US008642284B1

(12) United States Patent
Guarente et al.

(10) Patent No.: US 8,642,284 B1
(45) Date of Patent: Feb. 4, 2014

(54) METHODS FOR IDENTIFYING AGENTS THAT ALTER NAD-DEPENDENT DEACETYLATION ACTIVITY OF A SIR2 PROTEIN

(75) Inventors: Leonard Guarente, Chestnut Hill, MA (US); Shin-Ichiro Imai, St. Louis, MO (US); Christopher Armstrong, Jamaica Plain, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 767 days.

(21) Appl. No.: 09/735,786

(22) Filed: Dec. 13, 2000

Related U.S. Application Data

(63) Continuation-in-part of application No. 09/461,580, filed on Dec. 15, 1999, now Pat. No. 7,452,664.

(51) Int. Cl.
*C12Q 1/02* (2006.01)
*C12N 9/00* (2006.01)

(52) U.S. Cl.
USPC ............................................ 435/29; 435/183

(58) Field of Classification Search
None
See application file for complete search history.

(56) References Cited

U.S. PATENT DOCUMENTS

| | | | |
|---|---|---|---|
| 4,873,191 A | 10/1989 | Wagner et al. | |
| 5,010,175 A | 4/1991 | Rutter et al. | |
| 5,093,246 A | 3/1992 | Chech et al. | |
| 5,223,409 A | 6/1993 | Ladner et al. | |
| 5,270,163 A | 12/1993 | Gold et al. | |
| 5,270,170 A | 12/1993 | Schatz et al. | |
| 5,283,173 A | 2/1994 | Fields et al. | |
| 5,288,514 A | 2/1994 | Ellman | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,549,974 A | 8/1996 | Holmes | |
| 5,565,323 A | 10/1996 | Parker et al. | |
| 5,569,588 A | 10/1996 | Ashby et al. | |
| 5,593,853 A | 1/1997 | Chen et al. | |
| 5,705,350 A | 1/1998 | Mudryj et al. | |
| 5,744,300 A | 4/1998 | Linskens et al. | |
| 5,817,782 A | 10/1998 | Jazwinski et al. | |
| 5,840,493 A | 11/1998 | Davis et al. | |
| 5,874,210 A | 2/1999 | Guarente et al. | |
| 5,919,618 A | 7/1999 | Guarente et al. | |
| 5,965,543 A | 10/1999 | Campisi et al. | |
| 5,998,131 A | 12/1999 | Barr et al. | |
| 6,027,883 A | 2/2000 | Herrnstadt et al. | |
| 6,146,831 A | 11/2000 | Davis et al. | |
| 6,218,512 B1 | 4/2001 | Guarente et al. | |
| 6,228,583 B1 | 5/2001 | Guarente et al. | |
| 6,291,172 B1 | 9/2001 | Davis et al. | |
| 6,787,300 B2 | 9/2004 | Guarente et al. | |
| 6,835,563 B1 | 12/2004 | Lawn et al. | |
| 6,884,597 B1 | 4/2005 | Taya et al. | |
| 7,452,664 B2 | 11/2008 | Guarente et al. | |
| 7,572,575 B2 | 8/2009 | Guarente et al. | |
| 2003/0082668 A1 | 5/2003 | Tamai et al. | |
| 2003/0124101 A1 | 7/2003 | Gu et al. | |
| 2003/0207325 A1 | 11/2003 | Guarente et al. | |
| 2003/0228607 A1 | 12/2003 | Wagner et al. | |
| 2004/0091951 A1 | 5/2004 | Schultz | |
| 2005/0136429 A1 | 6/2005 | Guarente et al. | |
| 2005/0164969 A1 | 7/2005 | Guarente et al. | |
| 2006/0252076 A1 | 11/2006 | Guarente et al. | |
| 2007/0099830 A1 | 5/2007 | Guarente et al. | |
| 2009/0155834 A1 | 6/2009 | Guarente et al. | |
| 2010/0105036 A1 | 4/2010 | Guarente et al. | |
| 2010/0240029 A1 | 9/2010 | Guarente et al. | |
| 2011/0098190 A1 | 4/2011 | Guarente et al. | |

FOREIGN PATENT DOCUMENTS

| | | |
|---|---|---|
| WO | 9119735 | 12/1991 |
| WO | 9200091 | 1/1992 |
| WO | 9320242 | 10/1993 |
| WO | 9505459 | 2/1995 |
| WO | 9658850 | 2/1996 |
| WO | 9817823 | 4/1998 |
| WO | 9910482 | 3/1999 |
| WO | 0112851 | 2/2001 |
| WO | 0179842 | 10/2001 |
| WO | WO 02/31111 A2 | 4/2002 |
| WO | 02102981 | 12/2002 |
| WO | WO03004621 | 1/2003 |
| WO | 03046207 | 6/2003 |
| WO | 2005002527 | 1/2005 |
| WO | 2007146023 | 12/2007 |

OTHER PUBLICATIONS

Skolnick et al. (Trends in Biotechnology 18: 34-39, 2000).*
GenBank Accession No. AA105536 (1996).
GenBank Accession No. AA199012 (1997).
GenBank Accession No. AA260334 (1997).
GenBank Accession No. AI465098 (1999).
GenBank Accession No. AI465820 (1999).
GenBank Accession No. AI466061 (1999).
Aparicio et al., Modifiers of Position Effect are Shared Between Telomeric and Silent Mating-Type Loci in *S. cerevisiae*; Cell 66: 1279-1287 (1991).
Baker-Brachmann et al., The SIR2 Gene Family, Conserved From Bacteria to Humans, Functions in Silencing, Cell Cycle Progression, and Chromosome Stability; Genes & Development 9(23): 2888-2902 (1995).
Bork, Powers and Pitfalls in Sequence Analysis: The 70% Hurdle; Genome Research 10: 398-400 (2000).

(Continued)

*Primary Examiner* — Robert A Zeman
(74) *Attorney, Agent, or Firm* — Hamilton, Brook, Smith & Reynolds, P.C.

(57) ABSTRACT

Methods of identifying agents which alter the NAD-dependent deacetylation activity of a Sir2 protein or a fragment of a Sir2 protein are disclosed. The acetylated protein can be a nuclear protein, such as a histone protein, or a cytoplasmic protein. The Sir2 protein employed in the methods can include at least a core domain of a Sir2 protein, such as a human Sir2 protein.

18 Claims, 30 Drawing Sheets

(56) References Cited

OTHER PUBLICATIONS

Bowie et al., Deciphering the Message in Protein Sequences: Tolerance to Amino Acid Substitutions; Science 247: 1306-1310 (1990).
Braunstein et al., Transcriptional Silencing in Yeast is Associated with Reduced Nucleosome Acetylation; Genes & Development 7(4): 592-604 (1993).
Braunstein et al., Efficient Transcriptional Silencing in *Saccharomyces cerevisiae* Requires a Heterochromatin Histone Acetylation Pattern; Molecular & Cellular Biology 16(8): 4349-4356 (1996).
Bryk et al, Transcriptional Silencing of Ty1 Elements in the RDN1 Locus of Yeast; Genes Dev. 11: 255-269 (1997).
de Beus et al., Yeast NOP2 Encodes an Essential Nucleolar Protein with Homology to a Human Proliferation Marker; J. Cell Biology 127(6) (Part 2): 1799-1813 (1994).
Frye, Characterization of Five Human cDNAs with Homology to the Yeast SIR2 Gene: Sir2-like Proteins (Sirtuins) Metabolize NAD and May Have Protein ADP-Ribosyltransferase Activity; Biochemical & Biophysical Research Communications 260: 273-279 (1999).
Gottlieb and Easton-Esposito, A New Role for a Yeast Transcriptional Silencer Gene, SIR2, in Regulation of Recombination in Ribosomal DNA; Cell 56: 771-776 (1989).
Gotta et al., The Clustering of Telomeres and Colocalization with Rap1, Sir3, and Sir4 Proteins in Wild-Type *Saccharomyces cerevisiae*; J. Cell Biology 134(6): 1349-1363 (1996).
Grunstein, Yeast Heterochromatin: Regulation of Its Assembly and Inheritance by Histones; Cell 93: 325-328 (1998).
Hardy et al., A RAP1- interactig Protein Involved in Transcriptional Silencing and Telomere Length Regulation; Genes & Development 6: 801-814 (1992).
Ivy et al., Cloning and Characterization of Four SIR Genes of *Saccharomyces cerevisiae*; Molecular and Cellular Biology 6: 688-702 (1986).
Jamet-Vierny et al, Senescence in *Podospora anserina*: Amplification of a Mitochondrial DNA Sequence; Cell 21: 189-194 (1980).
Kadowaki et al., Nuclear mRNA Accumulation Causes Nucleolar Fragmentation in Yeast mtr2 Mutant; Molecular Biology of the Cell 5: 1253-1263 (1994).
Kaeberlein et al., The SIR2/3/4 Complex and SIR2 Alone Promote Longevity in Saccharomyces cerevisiae by Two Different Mechanisms; Genes & Development 13: 2570-2580 (1999).
Karpen and Allshire, The Case for Epigenetic Effects on Centromere Identity and Function; Trends Genet 13: 489-496 (1997).
Kennedy et al., Redistribution of Silencing Proteins from Telomeres to the Nucleolus is Associated with Extension of Life Span in *S. cerevisiae*; Cell 89: 381-391 (1997).
Martin et al., Relocalization of Telomeric Ku and SIR Proteins in Response to DNA Strand Breaks in Yeast; Cell 97: 621-633 (1999).
Mills et al., MEC1-Dependent Redistribution of the Sir3 Silencing Protein from Telomeres to DNA Double-Strand Breaks; Cell 97: 609-620 (1999).
Moretti et al., Evidence that a Complex of SIR Proteins Interacts with the Silencer and Telomere-Binding Protein RAP1; Genes & Development 8:2257-2269 (1994).
Oakes et al., Structural Alterations of the Nucleolus in Mutants of *Saccharomyces cerevisiae* Defective in RNA Polymerase I; Molecular and Cellular Biology 13(4): 2441-2455 (1993).
Park et al., Effects Effects of Mutations in DNA Repair Genes on Fomration of Ribosomal DNA Circles and Life Span in *Saccharomyces cerevisiae*; Molecular and Cellular Biology 19(5): 3848-3856 (1999).
Palladino et al., SIR3 and SIR4 Proteins Are Required for the Positioning and Integrity of Yeast Telomeres; Cell 75: 543-555 (1993).
Rine and Herskowitz, Four Genes Responsible for a Position Effect on Expression From HML and HMR in *Saccharomyces cerevisiae*; Genetics 116: 9-22 (1987).
Sherman and Pillus, An Uncertain Silence; Trends Genet. 13: 308-313 (1997).
Shou et al, Exit from Mitosis is Triggered by Tem1-Dependent Release of the Protein Phosphatase Cdc14 from Nucleolar RENT Complex; Cell 97: 233-244 (1999).
Sinclair et al., Accelerated Aging and Nucleolar Fragmentation in Yeast sgs1 Mutants; Science 277 (5330): 1313-1316 (1997).
Sinclair and Guarente, Extrachomosomal rDNA Circles—A Cause of Aging in Yeast; Cell 91: 1033-1042 (1997).
Smith and Boeke, An Unusual Form of Transcriptional Silencing in Yeast Ribosomal DNA; Genes and Development 11: 241-254 (1997).
Sweeney and Zakian, Extrachromosomal Elements Cause a Reduced Division Potential in nib1 Strains of *Saccharomyces cerevisiae*; Genetics 122: 749-757 (1989).
Tani et al., Nucleolar Accumulation of Poly (A) + RNA in Heat-Shocked Yeast Cells: Implication of Nucleolar Involvement in mRNA Transport; Molecular Biology of the Cell 6: 1515-1534 (1995).
Triolo and Sternglanz, Role of Interactions Between the Origin Recognition Complex and SIR1 in Transcriptional Silencing; Nature 381: 251-253 (1996).
Tsang and Escalante-Semerena, CobB, a New Member fo the SIR2 Family of Eucaryotic Regulatory Proteins, is Required to Compnsate for the Lack of Nicotinate Mononucleotide: 5,6-Dimethylbenzimidazole Phosphoribosyltransferase Activity in cobT Mutants During Cobalamin Biosynthesis in *Salmonella typhimurium* LT2\*; J. Biological Chemistry 273(48): 31788-31794 (1998).
Frye, Human Sir2-Like Proteins (sirtuins) are NAD-metabolizing protein (ADP-ribosyl) transferases; Proceedings of the American Association for Cancer Research; vol. 40; p. 436 (1999).
Sinclair et al., Molecular Mechanisms of Yeast Aging; Trends in Biochemical Science; vol. 23, No. 4, pp. 131-134 (1998).
Siliciano, J.D., et al., "DNA Damage Induces Phosphorylation of the Amino Terminus of p53", Genes Dev., 11:3471-3481 (Nov. 1997).
Simon, R.J., et al., "Peptoids: a Modular Approach to Drug Discovery" Proc. Natl. Acad. Sci. USA, 89:9367 (Oct. 1992).
Smith, J.S., et al., "A Phylogenetically Conserved NAD-Dependent Protein Deacetylase Activity in the Sir2 Protein Family", Proc. Natl. Acad. Sci. USA, 97:6658-6663 (Jun. 2000).
Sterner, D.E. and S.L. Berger, "Acetylation of histones and transcription-related factors", Microbiol. Mol. Biol. Rev., 64 (2), pp. 435-459 (Jun. 2000).
Sussel, L. and D. Shore, "Separation of Transcriptional Activation and Silencing Functions of the RAP1-Encoded Repressor/Activator Protein 1: Isolation of Viable Mutants Affecting Both Silencing and Telomere Length," Proc. Natl. Acad. Sci. USA, 88:7749-7753 (Sep. 1991).
Tanner, K.G., et al., "Silent Information Regulator 2 Family of NAD-Dependent Histone/Protein Deacetylases Generates a Unique Product, 1-O-acetyl-ADP-Ribose", Proc. Natl. Acad. Sci. USA, 97:14178-14182 (Dec. 2000).
Tao, W., et al., "Nucleocytoplasmic shuttling of oncoprotein HDM1 is required for HDM2-Mediated Degradation of P53", Proc. Natl. Acad. Sci. USA, 96(6):3077-3080 (Mar. 1999).
Tao, W., et al., "P19ARF Stabilizes p53 by Blocking Nucleo-Cytoplasmic Shuttling of Mdm2", Proc. Natl. Acad. Sci. USA, 96(12):6937-6941 (Jun. 1999).
Taunton, J., et al., "A Mammalian Histone Deacetylase Related to the Yeast Transcriptional Regulator Rpd3p", Science, 272:408-411 (Apr. 1996).
Thompson et al., "Germ line transmission and expression of a corrected HPRT gene produced by gene targeting in embryonic stem cells", Cell, 1989, vol. 56, pp. 313-321.
Tsai, D.E., et al., "In vitro Selection of an RNA Epitope Immunologically Cross-Reactive with a Peptide", Proc. Natl. Acad. Sci. USA, 89:8864-8868 (Oct. 1992).
Unger, T., et al., "Critical Role for Ser20 of Human p53 in the Negative Regulation of p53 by Mdm2", EMBO J., 18 (7):1805-1814 (1999).
Urrestarazu et al. EMBL/GenBank/DDBJ databases Accession No. Z28267, 1994.
Van Der Putten, H., et al., "Efficient Insertion of Genes Into the Mouse Germ Line Via Retroviral Vectors", Proc. Natl. Acad. Sci. USA, 82:6148-6152 (Sep. 1985).
Vaughn, T.J., et al., "Human Antibodies with Sub-nanomolar Affinities Isolated from a Large Non-immunized Phage Display Library," Nature Biotechnology, 14(3):309-314 (Mar. 1996).

(56) References Cited

OTHER PUBLICATIONS

Vaziri, H. et al. "Analysis of Genomic Integrity and p53-Dependent G1 Checkpoint in Telomerase-Induced Extended-Life-Span Human Fibroblasts", Mol. Cell. Biol., 19:2373-2379 (Mar. 1999).
Vaziri, H., et al., "ATM-Dependent Telomere Loss in Aging Human Diploid Fibroblasts and DNA Damage Lead to the Post-Translational Activation of p53 Protein Involving Poly (ADP-Ribose) Polymerase", EMBO J., 16:6018-6033 (1997).
Vogelstein, B., et al., "Surfing the p53 Network", Nature, 408:307-310 (Nov. 2000).
Vousden, K.H., "p53: Death Star", Cell, 103(5):691-694 (Nov. 2000).
Weindruch, R. et al., "The Retardation of Aging in Mice by Dietary Restriction: Longevity, Cancer, Immunity and Lifetime Energy Intake", Journal of Nutrition, 116(4):641-654 (Nov. 1985).
Wu. W., et al., "The p53-mdm-2 Autoregulatory Feedback Loop", Genes Dev., 7:1126-1132 (Apr. 1993).
Yang, X.H., et al., "Cloning and Characterization of Two Mouse Genes with Homology to the Yeast Sir2 Gene," Genomics, 69:355-369 (Nov. 2000).
Yin, Y., et al., "Involvement of p85 in p53-Dependent Apoptotic Response to Oxidative Stress", Nature, 391:707-710 (Feb. 1998).
Yu, A., et al., "Activation of p53 or loss of the Cockayne syndrome group B repair protein causes metaphase fragility of human U1, U2, and 58 genes", Mol. Cell, 5:801-810 (May 2000).
Yu, Y., et al., "PUMA Induces the Rapid Apoptosis of Colorectal Cancer Cell," Molecular Cell, 7:673-682 (Mar. 2001).
Zhang, Y., et al., "SAP30, a Novel Protein Conserved Between Human and Yeast, is a Component of a Histone Deacetylase Complex", Mol. Cell, 1:1021-1031 (Jun. 1998).
Ziegler, M., et al., "New Functions of a Long-Known Molecule—Emerging Roles of NAD in Cellular Signaling," Eur. J. Biochem., 267:1550-1564 (Jan. 2000).
Bairoch, A., "Go Hunting in Sequence Databases but Watch Out for the Traps," Trends in Genetics, 12(10): 425-427 (Oct. 1996).
Campbell, D.A. and J.C. Bermak, "Phosphonate Ester Synthesis Using a Modified Mitsunobu Condensation," J. Org. Chem., 59:658 (1994).
Carroll, S.F. and R.J. Collier, "Photoaffinity labeling of active site residues in ADP-ribosylating toxins", Methods Enzymol., 235:631-639 (1994).
Felici, J., "Selection of Antibody Ligands From a Large library of Oligopeptides Expressed on a Multivalent Exposition Vector", J. Mol. Biol., vol. 222, pp. 301-310 (1991).
Furka, A., et al. "General Method for Rapid Synthesis of Multicomponent Peptide Mixtures", Int. J. Pept. Prot. Res., 37:487-493 (1991).
Gallop, M.A., et al., "Applications of Combinatorial Technologies to Drug Discovery. I. Background and Peptide Combinatorial Libraries", J. Med. Chem., 37:1233 (Apr. 1994).
Giles, R.H., et al., "Conjunction dysfunction: CBP/p300 in human disease", Elsevier Science Ltd. vol. 14(5), pp. 178-183 (1998).
Gordon, J.W., "Transgenic Animals," Intl. Rev. Cytol., 115:171-229 (1989).
Guarente, L., "Diverse and Dynamic Functions of the Sir Silencing Complex", Nat. Genet., 23:281-285 (Nov. 1999).
Hagihara, M., et al., "Viylogous Polypeptides: An Alternative Peptide Backbone," J. Amer. Chem. Soc., 114: 6568-6570 (1992).
Hass, B.S., et al., "Effects of caloric restriction in animals on cellular function, oncogene expression, and DNA methylation in vitro", Mutat. Res., 295(4-6): 281-289 (Oct. 1993).
Hirschmann, R., et al., "Nonpeptidal Peptidomimetics with a β-D-Glucose Scaffolding. A Partial Somatostatin Agonist Bearing a Close Structural Relationship to a Potent, Selective Substance P Antagonist", J. Amer. Chem. Soc., 114:9217-9218 (1992).
Hollstein, M. et al., "New Approaches to Understanding p53 Gene Tumor Mutation Spectra", Mutat. Res., 431(2):199-209 (Jun. 1999).
Houghten, R.A., et al. "The Use of Synthetic Peptide Combinatorial Libraries for the Identification of Bioactive Peptides," Biotechniques, 13:412-421 (1992).

Kari, F.W., et al., "Roles for Insulin-Like Growth Factor-1 in Mediating the Anti-Carcinogenic Effects of Caloric Restriction", J. Nutr. Health Aging, 3(2):92-101 (1999).
Khanna, K.K. et al., "ATM Associates With and Phosphorylates P53: Mapping the Region of Interaction", Nat. Genet., 20(4):398-400 (Dec. 1998).
Kuo, M.H., et al., "Roles of histone acetyltransferases and deacetylases in gene regulation", BioEssays, vol. 20, pp. 615-626 (1998).
Lutzker, S.G., et al., "A functionally inactive p53 protein in teratocarcinoma cells is activated by either DNA damage or cellular differentiation", Nat. Med., 2:804-810 (Jul. 1996).
Mitsudomi, T., et al., "p53 Gene Mutations in Non-Small-Cell Lung Cancer Cell Lines and Their Correlation With the Presence of Ras Mutations and Clinical Features", Oncogene, 7:171-180 (1992).
NCBI Accession No. O46955, submitted Aug. 1995.
NCBI Accession No. P25339, submitted May 1996.
NCBI Accession No. P46955, submitted Aug. 1995.
Sharpless, N.E. and R.A. DePinho., "The INK4A/ARF Locus and Its Two Gene Products", Curr. Opin. Genet. Dev., 9(1):22-30 (1999).
Smith, T.F. and X. Zhang, "The Challengers of Genome Sequence Annotation or 'The Devil in the Details'," Nature Biotechnology, 15:1222-1223 (Nov. 1997).
Tibbetts, R.S., et al., "The DnaJ family of protein chaperones in Trypanosoma cruzi", Mol. Biochem. Parasitol., 91(2):319-326 (1998).
Tsai, D.E. and J.D. Keene, "In Vitro Selection of RNA Epitopes Using Autoimmune Patient Serum[1]", Immunology, 150:1137 (Feb. 1993).
Tsang, N.M., et al., "Abrogation of p53 Function by Transfection of HPV16 E6 Gene Enhances the Resistance of Human Diploid Fibroblasts to Ionizing Radiation", Oncogene, 10:2403-2408 (1995).
Weber, J.D., et al., "Nucleolar Arf Sequesters Mdm2 and Activates p53", Nat. Cell. Biol., 1(1):20-26 (May 1999).
Wolf, N.S. and W.R. Pendergrass, "The Relationships of Animal Age and Caloric Intake to Cellular Replication in Vivo and in Vitro: A Review", J. Gerontol. A Bio. Sci. Med. Sci., 54(11):B502-B517 (1999).
Yoshida, M., et al., "Trichostatin A and Trapoxin: Novel Chemical Probes for the Role of Histone Acetylation in Chromatin Structure and Function", Bioessays, 5:423-430 (Feb. 1995).
Zuckermann, R.N., et al., "Discovery of Nanomolar Ligands for 7-Transmembrane G-protein-coupled Receptors from a Diverse N-(Substituted)glycine Peptoid Library", J. Med. Chem., 37:2678-2685 (1994).
U.S. Office Action dated Feb. 28, 2011 for U.S. Appl. No. 12/408,575.
U.S. Office Action dated Oct. 31, 2007 for U.S. Appl. No. 09/461,580.
U.S. Office Action dated Jul. 17, 2006 for U.S. Appl. No. 09/461,580.
U.S. Office Action dated Nov. 15, 2005 for U.S. Appl. No. 09/461,580.
U.S. Office Action dated Mar. 26, 2004 for U.S. Appl. No. 09/461,580.
U.S. Office Action dated Nov. 6, 2001 for U.S. Appl. No. 09/461,580.
U.S. Office Action dated May 25, 2010 for U.S. Appl. No. 10/885,977.
U.S. Office Action dated Oct. 23, 2008 for U.S. Appl. No. 10/885,977.
U.S. Office Action dated Mar. 19, 2008 for U.S. Appl. No. 10/885,977.
U.S. Office Action dated Dec. 21, 2006 for U.S. Appl. No. 10/885,977.
U.S. Office Action dated Sep. 29, 2010 for U.S. Appl. No. 12/209,847.
Tanny, J.C. and Danesh, M., "Coupling of histone deacetylation to NAD breakdown by the yeast silencing protein Sir2: Evidence for acetyl transfer from substrate to an NAD breakdown product," PNAS (98)2: 415-420 (Jan. 16, 2001).
Lin, S., et al., "Requirement of NAD and SIR2 for Life-Span Extension by Calorie Restriction in Saccharomyces cerevisiae" Science, 289:2126-2128 (Sep. 2000).

(56) References Cited

OTHER PUBLICATIONS

Liu, L., et al., "p53 Sites Acetylated in vitro by PCAF and p300 are Acetylated in vivo in Response to DNA Damage", Mol. Cell. Biol., 19:1202-1209 (Feb. 1999).
Lo, C.W., "Transformation by Iontophoretic Microinjection of DNA: Multiple Integrations Without Tandem Insertions", Mol. Cell Biol., 3:1803-1814 (Oct. 1983).
Lohrum, M. and K.H. Vousden, "Regulation and Activation of p53 and its Family Members", Cell Death Differ., 6(12):1162-1168 (Oct. 1999).
Longtine, M.S., et al., "Telomere-Mediated Plasmid Segregation in *Saccharomyces cerevisiae* Involves Gene Products Required for Transcriptional Repression at Silencers and Telomeres," Genetics, 133:171-182 (Feb. 1993).
Lumpkin, C.K., et al., "Existence of High Abundance Antiproliferative mRNA's in Senescent Human Diploid Fibroblasts", Science, 232:393-395 (Apr. 1986).
Lundblad, V., et al., "A Mutant With a Defect in Telomere Elongation Leads to Senescence in Yeast," Cell, 57:633-643 (May 1989).
Luo, J., et al., "Deacetylation of p53 Modulates its Effect on Cell Growth and Apoptosis," Nature, 408:377-381 (Nov. 2000).
Marasco, W.A., et al., "Design, Intracellular Expression, and Activity of a Human Anti-Human Immunodeficiency Virus Type 1 gp120 Single-Chain Antibody", Proc. Natl. Acad. Sci. USA, 90:7889-7893 (Aug. 1993).
Marbois, B., et al., "The COQ7 Gene Encodes a Protein in *Saccharomyces cerevisiae* Necessary for Ubiquinone Biosynthesis", J. Biol. Chem., 271(6), pp. 2995-3004 (Feb. 1996).
Marks, P.A., et al., "Histone Deacetylase Inhibitors: Inducers of Differentiation or Apoptosis of Transformed Cells", J. Nat'l Cancer Inst., 92(15):1210-1216 (Aug. 2000).
Marshall, M., et al., "Functional Domains of SIR4, a Gene Required for Position Effect Regulation in *Saccharomyces cerevisiae*," Molecular and Cellular Biology, 7(12):4441-4452 (Dec. 1987).
McAinsh, A.D., et al., "DNA Damage Triggers Disruption of Telomeric Silencing and Mec1p-Dependent Relocation of Sir3p", Curr. Biol., 9:963-966 (Aug. 1999).
McConnell, S.J., et al., "Temperate-sensitive Yeast Mutants Defective in Mitochondrial Inheritance", J. Cell Biol. 111:967-976 (Sep. 1990).
Migliaccio, E., et al., "The p66shc Adaptor Protein Controls Oxidative Stress Response and Life Span in Mammals", Nature, 402:309-313 (Nov. 1999).
Miura, T. and R. Sato, "Cellular Senescence in Yeast Caused by Carbon-Source Starvation," J. Biochem., 76 (3):593-601 (1974).
Miura, T. and T. Yanagita, "Cellular Senescence in Yeast Caused by Carbon-Source Starvation," J. Biochem., 72 (1):141-148 (1972).
Morgenstern, J.P., et al., "Advanced Mammalian Gene Transfer: High Titre Retroviral Vectors with Multiple Drug Selection Markers and a Complementary Helper-Free Packaging Cell Line", Nucl. Acids Res., 18:3587-3596 (May 1990).
Mortimer, R.K. and J.R. Johnston, "Life Span of Individual Yeast Cells", Nature, 183:1751-1752 (1959).
Muller, I. and F. Wolf, "A Correlation Between Shortened Life Span and UV-Sensitivity in Some Strain of *Saccharomyces cerevisiae*", Mol. Gen. Genet., 160:231-234 (1978).
Muller, I., "Experiments on Ageing in Single Cells of *Saccharomyces cerevisiae*", Arch. Mikrobiol., 77:20-25 (Dec. 1971).
Muller, I., "Parental age and the life-span of zygotes of *Saccharomyces cerevisiae*", Antonie van Leeuwenhoek, 51:1-10 (1985).
Muller, I., et al., "Calendar Life Span Versus Budding Life Span of *Saccharomyces cerevisiae*," Mechanisms of Aging and Development, 12(1):47-52 (1980).
Nakamura, S., et al., "Multiple lysine mutations in the C-terminal domain of p53 interfere with MDM2-dependent protein degradation and ubiquitination", Mol. Cell. Biol., 20:9391-9398 (Dec. 2000).
Norwood, T.H., et al., "Dominance of the Senescent Phenotype in Heterokaryons Between Replicative and Post-Replicative Human Fibroblast-Like Cells", Proc. Natl. Acad. Sci. USA, 71:2231-2235 (Jun. 1974).

Oda, K., et al., "p53AIP1, a Potential Mediator of p53-Dependent Apoptosis, and its Regulation by Ser-46-Phosphorylated p53", Cell, 102(6), pp. 849-862 (Sep. 2000).
Oda, E., et al., "Noxa, a BH3-Only Member of the Bcl-2 Family and Candidate Mediator of p53-Induced Apoptosis", Science, 288(5468):1053-1058 (May 2000).
Okamoto, K. and D. Beach, "Cyclin G is a Transcriptional Target of the p53 Tumor Suppressor Protein", EMBO J., 13:4816-4822 (1994).
Olovnikov, A.M., "A Theory of Marginotomy: The Incomplete Copying of Template Margin in Enzymic Synthesis of Polynucleotides and Biological Significance of the Phenomenon", J. Theor. Biol. 41:181-190 (1973).
Oren, M., "Regulation of the p53 Tumor Suppressor Protein", J. Biol. Chem., 274:36031-36034 (Dec. 1999).
Orgel, L.E., "Ageing of Clones of Mammalian Cells", Nature, 243:441-445 (Jun. 1973).
Pabo, C.O. "Transcription Factors: Structural Families and Principles of DNA Recognition," Annu. Rev. Biochem., 61:1053-1075 (1992) (month not available).
Pearson et al., "PML regulates p53 acetylation and premature senescence induced by oncogenic Ras", Nature, 2000, vol. 406, pp. 207-210.
Pelissier, P., et al., "NCA3, a Nuclear Gene Involved in the Mitochondrial Exepression of Subunits 6 and 8 of the Fo-F1 ATP Synthase of *S. cerevisiae*", Curr. Genet. 27:409-416 (1995).
Pereira-Smith, O.M. and J.R. Smith, "Genetic Analysis of Indefinite Division in Human cells: Identification of Four Complementation Groups", Proc. Natl. Acad. Sci. USA 85:604-60462 (Aug. 1988).
Pohley, H., "A formal Mortality Analysis for Populations of Unicellular Organisms (*Saccharomyces cerevisiae*)", Mechanisms of Ageing and Development, 38:231-243 (1987).
Pomerantz, J., et al., "The Ink4a Tumor Suppressor Gene Product, p19Arf, Interacts with MDM2 and Neutralizes MDM2's Inhibition of p53", Cell, 92(6), pp. 713-723 (Mar. 1998).
Pringle, J.R., et al., "Fluorescence Microscopy Methods for Yeast", Methods in Cell Biology, 31:357-435 (1989).
Proft, M., et al., "CAT5, a New Gene Necessary for Derepression of Gluconeogenic Enzymes in *Saccharomyces cerevisiae*", EMBO J., 14(24):6116-6126 (1995).
Rodriguez, M.S., et al., "Multiple C-Terminal Lysine Residues Target p53 for Ubiquitin-Proteasome-Mediated Degradation", Mol. Cell. Biol., 20:8458-8467 (Nov. 2000).
Rogina, B., et al., "*Drosophila* Drop-Dead Mutations Accelerate the Time Course of Age-Related Markers", Proc. Natl. Acad. Sci. USA, 94:6303-6306 (Jun. 1997).
Sainsard-Chanet, A. and O. Begel, "Transformation of Yeast and Podospora: Innocuity of Senescence-Specific DNAs," Mol Gen Genet., 204:443-451 (1986).
Sakaguchi, K., et al., "DNA Damage Activates p53 Through a Phosphorylation-Acetylation Cascade", Genes Dev., 12:2831-2841 (Jul. 1998).
Schnell, R., et al., "Genetic and Molecular Characterizations of Suppressors of SIR4 Mutations in *Saccharomyces cerevisiae*," Genetics,122:29-46 (May 1989).
Scott, J.K. and G.P. Smith, "Searching for Peptide Ligands with an Epitope Library", Science, 249:386-390 (Jun. 1990).
Seeler, J.S. and A. Dejean, "The PML Nuclear Bodies: Actors or Extras?," Curr. Opin. Genet. Dev., 9(3):362-367 (Jun. 1999).
Serrano, M., et al., "Oncogenic ras Provokes Premature Cell Senescence Associated with Accumulation of p53 and p16I8NK4a", Cell, 88(5):593-602 (Mar. 1997).
Shieh, S., et al., "DNA Damage-Induced Phosphorylation of p53 Alleviates Inhibition MDM2", Cell, 91:325-334 (Oct. 1997).
Shieh, S., et al., "The Human Homologs of Checkpoint Kinases Chk1 and Cds1(Chk2) Phosphorylate p53 at Multiple DNA Damage-Inducible Sites", Genes Dev., 14:289-300 (2000).
Shore D., "The Sir2 protein family: A novel deacetylase for gene silencing and more", Proc. Natl. Acad. Sci. USA, 2000, vol. 97, pp. 14030-14032.
Allsopp, R.C., et al., "Telomere Length Predicts Replicative Capacity of Human Fibroblasts", Proc. Natl. Acad. Sci. USAa 89:10114-10118 (Nov. 1992).

(56) References Cited

OTHER PUBLICATIONS

Angello, J.C., et al., "Cell Enlargement: One Possible Mechanism Underlying Cellular Senescence", J. Cell. Physiol. 140:288-294 (Feb. 1989).
Angello, J.C., et al., "Proliferative Potential of Human Fibroblasts: An Inversive Dependence on Cell Size", J. Cell. Physiol. 132:125-130 (1987).
Ashcroft, M., et al.,"Stress Signals Utilize Multiple Pathways to Stabilize p53", Mol. Cell Biol., 20(9):3224-3233 (May 2000).
Avantaggiati, M.L., et al., "Recruitment of p300/CB0 in p53-Dependent Signal Pathways", Cell, 89:1175-1184 (Jun. 1997).
Barak, Y., et al., "mdm2 Expression is Induced by6 Wild Type p53 Activity", EMBO J., 12(2):461-468 (1993).
Bernstein, B.E., et al., "Genomewide Studies of Histone Deacetylase Function in Yeast", Proc. Natl. Acad. Sci. USA, 97:13708-13713 (Dec. 2000).
Bertrand, H., et al., "An Extrachromosomal Plasmid is the Etiological Precursor of kaIDNA Insertion Sequences in the Mitochrondial Chromosome of Senescent Neurospora", Cell, 47:829-837 (Dec. 1986).
Brower, M., et al., "Growth of cell lines and clinical specimens of human non-small cell lung cancer in a serum-free defined medium", Cancer Research, 46(2):798-806 (Feb. 1986).
Buckley, A.R., et al., "Alterations in pim-1 and c-myc Expression Associated with Sodium Butyrate-Induced Growth Factor Dependency in Autonomous Rat Nb2 Lymphoma Cells", Cell Growth Differ., 17: 1713-1721 (Dec. 1996).
Butler, L.M., et al., "Suberoylanilide Hydroxamic Acid, an Inhibitor of Histone Deacetylase Suppresses the Growth of Prostate Cancer Cells in Vitro and in Vivo", Cancer Res., 60:5165-5170 (Sep. 2000).
Cabib, E., et al., "A Molecular Model for Morphogenesis: The Primary Septum of Yeast", Curr. Top. Cell. Regul.,8:1-32 (1974).
Campisi, J., "Aging, Chromatin, and Food Restriction-Connecting the Dots", Science, 289, pp. 2062-2063 (Sep. 2000).
Canman, C.E., et al., "Activation of the ATM Kinase by Ionizing Radiation and Phosphorylation of p53", Science, 281:1677-1679 (Sep. 1998).
Chao, C., et al., "p53 Transcriptional Activity is Essential for p53-Dependent Apoptosis Following DNA Damage", EMBO J., 19:4967-4975 (Jul. 2000).
Chehab, N.H., et al., "Phosphorylation of Ser-20 Mediates Stabilization of Human p53 in Response to DNA Damage", Proc. Natl. Acad. Sci. USA, 96:13777-13782 (Nov. 1999).
Chen, Q.M., et al., "Apoptosis or Senescence-Like Growth Arrest: Influence of Cell-Cycle Position, p53, p21 and bax in H2O2 Response of Normal Human Fibroblasts", Biochem. J., 347:543-551 (2000).
Chen, X., et al., "sir2 Mutants of Kluyveromyces Lactis are Hypersensitive to KNA-Targeting Drugs", Mol. Cell. Biol., 14:4501-4508 (Jul. 1994).
Cheung, P., et al., "Signaling to Chromatin Through Histone Modifications", Cell, 103:263-271 (Oct. 2000).
Cho, C.Y., et al., "An Unnatural Biopolymer", Science, 261:1303-1305 (Sep. 1993).
Cristofalo, V.J. and D.Kritchevsky, "Cell Size and Nucleic Acid Content in the Diploid Human Cell Line WI-38 During Aging", Med. Exp. 19:313-320 (1969).
Cristofalo, V.J., et al., "Growth factors as Probes of Cell Aging", Exp. Gerontol. 24:367-374 (1989).
Cull, M.G., et al., "Screening for Receptor Ligands Using Large Libraries of Peptides Linked to the C Terminus of the lac Repressor", Proc. Natl. Acad. Sci. USA, 89:1865-1869 (Mar. 1992).
Cummings, D.J., et al., "Excision—Amplification of Mitochrondial DNA During Senescence in *Podospora anserina*", J. Mol. Biol., 185:659-680 (Mar. 1985).
Cwirla, S.E., et al., "Peptides on Phage: A Vast Library of Peptides for Identifying Ligands", Proc. Natl. Acad. Sci. USA, 87:6378-6382 (Aug. 1990).
Cziepluch, C., et al., "Sequencing Analysis of a 40.2 kb Fragment of Yeast Chromosome X Reveals 19 Open Reading Frames Including URA2 (5' end), TRK1, PBS2, SPT10, GCD14, RPE1, PHO86, NCA3, ASF1, CCT7, GZF3, Two tRNA Genes, Three Remnant Delta Elements and a Ty4 Rransposon", Yeast, 12:1471-1474 (Jun. 1996).
De Witt, S.H., et al., "'Diversomes': An Approach to Nonpeptide, Nonoligomeric Chemical Diversity", Proc. Natl. Acad. Sci. USA, 90:6909 (Aug. 1993).
Devlin, J.J., et al., "Random Peptide Libraries: a Source of Specific Protein Binding Molecules", Science, 249:404-406 (Jul. 1990).
Dhar, S., et al., "Inactivation of 14-3-3sigma Influences Telomere Behavior and Ionizing Radiation-Induced Chromosomal Instability", Mol. Cell. Biol., 20:7764-7772 (Oct. 2000).
Di Cristofano, A., et al., "Impaired Fas Response and Autoimmunity in Pten+/− Mice", Science, 285:2122-2125 (Sep. 1999).
Dimri, G.P., et al., "A Biomarker that Identifies Senescent Human Cells in Culture and in Aging Skin in vivo," Proc. Natl. Acad. Sci. USA, 92:9363-9367 (Sep. 1995).
D'Mello, N.P. et al., "Molecular Analysis of a Young-Specific Gene in the Yeast *Saccharomyces cerevisiae*," Abstracts of the 92nd General Meeting of the American Society for Microbiology, H-284, p. 230 (May 26-30, 1992).
Dumaz, N. and D.W. Meek, "Serine 15 Phosphorylation Stimulates p53 Transactivation But Does Not Directly Influence Interaction with HDM2", EMBO J., 18(24:7002-7010 (1999).
Edgington, S.M., "Is Biopharmaceutical Discovery Entering a New Evolutionary Stage?" Bio/Technology, 11:285 (Mar. 1993).
Egilmez, N.K. and S.M. Jazwinski, "Evidence for the Involvement of a Cytoplasmic Factor in the Aging of the Yeast *Saccharomyces cerevisiae*," Journal of Bacteriology, 171(1):37-42 (Jun. 1989).
Egilmez, N.K., et al., "Preparation and Partial Characterization of Old Yeast Cells", J. Gerontol. Biol. Sci. 45:B9-B17 (1990).
Egilmez, N.K. et al., "Specific Alterations in Transcript Prevalence During the Yeast Life Span," The Journal of Biological Chemistry, 264(24):14312-14317 (Apr. 1989).
El-Deriry, W.S., et al., "WAF1, a Potential Mediator of p53 Tumor Suppression", Cell, 75:817-825 (Nov. 1993).
Erb, E., et al., "Recursive Deconvolution of Combinatorial Chemical Libraries", Proc. Natl. Acad. Sci. USA, 91:11422-11426 (Nov. 1994).
Ferbeyre, G., et al., "MIL is Induced by Oncogenic ras and Promotes Premature Senescence", Genes Dev., 14:2015-2027 (Jun. 2000).
Finkel, T. and N.J. Holbrook, "Oxidants, Oxidative Stress and the Biology of Ageing", Nature, 408:239-247 (Nov. 2000).
Finnin, M.S., et al., "Structures of a Histone Deacetylase Homologue Bound to the TSA and SAHA Inhibitors", Nature, 401: 188-193 (Sep. 1999).
Fleming, J.E., et al., "Role of Oxidative Stress in Drosophila Aging," Mutation Research, 275:267-279 (May 1992).
Fodor, S.P.A., et al., "Multiplexed Biochemical Assays with Biological Chips", Nature, 364:555-556 (Aug. 1993).
Freedman, D.A., et al., "Functions of the MDM2 Oncoprotein", Cell. Mol. Life Sci., 55(1):96-107 (1999).
Friedman, D.B. and T.E. Johnson, "A Mutation in the age-1 Gene in *Caenorhabditis elegans* Lengthens Life and Reduces Hermaphrodite Fertility", Genetics, 118:75-86 (Jan. 1988).
GenBank Acc. No. AL133551, "Human DNA Sequence from Clone RP11-57G10 on Chromosome 10 Contains the SIRT1 Gene for Sirtuin (Silent Mating Type Information Regulation 2 Homolog) 1 (*S. cerevisiae*)," version of May 18, 2005).
GenBank Acc. No. BC026650, "*Mus musculus* Sirtuin 7 (Silent Mating Type Information Regulation 2, Homolog) 7 (*S. cerevisiae*)," version of Jun. 30, 2004.
GenBank Accession No. NP_036372; GI No. 6912662, first seen at NCBI on Feb. 7, 2000.
Giaccia, A.J. and M.B. Kastan, "The complexity of p53 modulation: emerging patterns from divergent signals", Genes Dev., 12:2973-2983 (Oct. 1998).
U.S. Office Action dated Jul. 25, 2011 for U.S. Appl. No. 12/209,847.
Goodman, R.H. and S. Smolik, "CBP/p300 in cell growth, transformation, and development", Genes Dev., 14 (13):1553-1577 (2000).
Gottschling, D.E., "Gene silencing: two faces of SIR2", Curr. Biol., 10: R708-R711 (2000).
Gu W., et al., "A Novel Human SRB/MED-Containing Cofactor Complex, SMCC, Involved in Transcription Regulation", Mol. Cell, 3:97-108 (Jan. 1999).

(56) References Cited

OTHER PUBLICATIONS

Gu W., et al., "Activation of p53 Sequence-Specific DNA Binding by Acetylation of the p53 C-Terminal Domain", Cell, 90:595-606 (Aug. 1997).
Gu, W., et al., "Synergistic Activation of Transcription by CBP and p53", Nature, 387:819-823 (Jun. 1997).
Guarente, L. and C.Kenyon, "Genetic Pathways That Regulate Ageing in Model Organisms", Nature,408:255-262 (Nov. 2000).
Guarente, L. "UASs and Enhancers: Common Mechanism of Transcriptional Activation in Yeast and Mammals", Cell, 52:303-305 (Feb. 1988).
Guarente, L., "Sir2 links chromatin silencing, metabolism, and aging", Genes Dev., 2000, vol. 14, pp. 1021-1026.
Guo, J.C., et al., "Dual Analyte Flow Injection Fluorescence Immunoassays Using Thiophilic Gel Reactors and Synchronous Scanning Detection", Analyst, 125(10):1707-1708 (Sep. 2000).
Hamlyn et al. EMBL/GenBank/DDBJ databases Accession No. Z46833 (Nov. 1994).
Harley, C.B., et al., "Telomeres Shorten During Ageing of Human Fibroblasts", Nature, 345:458-460 (May 1990).
Hayflick, I. and P.S. Moorhead, "The Serial Cultivation of Human Diploid Cell Trains", Exp. Cell Res., 25:585-621 (May 1961).
Hayflick, I., "The Limited in vitro Lifetime of Human Diploid Cell Strains", Exp. Cell Res., 37:614-636 (1965).
Hill, A.A., et al., "Genomic Analysis of Gene Expression in *C. elegans*", Science, 290: 809-812 (Oct. 2000).
Hirao, A., et al., "DNA damage-induced activation of p53 by the checkpoint kinase Chk2", Science, 287 (5459):1824-1827 (Mar. 2000).
Hirsch, H.R., "Accumulation of a Senescence Factor in Yeast Cells," Experimental Gerontology, 28(2):195-204 (1993).
Hollstein, M., et al., "Database of p53 Gene Somatic Mutations in Human Tumors and Cell Lines", Nucleic Acids Res., 22:3551-3555 (1994).
Holtzman, et al., "Synthetic-lethal interactions identify two novel genes, SLA1 and SLA2, that control membrane cytoskeleton assembly in *Saccharomyces cerevisiae*", J. Cell Bio., 122:635-644 (1993).
Honda, R. and H. Yasuda, "Association of p19(ARF) With Mdm2 Inhibits Ubiquitin Ligase Activity of Mdm2 for Tumor Suppressor p53", EMBO J., 18(1):22-27 (1999).
Houghten, R.A., et al., "Generation and Use of Synthetic Peptide Combinatorial Libraries for Basic Research and Drug Discovery", Nature, 354:84-88 (Nov. 1991).
Imai, S., et al., "Transcriptional silencing and longevity protein Sir2 is an NAD-dependent histone deacetylase", Nature, 403:795-800 (Feb. 2000).
Imai, S., et al., "Sir2: an NAD-Dependent Histone Deacetylase that Connects Chromatin Silencing, Metabolism, and Aging," Cold Spring Harbor Symp. Quant. Biol., 65:297-302 (2000).
International Search Report for PCT/US94/09351 Dated Jan. 23, 1995.
Ito, M., et al., "Identity between TRAP and SMCC Complexes Indicates Novel Pathways for the Function of Nuclear Receptors and Diverse Mammalian Activators", Mol. Cell., 3:361-370 (Mar. 1999).
Ivy, J.M., et al., "Map Positions of Yeast Genes SIR1, SIR3 and SIR4," Genetics III, 735-744 (Dec. 1985).
Jazwinski, M., "Longevity, Genes, and Aging", Science, 273:54-59 (Jul. 1996).
Jazwinski, S.M., "Genes of Youth: Genetics of Aging in Baker's Yeast," ASM News, 59(4):172-178 (1993).
Jazwinski, S.M., "Aging and Senescence of the Budding Yeast *Saccharomyces Cerevisiae*," Molecular Microbiology, 4 (3):337-343 (Oct. 1990).
Juan, L., et al., "Histone Deacetylases Specifically Down-Regulate p53-Dependent Gene Activation", J. Biol. Chem., 275(27):20436-20443 (Jul. 2000).
Kastan et al., "A mammalian cell cycle checkpoint pathway utilizing p. 53 and TGADD45 is defective in ataxia-telangiectasis", Cell, 1992, vol. 71, pp. 587-597.

Kenyon, C., et al., "A *C. elegans* Mutant That Lives Twice as Long as Wild Type", Nature,366:461-464 (Dec. 1993).
Kobet et al., "MDM2 inhibits p300-mediated p53 acetylation and activation by forming a ternary complex with the two proteins", Proc. Natl. Acad. Sci. USA, 2000, vol. 97, pp. 12547-12552.
Kofler, B., et al., "Purification and Characterization of NAD+: ADP-Ribosyltransferase (Polymerizing) from Dictyostelium Discoideum," Biochem, J., 293:275-281 (1993).
Kohl, N.E., et al., "Selective Inhibition of ras-Dependent Transformation by a Farnesyltransferase Inhibitor", Science, 260:1934 (Jun. 1993).
Koll, F., et al., "A 1100-bp Sequence of Mitochondiral DNA is Involved in Senescence Process in Podospora: Study of Senescent and Mutant Cultures", Plasmid,14:106-117 (Jun. 1985).
Kouzarides, T., "Acetylation: a Regulatory Modification to Rival Phosphorylation?" EMBO J., 19:1176-1179 (2000).
Kung, A.L., et al., "Gene Dose-Dependent Control of Hematopoiesis and Hematologic Tumor Suppression by CBP", Genes Dev., 14(3):272-277 (2000).
Lam, et al., "Rational design of potent, bioavailable, nonpeptide cyclic ureas as HIV protease inhibitors", Science, 1994, vol. 263, p. 380.
Lam, K.S., et al."A New Type of Synthetic Peptide Library for Identifying Ligand-Binding Activity", Nature, 354:82-84 (Nov. 1991).
Lambert, P.F., et al., "Phosphorylation of p53 Serine 15 Increases Interaction with CBP", J. Biol Chem., 273:33048-33053 (Dec. 1998).
Landry, J., et al., "The Silencing Protein SIR2 and its Homolog are NAD-Dependent Protein Deacetylases," PNAS, 97 (11):5807-5811 (May 2000).
Landry, J., et al., "Role of NAD(+) in the Deacetylase Activity of the SIR2-like Proteins", Biochem. Biophys. Res. Commun., 278:685-690 (Oct. 2000).
Lavitrano, M., et al., "Sperm Cells as Vectors for Introducing Foreign DNA into Eggs: Genetic Transformation of Mice", Cell, 57:717-723 (Jun. 1989).
Lazarus, C.M., et al., "Amplification of a Mitochondrial DNA Sequence in the Cytoplasmically Inherited Ragged Mutant of *Aspergillus amstelodami*", Eur. J. Biochem, 106:663-641 (1980).
Lee, S. and D.S. Gross, "Conditional Silencing: The HMRE Mating-Type Silencer Exerts a Rapidly Reversible Position Effect on the Yeast HSP82 Heat Shock Gene," Molecular and Cellular Biology, 13(2):727-738 (1993).
Lee, S.E., et al., "Role of Yeast SIR Genes and Mating Type in Directing DNA Double-Strand Breaks to Homologous and Non-Homologous Repair Paths", Curr. Biol., 9:767-770 (Jul. 1999).
Levine, AJ, "p53, the Cellular Gatekeeper for Growth and Division", Cell, 88:323-331 (Feb. 1997).
Li, Y., et al., "Long-Term Caloric Restriction Delays Age-Related Decline in Proliferation Capacity of Murine Lens Epithelial Cells in vitro and in vivo", Invest. Ophthalmol., 38(1)100-107 (Jan. 1997).
Liang, R., et al., "Parallel Synthesis and Screening of a Solid Phase Carbohydrate Library", Science, 274:1520-1522 (Nov. 1996).
Lill, N.L., et al., "Binding and Modulation of p53 by p300/CBP Coactivators", Nature, 387:823-827 (Jun. 1997).
Li, X., et al., Interventions in Aging and Age-Related Diseases: The Present and the Future, AGE, 28(1):1-75 (Mar. 2006).
U.S. Office Action dated Sep. 8, 2011 for U.S. Appl. No. 12/408,575.
U.S. Office Action dated Oct. 31, 2011 for U.S. Appl. No. 12/303,721.
Viswanathan, M., et al., "A Role for SIR-2.1 Regulation of ER Stress Response Genes in Determining *C. elegans* Life Span," *Development Cell*, vol. 9, pp. 605-615 (2005).
Rizki, G., et al., "The Evolutionarily Conserved Longevity Determinants HCF-1 and SIR-2.1/SIRT1 Collaborate to Regulate DAF-16/FOXO," *PLoS Genetics*, vol. 7, Issue 9, e1002235, pp. 1-16 (2011).
Burnett, C., et al., "Absence of Effects of Sir2 Overexpression on Lifespan in *C. elegans* and *Drosophila*," *Nature*, , vol. 477, pp. 482 (2011).
Viswanathan, M., et al., "Regulation of *Caenorhabditis elegans* Lifespan by Sir-2.1 Transgenes," *Nature*, vol. 477, pp. E1-E2 (2011).
Lombard, D. B., et al., "Longevity Hits a Roadblock," *Nature*, vol. 477, pp. 410-411 (2011).

(56) References Cited

OTHER PUBLICATIONS

Ledford, H., "Longevity Genes Challenged," [on-line], Sep. 21, 2011, Retrieved from the Internet URL: http://www.nature.com/news/2011/110921/full/news.2011.549.html;doi:10.1038/news.2011.549.

Notice of Allowance dated Mar. 15, 2012 for U.S. Appl. No. 12/408,575.

U.S. Office Action dated Dec. 15, 2004 for U.S. Appl. No. 10/191,121.

U.S. Office Action dated Aug. 15, 2008 for U.S. Appl. No. 11/404,146.

U.S. Office Action dated Jan. 25, 2008 for U.S. Appl. No. 11/404,146.

U.S. Office Action dated Jun. 27, 2007 for U.S. Appl. No. 11/404,146.

\* cited by examiner

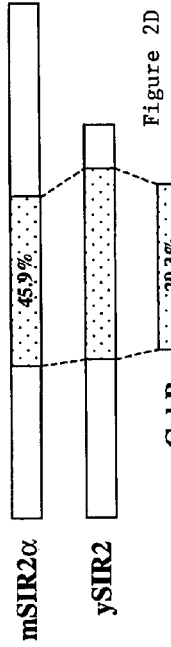
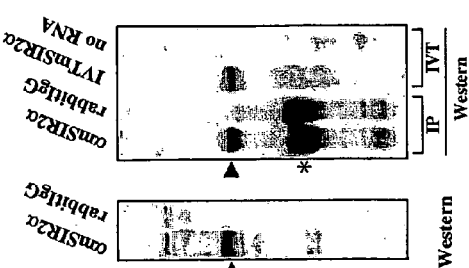
Figure 2A
Figure 2B
Figure 2C
Figure 2D

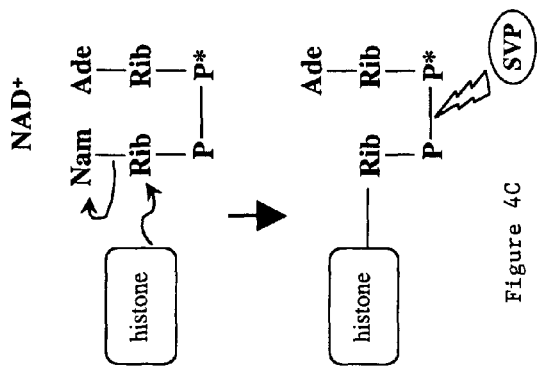
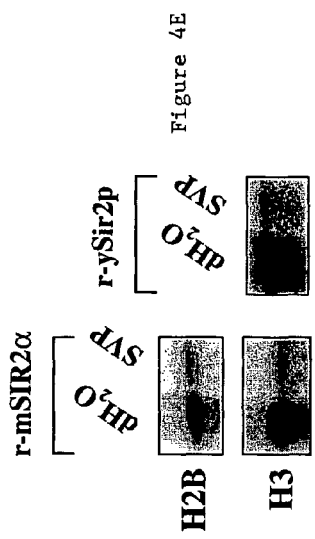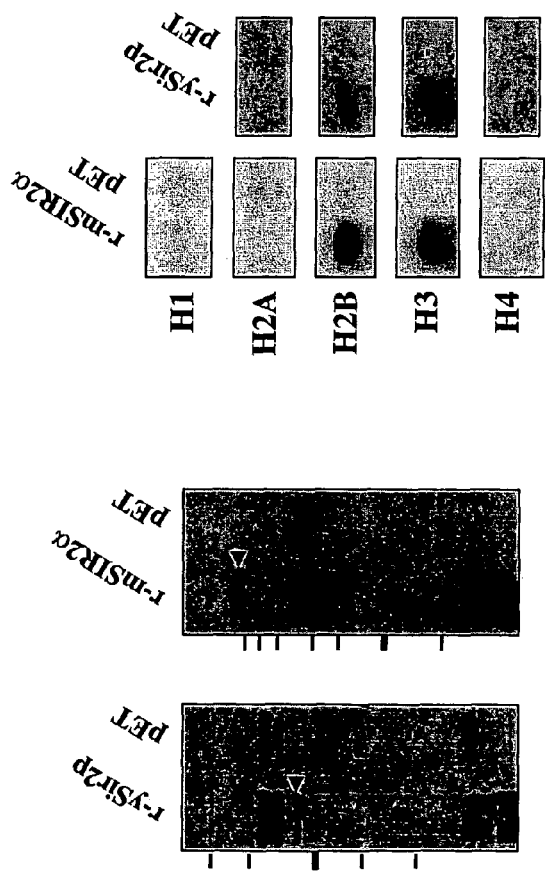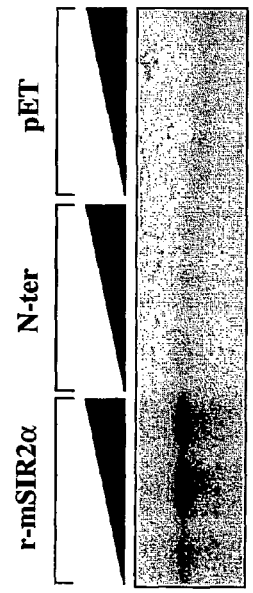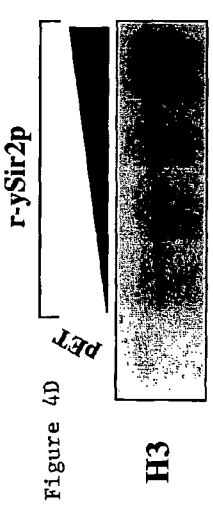
Figure 4A
Figure 4B
Figure 4C
Figure 4D
Figure 4E

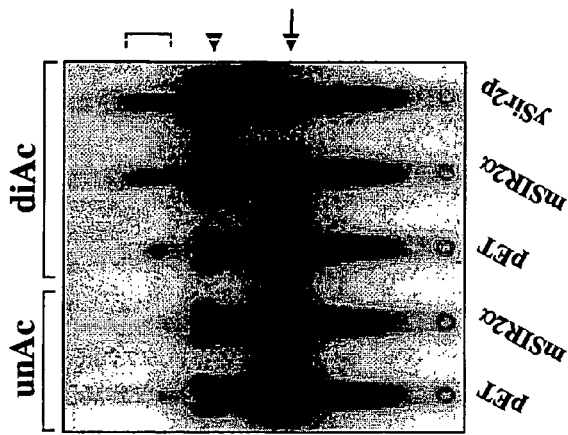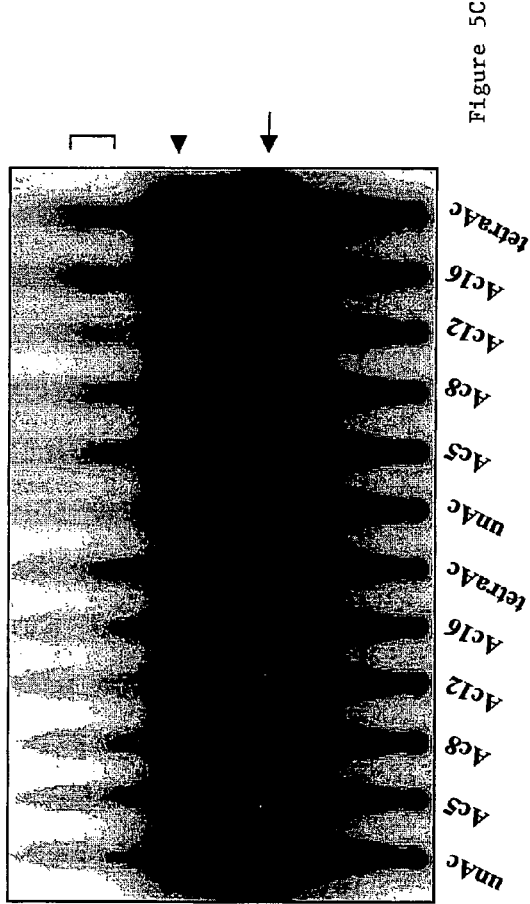
Figure 5A
Figure 5B
Figure 5C

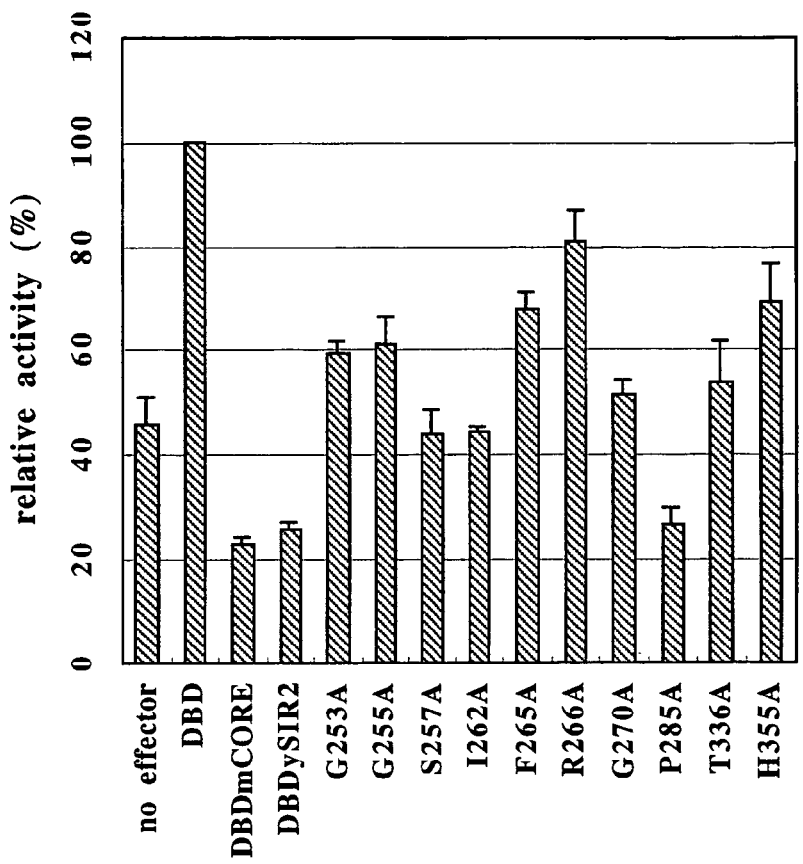
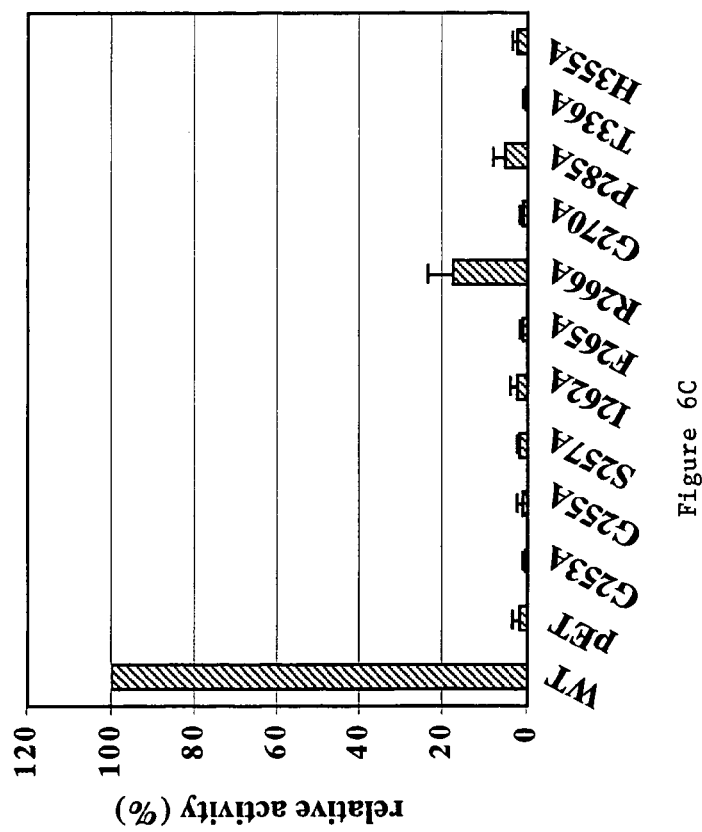
Figure 6D
Figure 6C peak 4          peak 5

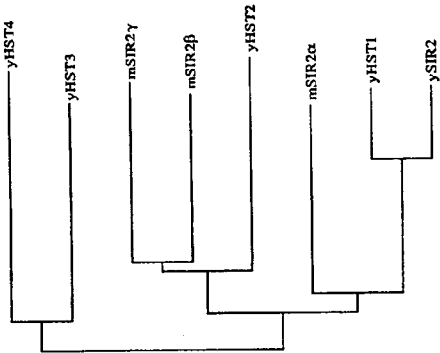
Figure 12a
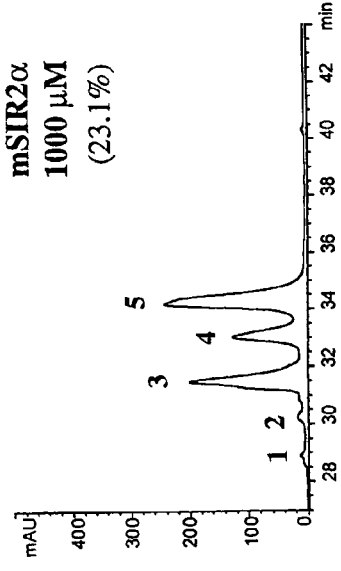
Figure 12b
Figure 12c

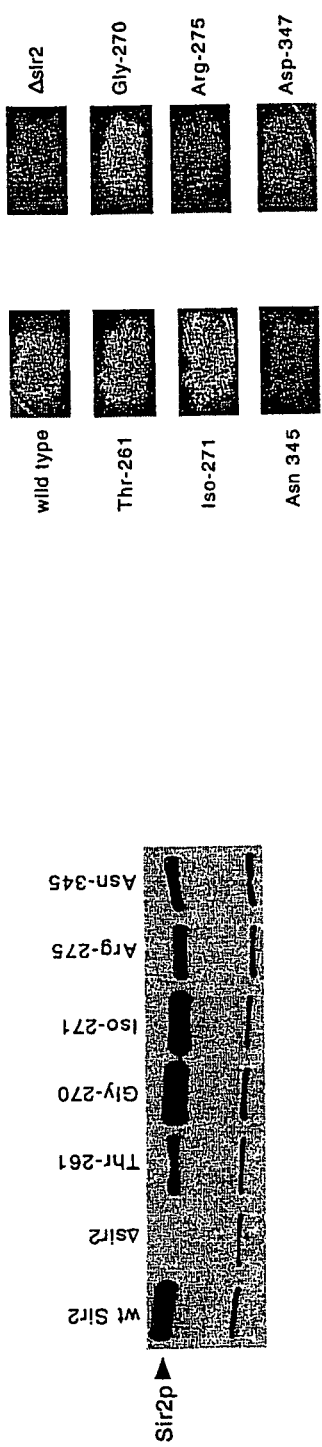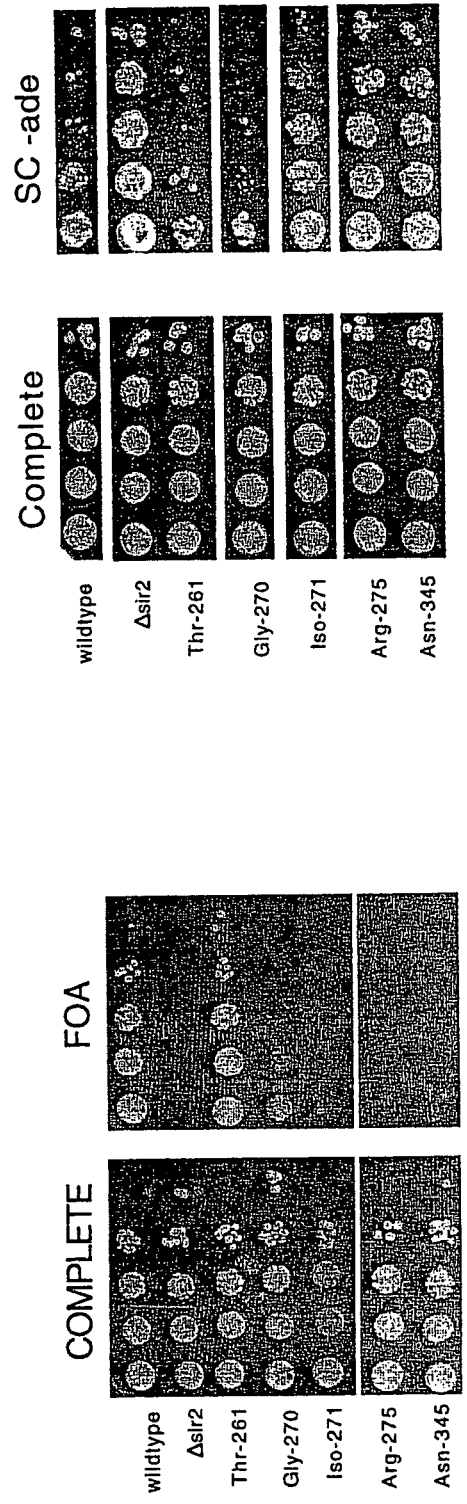
Figure 16a
Figure 16b
Figure 16c
Figure 16d

| Mutant | ADP-Rib. Activity (% of wt) | Deacetylase Activity (% of wt) | HM Silencing | Telomere Silencing | rDNA Silencing | rDNA Recombination | Mean Life Span (HML+) |
|---|---|---|---|---|---|---|---|
| sir2Δ | 0% | 2.7% | - | - | - | 1.15% | 11.4 |
| wildtype | 100% | 100% | + | + | + | 0.09% | 24.4 |
| Thr-261 | 4% | 17% | + | + | + | 0.09% | 19.8 |
| Gly-270 | 7% | 80% | + | +/- | + | 0.08% | 18.9 |
| Iso-271 | 8% | 36% | + | - | +/- | 0.22% | ND |
| Arg-275 | 100% | 67% | - | - | - | 1.03% | ND |
| Asn-345 | 0% | 3% | - | - | - | 1.22% | ND |
| Asp-347 | 0% | 3% | - | ND | ND | ND | ND |

```
         10        20        30        40        50        60
GCGGAGCAGAGGAGGCGAGGGCGGAGGGCCAGAGAGGCAGTTGGAAGATGGCGGACGAGG
                                                  M  A  D  E  V 70        80        90       100       110       120
TGGCGCTCGCCCTTCAGGCCGCCGGCTCCCCTTCCGCGGCGGCCGCCATGGAGGCCGCGT
 A  L  A  L  Q  A  A  G  S  P  S  A  A  A  A  M  E  A  A  S 130       140       150       160       170       180
CGCAGCCGGCGGACGAGCCGCTCCGCAAGAGGCCCCGCCGAGACGGGCCTGGCCTCGGGC
 Q  P  A  D  E  P  L  R  K  R  P  R  R  D  G  P  G  L  G  R 190       200       210       220       230       240
GCAGCCCGGGCGAGCCGAGCGCAGCAGTGGCGCCGGCGGCCGCGGGGTGTGAGGCGGCGA
 S  P  G  E  P  S  A  A  V  A  P  A  A  A  G  C  E  A  A  S 250       260       270       280       290       300
GCGCCGCGGCCCCGGCGGCGCTGTGGCGGGAGGCGGCAGGGGCGGCGGCGAGCGCGGAGC
 A  A  A  P  A  A  L  W  R  E  A  A  G  A  A  A  S  A  E  R 310       320       330       340       350       360
GGGAGGCCCCGGCGACGGCCGTGGCCGGGGACGGAGACAATGGGTCCGGCCTGCGGCGGG
 E  A  P  A  T  A  V  A  G  D  G  D  N  G  S  G  L  R  R  E 370       380       390       400       410       420
AGCCGAGGGCGGCTGACGACTTCGACGACGACGAGGGCGAGGAGGAGGACGAGGCGGCGG
 P  R  A  A  D  D  F  D  D  D  E  G  E  E  E  D  E  A  A  A 430       440       450       460       470       480
CGGCAGCGGCGGCGGCAGCGATCGGCTACCGAGACAACCTCCTGTTGACCGATGGACTCC
 A  A  A  A  A  A  I  G  Y  R  D  N  L  L  L  T  D  G  L  L 490       500       510       520       530       540
TCACTAATGGCTTTCATTCCTGTGAAAGTGATGACGATGACAGAACGTCACACGCCAGCT
 T  N  G  F  H  S  C  E  S  D  D  D  D  R  T  S  H  A  S  S 550       560       570       580       590       600
CTAGTGACTGGACTCCGCGGCCGCGGATAGGTCCATATACTTTTGTTCAGCAACATCTCA
 S  D  W  T  P  R  P  R  I  G  P  Y  T  F  V  Q  Q  H  L  M 610       620       630       640       650       660
TGATTGGCACCGATCCTCGAACAATTCTTAAAGATTTATTACCAGAAACAATTCCTCCAC
 I  G  T  D  P  R  T  I  L  K  D  L  L  P  E  T  I  P  P  P 670       680       690       700       710       720
CTGAGCTGGATGATATGACGCTGTGGCAGATTGTTATTAATATCCTTTCAGAACCACCAA
 E  L  D  D  M  T  L  W  Q  I  V  I  N  I  L  S  E  P  P  K 730       740       750       760       770       780
AGCGGAAAAAAAGAAAAGATATCAATACAATTGAAGATGCTGTGAAGTTACTGCAGGAGT
 R  K  K  R  K  D  I  N  T  I  E  D  A  V  K  L  L  Q  E  C 790       800       810       820       830       840
GTAAAAAGATAATAGTTCTGACTGGAGCTGGGGTTTCTGTCTCCTGTGGGATTCCTGACT
 K  K  I  I  V  L  T  G  A  G  V  S  V  S  C  G  I  P  D  F 850       860       870       880       890       900
TCAGATCAAGAGACGGTATCTATGCTCGCCTTGCGGTGGACTTCCCAGACCTCCCAGACC
 R  S  R  D  G  I  Y  A  R  L  A  V  D  F  P  D  L  P  D  P
```

Figure 21a

```
         910       920       930       940       950       960
CTCAAGCCATGTTTGATATTGAGTATTTTAGAAAAGACCCAAGACCATTCTTCAAGTTTG
   Q  A  M  F  D  I  E  Y  F  R  K  D  P  R  P  F  F  K  F  A 970       980       990      1000      1010      1020
CAAAGGAAATATATCCCGGACAGTTCCAGCCGTCTCTGTGTCACAAATTCATAGCTTTGT
   K  E  I  Y  P  G  Q  F  Q  P  S  L  C  H  K  F  I  A  L  S 1030      1040      1050      1060      1070      1080
CAGATAAGGAAGGAAAAACTACTTCGAAATTATACTCAAAATATAGATACCTTGGAGCAGG
   D  K  E  G  K  L  L  R  N  Y  T  Q  N  I  D  T  L  E  Q  V 1090      1100      1110      1120      1130      1140
TTGCAGGAATCCAAAGGATCCTTCAGTGTCATGGTTCCTTTGCAACAGCATCTTGCCTGA
   A  G  I  Q  R  I  L  Q  C  H  G  S  F  A  T  A  S  C  L  I 1150      1160      1170      1180      1190      1200
TTTGTAAATACAAAGTTGATTGTGAAGCTGTTCGTGGAGACATTTTTAATCAGGTAGTTC
   C  K  Y  K  V  D  C  E  A  V  R  G  D  I  F  N  Q  V  V  P 1210      1220      1230      1240      1250      1260
CTCGGTGCCCTAGGTGCCCAGCTGATGAGCCACTTGCCATCATGAAGCCAGAGATTGTCT
   R  C  P  R  C  P  A  D  E  P  L  A  I  M  K  P  E  I  V  F 1270      1280      1290      1300      1310      1320
TCTTTGGTGAAAACTTACCAGAACAGTTTCATAGAGCCATGAAGTATGACAAAGATGAAG
   F  G  E  N  L  P  E  Q  F  H  R  A  M  K  Y  D  K  D  E  V 1330      1340      1350      1360      1370      1380
TTGACCTCCTCATTGTTATTGGATCTTCTCTGAAAGTGAGACCAGTAGCACTAATTCCAA
   D  L  L  I  V  I  G  S  S  L  K  V  R  P  V  A  L  I  P  S 1390      1400      1410      1420      1430      1440
GTTCTATACCCCATGAAGTGCCTCAAATATTAATAAATAGGGAACCTTTGCCTCATCTAC
   S  I  P  H  E  V  P  Q  I  L  I  N  R  E  P  L  P  H  L  H 1450      1460      1470      1480      1490      1500
ATTTTGATGTAGAGCTCCTTGGAGACTGCGATGTTATAATTAATGAGTTGTGTCATAGGC
   F  D  V  E  L  L  G  D  C  D  V  I  I  N  E  L  C  H  R  L 1510      1520      1530      1540      1550      1560
TAGGTGGTGAATATGCCAAACTTTGTTGTAACCCTGTAAAGCTTTCAGAAATTACTGAAA
   G  G  E  Y  A  K  L  C  C  N  P  V  K  L  S  E  I  T  E  K 1570      1580      1590      1600      1610      1620
AACCTCCACGCCCACAAAAGGAATTGGTTCATTTATCAGAGTTGCCACCAACACCTCTTC
   P  P  R  P  Q  K  E  L  V  H  L  S  E  L  P  P  T  P  L  H 1630      1640      1650      1660      1670      1680
ATATTTCGGAAGACTCAAGTTCACCTGAAAGAACTGTACCACAAGACTCTTCTGTGATTG
   I  S  E  D  S  S  S  P  E  R  T  V  P  Q  D  S  S  V  I  A 1690      1700      1710      1720      1730      1740
CTACACTTGTAGACCAAGCAACAAACAACAATGTTAATGATTTAGAAGTATCTGAATCAA
   T  L  V  D  Q  A  T  N  N  N  V  N  D  L  E  V  S  E  S  S 1750      1760      1770      1780      1790      1800
GTTGTGTGGAAGAAAAACCACAAGAAGTACAGACTAGTAGGAATGTTGAGAACATTAATG
   C  V  E  E  K  P  Q  E  V  Q  T  S  R  N  V  E  N  I  N  V 1810      1820      1830      1840      1850      1860
TGGAAAATCCAGATTTTAAGGCTGTTGGTTCCAGTACTGCAGACAAAAATGAAAGAACTT
   E  N  P  D  F  K  A  V  G  S  S  T  A  D  K  N  E  R  T  S 1870      1880      1890      1900      1910      1920
CAGTTGCAGAAACAGTGAGAAAATGCTGGCCTAATAGACTTGCAAAGGAGCAGATTAGTA
   V  A  E  T  V  R  K  C  W  P  N  R  L  A  K  E  Q  I  S  K
```

Figure 21b

```
      1930      1940      1950      1960      1970      1980
AGCGGCTTGAGGGTAATCAATACCTGTTTGTACCACCAAATCGTTACATATTCCACGGTG
   R  L  E  G  N  Q  Y  L  F  V  P  P  N  R  Y  I  F  H  G  A 1990      2000      2010      2020      2030      2040
CTGAGGTATACTCAGACTCTGAAGATGACGTCTTGTCCTCTAGTTCCTGTGGCAGTAACA
   E  V  Y  S  D  S  E  D  D  V  L  S  S  S  S  C  G  S  N  S 2050      2060      2070      2080      2090      2100
GTGACAGTGGCACATGCCAGAGTCCAAGTTTAGAAGAACCCTTGGAAGATGAAAGTGAAA
   D  S  G  T  C  Q  S  P  S  L  E  E  P  L  E  D  E  S  E  I 2110      2120      2130      2140      2150      2160
TTGAAGAATTCTACAATGGCTTGGAAGATGATACGGAGAGGCCCGAATGTGCTGGAGGAT
   E  E  F  Y  N  G  L  E  D  D  T  E  R  P  E  C  A  G  G  S 2170      2180      2190      2200      2210      2220
CTGGATTTGGAGCTGATGGAGGGGATCAAGAGGTTGTTAATGAAGCTATAGCTACAAGAC
   G  F  G  A  D  G  G  D  Q  E  V  V  N  E  A  I  A  T  R  Q 2230      2240      2250      2260      2270      2280
AGGAATTGACAGATGTAAACTATCCATCAGACAAATCATAACACTATTGAAGCTGTCCGG
   E  L  T  D  V  N  Y  P  S  D  K  S  *

2290      2300      2310      2320      2330      2340
ATTCAGGAATTGCTCCACCAGCATTGGGAACTTTAGCATGTCAAAAAAATGAATGTTTAC 2350      2360      2370      2380      2390      2400
TTGTGAACTTGAACAAGGAAATCTGAAAGATGTATTATTTATAGACTGGAAAATAGATTG 2410      2420      2430      2440      2450      2460
TCTTCTTGGATAATTTCTAAAGTTCCATCATTTCTGTTTGTACTTGTACATTCAACACTG 2470      2480      2490      2500      2510      2520
TTGGTTGACTTCATCTTCCTTTCAAGGTTCATTTGTATGATACATTCGTATGTATGTATA 2530      2540      2550      2560      2570      2580
ATTTTGTTTTTTGCCTAATGAGTTTCAACCTTTTAAAGTTTTCAAAAGCCATTGGAATGT 2590      2600      2610      2620      2630      2640
TAATGTAAAGGGAACAGCTTATCTAGACCAAAGAATGGTATTTCACACTTTTTTGTTTGT 2650      2660      2670      2680      2690      2700
AACATTGAATAGTTTAAAGCCCTCAATTTCTGTTCTGCTGAACTTTTATTTTTAGGACAG 2710      2720      2730      2740      2750      2760
TTAACTTTTTAAACACTGGCATTTTCCAAAACTTGTGGCAGCTAACTTTTTAAAATCACA 2770      2780      2790      2800      2810      2820
GATGACTTGTAATGTGAGGAGTCAGCACCGTGTCTGGAGCACTCAAAACTTGGGCTCAGT 2830      2840      2850      2860      2870      2880
GTGTGAAGCGTACTTACTGCATCGTTTTTGTACTTGCTGCAGACGTGGTAATGTCCAAAC 2890      2900      2910      2920      2930      2940
AGGCCCCTGAGACTAATCTGATAAATGATTTGGAAATGTGTTTCAGTTGTTCTAGAAACA 2950      2960      2970      2980      2990      3000
ATAGTGCCTGTCTATATAGGTCCCCTTAGTTTGAATATTTGCCATTGTTTAATTAAATAC 3010      3020      3030      3040      3050      3060
CTATCACTGTGGTAGAGCCTGCATAGATCTTCACCACAAATACTGCCAAGATGTGAATAT 3070      3080      3090      3100      3110      3120
GCAAAGCCTTTCTGAATCTAATAATGGTACTTCTACTGGGGAGAGTGTAATATTTTGGAC 3130      3140      3150      3160      3170      3180
TGCTGTTTTTCCATTAATGAGGAAAGCAATAGGCCTCTTAATTAAAGTCCCAAAGTCATA
```

Figure 21c

```
      3190      3200      3210      3220      3230      3240
AGATAAATTGTAGCTCAACCAGAAAGTACACTGTTGCCTGTTGAGGATTTGGTGTAATGT 3250      3260      3270      3280      3290      3300
ATCCCAAGGTGTTAGCCTTGTATTATGGAGATGAATACAGATCCAATAGTCAAATGAAAC 3310      3320      3330      3340      3350      3360
TAGTTCTTAGTTATTTAAAAGCTTAGCTTGCCTTAAAACTAGGGATCAATTTTCTCAACT 3370      3380      3390      3400      3410      3420
GCAGAAACTTTTAGCCTTTCAAACAGTTCACACCTCAGAAAGTCAGTATTTATTTTACAG 3430      3440      3450      3460      3470      3480
ACTTCTTTGGAACATTGCCCCCAAATTTAAATATTCATGTGGGTTTAGTATTTATTACAA 3490      3500      3510      3520      3530      3540
AAAAATGATTTGAAATATAGCTGTTCTTTATGCATAAAATACCCAGTTAGGACCATTACT 3550      3560      3570      3580      3590      3600
GCCAGAGGAGAAAAGTATTAAGTAGCTCATTTCCCTACCTAAAAGATAACTGAATTTATT 3610      3620      3630      3640      3650      3660
TGGCTACACTAAAGAATGCAGTATATTTAGTTTTCCATTTGCATGATGTGTTTGTGCTAT 3670      3680      3690      3700      3710      3720
AGACAATATTTTAAATTGAAAAATTTGTTTTAAATTATTTTTACAGTGAAGACTGTTTTC 3730      3740      3750      3760      3770      3780
AGCTCTTTTTATATTGTACATAGACTTTTATGTAATCTGGCATATGTTTTGTAGACCGTT 3790      3800      3810      3820      3830      3840
TAATGACTGGATTATCTTCCTCCAACTTTTGAAATACAAAAACAGTGTTTTATACTAAAA 3850      3860      3870
AAAAAAAAAGTCGACGCGGCCGCGAATTC
```

Figure 21d

```
         10         20         30         40         50         60
CCACGCGTCCGCGGACGCGTGGGCACGGGACAGAGCAGTCGGTGACAGTCCCGAGGGCCC
   T  R  P  R  T  R  G  H  G  T  E  Q  S  V  T  V  P  R  A  P 70         80         90        100        110        120
CCACCCCGTTCCCATGGCCGAGCCGGACCGATTCAGACTCGGACACTGAGGGAGGAGCCA
   T  P  F  P  W  P  S  R  T  D  S  D  S  D  T  E  G  G  A  T 130        140        150        160        170        180
CTGGTGGAGAGGCAGAGATGGACTTCCTGAGGAATTTATTCACCCAGACCCTGGGCCTGG
   G  G  E  A  E  M  D  F  L  R  N  L  F  T  Q  T  L  G  L 190        200        210        220        230        240
GTTCCCAAAAGGAGCGTCTTCTAGACGAGCTGACCCTCGAAGGAGTGACACGCTACATGC
 S  Q  K  E  R  L  L  D  E  L  T  L  E  G  V  T  R  Y  M  Q 250        260        270        280        290        300
AGAGCGAGCGCTGCCGCAAGGTCATCTGTTTGGTGGGAGCCGGAATCTCCACGTCCGCGG
   S  E  R  C  R  K  V  I  C  L  V  G  A  G  I  S  T  S  A  G 310        320        330        340        350        360
GTATCCCTGACTTCCGCTCCCCGTCCACTGGCCTCTATGCAAACCTGGAGAAGTACCACC
   I  P  D  F  R  S  P  S  T  G  L  Y  A  N  L  E  K  Y  H  L 370        380        390        400        410        420
TTCCTTACCCAGAGGCCATCTTTGAGATCAGCTACTTCAAGAAACATCCGGAACCCTTCT
   P  Y  P  E  A  I  F  E  I  S  Y  F  K  K  H  P  E  P  F  F 430        440        450        460        470        480
TTGCCCTTGCCAAGGAGCTCTATCCCGGGCAGTTCAAGCCAACCATCTGCCACTACTTCA
   A  L  A  K  E  L  Y  P  G  Q  F  K  P  T  I  C  H  Y  F  I 490        500        510        520        530        540
TCCGCCTGCTGAAGGAGAAGGGGCTGCTGCTGCGCTGCTACACGCAGAACATAGACACGC
   R  L  L  K  E  K  G  L  L  L  R  C  Y  T  Q  N  I  D  T  L 550        560        570        580        590        600
TGGAACGAGTGGCGGGGCTGGAGCCCCAGGACCTGGTGGAGGCCCACGGCACCTTCTACA
   E  R  V  A  G  L  E  P  Q  D  L  V  E  A  H  G  T  F  Y  T 610        620        630        640        650        660
CATCACACTGTGTCAACACCTCCTGCAGAAAAGAATACACGATGGGCTGGATGAAAGAGA
   S  H  C  V  N  T  S  C  R  K  E  Y  T  M  G  W  M  K  E  K 670        680        690        700
AGATTTCTCAGAAGCAACTCCCAGGTGTGAGCAGTGTCA
   I  S  Q  K  Q  L  P  G  V  S  S  V
```

METHODS FOR IDENTIFYING AGENTS THAT ALTER NAD-DEPENDENT DEACETYLATION ACTIVITY OF A SIR2 PROTEIN

RELATED APPLICATIONS

This application is a continuation-in-part of U.S. Ser. No. 09/461,580, filed Dec. 15, 1999, now U.S. Pat. No. 7,452,664, the entire teachings of which are hereby incorporated by reference in their entirety.

GOVERNMENT SUPPORT

This invention was made with government support under grant number R01 AG011119 awarded by the National Institutes of Health. The government has certain rights in the invention.

BACKGROUND OF THE INVENTION

Aging involves progressive and irreversible loss of cellular processes and physiological functions that ultimately increase the likelihood of death. Molecular correlates of aging, including an increase in chromosomal structural abnormalities, the frequency of single-strand DNA breaks, a decline in DNA methylation, and a loss of DNA telomeric sequences, have been described in a range of eukaryotic organisms from mammals, such as humans, to unicellular organisms, such as yeast.

Although several mechanisms have been postulated as mediators of aging (e.g., somatic mutation theory, error catastrophe theory, intrinsic DNA rearrangement theory), none have led to interventions or therapies to slow aging and increase life span. In humans, declining health in aging individuals has a significant impact on the cost and implementation of geriatric health care.

Thus, there is a need to identify agents which alter (e.g., agonize, antagonize) the level of substrates and cellular mediators associated with the aging process. The identification of such agents is important in the development of specific and effective treatment regimens to decrease aging or increase the life span of a cell or an organism, and to further define pathways which lead to aging in a cell or organism.

SUMMARY OF THE INVENTION

The present invention relates to a method of altering the NAD-dependent acetylation status of proteins, a method of identifying agents which alter the NAD-dependent acetylation status of proteins, a method of identifying agents which alter mono-ADP-ribosylation of nuclear proteins, a method of alter aging or altering life span, as well as to methods of altering mono-ADP-ribosylation of proteins, a method of altering aging of a cell or organism, and a method of altering life span of a cell or organism. Examples of suitable proteins, the acetylation of status of which is altered in the method of the invention, include nuclear and cytoplasmic proteins. Examples of suitable nuclear proteins include histone and p53. In one embodiment, the histone protein, or proteins, are selected from the group consisting of H2A, H2B, H3, H4 and p53. Examples of organisms and cells in which aging or life span can be altered include yeast, c. elegans, and mammalian organisms and cells.

In preferred embodiments, the invention relates to methods of identifying agents which alter the NAD-dependent acetylation status of histone proteins by altering the activity of Sir2, increase mono-ADP-ribosylation of nuclear histone proteins, decrease aging or increase life span in a cell or organism, as well as to methods of increasing mono-ADP-ribosylation, decreasing aging or increasing life span of a cell or organism. In preferred embodiments, increasing mono-ADP-ribosylation or NAD-dependent deacetylation of acetylated proteins (e.g. nuclear proteins such as histones, p53) decreasing aging or increasing life span of a cell or organism comprise administering to the cell or organism Sir2 or a mono-ADP-ribosyltransferase or an agonist of Sir2 and/or mono-ADP-ribosyltransferase activity, and combinations thereof. In one embodiment, the method of the invention is a method of altering the NAD-dependent acetylation status of at least one amino acid residue in an acetylated protein (e.g., a nuclear protein such as a histone protein or p53) by altering the activity of a Sir2 protein or a Sir2-like protein. The histone protein can be, for example, selected from the group consisting of a H2B, H3 and H4 histone protein. In a preferred embodiment, the amino acid residue is a lysine amino acid residue. In a particularly preferred embodiment, the lysine amino acid residue is lysine 9 and/or lysine 14 of a H3 histone protein and/or lysine 16 of a H4 histone protein. The NAD-dependent acetylation status is removal of an acetyl group and/or addition of an acetyl group.

In a preferred embodiment, NAD-dependent acetylation status of the acetylated protein (e.g., a nuclear protein such as a histone protein or p53) is altered by altering the activity of Sir2α protein. In another embodiment, the NAD-dependent acetylation status is altered by altering the activity of a mutant Sir2α protein selected from the group consisting of G253A, G255A, S257A, I262A, F265A, R266A, G270A, P285A, T336A, H355A, Thr-261, Iso-271, Arg-275, Asn-345 and Asp-347.

In another embodiment, the invention relates to a method of identifying an agent which alters the activity of a Sir2 protein or a Sir2-like protein by assessing the NAD-dependent acetylation status of at least one amino acid in an acetylated protein (e.g., a nuclear protein such as a histone protein or p53), comprising combining the acetylated protein, the Sir2 protein or the Sir2-like protein, NAD or a NAD-like compound and the agent to be tested, thereby producing a combination; detecting the NAD-dependent acetylation status of an amino acid in the acetylated protein; and comparing the NAD-dependent acetylation status in the presence of the agent to be tested with the NAD-dependent acetylation status of the amino acid in the acetylated protein in the absence of the agent to be tested, wherein a difference in the NAD-dependent acetylation status of the amino acid of the acetylated protein between the presence of the agent and the absence of the agent indicates that the agent alters the NAD-dependent acetylation status of at least one amino acid of the acetylated protein.

Another aspect of the invention relates to a method of identifying an agent which alters life span of a cell by assessing the NAD-dependent acetylation status of at least one amino acid in an acetylated protein (e.g., a nuclear protein such as a histone protein or p53), comprising combining the histone protein, a Sir2 protein or Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the acetylation status of the amino acid in the histone protein in the absence of the agent to be tested, wherein a difference in the acetylation status of the amino acid of the histone protein between the presence of the agent and the absence of the agent is an indicator that the agent alters the life span of the cell. The invention further relates to administering the agents identified by the method to a cell and assessing the NAD-dependent acetylation status of at least one amino acid in a histone protein of the cell.

In a further embodiment, the invention relates to a method of identifying an agent which alters the activity of a Sir2 protein or a Sir2-like protein by assessing the NAD-dependent acetylation status of at least one amino acid in a histone protein, comprising combining the histone protein, the Sir2 protein or the Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the NAD-dependent acetylation status of the amino acid in the histone protein in the absence of the agent to be tested, wherein a difference in the NAD-dependent acetylation status of the amino acid of the histone protein between the presence of the agent and the absence of the agent indicates that the agent alters the NAD-dependent acetylation status of at least one amino acid of the histone protein.

In yet another embodiment, the invention relates to a method of identifying an agent which alters aging of a cell by assessing the NAD-dependent acetylation status of at least one amino acid in an acetylated protein (e.g., a nuclear protein such as a histone protein or p53), comprising combining the histone protein, a Sir2 protein or Sir2-like protein, NAD or a NAD-like compound and the agent to be tested, thereby producing a combination; detecting the NAD-dependent acetylation status of an amino acid in the histone protein; and comparing the NAD-dependent acetylation status in the presence of the agent to be tested with the acetylation status of the amino acid in the histone protein in the absence of the agent to be tested, wherein a difference in the acetylation status of the amino acid of the histone protein between the presence of the agent and the absence of the agent is an indicator that the agent alters aging of the cell. In one embodiment, the identified agent increases aging of the cell. In another embodiment, the identified agent decreases aging of the cell.

In another embodiment, the invention relates to a method of altering the NAD-dependent acetylation status of at least one amino acid residue in an acetylated protein (e.g., a nuclear protein such as a histone protein or p53) comprising combining the acetylated protein, a Sir2 protein or Sir2-like protein and a NAD or a NAD-like compound.

In yet another embodiment, the methods of the invention include methods for identifying an agent which alters mono-ADP-ribosylation of a nuclear protein in a cell or an organism, comprising combining a cell or organism and an agent to be tested; determining a level of mono-ADP-ribosylation of a nuclear protein in the cell or in one or more cells of the organism; and comparing the level of mono-ADP-ribosylation in the presence of the agent with the level of mono-ADP-ribosylation of the nuclear protein in the absence of the agent. A difference in the level of mono-ADP-ribosylation of the nuclear protein in the presence of the agent as compared with in the absence of the agent indicates that the identified agent alters mono-ADP-ribosylation of the nuclear protein. In a preferred embodiment, the identified agent is an agonist of mono-ADP-ribosylation. In another embodiment, the identified agent is an antagonist of mono-ADP-ribosylation.

In another embodiment, the invention relates to methods for identifying an agent which alters life span of a cell or an organism, comprising combining a cell or organism and an agent to be tested; determining a level of mono-ADP-ribosylation of a nuclear protein in the cell or in one or more cells of the organism; and comparing the level of mono-ADP-ribosylation in the presence of the agent with the level of mono-ADP-ribosylation of the nuclear protein in the absence of the agent. A difference in the level of mono-ADP-ribosylation of the nuclear protein in the presence of the agent as compared with the absence of the agent indicates that the agent alters mono-ADP-ribosylation of the nuclear protein and, therefore, alters the life span of the cell or organism. In a preferred embodiment, the identified agent is an agonist of mono-ADP-ribosylation. In another embodiment, the identified agent is an antagonist of mono-ADP-ribosylation.

The invention also relates to a method of identifying an agent which increases life span of a cell or an organism by increasing mon-ADP-ribosylation of a nuclear protein, comprising the steps of combining a cell or organism and an agent to be tested; determining a level of mono-ADP-ribosylation of a nuclear protein in the cell or in one or more cells of the organism in the presence of the agent and in the absence of the agent; identifying an agent which increases mono-ADP-ribosylation of a nuclear protein; administering said agent to a cell or an organism; and determining the life span of said cell, wherein an agent which increases the life span of said cell or organism relative to the mean life span of said cell or organism or relative to the life span of said cell or organism in the absence of the agent is identified as an agent which increases life span of a cell or organism by increasing mon-ADP-ribosylation of a nuclear protein.

In another embodiment, the invention relates to a method of identifying an agent which alters life span of an organism. The organism and an agent to be tested are combined and the NAD-dependent acetylation status of a protein in the organism and compared with an NAD-dependent acetylation status of the protein in the absence of the agent to be tested. A difference in the NAD-dependent acetylation status of the protein in the presence of the agent and the absence of the agent indicates that the agent alters the life span of the organism.

The invention also relates to a method of identifying an agent which decreases life span of a cell or an organism by decreasing mono-ADP-ribosylation of a nuclear protein, comprising the steps of combining a cell or organism and an agent to be tested; determining a level of mono-ADP-ribosylation of a nuclear protein in the cell or in one or more cells of the organism in the presence of the agent and in the absence of the agent; identifying an agent which decreases mono-ADP-ribosylation of a nuclear protein; administering said agent to a cell or an organism; and determining the life span of said cell, wherein an agent which decreases the life span of said cell or organism relative to the mean life span of said cell or organism or relative to the life span of said cell or organism in the absence of the agent is identified as an agent which decreases life span of a cell or organism by decreasing mono-ADP-ribosylation of a nuclear protein.

Also encompassed by the present invention is a method of identifying an agent which alters aging of a cell, comprising the steps of combining a cell and an agent to be tested; determining a level of mono-ADP-ribosylation of a nuclear protein in the cell; and comparing the level of mono-ADP-ribosylation in the presence of the agent with a level of mono-ADP-ribosylation of the nuclear protein in the absence of the agent to be tested. A difference in the level of mono-ADP-ribosylation of the nuclear protein between the presence of the agent and the absence of the agent indicates that the agent alters aging of the cell. In a particular embodiment, the identified agent decreases aging of the cell. In another embodiment, the identified agent increases aging of the cell.

Another aspect of the invention includes a method of increasing the life span of a cell, comprising administering to the cell an effective amount of an agent which increases mono-ADP-ribosylation of a nuclear protein. The agent to be administered is identified by a method comprising the steps of combining a cell and an agent to be tested; determining a level of mono-ADP-ribosylation of a nuclear protein in the cell; and comparing the level of mono-ADP-ribosylation in the presence of the agent with a level of mono-ADP-ribosylation of the nuclear protein in the absence of the agent to be tested, wherein an increase in mono-ADP-ribosylation in the presence of the agent relative to that in the absence of the agent is an indicator that the agent increases the life span of the cell.

The invention also relates to a method of decreasing aging of a cell, comprising administering to the cell an effective amount of an agent which increases mono-ADP-ribosylation of a nuclear protein. The agent to be administered is identified by a method comprising the steps of combining a cell and an agent to be tested; determining a level of mono-ADP-ribosylation of a nuclear protein in the cell; and comparing the level of mono-ADP-ribosylation in the presence of the agent with a level of mono-ADP-ribosylation of the nuclear protein in the absence of the agent to be tested, wherein an increase in mono-ADP-ribosylation in the presence of the agent relative to that in the absence of the agent is an indicator that the agent decreases aging of the cell.

The invention further pertains to a method of increasing the life span of a cell or an organism comprising administering to the cell or organism a mono-ADP-ribosyltransferase or an agonist of mono-ADP-ribosyltransferase activity in an amount effective to increase the life span of the cell or organism.

In yet another embodiment, the present invention pertains to a method of increasing the life span of a cell or organism comprising administering to the cell or organism an agonist of mono-ADP-ribosylation of histone protein H2B in an amount effective to increase the life span of the cell or organism.

Another embodiment of the invention pertains to a method of decreasing aging of a cell or organism comprising administering to the cell or organism a mono-ADP-ribosyltransferase or an agonist of mono-ADP-ribosyltransferase activity in an amount effective to decrease aging of the cell or organism.

Also encompassed by the present invention is a method of decreasing aging of a cell or organism comprising administering to the cell or organism an agonist of mono-ADP-ribosylation of histone protein H2B in an amount effective to decrease aging of the cell or organism.

The invention also relates to a method of inhibiting the formation, replication and/or accumulation of rDNA circles in a cell comprising administering to the cell a mono-ADP-ribosyltransferase or an agonist of mono-ADP-ribosyltransferase activity in an amount effective to inhibit the formation, replication and/or accumulation of rDNA circles.

Another aspect of the invention is a method for decreasing recombination between rDNA in a cell comprising administering to the cell a mono-ADP-ribosyltransferase or an agonist of mono-ADP-ribosyltransferase activity in an amount effective to decrease recombination between rDNA.

An additional embodiment of the invention is a method of identifying an agent which alters aging of an organism. The organism and an agent to be tested are combined and the NAD-dependent acetylation status of a protein in the organism is determined and compared to the NAD-dependent acetylation status of the protein in the absence of the agent to be tested. A difference in the NAD-dependent acetylation status of the protein in the presence of the agent and the absence of the agent indicates that the agent alters aging of the organism.

In yet another embodiment, the invention relates to a method of increasing the life span of an organism. A first organism and an agent to be tested are combined. The NAD-dependent acetylation status of a protein in the organism is determined and compared to the NAD-dependent acetylation status of the protein in the absence of the agent to be tested. An agent which increases the deacetylation of the protein is identified and administered to a second organism, whereby the lifespan of the second organism is increased by the agent.

In still another embodiment, the invention relates to a method of decreasing aging of an organism. A first organism and an agent to be tested are combined and the NAD-dependent acetylation status of a protein in the organism is determined and compared to the NAD-dependent acetylation status in the protein in the absence of the agent to be tested. An agent which increases the deacetylation status of the protein is identified and administered to a second organism, wherein the life span of the second organism is decreased by the agent.

In another embodiment, the invention relates to a method of increasing the life span of an organism comprising administering to the organism a mono-ADP-ribosyltransferase or an agonist of a mono-ADP-ribosyltransferase in an amount effective to increase the life span of the organism.

In yet another embodiment, the invention relates to a method of increasing the life span of an organism comprising administering to the organism an NAD-dependent deacetylase or an agonist of an NAD-dependent deacetylase.

In still another embodiment, the invention relates to a method of decreasing aging of an organism comprising administering to the organism an NAD-dependent deacteylase or an agonist of an NAD-dependent deacetylase.

In another embodiment, the invention relates to a method of inhibiting formation, replication and/or accumulation of rDNA circles in an organism comprising administering to the organism an NAD-dependent deacetylase.

In a further embodiment, the invention relates to a method for decreasing recombination between rDNA in an organism comprising administering to the organism an NAD-dependent deacetylase.

In still another embodiment, the invention relates to a method of identifying an agent which is an agonist of Sir2 activity. A yeast cell and an agent to be tested are combined and the presence of red colonies in the combination is determined. The presence of red colonies indicates the agent is an agonist of Sir2 activity.

An additional embodiment of the invention is a method of identifying an agent which is an antagonist of Sir2 activity. A yeast cell and an agent to be tested are combined and the presence of white colonies in the combination is determined. The presence of white colonies indicates the agent is an antagonist of Sir2 activity.

The present invention also provides an isolated murine Sir2 protein, preferably the murine Sir2α protein (SEQ ID NO: 26) and the nucleic acid sequence encoding the Sir2α (SEQ ID NO: 25).

The invention also pertains to isolated nucleic acid molecules of murine SIR2 genes operably linked to a regulatory sequence and methods of preparing Sir2 proteins by culturing recombinant host cells that include isolated nucleic acid molecules of murine SIR2 genes.

Also encompassed by the present invention are antibodies, or antigen-binding fragments thereof, which selectively bind a murine Sir2 protein or a murine Sir2-like protein.

The invention described herein provides novel methods to readily identify agents that alter the NAD-dependent acetylation status of nuclear proteins and/or the mono-ADP-ribosylation of a nuclear protein; and to utilize the identified agents to alter NAD-dependent acetylation, ADP-ribosylation, aging and thereby increase life span. For example, the invention provides unique and efficient ways to forestall senescence and extend life in cells and organisms.

BRIEF DESCRIPTION OF THE FIGURES

FIG. 2A is the deduced amino acid sequence of mSir2α (SEQ ID NO: 1) with the predicted nuclear localization signal underlined.

FIG. 2B is a Western blot of the mSir2α protein (120 kD) immunoprecipitated (IP) from cell extracts of murine NIH3T3 cells and in vitro translated (IVF) probed with a polyclonal antibody against the N-terminal 131 amino acids of the protein (αmSir2α).

FIG. 2C is an alignment of the evolutionarily conserved core domains of yeast (ySir2, GENBANK® Accession Nos: X01419, M21316, SEQ ID NO: 2; yHST1, GENBANK® Accession Nos: U39041, L47120, SEQ ID NO: 3); murine (mSir2α, SEQ ID NO: 4) and *Salmonella* (CobB, GENBANK® Accession No: U89687, SEQ ID NO: 5) Sir2 proteins. Identical amino acids are boxed. A putative NAD binding cleft is indicated by asterisks. Less conserved amino acids are shaded.

FIG. 2D is a schematic alignment of the core domain of mSir2α, ySir2p and CobB proteins.

FIG. 4A is a COOMASSIE® blue stained gel of 6×His-tagged recombinant yeast (r-y Sir2p) and murine (r-m Sir2α) Sir2 proteins purified with Ni-NTA agarose under native conditions. Arrowheads indicate each full-length protein.

FIG. 4B depicts the results of ADP-ribosylation of histone proteins H1, H2A, H2B, H3 and H4 by recombinant r-ySir2p and r-mSir2α.

FIG. 4C illustrates ADP-ribosyltransferases cleaving nicotinamide (Nam) from NAD$^+$ (Ade-Rib-P*) creating a linkage between ribose (Rib) and histone proteins.

FIG. 4D illustrates the dose-dependent modification of H2B and H3 by recombinant yeast r-ySir2p and murine r-mSir2α proteins.

FIG. 4E illustrates the effects of snake venom phosphodiesterase (SVP) on the removal of radiolabeled $^{32}$P-NAD from Sir2-modified H2B and H3.

FIG. 5A depicts the amino acid sequences of the N-terminal tails of H3 (SEQ ID NO: 6) and H4 (mono AC, SEQ ID NO: 7, tetra Ac, SEQ ID NO: 8) peptides. The asterisks depict the site of acetylation (mono Ac, tetra Ac) to generate peptides with and without acetylated lysines. Human H3 GENBANK® Accession No: M26150, mouse H3 GENBANK® Accession Nos: M23459, 32460, 32461, 32462. Human H4 GENBANK® Accession Nos: M60749, M16707, mouse H4 GENBANK® Accession No: U62672.

FIG. 5B depicts the effects of mSir2α and ySir2p on diacetylated H3 peptide (diAc), but not unacetylated H3 (unAc). A bracket, an arrowhead, and an arrow at right indicate modified peptides, hydrolyzed and/or decomposed products of $^{32}$P-NAD, and unhydrolyzed $^{32}$P-NAD, respectively.

FIG. 5C illustrates mSir2α modification of Lys16-acetylated H4 peptide (Ac16). Unacetylated (unAc), monoacetylated (Ac5, Ac8, Ac12, or Ac16), and tetraacetylated (tetraAc) peptides were added in the reactions with the control eluate (pET) or the mSir2α, respectively.

FIG. 6C illustrates the quantitation of the ADP-ribosylation activities of the mSir2α mutants (G253A, G255A, S257A, I262A, F265A, R266A, G270A, P285A, T336A, H355A) compared to wild type (WT) and control pET.

FIG. 6D illustrates the in vivo transcriptional repression by the mSir2α wildtype and mutant core domain fused to the GAL4 DNA binding domain (DBD).

FIG. 8a is a COOMASSIE® blue-stained SDS-PAGE gel of purified recombinant yeast (rSir2p) protein, mouse Sir2 (mSir2α) proteins and vector controls. Full length proteins are indicated by dots.

FIGS. 8b, 8c, 8d, 8e and 8f are HPLC chromatograms showing absorbance at 220 nm of products of deacetylation assays with yeast Sir2p and the indicated concentrations of NAD. The efficiencies of the reactions are calculated from the areas under peaks 1, 2, and 4.

FIG. 8g is a schematic of contents of peaks 1-5 shown in chromatograms.

FIGS. 9a and 9b depict peak 3 of the HPLC chromatogram of the deacetylase reaction at 1 mM NAD. The molecular weights of the two products in peak 3 correspond to the starting peptide (2370) and the doubly deacetylated dimer (2-times the molecular weight of the starting peptide, 4740, minus the difference between the molecular weight of two acetyl moieties versus two hydrogens, 84, yielding 4656).

FIG. 9c Peak 4 of the same reaction. The molecular weight of peak 4 (4698) corresponds to singly deacetylated dimer peptide.

FIG. 9d Peak 5 of the same reaction corresponds to dimer peptide (molecular weight 4740).

FIG. 11d shows the ADP-ribosylated peptide indicated by a bracket on a longer exposure (left), and NAD and its hydrolysed product are indicated by an arrow and an arrowhead on a shorter exposure, respectively (right).

FIGS. 12a, 12b, and 12c show the deacetylation activity of the mouse Sir2p homolog, mSir2α.

FIG. 12a is the amino acid sequence of mSir2α (SEQ ID NO: 1). The evolutionarily conserved core domain of mSir2α is boxed.

FIG. 12b show the phylogenetic tree of yeast and mouse Sir2 core domains. The core domain sequences of three mouse homologs termed α, β, and γ are compared on CLUSTAL X and NJPLOT programs to generate the phylogenetic tree.

FIG. 12c illustrates the HPLC chromatogram of the product of deacetylation assay with 10 µg of recombinant mSir2α protein at 1 mM NAD. The calculated efficiency of the reaction is indicated.

FIG. 14a is the amino acid sequence of the core domains of ySir2p (ySir2; SEQ ID NO: 11), mSir2α (SEQ ID NO: 12) and CobB (SEQ ID NO: 13) aligned and six highly conserved residues, indicated by arrowheads, were mutated to alanine.

FIG. 14b shows the 6×His (SEQ ID NO: 39) tagged versions of wild type ySir2p (wt) and the six mutant Sir2p (Thr-261, Gly-270, Iso-271, Arg-275, Asn-345, Asp-347) and a vector control (vector) expressed in E. coli, purified over a Nickel-NTA column and analyzed on a 7% polyacrylamide SDS gel to assess expression levels.

FIG. 14c depicts the ability of ySir2p and mutant Sir2p proteins to modify histone H3 with $^{32}$P labeled NAD.

FIGS. 16a, 16b, 16c and 16d illustrate the effect of mutations on deacetylation in vitro and silencing in vivo. Wildtype (wt) and mutant Sir2 (Thr-261, Gly-270, Iso-271, Arg-275, Asn-345) were integrated into sir2Δ W303R strains.

FIG. 16a is a Western blot of 25 µg of whole cell extract from wildtype, sir2Δ and Sir2 mutants probed with Sir2 antibody. The upper band corresponds to Sir2p and a lower background band is included as a loading control.

FIG. 16b illustrates silencing at HMLα by mating the strains with tester strains of the opposite mating type and monitoring growth of diploids on selective media.

FIG. 16c illustrates telomere-silencing by the ability of strains with telomeric URA3 to grow on media containing 5-FOA, which is toxic when URA3 is expressed, but harmless when URA3 is silenced.

FIG. 16d illustrates rDNA silencing was monitored in a strain with the ADE2 marker located within the rDNA array. RPD3 was disrupted to enhance silencing differences between the wildtype and sir2Δ strains. sir2 mutant strains were spotted on complete and -ade media to monitor effects on silencing.

FIG. 17a illustrates W303R with ADE2 at rDNA tested for rDNA recombination rates by counting the frequency of loss of the marker in the first generation after plating.

FIG. 17b illustrates the life span of wildtype, sir2Δ, and mutants 261, 270, and 275 measured in hmlÆ strains where the a/α effects are eliminated.

FIG. 17c illustrates the life span of wildtype, sir2Δ, and mutants 261 and 270 measured in HML+ strains as a sensitive test of a/α silencing.

FIG. 18 is a summary of in vitro and in vivo data regarding ADP-ribosyltransferase, deacetylase, HM silencing, telomere silencing, rDNA silencing, rDNA recombination and mean life span for Sir2 wildtype and mutant Sir2 proteins (Thr-261, Gly-270, Iso-271, Arg-275, Asn-345, Asp-347).

FIG. 19 depicts the amino acid sequence alignment of the core domain of ySir2 (SEQ ID NO: 14), yHST1 (SEQ ID NO: 15), yHST2 GENBANK® Accession NO: U39063, (SEQ ID NO: 16), yHST3 GENBANK® Accession No: U39062, (SEQ ID NO: 17), yHST4 GENBANK® Accession No: NC_001136 (SEQ ID NO: 18), mSir2alpha (mSir2α, SEQ ID NO: 19), mSir2beta (mSir2β, SEQ ID NO: 20), mSirg (mSir2γ, SEQ ID NO: 21), and deduced amino acid sequences of Sir2-like core domains (GENBANK® Accession No: A1465098, SEQ ID NO: 22; GENBANK® Accession No: A1465820, SEQ ID NO: 23; GENBANK® Accession No: A1466061, SEQ ID NO: 24).

FIGS. 21a, 21b, 21c, and 21d depict the nucleotide sequence (GenBank Accession No: AF214646, SEQ ID NO: 25) and amino acid sequence (SEQ ID NO: 26) of murine Sir2α.

FIG. 22 depicts the nucleotide sequence (SEQ ID NO: 34) and amino acid sequence (SEQ ID NO: 35) of an EST CDNA clone 557657 (Genome Systems, Inc.).

DETAILED DESCRIPTION OF THE INVENTION

Figures 1A, 1B:
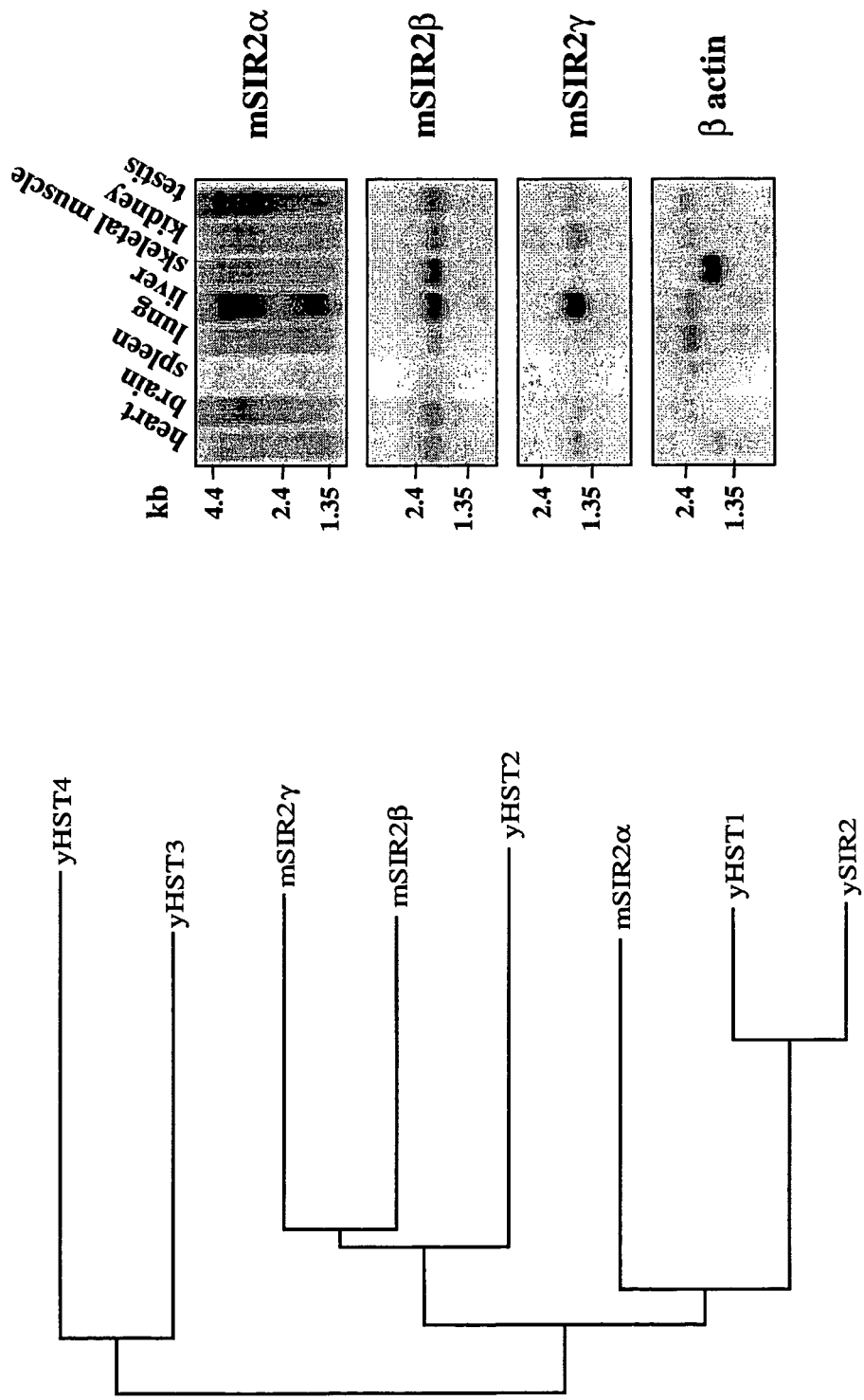
FIG. 1A is a diagrammatic representation of the phylogenetic tree of yeast and murine Sir2 protein core domains.
FIG. 1B is a Northern blot analysis of the tissue distribution of murine SIR2α, β and γ mRNA transcripts.

The invention relates to the discovery that Sir2 proteins, which play a part in the life span control mechanisms in eukaryotic cells, alter the NAD-dependent acetylation status of histone proteins and mono-ADP-ribosylation of nuclear proteins. In particular, the invention pertains to the discovery that Sir2 (e.g., murine Sir2α) alters the NAD-dependent acetylation status (e.g., removes and/or adds an acetyl group) of proteins (e.g., nuclear proteins such as histone proteins H2B, H2A, H3 or H4) and mono-ADP-ribosylation of nuclear histone proteins. In particular, the mono-ADP-ribosylation of nuclear proteins is performed by the core domain of Sir2, the Sir2 protein, a fragment of the Sir2 protein (e.g., SEQ ID NOS: 1, 2, 4, 9, 10, 11, 12, 14, 19, 20, 21 or 26), or an agonist of Sir2. As a result of this discovery, methods for identifying agents (e.g., agonists) which alter the NAD-dependent acetylation status of nuclear proteins, such as histone proteins, and/or their mono-ADP-ribosylation are available to provide methods and compositions to alter (e.g., slow) aging and alter (e.g., increase) life span of cells (e.g., mammalian cells) and organisms (e.g., C. elegans).

The present invention relates to a method of altering the NAD-dependent acetylation status of at least one amino acid residue of a histone protein by altering the activity of a Sir2-protein or Sir-2 like protein. In a particular embodiment, the NAD-dependent acetylation status of H3 and/or H4 is altered. Specifically encompassed by the invention is the alteration of lysine residues in the N-terminus of H3 (e.g., lysine 9 and/or 14) and H4 (e.g., lysine 16).

"NAD-dependent" as used herein refers to a requirement for NAD (nicotinamide adenine dinucleotide) compound (an "NAD compound") in a reaction. The reaction can performed or take place in the presence (e.g., in vivo) or the absence (e.g., in vitro) of cells. A "NAD-like compound" is also within the scope of the invention and refers to a compound (e.g., a synthetic or naturally occurring chemical, drug, protein, peptide, small organic molecule) which possesses structural similarity (e.g., adenine, ribose and phosphate groups) or functional similarity (e.g., oxidation of substrates, NAD-dependent deacetylation of histone proteins). For example, NAD-like compounds can be NADH, NADP, NADPH, non-hydrolyzable NAD and fluorescent analogs of NAD (e.g., 1, N6-etheno NAD).

The term "NAD-dependent acetylation status" refers to the requirement of NAD to either transfer (also referred to herein as the addition) or remove (also referred to herein as deacetylation) at least one acetyl group (e.g., $CH_3CO-$) to or from a substrate having OH or $NH_2$ groups (e.g., at least one amino acid residue of a nuclear protein such as p53 or histone proteins such as H2B, H2A, H3 and/or H4). Thus, "acetylation status" can be either acetylation or deacetylation of a substrate.

In a particular embodiment, the amino acid residue of which acetylation status is altered is a basic amino acid (e.g., lysine, arginine, histidine). In a preferred embodiment, the acetylation status of lysine residues of nuclear proteins such as p53 or histone proteins H1, H2A, H2B, H3 or H4 are altered. In a more preferred embodiment, the acetylation status of lysine residues at the amino terminus of H3 and H4 is altered In particular, lysine 9 and/or lysine 14 of H3 and/or lysine 16 of H4. Any suitable amino acid residue (e.g. having OH or $NH_2$ groups) capable of undergoing an alteration in acetylation status in a cell, organism or animal, under in vitro conditions (e.g., outside a cell, organism, or animal) is within the scope of the invention.

The invention also relates to a method of identifying an agent which alters the activity of a Sir2 protein or a Sir2-like protein by assessing the NAD-dependent acetylation status of at least one amino acid in a histone protein. The method can further include combining the histone protein, the Sir2 protein or the Sir2-like protein, NAD or a NAD-like compound and the agent to be tested to produce a combination; detecting the NAD-dependent acetylation status of an amino acid in the histone protein; and comparing the NAD-dependent acetylation status in the presence of the agent to be tested with the NAD-dependent acetylation status of the amino acid in the histone protein in the absence of the agent to be tested, wherein a difference in the NAD-dependent acetylation status of the amino acid of the histone protein between the presence of the agent and the absence of the agent indicates that the agent alters the NAD-dependent acetylation status of at least one amino acid of the histone protein.

The agent identified by the methods of the invention can add an acetyl group or remove an acetyl group from at least one amino acid residue (e.g., lysine) of a nuclear protein such as p53 or a histone protein (e.g., H2B, H3 or H4).

The invention further relates to a method of identifying an agent which alters life span of a cell or an organism by altering the activity of a Sir2 protein or a Sir2-like protein by assessing the NAD-dependent acetylation status of at least one amino acid (e.g., lysine) in a nuclear protein such as p53 or a histone protein (e.g., H2B, H3 or H4). In one embodiment the organism is a yeast cell. In a preferred embodiment, the methods of the invention alter the life span of the organism C. elegans.

In the method, the histone protein, a Sir2 protein or Sir2-like protein, NAD or a NAD-like compound and the agent to be tested are combined to produce a combination, the NAD-dependent acetylation status of an amino acid in the histone protein is detected (e.g., electron-spray or matrix assisted laser desorption/ionization (MALDI) mass spectroscopy); and compared the NAD-dependent acetylation status in the presence of the agent to be tested with the acetylation status of the amino acid in the histone protein in the absence of the agent to be tested. A difference in the acetylation status of the amino acid of the histone protein between the presence and absence of the agent alters the life span of the cell or the organism. The agent tested can increase the lifespan of a cell or an organism (e.g., C. elegans) by NAD-dependent deacetylation of the histone protein. Alternatively, or additionally, the agent can decrease the lifespan of the cell or the organism by NAD-dependent acetylation of histone proteins. The agent can be an agonist of Sir2 activity or the agent can be an antagonist of Sir2 activity.

The invention also provides a method of identifying an agent which alters aging of a cell or organism (e.g., C. elegans) by altering the activity of Sir2 or a Sir-2 like protein by assessing the NAD-dependent acetylation status of at least one amino acid (e.g., lysine) in a protein such as a nuclear protein. The nuclear protein can be, for example, p53 or a histone protein (e.g., H2B, H3 or H4). The histone protein, a Sir2 protein or Sir2-like protein, NAD or a NAD-like compound and the agent to be tested are combined to produce a combination, the NAD-dependent acetylation status of an amino acid in the histone protein is detected (e.g., electron-spray mass spectroscopy); and compared the NAD-dependent acetylation status in the presence of the agent to be tested with the acetylation status of the amino acid in the histone protein in the absence of the agent to be tested. A difference in the acetylation status of the amino acid of the histone protein in the presence of the agent alters aging of the cell or organism (e.g., C. elegans). The agent tested can increase the aging of a cell or an organism (e.g., C. elegans) by NAD-dependent acetylation of the histone protein. Alternatively, the agent can decrease aging of the cell or the organism by NAD-dependent deacetylation of histone proteins. The agent can be an agonist of Sir2 or an antagonist of Sir2.

Agents identified by the in vitro methods of the invention, such as the method described above, can be further evaluated for their ability to alter the NAD-dependent acetylation status in a cell or an organism (e.g., *C. elegans*) by administering the identified agents to a cell or an organism and monitoring the NAD-dependent acetylation status of at least one amino acid in a histone protein of the cell or the organism. It is expected that agents identified in vitro as agents which alter the NAD-dependent acetylation status of a histone protein will alter the NAD-dependent alteration status of histone protein in vivo. Likewise, it is expected that the agents which alter NAD-dependent acetylation status of histone proteins by the methods described herein will alter the lifespan and aging of a cell or organism.

The invention also relates to a method of altering the NAD-dependent acetylation status of at least one amino acid residue in a histone protein comprising combining the histone protein, a Sir2 protein or Sir2-like protein and a NAD or a NAD-like compound. The method can be used in vitro (e.g., the absence of cells or an animal) or in vivo (e.g., in cells or animals).

The present invention also relates to a method of identifying agents which alter mono-ADP-ribosylation of one or more nuclear proteins in a cell. The cell can be in an organism or can be an isolated cell or a collection of cells outside an organism. In a preferred embodiment, the organism is *C. elegans*. The cell or organism and agent to be tested are combined and the level of mono-ADP-ribosylation of a nuclear protein, such as p53 or one or more histone proteins (e.g., H2B, H2A, H3, H4), is determined and compared to the level of mono-ADP-ribosylation of that protein or proteins in the absence of the agent. A difference in the level of mono-ADP-ribosylation in the presence and absence of the agent indicates that the agent alters the mono-ADP-ribosylation of the nuclear protein. That is, if the level of mono-ADP-ribosylation is greater in the presence of the agent than in the absence of the agent, the agent is an agonist of mono-ADP-ribosylase activity. Similarly, if the level of mono-ADP-ribosylation is greater in the absence of the agent than in the presence of the agent, the agent is an antagonist of mono-ADP-ribosylation.

Alternatively, the method of identifying agents which alter NAD-dependent acetylation status of a histone protein and/or mono-ADP-ribosylation of one or more nuclear proteins can be carried out at the organism (e.g. animal) level. An agent to be tested is administered to an organism, and the alteration in NAD-dependent acetylation of a histone protein and/or the level of mono-ADP-ribosylation of one or more nuclear proteins, such as one or more histone proteins, in cells of the organism is determined and compared to the acetylation status of a histone protein and/or the level of mono-ADP-ribosylation of that protein or proteins in the absence of the agent. A difference in the acetylation status of a histone protein and/or the level of mono-ADP-ribosylation in the presence and absence of the agent indicates that the agent alters NAD-dependent acetylation status of histone proteins and/or the mono-ADP-ribosylation of the nuclear protein.

Agents to be tested for activity in the assays described herein can include proteins (including post-translationally modified proteins), peptides (including chemically or enzymatically modified peptides), or small molecules (including carbohydrates, steroids, lipids, anions or cations, drugs, small organic molecules, oligonucleotides, antibodies, and genes encoding proteins of the agents or antisense molecules), including libraries of compounds. The agents can be naturally occurring (e.g., found in nature or isolated from nature) or can be non-naturally occurring (e.g., synthetic, chemically synthesized or man-made). Agents which alter the level of NAD-dependent acetylation status of histone proteins or the mono-ADP-ribosylation of nuclear proteins of the invention can be agonists (e.g., stimulators/enhancers) or antagonists (e.g., inhibitors) of NAD-dependent acetylation or mono-ADP-ribosylase activity. In a particular embodiment, the agents are agonists or antagonists of Sir2 (e.g., mSir2α, ySir2) dependent NAD-dependent acetylation and mono-ADP-ribosylation of proteins. The proteins can be nuclear proteins such as p53 or histone proteins (e.g., H2A, H2B, H3, H4).

The term "agonist" as used herein, refers to an agent which simulates or mimics NAD-dependent acetylation or deacetylation of histone proteins (e.g., mSir2, ySir2, human Sir2), a mono-ADP-ribosylase (e.g., mSir2α, ySir2, human Sir2) by, for example, deacetylating H3 or H4 (e.g., removal an acetyl group from at least one lysine residue in the amino terminus) and/or catalyzing the transfer of an adenosine diphosphate ribose unit from an ADP donor (e.g., NAD) to an amino acid residue (e.g., lysine) of a substrate (e.g., p53, histone protein H2B, H3, H4). Alternatively, or additionally, an agonist can be an agent which stimulates, augments, enhances, increases, intensifies or strengthens NAD-dependent acetylation/deacetylation and/or mono-ADP-ribosylase activity or the interaction between a nuclear protein and a NAD-dependent acetylase, mono-ADP-ribosyltransferase, or alters a mono-ADP-ribosylase in a manner (e.g., results in a conformational change) which augments the activity of the mono-ADP-ribosylase such that the nuclear protein is mono-ADP-ribosylated at a higher rate or in greater quantities than in the absence of the agonist. An agonist can also enhance the rate of removal of acetyl groups from amino acid residues of histone proteins.

An agonist can also enhance the availability or accessability of a mono-ADP-ribosylase to a substrate, or a substrate to a mono-ADP-ribosylase, thereby further increasing the level of mono-ADP-ribosylation of a nuclear protein. For example, a substance possessing agonist activity can increase the rate at which ADP-ribose is transferred to an amino acid residue of a histone protein, such as H2B, H2A, H3, or H4 beyond that observed in the absence of the agonist.

The term "antagonist", as used herein, includes a substance which blocks, diminishes, inhibits, hinders, limits, decreases, reduces, restricts or interferes with the NAD-dependent acetylation/deacetylation of histone proteins and/or enzymatic activity of a mono-ADP-ribosylase, alters the substrate (e.g., p53, a histone protein such as H2B, H2A, H3 or H4). An antagonist can act in a manner which prevents Sir2 from deacetylating an amino acid residue in a histone protein and/or a mono-ADP-ribosylase (e.g., mSir2α, ySir2, human Sir2) from acting on the substrate, or interferes with the accessibility of the substrate (e.g., H2B, H2 or H4) to Sir2 for alterations in NAD-dependent acetylation status and/or the mono-ADP-ribosyltransferase, or any combination thereof.

Alternatively or additionally, an antagonist can prevent, impede or interfere with the interaction between Sir2 and NAD, a mono-ADP-ribosyltransferase and a nuclear protein substrate by altering the Sir2 or mono-ADP ribosyltransferase (e.g., conformationally), thereby preventing the Sir2 and/or a mono-ADP-ribosyltransferase from altering the NAD-dependent acetylation status of a histone protein and/or catalyzing the transfer of an adenosine diphosphate ribose unit from an ADP donor (e.g., NAD) to an amino acid residue (e.g., threonine) of a substrate (e.g., a nuclear protein such as a histone protein). For example, a substance possessing antagonist activity can decrease the rate at which the status of NAD-dependent acetylation (e.g., deacetylation) takes place.

An agonist can also prevent, impede or interfere with ADP-ribose transfer to an amino acid residue of a nuclear protein such as p53 or a histone protein (e.g., H2B, H2A, H3 or H4) relative to that observed in the absence of the antagonist.

The agonist or antagonists of the present invention can also alter transcription of NAD-dependent acetylases and/or mono-ADP-ribosyltransferase genes (e.g., SIR2), the mRNA stability of NAD-dependent acetylases and/or mono-ADP-ribosyltransferase transcripts, or degradation of the enzyme as a means to alter NAD-dependent acetylase and/or mono-ADP-ribosyltransferase activity. For example, an agonist can increase the level (e.g., total cellular pool) of deacetylated histone proteins by increasing the activity of Sir2 in an NAD-dependent manner. Likewise agonists of the invention can also mono-ADP-ribosylated nuclear protein by increasing transcription of mono-ADP-ribosyltransferase enzyme genes (e.g., SIR2α) or decreasing enzyme degradation in a cell or an organism.

Similarly, an antagonist can decrease the levels of deacetylated histone proteins or increase the amount of acetylated histone proteins. Antagonists can also decrease the levels of mono-ADP-ribosylation of a nuclear protein by down regulating transcription of mono-ADP-ribosyltransferase genes or increasing degradation of the enzyme.

The cell used in the methods of the invention can be a yeast cell (e.g., *Saccharomyces cerevisiae*) or a mammalian cell, including somatic or embryonic cells, Chinese hamster ovary cells, HeLa cells, human 293 cells and monkey COS-7 cells. A collection of cells can form a tissue or an organism. The organism can be, for example, a vertebrate animal (e.g., a mammal, such as mice, rats, pigs dogs, cats, primates, and humans), nonvertebrate animal, such as an insect (e.g., *Drospholia melanogaster*), nematode (e.g., *C. elegans*), or yeast (e.g., *Saccharomyces cerevisioa*). A "tissue" refers to a collection of similar cell types (such as epithelium, connective, muscle and nerve tissue).

Figure 19:
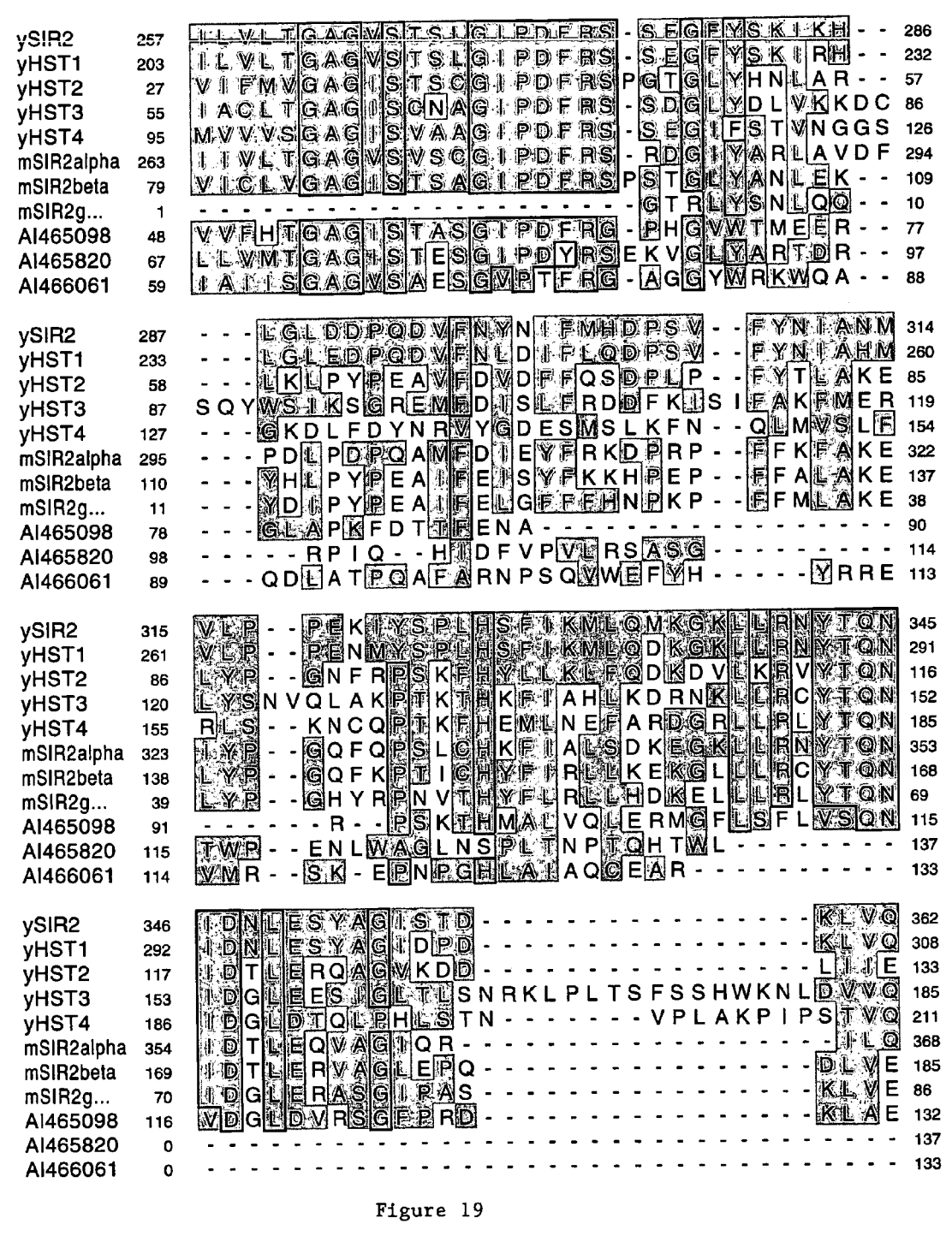

The term "mono-ADP-ribosylation", as used herein, refers to the transfer of one adenosine diphosphate ribose unit from an ADP donor (e.g., NAD) to an amino acid residue (e.g., threonine) of a substrate (e.g., one or more histone proteins such as H2B). A "mono-ADP-ribosyltransferase" (also referred to herein as mono-ADP ribosylase is a protein (also referred to herein as a polypeptide) which catalyzes the mono-ADP-ribosylation. For example, mono-ADP-ribosyltransferases encompassed by the invention include murine (m) SIR2 genes and proteins (e.g., mSir2α, mSir2β, mSir2γ), human Sir2 genes (Frye, *Biochem. Biophys. Res. Commun.* 260:273-279 (1999)) and proteins, yeast genes and proteins that are Homologous to SIR2 (HST) (e.g., HST1, HST2, HST3, HST4), and nucleic acid molecules having accession numbers AI466061, AI465820, or AI465098. (See FIG. 19). Database accession numbers for the nucleotide and amino acid sequences for some of these mono-ADP-ribosyltransferases are known. (Frye, *Biochem. Biophys. Res. Commun.* 260:273-279 (1999)). A mSIR2β EST CDNA clone (SEQ ID NO: 34, 35) 557657 can be purchased from Genome Systems, Inc.

Other known mono-ADP-ribosyltransferases include bacterial toxins, such as cholera, pertussis and diphtheria toxins and mammalian glycosylphosphatidylinositol (GP1)-anchored mono-ADP-ribosyltransferases (Domenighini, et al., *Microbiology* 21:667-674 (1996); Moss, et al., *Mol. Cell Biochem.* 193:109-113 (1999)). It is understood that any protein that mono-ADP-ribosylates nuclear proteins, in particular histone proteins such as H2B, H2A, or H3, is within the scope of the invention.

A "level of mono-ADP-ribosylation" refers to an amount of a substrate to which an adenosine diphosphate ribose has been transferred. The level of mono-ADP-ribosylation can be assessed using methods known in the art, such as in vitro labeling techniques, for example, by monitoring the addition of [$^{32}$P]NAD+ to a substrate (e.g., H2A, H2B, H3). By way of illustration only, the ADP-ribosylase activity of an agent and the level of mono-ADP-ribosylation of a substrate can be determined by adding a protein to be evaluated (about 0-1 g) to a reaction buffer comprising 50 mM Tris-HCl, pH 8.0, 4 mM MgCl$_2$, 0.2 mM DTT, 1 µM cold or nonradiolabeled NAD, 0.08 µM [$^{32}$P]NAD and admixing or gently vortexing to dilute, resuspend or mix the protein. Substrates (e.g., histone proteins at a concentration of about 0-1 g) are then added and the reaction mixture is incubated at ambient temperature (18-25° C.) for 30-120 minutes. The presence or absence of ADP-ribosylation products (e.g., ADP-ribosylated nuclear proteins) is detected using autoradiography. Differences in the levels of mono-ADP-ribosylation, for example in the presence and absence of an agent to be tested, can be determined using suitable techniques, including, but not limited to, densitometric scanning of autoradiographs or phosphoimaging techniques of gels. (See, Ausubel, et al., "Current Protocols in Molecular Biology" John Wiley & Sons (1999)). Techniques to perform the mono-ADP-ribosylation assays are detailed in the Exemplification Section.

Figures 4F, 4G:
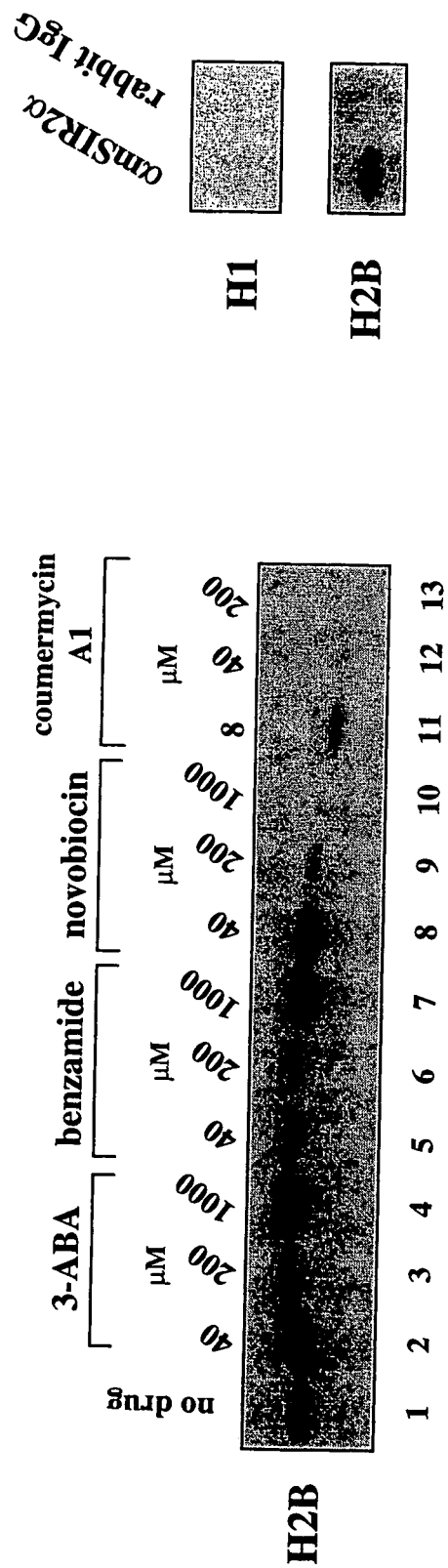
FIG. 4F depicts the effects of mono-ADP-ribosylation inhibitors (novobiocin and coumermycin A1), but not poly-ADP-ribosylation inhibitors (3-aminobenzamide (3-ABA) and benzamide), on mSir2α ADP-ribosylation of H2B.
FIG. 4G depicts the mono-ADP-ribosyltransferase activity of mSir2α immunoprecipitated by an antiserum to mSir2α (αmSir2α) from NIH3T3 whole cell extracts.

Confirmation of mono-ADP-ribosylation of substrates and, thus, mono-ADP-ribosyltransferase activity of an agent, can be performed, for example, by adding a suitable amount of snake venom phosphodiesterase (e.g., 2 mg/ml, specific activity 1.5 U/mg) to the resulting product of the reaction mixture described above. The reaction product and phosphodiesterase are incubated at about 37° C. for about an hour. Absence of an autoradiographic band following phosphodiesterase digestion, as compared with presence of an autoradiographic band in the absence of digestion, indicates that the substrate was mono-ADP-ribosylated (FIG. 4E). Mono-ADP-ribosylase activity can also be verified by the addition of one or more specific mono-ADP-ribosylation inhibitors, including, but not limited to, novobiocin and coumermycin A1, to in vitro assays described above (FIG. 4F). The inhibitor (s) can be added before or after the addition of the substrate. The absence of a band in an autoradiograph following the addition of a specific mono-ADP-ribosylation inhibitor indicates that the agent has mono-ADP-ribosylase activity. Thus, the mono-ADP-ribosyltransferase activity of agents is evaluated by mono-ADP-ribosylation of substrate proteins as described in the Exemplification Section.

In a preferred embodiment, agonists of the invention are agonists of Sir2 NAD-dependent acetylation of histone proteins and Sir2 mono-ADP-ribosyltransferase activity. The identification of agonists or antagonists of Sir2 activity can be initially evaluated using yeast cells. In the presence of an agonist of Sir2 activity, a yeast cell will produce a red colonies, whereas antagonists of Sir2 will result in a white colony. When the ADE2 gene is inserted into one of the three Sir2-regulated silencing loci (e.g., telomere rDNA, or HM mating loci) it is silenced in the presence of the agonists, which eventually leads to yeast cells accumulating red pigment. When the ADE2 gene is transcribed in the presence of antagonists, yeast cells metabolizing the intermediate red pigments and become white in color. Prescreening agents employing color selection of yeast cells will be particularly useful for large scale screening of agents which alter the activity of NAD-acetylation of histone proteins and mono-ADP-ribosyltransferases that ADP-ribosylate nuclear proteins. Following a color selection screening protocol agents can be further evaluated for their ability to alter NAD-dependent acetylation of histone proteins and the level of mono-ADP-ribosylation of nuclear proteins using techniques described herein.

The mono-ADP-ribosyltransferases described herein catalyze the addition of ADP-ribose to cellular proteins, specifically nuclear proteins. A "nuclear protein" refers to any protein, polypeptide or peptide that is located in or performs a function in the nucleus of a eukaryotic cell (e.g., a yeast cell, a zebrafish cell, a *C. elegans* cell, *Drosophila melanogaster* cell, or a mammalian cell, such as a murine cell or a human cell). In a preferred embodiment, the nuclear proteins are histone proteins. Histone proteins are highly conserved DNA-binding nuclear proteins that form the nucleosome, the basic subunit of the chromatin. Histone proteins can be one or more core histone proteins (e.g., H2A, H2B, H3, H4) or an outer histone protein (e.g., H1), or combinations thereof. In a more preferred embodiment, the substrate for mono-ADP-ribosylation is histone H2B or H3. In a preferred embodiment, the substrate for NAD-dependent deacetylation is a protein such as an acetylated p53 protein or an acetylated histone protein.

The term "alters" is defined as a change in an activity (e.g., NAD-dependent acetylation status of at least one amino acid of a protein such as a nuclear protein, p53, a histone protein, mono-ADP-ribosylation) or phenomena (e.g., aging, life span), for example, relative to an activity or phenomena in the absence of an agent to be tested. Alteration includes both an increase and a decrease (e.g., complete abolishment), either qualitatively, quantitatively or both, in the activity or phenomena being monitored.

The agent to be tested (e.g., an agonist or antagonist) can be combined with the cell before or after the addition of the substrate (e.g., a histone protein such as H2B, H3, and/or H4). Experimental conditions for evaluating test substances, such as buffer (e.g., 50 mM Tris-HCl, pH 8.0) or media, concentration (about 0-1 g), temperature (about 18-25° C.), and incubation (about 30-120 minutes) requirements, can, initially, be similar to those described in the Exemplification Section herein relating to NAD-dependent acetylation status of histone proteins and mono-ADP-ribosylation of histone proteins by mSir2α or ySir2. One of ordinary skill in the art can determine empirically how to vary experimental conditions depending upon the biochemical nature of the agent and the particular cell used in the methods described herein.

If the agent to be tested is being administered to an organism, various methods and routes of administration are known in the art. The agent will preferably be formulated in a pharmaceutical composition. For instance, suitable agents can be formulated with a physiologically acceptable medium to prepare a pharmaceutical composition. The particular physiological medium may include, but is not limited to, water, buffered saline, polyols (e.g., glycerol, propylene glycol, liquid polyethylene glycol) and dextrose solutions. The effective amount and optimum concentration of the active ingredient (s) (e.g., the agent) in the chosen medium can be determined empirically, according to procedures well known to medicinal chemists, and will depend on the ultimate pharmaceutical formulation desired. Methods of administration of compositions for use in the invention include, but are not limited to, intradermal, intramuscular, intraperitoneal, intravenous, subcutaneous, intraocular, oral and intranasal. Other suitable methods of introduction can also include rechargeable or biodegradable devices and slow release polymeric devices. The pharmaceutical compositions of this invention can also be administered as part of a combinatorial therapy with other agents.

The invention further relates to the discovery that increased NAD-dependent deacetylation of histone protein by Sir2 and/or mono-ADP-ribosylation of one or more nuclear proteins (e.g., histone proteins) correlates with decreased rDNA recombination, increased life span and decreased aging at the cellular level. Thus, agents which increase NAD-dependent deacetylation of histone proteins by Sir2 and/or mono-ADP-ribosylation of nuclear proteins are expected to be agents which decrease rDNA recombination, increase life span and decrease aging. Accordingly, in another embodiment, the methods of the invention relate to identifying agents which alter the life span of a cell or an organism. It is envisioned that the methods of the invention can be used for any cell that undergoes aging, for example, a mammalian cell (e.g., from a human), a zebrafish cell, a *C. elegans* cell, or *Drosophila melanogaster* cell in, for example, experimental systems.

The cell or organism is combined with the agent to be tested and the level of NAD-dependent acetylation or deacetylation of histone proteins by Sir2 and/or mono-ADP-ribosylation of one or more nuclear proteins is determined in the presence of the agent and compared to the level in an appropriate control in the absence of the agent. A difference in the level NAD-dependent acetylation of histone proteins and/or of mono-ADP-ribosylation of the nuclear protein in the presence of the agent indicates that the agent alters NAD-dependent acetylation of histone proteins and/or the mono-ADP-ribosylation of a nuclear protein of a cell or an organism and that the agent alters life span of the cell or organism.

Figure 20:
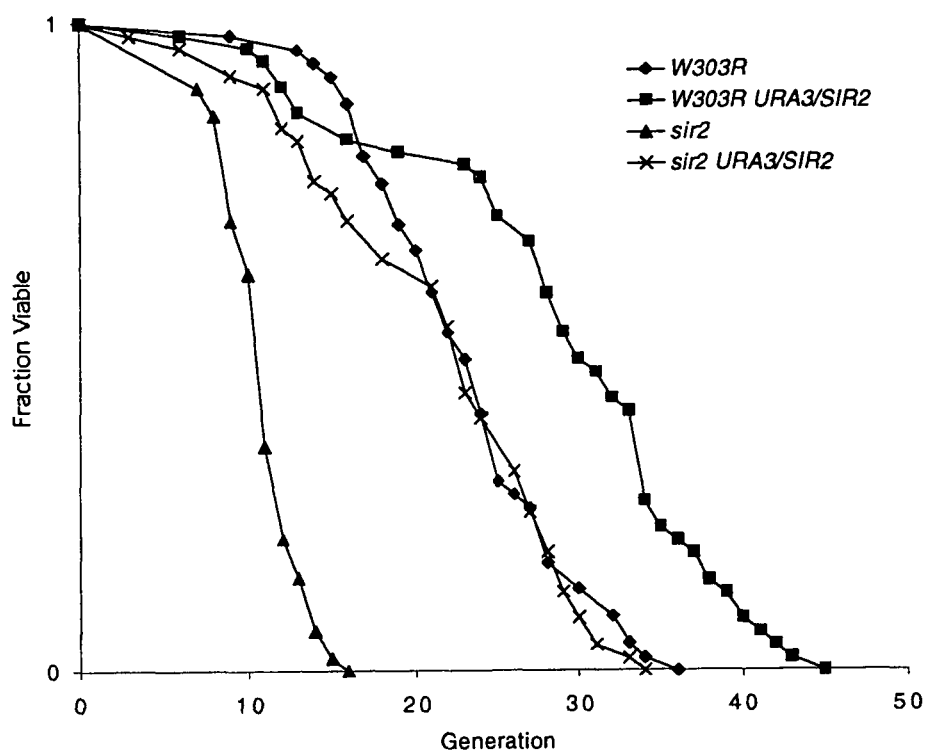
FIG. 20 depicts the effects of multiple copies of Sir2 on yeast life span.

Methods of determining life span of a cell or an organism are known in the art. With regard to a yeast cell, for example, "life span" refers to the number of generations, or divisions of a mother cell, which give rise to daughter cells. Techniques to assess the life span of yeast cells, including growth conditions for particular strains, are well known and include stress-resistance methods, cell surface labeling methods and temperature sensitive methods. (See, for example, Guarente et al., U.S. Pat. No. 5,874,210 (1999), the teachings of which are incorporated herein in their entirety). The life span of a yeast cell in the presence of an agent can be initially identified, e.g., by the mean number of generations using a colony color selection strategy. The ability of an agent to alter (e.g., increase) the life span of a cell, as described herein, is measured as an increase in the mean life span of a cell(s) as compared with the mean life span of a cell(s) not combined with the test agent. For example, the life span of the yeast *Saccharomyces cerevisiae* can be increased at least 2-3 fold in the presence of two copies of the yeast or mammalian (e.g., murine, human) NAD-dependent deacetylase and/or mono-ADP-ribosyltransferase SIR2 gene compared to cells lacking the SIR2 gene (FIG. 20). When SIR2 is deleted from yeast haploid cells the life span of cells is reduced by about 50% compared to wild type. When an extra copy of the SIR2 gene is introduced into wild type yeast haploid cells (the yeast cells have two copies of the gene), the cells display a longer life span than wild type (Kennedy, et al., *Cell* 90:485-496, (1995); Kaeberlein, et al., *Genes & Development,* 13:2370-2580, (1999)).

The life span of mammalian cells (e.g., human and murine diploid fibroblasts, epithelial cells and lymphocytes) refers to the number of population doublings until the cells are in a growth-arrested state such as "cellular senescence" (Hayflick et al., *Experimental Cell Research,* 25:585-621, (1961); Todaro, et al., *Journal of Cell Biology,* 17: 299-313, (1963); Rohme, *Proc. Natl. Acad. Sci. USA,* 78:5009-5013, (1981)). For some mammalian cells which obtain the ability to proliferate indefinitely in culture (e.g., cell lines established from cancers and cell lines engineered chemically or genetically to have infinite life span), the life span can be artificially terminated by the methods of the invention. In this case, the life span is defined as the average doubling cycles before the cells die by the induction of cellular senescence or apoptosis.

The life span of an organism (e.g., vertebrate organism, such as a human, or a nonvertebrate organism, such as an insect, nematode or fish) refers to the average (also referred to herein as mean) duration of life of a given organism. For example, the average life span of a male human being is about 71.8 years, and the average life span of a female human being is about 78.6 years and the average life span of a mouse is about 0.7-2.7 years (Finch, "Longevity, Senescence and the Genoma," Univ. of Chicago Press, Chicago, Ill. (1990)).

In one embodiment, the agent increases the life span of the cell or organism by increasing the NAD-dependent deacetylation of histone proteins, in particular at least one amino acid at the N-terminal lysine residues of H3 (e.g., lysine 9 and/or lysine 14) and/or H4 (e.g., lysine 16), by increasing the activity of Sir2. In another embodiment, the agent increases the lifespan of the cell or organism by increasing the level of mono-ADP-ribosylation or NAD-dependent deacetylation of a nuclear protein, such as p53, H2B or H3, in particular mono-ADP-ribosylation of a lysine residues in H3 and/or H4. An increase in life span would be a duration of a particular life beyond the average for that cell or organism.

In another embodiment, the agent decreases the life span of the cell or organism by decreasing the activity of Sir2, thereby altering NAD-dependent acetylation (e.g., deacetylation) of histone proteins, in particular at least one amino acid at the N-terminus of H3 (e.g., lysine 9 and/or lysine 14) and/or H4 (e.g., lysine 16). In an additional embodiment, the agent decreases the level of mono-ADP-ribosylation of a nuclear protein, such as H2B or H3. In yet another embodiment, the agent increases the NAD-dependent deacetylation of an acetylated protein (e.g., a nuclear protein such as p53 or a histone protein). An increase in the NAD-dependent deacetylation of a protein can increase the lifespan of the cell or organism. In a preferred embodiment, the NAD-dependent deacetylase is a Sir2 protein (e.g., Sir2α, Sirβ, Sirδ). A decrease in life span would a duration of a particular life less than average for that cell organism.

The invention also pertains to a method of identifying an agent which alters aging of a cell or an organism. The cell or organism and agent to be tested are combined and the level of NAD-dependent acetylation of histone proteins and/or the level of mono-ADP-ribosylation of a nuclear protein (e.g., H2B, H2A or H3) is determined and compared to the NAD-dependent acetylation status of a histone protein and/or the level of mono-ADP-ribosylation of the nuclear protein in the absence of the agent. A difference in the NAD-dependent acetylation status and/or level of mono-ADP-ribosylation in the presence and absence of an agent indicates that the agent alters aging of the cell or organism.

"Aging" refers to all time-dependent changes to which biological entities, from molecules to ecosystems, are subject, though the mechanisms and consequences to function may be vastly different (Medawar, "An Unsolved Problem of Biology", H. K. Lewis, London, (1952). Additionally or alternatively, aging refers to the process of growing old or senencing. Aging is associated with particular phenotypes in a cell or organism. In a cell, aging can be characterized by an increase in cell size, a slowing of the cell cycle, shortening of telomeres, and/or expression of some particular categories of genes (Stanulis-Praeger, *Mech. Ageing Dev.* 38:1-48, (1987); Faraher, et al., *BioEssay,* 20:985-991, (1998)). The changes in heterochromatin structure and mitochondria can also be associated with aging (Imai, et al., *Experimental Gerontology,* 33:555-570, (1998); Wallace, et al., *Biofactors,* 7:187-190, (1998)). In yeast cells, sterility, the appearance of surface wrinkles, blebs and bud scars, nucleolar enlargement and fragmentation, and formation, replication, and accumulation of rDNA circles are also associated with aging (Sinclair, Mills and Guarente, *Annu. Rev. Microbiol.,* 52533-560, (1998)).

In yeast, aging is defined by the relatively fixed number of cell divisions undergone by mother cells (Müller et al., *Aging Dev.* 12:47 (1980)), as well as characteristic changes during their life span (Jazwinski, *Science* 273:54 (1996)), such as cell enlargement (Mortimer and Johnson, *Nature* 183:1751 (1959)) and sterility (Müller, *J. Microbiol. Serol.* 51:1 (1985)). Techniques to determine aging in a yeast cell are well-known and are described, for example, in Guarente et al., U.S. Pat. No. 5,874,210 (1999), Smeal, et al., *Cell* 84:633-642 (1996); Sinclair, et al., *Science* 277:1313-1316 (1997); Sinclair, et al., *Cell* 91:1033-1042 (1997)), the teachings of all of which are incorporated herein in their entirety.

Aging of an organism refers to the deterioration of the organism associated with changes in structures and functions (e.g., phenotype) that are characteristic of a particular organism. Such characteristics can include, for example, hair loss, graying of hair, osteoporosis, cataracts, atherosclerosis, loss of skin elasticity and a propensity for certain cancers.

The agents identified by the methods of the present invention can be used to alter the aging of a cell or an organism by altering the level Sir2 activity, NAD-dependent acetylation status of histone proteins and/or of mono-ADP-ribosylation of a nuclear protein. In a preferred embodiment, the agents identified by the methods of the invention decrease aging of the cell or organism. In another embodiment, the agents identified by the methods of the invention increase aging of the cell or organism.

Due to their ease of experimental manipulation, similar structural features associated with aging in mammalian cells (Guarente et al., U.S. Pat. No. 5,874,210 (1999)), and an Sir2 protein which shares sequence (nucleic acid and amino acid) and enzymatic (e.g., NAD-dependent acetylation of histone proteins, mono-ADP-ribosyltransferase) with a mammalian Sir2 proteins (e.g., mSir2α, mSir2β), the yeast cell is a suitable cellular model to identify agents which alter NAD-dependent acetylation of histone proteins or mono-ADP-ribosylation of nuclear proteins, increase life span and decrease aging in mammalian cells and organisms as well as nonmammalian cells and organisms (e.g., insect, nematode, fish, *C. elegans*). Moreover, a mammalian (e.g., mSir2α) NAD-dependent deacetylase and/or mono-ADP-ribosylase increases the life span and slows aging of yeast cells. Thus, mammalian and yeast Sir2 proteins mediate similar biological activities.

Likewise, due to their ease of experimental manipulation, the presence of genes with similarity and identity to the Sir2 genes (also referred to herein as "Sir2 like") (see exemplification), in particular yeast Sir2 genes, the presence of a duplication(s) of the Sir2 like genes in the *C. elegans* genome and the ability of endogenous (e.g., duplications) or exogenous extra copies of Sir2 (e.g., yeast Sir 2) to extend life span in *C. elegans* (see exemplification), *C. elegans* is also a suitable model system to assess the effects of agents which alter (e.g., increase or decrease) the life span of a cell or an organism by assessing the effect of an agent on the life span of *C. elegans*. The agent can alter the activity of Sir2 in *C. elegans* thereby altering the life span of *C. elegans*. Alterations in the activity of Sir2 in *C. elegans* can be, for example, by altering the NAD-dependent acetylation status of at least one histone protein. Agents which extend the life span of *C. elegans* can be further assessed for their ability to alter the NAD-dependent acetylation status of at least one amino acid of a histone protein.

As defined herein, mammals include rodents (such as rats, mice or guinea pigs), domesticated animals (such as dogs or cats), ruminant animals (such as horses, cows) and primates (such as monkeys or humans).

Thus, the agents identified by the methods described herein, which increase life span or decrease aging as described above, can be used to increase the life span or decrease aging of cells, e.g., mammalian cells including human cells, or vertebrate (e.g., mice, humans, guinea pigs, rats) or invertebrate (e.g., insects, nematodes, *C. elegans*) organisms. For example, cells or organisms to be treated can be combined with an effective amount of an agent that increases the activity of Sir2, increases the NAD-dependent deacetylation of histone proteins, and/or level of mono-ADP-ribosylation of a nuclear protein, thereby increasing their life span or decreasing their aging relative to untreated cells or organisms.

An "effective amount" of an agent, as used herein, is defined as that quantity of an agent which increases life span or decreases aging, to any degree, in the cell or organism being treated by increasing, to any degree, the NAD-dependent deacetylation of a protein such as a nuclear protein (e.g., p53 or a histone protein) by Sir2 or a Sir2-like protein and/or the level of mono-ADP-ribosylation of a nuclear protein (e.g., H2B, H2A, H3, or H4). In a preferred embodiment, lysines at position 9 and/or 14 in H3 are deacetylated and/or lysine at position 16 in H4 is deacetylated. For example, an effective amount of an agonist of a mono-ADP-ribosyltransferase in a cell or an organism can inhibit certain characteristics associated with aging, for example, the formation of rDNA with, or without, inhibiting other characteristics, such as the replication and/or accumulation of rDNA. Similarly, an effective amount of an agent that increases the NAD-dependent deacetylation of histone proteins (e.g., H2B, H3 and/or H4) and/or the levels of mono-ADP-ribosylation of a nuclear protein can decrease aging in an organism by slowing hair loss, with or without, diminishing graying or hair, cataracts or atherosclerosis.

It is envisioned that the agents identified by the methods of the present invention can be administered to cells or organisms which age naturally (e.g., normally) or age prematurely or abnormally (e.g., as a result of Werner's syndrome in mice or humans) due to genetic permutations. Thus, the agents identified by the methods of the present invention, can be useful in anti-aging therapies and for the treatment of aging diseases, such as Werner's syndrome, to prevent, halt, hasten, slow or ameliorate premature aging. Additionally, or alternatively, the identification of agents which alter the NAD-dependent acetylation status of histone proteins (e.g., lysines 9 and/or 14 of H3, lysine 16 of H4) and/or the mono-ADP-ribosylation of nuclear proteins can be also be useful for the continued study of cellular and organismal aging processes.

Thus, the present invention also pertains to methods of increasing the life span or decreasing the aging of a cell or an organism by administering an effective amount of an agent that increases the NAD-dependent deacetylation of histone proteins and/or increases the mono-ADP-ribosylation of a nuclear protein. The agent is identified by combining an agent to be tested with a cell or an organism and determining the level of NAD-dependent deacetylation of histone proteins (e.g., H3, H4) and/or mono-ADP-ribosylation of a nuclear protein in the presence of the agent which is compared to the NAD-dependent acetylation of a histone protein and/or level of mono-ADP-ribosylation of a nuclear protein in the absence of the agent. The presence of an agent which increases life span or decreases aging increases the activity of Sir2 thereby increasing the deacetylation of histone proteins or increases the level mono-ADP-ribosylated nuclear protein (e.g., H2B, H2A, H3, H4).

The present invention also pertains to methods of increasing the life span or decreasing aging of a cell or an organism by administering to the cell or organism an agonist of Sir2 that increases the NAD-dependent deacetylation of histone proteins, a mono-ADP-ribosyltransferase (e.g., Sir2) or an agonist of a mono-ADP-ribosyltransferase of a nuclear protein. In a preferred embodiment, the nuclear protein is p53 or a histone protein, in particular H2A, H2B, H3 or H4. In a more preferred embodiment, the acetylation status of lysine residues at positions 9 and/or 14 of H3 are altered and the lysine at position 16 of H4 is altered by altering the activity of Sir2. Preferably the mono-ADP-ribosyltransferase is a Sir2 protein (e.g., Sir2α, Sir2β, Sir2γ). Specifically, the core domain of a Sir2 protein (FIG. 2B, 6A, 14*a*, 19; SEQ ID NOS: 2, 3, 4, 5, 9, 10, 11, 12, 13, 14, 15, 16, 17, 18, 19, 20, 21, 22, 23 and 24) alters the NAD-dependent acetylation status of histone proteins, the mono-ADP-ribosyltransferase or the agonist of NAD-dependent acetylation status of histone proteins and/or mono-ADP-ribosyltransferase activity of the core domain of Sir2.

Because aging in cells and organisms is associated with the formation, replication and/or accumulation of ribosomal DNA (rDNA) circles, the present invention relates to methods of inhibiting the formation, replication and/or accumulation of rDNA circles in a cell or an organism by administering an effective amount of a mono-ADP-ribosyltransferase or agonist of NAD-dependent acetylation status of histone proteins and/or a mono-ADP-ribosyltransferase to a cell or organism. rDNA circles accumulate exponentially in old yeast mother cells and are responsible for age-related enlargement and fragmentation of the nucleolus, and appear to nucleate the fragmented nucleolus. (Sinclair, et al., *Cell* 91:1033-1042 (1997)). For example, agents which have been identified by methods described herein as agonists of NAD-dependent deacetylation and/or of mono-ADP-ribosylation of nuclear proteins can be administered to a cell or an organism to suppress the formation, replication and/or accumulation of rDNA circles. The cell samples thus treated are then examined for longer-lived, slower aged colonies, using any of the methods described herein or other appropriate methods.

The invention further relates to a method of suppressing recombination between rDNA in a cell or an organism comprising administering to the cell or the organism a mono-ADP-ribosyltransferase or an agonist of NAD-dependent deacetylation of histone proteins and/or a mono-ADP-ribosyltransferase. Recombination between rDNA is a characteristic of aging in cells. In yeast cells, sterility associated aging is due to a loss of transcriptional silencing at HMRa and HMLα loci, and the resulting expression of both a and α mating-type information (Smeal et al., *Cell* 84:633 (1996)). The Sir2 protein silences genes inserted at rDNA (Bryk et al., *Genes Dev.* 11:255 (1997); Smith and Boeke, *Genes Dev.* 11:241 (1997)) and suppresses recombination between rDNA repeats (Gottleib and Esposito, *Cell* 56:771 (1989)). Thus, suppressing recombination between rDNA by administering a mono-ADP-ribosyltransferase or an agonist of a NAD-dependent deacetylation of histone proteins and/or mono-ADP-ribosyltransferase can also decrease aging and increase life span.

Agents which alter the NAD-dependent acetylation status of histone proteins and/or mono-ADP-ribosylation of nuclear proteins (e.g., agonist of NAD-dependent deacetylation and/or mono-ADP-ribosyltransferase activity) can be formulated into compositions. Such compositions can also comprise a pharmaceutically acceptable carrier, and are referred to herein as pharmaceutical compositions. The agonist or antagonist compositions of the present invention can be administered intravenously, parenterally, orally, nasally, by inhalation, by implant, by injection, or by suppository. The agonist or antagonist compositions can be administered in a single dose or in more than one dose over a period of time to achieve a level of NAD-dependent deacetylation of histone proteins and/or mono-ADP-ribosylation of nuclear protein which is sufficient to confer the desired effect.

Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and if desired, mixed with auxiliary substances, e.g., lubricants, preservatives, stabilizers, wetting substances, emulsiers, salts for influencing osmotic pressure, buffers, coloring, and/or aromatic substances and the like which do not deleteriously react with the agonist or antagonist compounds. They can also be combined where desired with other active substances, e.g., enzyme inhibitors, to reduce metabolic degradation.

For parenteral application, particularly suitable are injectable, sterile solutions, preferably oily or aqueous solutions, as well as suspensions, emulsions, or implants, including suppositories. Ampules are convenient unit dosages.

It will be appreciated that the actual effective amounts of an agonist or antagonist of NAD-dependent acetylation status of histone proteins and/or mono-ADP-ribosylation of nuclear proteins in a specific case can vary according to the specific agonist or antagonist being utilized, the particular composition formulated, the mode of administration and the age, weight and condition of the patient, for example. For example, an effective amount of an agonist is an amount of agonist capable of slowing aging or extending the life span of a cell or an organism by altering the NAD-dependent acetylation status and/or mono-ADP-ribosylating substrates such as nuclear proteins (e.g., p53, histone proteins, preferably H2A, H2B, H3). Dosages of suitable agonists or antagonists of NAD-dependent deacetylation of histone proteins and/or mono-ADP-ribosylation of nuclear proteins for a particular patient can be determined by one of ordinary skill in the art using conventional considerations, (e.g. by means of an appropriate, conventional pharmacological protocol).

The present invention further relates to novel murine SIR2 (Silent Information Regulator) genes (e.g., mSIR2α, mSIR2β) and their protein products. The invention also relates to the discovery that mSir2α and yeast Sir2 (ySir2) proteins possess mono-ADP-ribosyltransferase activity, in particular mSir2α and ySir2 mono-ADP-ribosylate histone proteins (e.g., H2B, H3, H4) or NAD-dependent deacetylase activity. As shown in the Exemplification Section, transfection of yeast cells, which lack SIR2, with ySIR2 genes, slows aging and extends the life span of cell. Specifically, the administration of two copies of the ySIR2 gene increases life expectancy of the cell about 1.5 fold over cells with a single copy of the SIR2 gene and about 2-3 fold above cells which do not contain the SIR2 gene. Further, the duplication of genes which share identity and similarity to known SIR2 genes in *C. elegans* as well as the introduction of extra copies of a SIR2 gene extends the life span of *C. elegans*. Thus, the SIR2 gene of the present invention plays a critical role in the life span and aging of a cell and, thus, of a multicellular organism such as a *C. elegans* or a mammal.

The terms "SIR2" and "Sir2 amino acid sequence or Sir2 protein" refer to the SIR2 gene and its protein product, respectively. SIR2 or Sir2 refers to the any of the yeast (e.g., *S. cerevisiae*) SIR2 or Sir 2. "mSIR2" or "mSir2" refers to any murine SIR2 (e.g., SIR2α, SIR2β, SIR2γ). The terms "SIR2 nucleic acid", "nucleotide sequence of SIR2" or the "corresponding SIR2 nucleic acid", refer to the nucleic acid sequence that encodes the Sir2 protein.

The present invention also relates to the nucleic acid sequences encoding murine Sir2 proteins (e.g., mSir2α, mSir2β, mSir2γ). In particular a full length cDNA and genomic DNA nucleic acid sequence of mSIR2α and a partial cDNA sequence of SIR2β. The murine Sir2 proteins (e.g., mSir2α, mSir2β, mSir2γ) are encoded by at least three different genes. The nucleic acid sequence (SEQ ID NO.: 25) that encodes mSir2α protein (SEQ ID NO.: 26) can be found in FIG. 21.

The Sir2 proteins have functional domains. For example, one domain can be the core domain and another domain can be the amino-terminus or carboxy-terminus. The core-domain of the Sir2 protein (e.g., mSir2α) can alter the NAD-dependent acetylation status of histone proteins and/or mono-ADP-ribosyltransferase activity. The invention is also intended to embody the functional domains (e.g., core-domain of Sir2), as described herein. The amino acid sequence of the core domain of the mSir2α protein (SEQ ID NOS.: 4, 9, 12 and 19) is depicted in FIGS. 2C, 6, 14*a* and 19. Amino acid sequences (SEQ ID NOS: 2, 3, 5, 10, 11, 13, 14, 15, 16, 17, 18, 20, 21, 22, 23 and 24) which share structural identity to the nucleic acid and amino acid sequences of mSir2α are depicted in FIGS. 2C, 6A, 14*a* and 19.

The term "isolated", as it refers to a Sir2 protein, means a protein, as found in nature, but separated away from other proteins and cellular material of their source of origin. The isolated Sir2 proteins include essentially pure protein from cells, proteins produced by chemical synthesis, by combinations of biological and chemical synthesis and/or by recombinant methods.

The invention is intended to encompass Sir2 proteins, and proteins and polypeptides having amino acid sequences analogous (also referred to herein as similar or homologous) to the amino acid sequences of the Sir2 protein (e.g., mSir2α, ySir2) and functional equivalents or fragments thereof. Such proteins are defined herein as Sir2-like proteins, Sir2 homologs (e.g., analogues) or derivatives. Any protein possessing the Sir2 consensus sequence GAGISTS(L/A)GIPDFR (SEQ ID NO: 27) or YTQNID (SEQ ID NO: 28) (Brachmann, et al., *Genes & Development* 9:2888-2902 (1995) and which is capable of NAD-dependent deacetylation and/or mono-ADP-ribosylation of nuclear proteins is within the scope of the invention.

It is also envisioned that other Sir proteins (e.g., Sir1, Sir3, Sir4) or Sir-like proteins and the nucleic acids (e.g., SIR1, SIR3, SIR4) which encode Sir proteins, other than Sir2 or Sir2-like proteins, are within the scope of the invention.

Analogous or homologous amino acid sequences are further defined herein to mean amino acid sequences with sufficient identity to the Sir2 amino acid sequences so as to possess the biological activity of a Sir2 protein (e.g., mono-ADP-ribosylation of histone proteins). For example, an analogous peptide can be produced with "silent" changes in amino acid sequence wherein one, or more, amino acid residues differ from the amino acid residues of the Sir2 protein, yet still possess the biological activity of Sir2. Examples of such differences include additions, deletions or substitutions of residues of the amino acid sequence of Sir2. Also encompassed by the invention are analogous proteins that exhibit greater, or lesser, NAD-dependent deacetylation of histone proteins and/or mono-ADP-ribosyltransferase activity (e.g., biological activity) of the Sir2 protein of the present invention. Such structurally and functionally related proteins are also referred to herein as "Sir2-like" proteins.

The "biological activity" of a Sir2 protein is defined herein to mean the ability to alter the NAD-dependent acetylation status of a histone protein and/or the mono-ADP-ribosylates a substrate such as a histone protein (e.g., p53, H2B, H2A, H3, H4). In particular, the biological activity of mSir2α is the ability to alter the NAD-dependent acetylation status of lysine residues in the N-terminus of H3 (e.g., lysine 9 and/or 14) and/or H4 (e.g., lysine 16) and/or mono-ADP-ribosylate an amino acid residue of p53, H2B, H3 or H4. Additionally, or alternatively, the biological activity also means the ability to slow aging or extend life span by, for example, repressing recombination of rDNA, or inhibiting the formation, replication and/or accumulation of rDNA circles of a cell (e.g., a yeast cell, a cell from a mammal, a cell from C. elegans) or an organism (e.g., C. elegans). The biological function of Sir2 is illustrated and further defined by the Exemplification Section. In particular, extension of the life span of yeast cells and C. elegans which have multiple copies or duplication of a SIR2 or SIR2-like gene.

The invention also encompasses biologically active polypeptide fragments of the Sir2 protein, as described herein. Such fragments can include only a part of a full length amino acid sequence of Sir2 and yet possess the ability to NAD-dependent deacetylation and/or mono-ADP-ribosylate a substrate. Specifically encompassed by the invention are fragments of Sir2 comprising the core domain of Sir2.

The term "core domain" (also referred to herein as "core") refers to the evolutionarily conserved domains of Sir2 or Sir2-like proteins which can be identified, for example, by the comparison of amino acid sequences by, for example, CLUSTAL X, BLAST, PSI-BLAST or FASTA algorithms. The "core domain" is the domain that shows significant identity and/or homology to about 240-270 amino acids of Sir2 or Sir2-like proteins (about 20-50% or higher as amino acid identity, see FIG. 2) and/or possesses the consensus sequence GAG(V/I)S(T/V)S (L/C/A)GIPDFRS (SEQ ID NO:38) and YTQNID (SEQ ID NO: 28) (Brachmann, et al., *Genes & Development* 9:2888-2902, (1995)). The "core domain" of Sir2 proteins has NAD-dependent deacetylation and/or mono-ADP-ribosylation activities. Any protein with a "core domain" of a Sir2 protein, a fragment of the core domain, or any functional or structural equivalent which is capable of NAD-dependent deacetylation and/or mono-ADP-ribosylation of nuclear proteins is within the scope of the invention.

The Sir2 protein and nucleic acid sequence include homologues, as defined herein. The homologous proteins and nucleic acid sequences can be determined using methods known to those of skill in the art. Initial homology searches can be performed at NCBI against the GENBANK® (release 87.0), EMBL (release 39.0), and SwissProt™ (release 30.0) databases using the BLAST and PSI-BLAST network services. (See, for example, Altshul, et al., *J. Mol. Biol.* 215: 403 (1990); Altschul et al. *Nucleic Acid Res.* 25: 3389-3402 (1997); Altschul, *Nucleic Acids Res.* 25:3389-3402 (1998), the teachings of which are incorporated herein by reference). Computer analysis of nucleotide sequences can be performed using the MOTIFS and the FindPatterns subroutines of the Genetics Computing Group (GCG®, version 8.0) software. Protein and/or nucleotide comparisons can also be performed according to CLUSTAL algorithms (Higgins, et al., *Gene,* 73: 237-244 (1988)). Homologous proteins and/or nucleic acid sequences to the Sir2 protein and/or nucleic acid sequences that encode the Sir2 protein are defined as those molecules with greater than 25% sequences identity, also referred to herein as similarity, (e.g., 30%, 40%, 50%, 60%, 70%, 80% or 90% homology). The percent identity between the yeast (S. cerevisiae) SIR2 sequence and the murine SIR2α and SIR2β sequence is 45.9% (FIG. 2D). These particular sequence similarities and identities were determined using the CLUSTAL algorithm.

Homology was determined in accordance with the methods described in above (e.g., BLAST, PSI-BLAST algorithms). Homologs of mSIR2α can be, for example, mSIRγ, mSIR2β, ySIR2, yHST1, yHST2, yHST3, yHST4 (amino acid sequences depicted in SEQ ID NOS: 2, 3, 5, 10, 11, 13, 14, 15, 16, 17, 18, 20, 21, 22, 23 and 24; FIGS. 2C, 6A, 14a and 19) and human SIR2 nucleic acid or protein (Frye, *Biochem. Biophys. Res. Commun.* 260:273-279 (1999)).

Sequence identity of homologs of SIR2 can be to the entire nucleic acid or amino acid sequence, or to the core domain of the protein. In one embodiment, the BLAST or PSI-BLAST parameters are set such that they yield a sequence having at least about 60% sequence identity with the corresponding known mSIR2α sequence, preferably, at least about 70% sequence. In another embodiment, the percent sequence identity is at least about 85%, and in yet another embodiment, at least about 95%. Such molecules are also referred to herein as Sir2-like proteins. Thus, the Sir2-like proteins possess structural identity with the SIR2 molecules (e.g., nucleic acid or amino acid identity) described herein. The Sir2-like proteins are capable of altering the NAD-dependent acetylation status of at least one amino acid in a histone protein (e.g. lysine 9 and/or 14 of H3, lysine 16 of H4) and/or mono-ADP-ribosylating substrates (e.g., histone proteins), thus extending the life span or slowing the aging of a cell (e.g., yeast cell) or an organism (e.g., C. elegans).

Biologically active derivatives or analogs of the Sir2 protein can be made using peptide mimetics, designed and produced by techniques known to those of skill in the art. (see e.g., U.S. Pat. Nos. 4,612,132; 5,643,873 and 5,654,276, the teachings of which are incorporated herein by reference). These peptide mimetics can be based, for example, on a specific Sir2 amino acid sequence such as the core domain of Sir2α. These peptide mimetics can possess biological activity similar to the biological activity of the corresponding peptide compound, but possess a "biological advantage" over the corresponding Sir2 amino acid sequence with respect to one, or more, of the following properties: solubility, stability and susceptibility to hydrolysis and proteolysis.

It is also envisioned that any NAD-dependent deacetylase that alters the acetylation status of at least one amino acid of a histone protein and/or a mono-ADP-ribosyltransferase or Sir2-like protein containing proteins functionally equivalent to the Sir2 proteins described herein will be within the scope of the invention. The phrase "functionally equivalent" as used herein refers to any molecule (e.g., peptide, peptide mimetic, protein and nucleic acid sequence encoding the protein) which mimics the NAD-dependent deacetylation activity of Sir2 and/or mono-ADP-ribosyltransferase activity of the Sir2α proteins and/or functional domains of Sir2 (e.g., the carboxy-terminus) described herein (such as Sir2β, Sir2γ, HST1, HST2, HST3) or which exhibit nucleotide or amino acid sequence identity to Sir2α such as Sir2β, Sir2γ, for example.

The Sir2 protein or Sir2-like protein can also be mutated to down-regulate or affect one or more properties of the protein, while other properties still exist. In particular, the Sir2 protein can be mutated at a position in the sequence that prevents it from catalyzing the transfer of an ADP ribose from a donor, such as NAD, to a substrate and/or from acetylating or deacetylating at least one amino acid of a histone protein (e.g., lysine 9 and/or 14 of H3, lysine 16 of H4).

Thus, another embodiment of the present invention encompasses mutants of Sir2 proteins with altered NAD-dependent deacetylation activity and/or mono-ADP-ribosyltransferase activity. Mutants with NAD-dependent deacetylation activity and/or mono-ADP-ribosyltransferase activity greater than that of wildtype (e.g., nonmutant, naturally occurring) Sir2 are referred to as having "increased" NAD-dependent deacetylation activity or "increased" mono-ADP-ribosyltransferase activity. Mutants with a mono-ADP-ribosyltransferase activity less than that of wildtype Sir2 are referred to as having "decreased" NAD-dependent deacetylation activity or "decreased" mono-ADP-ribosyltransferase activity. The mutants of the present invention can be used, for example, to further understand the mechanism of substrate specificity and cellular pathways influenced by NAD-dependent deacetylation of histone proteins and/or mono-ADP-ribosylation of substrates, such as histone proteins.

The term "mutant", as used herein, refers to any modified nucleic acid sequence encoding a Sir2 protein or Sir2-like protein. For example, the mutant can be a protein produced as a result of a point mutation or the addition, deletion, insertion and/or substitution of one or more nucleotides encoding the Sir2 protein, or any combination thereof. Modifications can be, for example, conserved or non-conserved, natural or unnatural.

As used herein a mutant also refers to the protein encoded by the mutated SIR2 nucleic acid. That is, the term "mutant" also refers to a protein (also referred to herein as polypeptide) which is modified at one, or more, amino acid residues from the wildtype (e.g., naturally occurring) Sir2 protein. In a preferred embodiment, mutants are generated by mutations in mSir2α or ySir2 proteins. In a particular embodiment, the core domain of the mSir2α protein, as described herein, has a mutation resulting in a altered mono-ADP-ribosyltransferase activity. For example, in this embodiment the mSir2α mutant is a mutant of mSir2α resulting from a point mutation substituting the glycine at position 253 in the core domain of mSir2α with alanine residue to generate the G253A Sir2α mutant. Sir2 mutants can be made by mutations to one, or more, amino acid residues selected from a group consisting of glycine, serine, proline, isoleucine, phenylalanine, threonine, or histidine, or any combination thereof.

As used herein the designation for the amino acid substitutions for the Sir2 mutants is indicated as, for example, "G253A", wherein the letter to the left of the number indicates the amino acid in the wildtype Sir2 protein (e.g., "G" or glycine); the number indicates the position of the amino acid in the wildtype Sir2 protein (e.g., position 253); and the letter to the right of the number indicates the amino acid residue which replaces the wildtype (e.g., "A" or alanine).

Additionally, or alternatively, the mutants are designated by the amino acid which is mutated to an alanine residue, for example Thr-261, Gly-270, Iso-271, Arg-275 or Asn-345. Specifically encompassed by the invention are mSir2α mutants G253A, G255A, S257A, I262A, F265A, R266A, G270A (also referred to herein as Gly-270), P285A, T336A, H355A; and ySir2 mutants Thr-261, Iso-271, Arg-275, Asn-345 and Asp-347.

Using well-known techniques to align amino acids, amino acid residues suitable for mutation as described herein for mSir2α or ySir2 proteins can be determined for other Sir2 (e.g., Sir2β, Sir2γ) or Sir2-like (e.g., HST1, HST2) proteins. Nucleic acid sequences encoding the Sir2 proteins can be mutated; the mutated nucleic acid constructs expressed under standard experimental conditions well known to the skilled artisan; and the resulting mutant proteins evaluated for NAD-dependent deacetylation of histone proteins and/or mono-ADP-ribosyltransferase activity, the ability to slow aging, or extend life span as described herein.

It is also envisioned that fragments of the Sir2 proteins can be used in the methods of the invention. "Fragments" of Sir2 proteins, as used herein, refer to any part of the Sir2 protein capable of altering the NAD-dependent acetylation status of at least one amino acid residue of a histone protein (e.g., lysine 9 and/or 14 of H3, lysine 16 of H4) and/or mono-ADP-ribosylating a substrate (e.g., p53, H2B, H3, or H4). For example, the core domain of the Sir2 protein is considered a fragment of Sir2.

A Sir2 protein can be in the form of a conjugate or a fusion protein which can be manufactured by known methods. Fusion proteins can be manufactured according to known methods of recombinant DNA technology. For example, fusion proteins can be expressed from a nucleic acid molecule comprising sequences which code for a biologically active portion of the Sir2 protein and a fusion partner, for example, a portion of an immunoglobulin or a peptide linker. A nucleic acid construct encoding a Sir2 fusion protein can be introduced into a host cell, expressed, isolated or purified from a cell by means of an affinity matrix employing antibodies to Sir2 or the fusion partner (e.g., IgG).

Antibodies can be raised to the Sir2 protein, Sir2-like protein, analogs, and portions thereof, using techniques known to those of skill in the art. (See, for example, Kohler et al., *Nature* 256:495-497 (1975); Cole et al., "Monoclonal Antibodies and Cancer Therapy", Alan R. Liss, Inc., pp. 77-96 (1985); Ausubel et al., "Current Protocols in Molecular Biology", John Wiley & Sons, Inc. (1999)). A mammal, such as a murine, rat, hamster or rabbit, can be immunized with an immunogenic form of the protein (e.g., mSir2α, mSirβ, or a peptide comprising an antigenic fragment of the protein which is capable of eliciting an antibody response). Techniques for conferring immunogenicity on a protein or peptide include conjugation to carriers, such as BSA or keyhole limpet hemocyanin, or other techniques, such as the use of Freud's adjuvant or Titermax™, well known in the art. The progress of immunization can be monitored by detection of antibody titers in plasma or serum. Standard ELISA, RIA or Western blots can be used with the Sir2 protein to assess the levels of antibody.

In a preferred embodiment, the antibody, or antigen-binding fragment, selectively binds murine Sir2 proteins, such as mSir2α and mSir2β. An "antigen-binding fragment" of an antibody refers to an antibody which binds to any part of the Sir2 protein.

The antibodies of the invention can be human and nonhuman antibodies. The antibodies can be polyclonal, monoclonal, chimeric (e.g., human chimeric antibodies), or fragments thereof. These antibodies can be used to purify or identify the Sir2 protein contained in a mixture of proteins, using techniques well known to those of skill in the art. These antibodies, or antigen-binding fragments thereof, can be used to detect the presence or absence of the Sir2 protein using standard immunochemistry, Western blot methods, ELISA, or RIA. For example, and ELISA and RIA assays can be used to quantitate the amount of Sir2 in a cellular or nuclear extract.

As used herein, an "isolated" nucleic acid molecule (e.g., gene, nucleotide sequence, nucleic acid sequence), when referring to an Sir2 protein encoded by a nucleic acid sequence, is a nucleic acid molecule which is not flanked by nucleic acid molecules which normally (e.g., naturally occurring) flank the gene or nucleotide sequence (e.g., as in genomic sequences) and/or has been completely or partially purified from other transcribed sequences (e.g., as in a cDNA library). Thus, an isolated nucleic acid molecule, gene or nucleotide sequence can include a nucleic acid molecule, gene or nucleotide sequence which is synthesized chemically or by recombinant means. Nucleic acid molecules contained in a vector are included in the definition of "isolated" as used herein. Also, isolated nucleic acid molecules include recombinant nucleic acid molecules and heterologous host cells, as well as partially or substantially or purified nucleic acid molecules in solution. In vivo and in vitro RNA transcripts of the invention are also encompassed by "isolated" nucleic acid molecules. Such isolated nucleic acid molecules are useful for introduction into host cells, the manufacture of the encoded Sir2 protein, as probes for isolating homologues sequences (e.g., from other mammalian species or other organisms), for gene mapping (e.g., by in situ hybridization), or for detecting the presence (e.g., by Southern blot analysis) or expression (e.g., by Northern blot analysis, RNase protection assays) of related SIR2 genes in cells or tissue.

The present invention also encompasses isolated nucleic acid sequences encoding the Sir2 proteins described herein, and fragments of nucleic acid sequences encoding biologically active Sir2 proteins. Fragments of the nucleic acid sequences, described herein, as useful as probes to detect the presence of SIR2. Specifically provided for in the present invention are DNA/RNA (also referred to herein as nucleic acid) sequences encoding mSir2α and mSir2β proteins, the fully complementary strands of these sequences, and allelic variations thereof. Also encompassed by the present invention are nucleic acid sequences, genomic DNA, cDNA, RNA or a combination thereof, which are substantially complementary to the nucleic acid sequences (e.g., DNA, RNA) encoding Sir2 (e.g., mSir2α, mSir2β), and which specifically hybridize with the SIR2 nucleic acid sequences under conditions of stringency known to those of skill in the art, those conditions being sufficient to identify nucleic acid sequences with substantial nucleic acid identity. As defined herein, substantially complementary means that the sequence need not reflect the exact sequence of the SIR2 nucleic acid, but must be sufficiently similar in identity of sequence to hybridize with SIR2 nucleic acid under stringent conditions. Conditions of stringency are described, for example, in Ausubel, et al., "Current Protocols in Molecular Biology", John Wiley & Sons, Inc. (1999). Non-complementary bases can be interspersed in the sequence, or the sequences can be longer or shorter than SIR2 nucleic acid, provided that the sequence has a sufficient number of bases complementary to SIR2 to hybridize therewith.

The SIR2 nucleic sequence, or a fragment thereof, can be used as a probe to isolate additional SIR2 homologs. For example, a cDNA or genomic DNA library from the appropriate organism can be screened with labeled SIR2 nucleic acid probes (e.g., DNA or RNA) to identify homologous genes, as described, for example, in Ausubel, F. M., et al., "Current Protocols in Molecular Biology", John Wiley & Sons, (1999).

Typically the nucleic acid probe comprises a nucleic acid sequence of sufficient length and complementary to specifically hybridize to nucleic acid sequences which encode mSir2α (SEQ ID NO: 25), mSir2β, mSir2γ, ySir2 or human Sir2. The requirements of sufficient length and complementarity can be easily determined by one of skill in the art.

Uses of nucleic acids encoding cloned Sir2 proteins or fragments include one or more the following: (1) producing proteins which can be used, for example, for structure determination, to further assess Sir2 NAD-dependent deacetylation activity and/or mono-ADP-ribosyltransferase activity, or to obtain antibodies binding to the Sir2 protein; (2) to determine the nucleotide sequence encoding a Sir2-like protein which can be used, for example, as a basis for comparison with other proteins to determine conserved regions, determine unique nucleotide sequences for normal and altered proteins, and to determine nucleotide sequences to be used as target sites for antisense nucleic acids, ribozymes, hybridization detection probes, or PCR amplification primers; (3) as hybridization detection probes to detect the presence of a native protein and/or a related protein in a sample; and (4) as PCR primers to generate particular nucleic acid sequence regions, for example, to generate regions to be probed by hybridization detection probes.

The Sir2 proteins and/or nucleic acid sequences include fragments thereof, (e.g., core domains of Sir2 proteins). Preferably, the nucleic acid contains at least 14, at least 20, at least 27, and at least 45, contiguous nucleic acids of a sequence provided in SEQ ID NO.: 25. Advantages of longer-length nucleic acid include producing longer-length protein fragments having the sequence of a Sir2 protein which can be used, for example, to produce antibodies; increased nucleic acid probe specificity under high stringent hybridization assay conditions; and more specificity for related the SIR2 nucleic acid under lower stringency hybridization assay conditions.

Another aspect of the present invention features a purified nucleic acid encoding a Sir2 protein or fragment thereof. Specifically, mSIR2α (SEQ ID NO: 25), mSIR2γ and/or mSIR2β. Due to the degeneracy of the genetic code, different combinations of nucleotides can code for the same protein. Thus, numerous protein fragments having the same amino acid sequences can be encoded for by difference nucleic acid sequences. In preferred embodiments, the nucleic acid encodes at least 12, at least 18, or at least 54 contiguous amino acids of SEQ ID NO.: 25.

Another aspect of the present invention features a purified nucleic acid having a nucleic acid sequence region of at least 12 contiguous nucleotides substantially complementary to a sequence region in SEQ ID NO.: 25. By "substantially complementary" is meant that the purified nucleic acid can hybridize to the complementary sequence region in nucleic acid sequences of SEQ ID NO.: 25, under stringent hybridizing conditions. Such nucleic acid sequences are particularly useful as hybridization conditions, only highly complementary nucleic acid sequences hybridize. Preferably, such conditions prevent hybridization of nucleic acids having 4 mismatches out of 20 contiguous nucleotides, more preferably 2 mismatches out of 20 contiguous nucleotides, most preferably one mismatch out of 20 contiguous nucleotides. In preferred embodiments, the nucleic acid is substantially complementary to at least 20, at least 27, or at least 45 contiguous nucleotides provided in SEQ ID NO.: 25.

Another aspect of the present invention features a purified protein having at least about 5-20 contiguous amino acids of an amino acid sequence provided in SEQ ID NOS.: 1, 2, 3, 4, 5, 9, 10, 11, 12, 13, 14, 15, 16, 17, 18, 19, 20, 21, 22, 23, 24, 26, 27 or 28. By "purified" in reference to a protein is meant that the protein is in a form (e.g., its association with other molecules) distinct from naturally occurring protein. Preferably, the protein is provided as substantially purified preparation representing at least 75%, more preferably 85%, most preferably 95% or the total protein in the preparation. In preferred embodiments, the purified protein has at least 5 contiguous amino acids of SEQ ID NO.: 27 or 28.

Preferred protein fragments include those having functional Sir2 activity (e.g., alter the NAD-dependent acetylation status of histone proteins such as H3 or H4; mono-ADP-ribosylate nuclear proteins such as p53, H2B, H3 or H4), or epitope for antibody recognition. Such protein fragments have various uses such as being used to obtain antibodies to a particular region and being used to form chimeric proteins with fragments of other proteins create a new protein having unique properties, such as a longer half-life.

Nucleic acid molecules can be inserted into a construct which can, optionally, replicate and/or integrate into a recombinant host cell, by known methods. The host cell can be a eukaryote or prokaryote and includes, for example, yeast (such as *Pichia pastorius* or *Saccharomyces cerevisiae*) bacteria (such as *Escherichia coli* or *Bacillus subtilis*), animal cells or tissue, insect Sf9 cells (such as baculoviruses infected SF9 cells), worms (e.g., *C. elegans*) or a mammalian cells (somatic or embryonic cells, Chinese hamster ovary cells, HeLa cells, human 293 cells, monkey COS-7 cells and mouse NIH 3T3 cells).

The invention also provides vectors or plasmids containing one or more of each of the SIR2 genes. Suitable vectors for use in eukaryotic and prokaryotic cells are known in the art and are commercially available or readily prepared by a skilled artisan. Additional vectors can also be found, for example, in Ausubel, F. M., et al., "Current Protocols in Molecular Biology", John Wiley & Sons, Inc. (1999) and Sambrook et al., "Molecular Cloning: A Laboratory Manual," 2nd Ed. (1989), the teachings of which are incorporated herein by reference in their entirety.

Another aspect of the present invention features a recombinant host cell comprising an isolated nucleic acid molecule of a SIR2 gene operably linked to a regulatory sequence. "Operably linked" is intended to mean that the nucleotide sequence(s) is linked to a regulatory sequence in a manner which allows expression of the nucleic acid sequence(s). The recombinant host cell is made up of an isolated nucleic acid sequence encoding at least about 5-20 contiguous amino acids provided in SEQ ID NO.: 1, 2, 3, 4, 5, 9, 10, 11, 12, 13, 14, 15, 16, 17, 18, 19, 20, 21, 22, 23, 24, 26, 27 or 28 and a cell able to express the nucleic acid. Cells containing a functioning Sir2 protein can be used, for example, to screen to agonists or antagonists of Sir2 activity.

The nucleic acid molecule can be incorporated or inserted into the host cell by known methods. Examples of suitable methods of transfecting or transforming cells include calcium phosphate precipitation, electroporation, microinjection, infection, lipofection and direct uptake. "Transformation" or "transfection" as used herein refers to the acquisition of new or altered genetic features by incorporation of additional nucleic acids, e.g., DNA. "Expression" of the genetic information of a host cell is a term of art which refers to the directed transcription of DNA to generate RNA which is translated into a protein. Methods for preparing such recombinant host cells and incorporating nucleic acids are described in more detail in Sambrook et al., "Molecular Cloning: A Laboratory Manual," 2nd Ed. (1989) and Ausubel, et al. "Current Protocols in Molecular Biology," (1999), for example. The host cell is then maintained under suitable conditions for expression of Sir2. Generally, the cells are maintained in a suitable buffer and/or growth medium or nutrient source for growth of the cells and expression of the gene product(s). The growth media are not critical to the invention, are generally known in the art and include sources of carbon, nitrogen and sulfur. Examples include Luria broth, Superbroth, Dulbecco's Modified Eagles Media (DMEM), RPMI-1640, M199 and Grace's insect media. The growth Media may contain a buffer, the selection of which is not critical to the invention. The pH of the buffered Media can be selected and is generally one tolerated by or optimal for growth for the host cell.

The mSIR2α gene can be expressed in mammalian or insect cells, any mammalian or insect expression plasmid or viral vector driven by native mSIR2α promoter can be used, any of other mammalian or insect promoters and enhances, any of viral promoters, or any of artificial inducible promoters can be used. The host cells can be cells of murine, human, or any of other organisms including insects cultured in conventional or specialized in vitro culture conditions. The cells transfected with a mSIR2 expression plasmid or infected by the virus containing a mSIR2α expression vector.

The host cell is maintained under a suitable temperature and atmosphere. Alternatively, the host cell is aerobic and the host cell is maintained under atmospheric conditions or other suitable conditions for growth. The temperature should also be selected so that the host cell tolerates the process and can be, for example, between about 13°-40° C.

The invention also relates to a method of preparing a Sir2 protein using the recombinant host cells described above. The recombinant host cells are biological factories to produce proteins encoded for by the isolated nucleic acid molecule of SIR2.

The chromosomes of higher eukaryotes are compartmentalized into two cytogenetically distinct regions, euchromatin and heterochromatin. Heterochromatin was initially described as chromosomal regions that failed to decondense after mitosis (Heitz, E. *Jb. Wiss. Bot.* 69:728 (1928)) Subsequent studies have revealed that heterochromatin is formed on highly repetitive DNA, such as centromeres and telomeres, replicates late in the cell cycle and is transcriptionally inactive (Hennig, W. *Heterochromatin. Chromosoma* 108:1-9 (1999)). Although many questions about the functional and structural properties of heterochromatin are unresolved, progress in understanding its molecular nature has been made in studies of yeast (Karpen, G., et al., *Trends Genet* 13: 489-496 (1997)); (Grunstein, M. *Cell* 93, 325-328 (1998)) and *Drosophila* (Wakimoto, B. T., *Cell* 93: 321-324 (1998)). In *Drosophila*, genes juxtaposed to centromeric heterochromatin through chromosomal rearrangement or transposition become inactivated. The phenomenon, known as position effect variegation (PEV) (Muller, H. J., *J. Genet* 22: 299-335 (1930)), results from the spreading of heterochromatin across the rearrangement breakpoint. Genetic screens have identified large numbers of PEV modifiers some of which have been cloned and characterized (Reuter, G., et al., *BioEssays* 14: 605-612 (1992); (Weiler, K. S., et al., *Annu. Rev. Genet.* 29: 577-605 (1995); (Wallrath, L. L., *Curr. Opin. Genet. Dev.* 8: 147-153 (1998)). Heterochromatin protein 1 (HP1) are one of the best-characterized heterochromatin components and known to localize at centromeres and telomeres (James, T. C., et al., *Mol. Cell. Biol.* 6: 3862-3872 (1986); (James, T. C., et al., *Eur. J. Cell Biol.* 50: 170-180 (1989); (Fanti, L., et al., *Mol. Cell* 2: 527-538 (1998)). HP1-related proteins have been identified from a wide variety of organisms including mammals, and a region termed the chromodomain is highly conserved in HP1 family members (Singh, P. B., et al., *Nucleic Acids Res.* 19: 789-794 (1991)). The chromodomain is also shared by a related set of chromatin factors, the Polycomb group (Pc-G) (Pirrotta, V., *Cell* 93: 333-336 (1998)). Pc-G is required to maintain the repressed state of homeotic genes through many cell divisions in the developmental stages of *Drosophila* (Orlando, V., et al., *Cell* 75: 1187 (1993)).

Transcriptional silencing in budding yeast is associated with genomic domains of structurally altered chromatin akin to heterochromatin in higher cells (Sherman, J. M., et al., *Trends Genet.* 13: 308-313 (1997)).

The principle genes required for silencing SIR2, SIR3, and SIR4 encode members of a complex that is targeted to the specific chromosomal domains that are silenced (Ivy, J. M., et al., *Mol. Cell. Biol.* 6: 688-702 (1986); (Gotta, M., et al., *J. Cell Biol.* 134: 1349-1363 (1996); (Rine, J., et al., *Genetics* 116: 9-22 (1987); (Aparicio, O. M., et al., *Cell* 66: 1279-1287 (1991)). For example, silencing at the extra copies of α and a mating type genes at HMLα and HMRa is mediated by the binding of these three Sir proteins, plus a fourth, Sir1p, to a set of DNA binding factors including Rap1p, ORC, and Abf1p (Triolo, T., et al., *Nature* 381: 251-253 (1996)).

In contrast, at telomeres Sirs 2p, 3p, and 4p bind to tandem Rap1p molecules arrayed at the telomeric repeat tract (Hardy, C. F. J., et al., *Genes Dev.* 6: 801 (1992); (Moretti, P., et al., *Genes Dev.* 8: 2257 (1994)). Finally, at the rDNA, Sir2p, but not the other Sir proteins, is bound to a specific region in the rDNA spacer in a complex termed RENT which includes another protein, Net1p (Shou, W., et al., *Cell* 97: 233-244 (1999)).

The function of SIR-mediated silencing at HM loci is to prevent the expression of both a and α mating types, which would lead to non-mating, pseudo-diploid strains. The role of the Sir complex at telomeres is less apparent. Interestingly, the telomeric Sir complex, along with the Ku protein, moves to sites of double strand DNA breaks to aid their repair by the non-homologous end joining pathway, suggesting that telomeric Sir complex exists as a poised DNA repairosome (Mills, K. D., et al., *Cell* 97: 609-620 (1999); (Martin, S. G., et al., *Cell* 97: 621-633 (1999)).

Sir2p in the rDNA silences marker genes inserted there (Bryk, M., et al., *Genes Dev.* 11: 255-269 (1997); (Smith, J. S., et al., *Genes Dev.* 11: 241-254 (1997)) and, plays an important role in repressing recombination within the 100-200 tandemly repeated copies of the rDNA sequences in chromosome XII (Gottlieb, S., et al., *Cell* 56: 771-776 (1989)).

Replicative life span in yeast mother cells (the number of times a mother cell divides to give daughters) is limited, at least in part, by the accumulation of extrachromosomal rDNA circles (ERCs) in nuclei of aging mothers (Sinclair, D. A., et al., *Science* 277: 1313-1316 (1997)). These accumulated ERCs result from the excision of circles from the chromosomal rDNA array by homologous recombination (Park, P. U., et al., *Mol. Cell. Biol.* 19: 3848-3856 (1999)), the subsequent replication of ERCs in future cell divisions, and the preferential segregation of ERCs to mother cells.

SIR2, SIR3, and SIR4 play a key role in determining the life span of yeast mother cells (Kennedy, B. K., et al., *Cell* 89: 381-391 (1997); (Kaeberlein, M., et al., *Genes Dev.* 13: 2570-2580 (1999)). Deleting SIR3 or SIR4 shortens the life span by about 25%, and deleting SIR2 shortens the life span by about 50%. The shortening in the sir3 and sir4 mutants is due to the simultaneous expression of a and α mating type information, which somehow causes an increase in recombination in the rDNA leading most likely to an earlier accumulation of a lethal number of ERCs (Kaeberlein, M., et al., *Genes Dev.* 13: 2570-2580 (1999)).

The shortening in sir2 mutants is due to the absence of Sir2p in the rDNA leading to the elevated rate of recombination at that locus and the rapid generation of ERCs. The short life span of sir2 mutants is suppressed by deletions of FOB1 (Kaeberlein, M., et al., *Genes Dev.* 13: 2570-2580 (1999)), which encodes a protein that creates a unidirectional barrier to DNA replication in the rDNA (Kobayashi, T., et al., *Genes Cells* 1: 465-474 (1996)). Evidently this barrier is a signal that provokes recombination in the rDNA and the generation of ERCs (Defossez, P. A., et al., *Mol. Cell* 3: 447-455 (1999)), and the role of Sir2p is to counteract this hyperrecombination. In the absence of Fob1p (and the replication barrier) Sir2p is no longer needed to prevent the formation of ERCs. The addition of a second copy of SIR2 to cells extends the replicative life span of mothers well beyond that of the wild type, indicating that Sir2p is the limiting factor for life span (Kaeberlein, M., et al., *Genes Dev.* 13: 2570-2580 (1999)).

Since chromatin at HML and HMR is hypoacetylated (Braunstein, M., et al., *Mol. Cell. Biol.* 16: 4349-4356 (1996); (Braunstein, M., et al., *Genes Dev* 7: 592-604 (1993)), Sir2p was hypothesized to be a histone deacetylase. However, it is also possible that hypoacetylation of chromatin results from some other effect, such as the exclusion of acetylases by the inaccessible structure of these chromosomal regions or the recruitment of other deacetylases.

More recent studies identified SIR2 orthologs in yeast and homologs in many species, including bacteria, which all share a core homology of about 270 amino acids. The four *S. cerevisiae* orthologs HST1-4 do not play any role in yeast silencing, with the exception that high level expression of HST1 can partially compensate for the absence of SIR2 (Brachmann, C. B., et al., *Genes Dev.* 9: 2888-2902 (1995)). The bacterial homolog, cobB, can apparently function in cells in a biosynthetic step that transfers phosphoribose from nicotinate mononucleotide to dimethyl benzimidazole (Tsang, A. W., et al., *J. Biol. Chem.* 273: 31788-31794 (1998)). The present invention, documents that yeast Sir2p and its mouse homologue mSir2α are mono-ADP-ribosyltransferases and NAD hydrolases with specifically acetylated histone substrates. Amino acid changes in mSir2α that disrupt this enzymatic activity also reduce function in vivo. The modification of the acetylation status of N-terminal tails of histones by Sir2 can trigger genomic silencing in yeast and heterochromatin formation more generally in eukaryotic organisms.

As described herein, yeast Sir2p and its mouse Sir2α homologue possess ADP-ribosyltransferase and NAD hydrolase. These activities are stimulated by N-terminal peptides of histones H3 and H4. In particular, acetylated lysines of histone proteins Lys9Ac and Lys14Ac of H3 and Lys16 of the H4. Transfer to histone H2B is also observed. Studies using enzyme inhibitors and snake venom phosphodiesterase show that Sir2p and mSir2α are mono-ADP ribosyltransferases.

Sir2 Proteins are Novel Nuclear Mono-ADP-Ribosyltransferases with Histone Substrates Yeast and mouse Sir2 proteins are shown herein to be mono-ADP-ribosyltransferases by several criteria. First, the proteins transfer $^{32}$P-labeled ADP-ribose from NAD to histones H2B and H3. The endogenous mSir2α protein immunoprecipitated from NIH3T3 cell extracts shows the same activity. Second, this modification can be removed by snake venom phosphodiesterase, which digests the phosphodiester bond in the ADP-ribose moiety. Third, the reactions are sensitive to mono-ADP-ribosylation inhibitors, but not to poly (ADP-ribose)polymerase (PARP) inhibitors. ySir2p and mSir2α provide the first examples of nuclear mono-ADP-ribosyltransferases in yeast and mammals.

In the mammalian nucleus, PARPs are likely involved in DNA repair (Menissier-de Murcia, J., et al., *Proc. Natl. Acad. Sci. USA* 94: 7303-7307 (1997); (Wang, Z. Q., et al., *Genes Dev.* 11: 2347-2358 (1997)), replication (Yoshida, S., et al., *Mol. Cell. Biochem.* 138: 39-44 (1994)), transcription (Oliver, F. J., et al., *Embo J.* 18: 4446-4454 (1999)), apoptosis (Germain, M., et al., *J. Biol. Chem.* 274: 28379-28384 (1999)) and telomere maintenance (Di Fagagna, F. D. A., et al., *Nat. Genet.* 23: 76-80 (1999)). On the other hand, it has been reported that alkylating agents induce mono-ADP-ribosylation of histones H1, H2B, and H3 (Kreimeyer, A., et al., *J. Biol. Chem.* 259: 890-896 (1984); (Adamietz, P., et al., *J. Biol. Chem.* 259:6841-6846 (1984)). Interestingly, many viral, bacterial, and eukaryotic enzymes such as diphtheria, pertussis, and cholera toxins (DT, PT, and CT, respectively) and vertebrate arginine-specific mono-ADP-ribosyltransferases catalyze similar reactions (Domenighini, M., et al., *Mol. Microbiol* 21: 667-674 (1996)).

These ADP-ribosyltransferases share structural motifs in their catalytic domains and can be classified into two groups: the DT group and the CT group (Domenighini, M., et al., *Mol. Microbiol* 21: 667-674 (1996); (Moss, J., et al., *Mol. Cell Biochem.* 193: 109-113 (1999)). The DT group includes diphtheria toxin and the family of PARPs, while the CT group includes CT, PT, and other eukaryotic mono-ADP-ribosyltransferases. ySir2p and mSir2α share at least one motif of the CT group (see FIG. 2C), hydrophobic-Ser-Thr-Ser-hydrophobic (VSTSL, SEQ ID NO: 30, in ySir2p and VSVSC, SEQ ID NO: 31, in mSir2α), which forms the NAD-binding cleft. The mutation of the first serine, which is known to be important for positioning NAD, abolishes the mono-ADP-ribosylation activity of the mSir2α (see FIG. 6C).

The mutagenesis of highly conserved residues in the mSir2α core domain revealed that mutations in 10 of 10 residues affected the mono-ADP-ribosylation activity. In mouse cells, 9 of these 10 mutants were inactive in a transient assay for repression of a reporter, suggesting that the enzymatic activity is critical in vivo. The mutant, P285A, could misfold in *E. coli* and thus be inactive. Genetic analysis of the core of yeast Sir2p indicates that the four conserved cysteines at positions 372, 374, 396, and 398 are crucial for silencing in vivo. Further, chimeras in which a human Sir2 core domain is substituted for the yeast domain can function in silencing at HM loci, but not at telomeres or rDNA.

Specific Acetylation of H3 and H4 Tails Stimulates Sir2 Activities

A striking feature of the specificity of ADP-ribosylation of H3 was revealed by the use of N-terminal peptides (residues 1-20). Sir2 modified the H3 N-terminal tail peptide when Lys9 and Lys14 were acetylated but not when the peptide was unacetylated. These lysines are acetylated and important for silencing in vivo (Thompson, J. S., et al., *Nature* 369: 245-247 (1994)). In addition, a large fraction of the NAD was hydrolyzed specifically in the presence of the diacetylated peptide and either yeast or mouse Sir2. This latter activity can reflect inefficient transfer of ADP-ribose to the peptide substrate or can present another yet unknown activity of Sir2 proteins in the modification of histones. These data show that the N-terminal tail of H3 is a biologically relevant target of Sir2 proteins in vivo.

An H4 peptide (residues 1-20) acetylated on Lys16 stimulated both ADP-ribosyltransferase and NAD hydrolase activities of Sir2, but H4 peptides acetylated on Lys5, Lys8, or Lys12 did, at best, very weakly. A tetra-acetylated H4 peptide (aceylated Lys5, 8, 12 and 16) was also a poor substrate. Lys16 is a highly acetylated residue in mammalian chromatin. In constitutive heterochromatin, H4 is hypoacetylated at all four lysines, but in facultative heterochromatin Lys5, 8, and 12 are hypoacetylated, while Lys16 is not. Thus, these data illustrate the role of Sir2 in regulating the state of facultative heterochromatin, consistent with the observed intracellular localization of the protein. In yeast mutations of Lys16 to an uncharged residue, glutamine, reduce silencing, and mutation to arginine, even though positive charge is retained, also reduces silencing. Mutations in Lys5, 8, or 12 to arginine, in contrast, exert smaller effects on silencing. These findings are consistent with the idea that the acetylated Lys16 residue of H4 is critical for recognition by Sir2.

Figure 7:
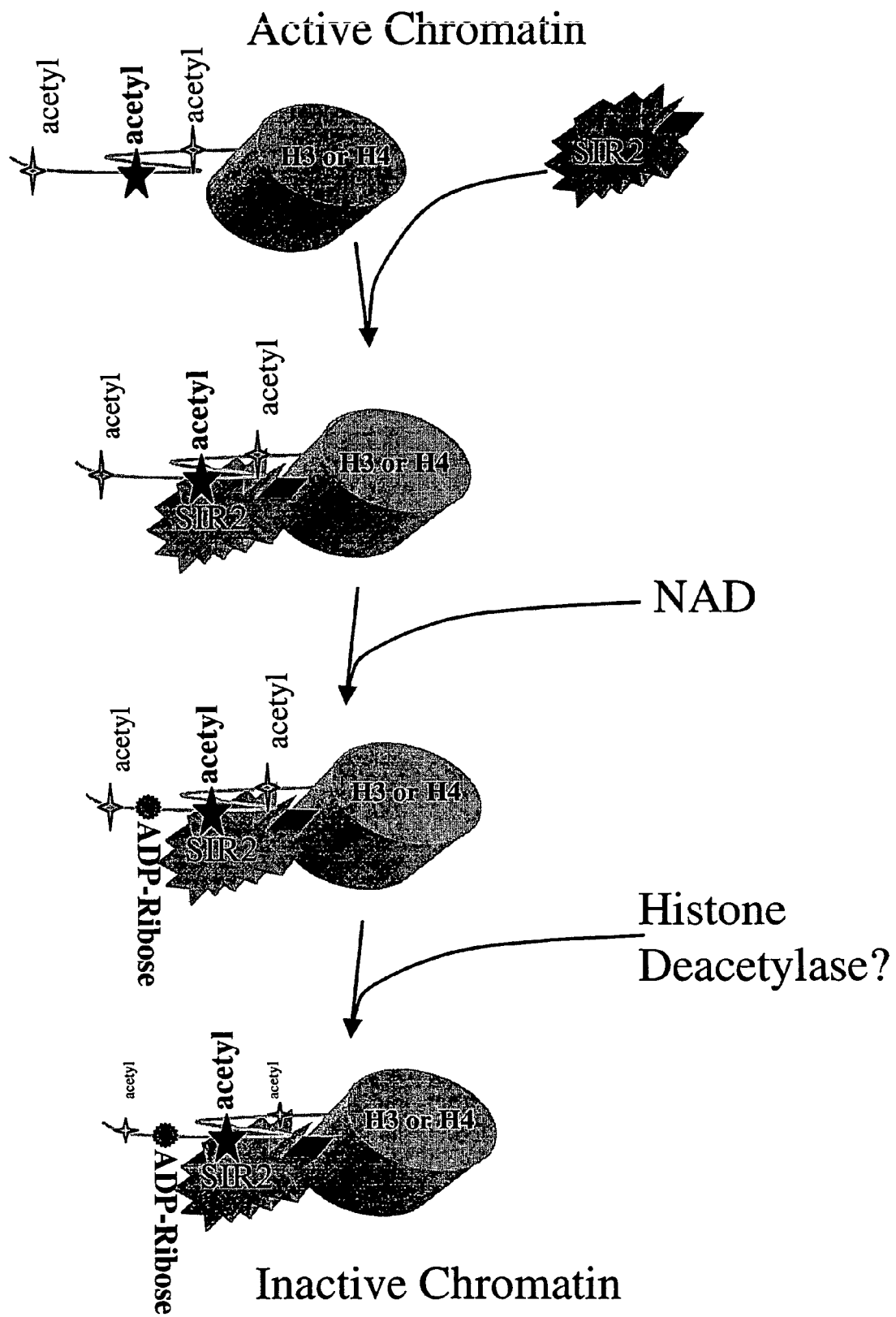
FIG. 7 is a diagrammatic representation of a model of Sir2-mediated modification of histone proteins H3 and H4.

ADP-ribosylation of histone N-terminal tails can lead to heterochromatin and gene silencing by interacting with histone residues that are constitutively acetylated, like Lys16 of mammalian 1-14, thereby inducing ADP-ribosylation by Sir2 proteins in one or more adjacent residues in the N-terminal tail (FIG. 7). In active chromatin, the lysines in the N-terminal tails of H3 and H4 are acetylated (depicted by stars at top). Sir2 recognizes H3 and H4 tails containing specifically acetylated lysines (indicated by a large star). Sir2 ADP-ribosylates these N-terminal tails, causing the formation of heterochromatin, perhaps by the recruitment of histone deacetylases.

The ADP-ribosylation in turn facilitates silencing, for example, by restricting access of histone acetylases or by recruiting deacetylases, leading to the hypoacetylated state of other lysine residues in the tail and thus a tighter chromatin structure. ADP-ribosylation and deacetylation are targeted to specific regions of the genome by the selective recruitment of Sir2. In yeast, Sir3p and Sir4p facilitating targeting of Sir2p to telomeres and HM loci, and Net1p and perhaps other components of the RENT complex recruit Sir2p to the rDNA. Consistent with this model, overexpression of Sir2 induces a more global hypoacetylation of histones H2B, H3 and H4 in yeast.

The model depicted in FIG. 7 is consistent with the silencing phenotypes of several yeast mutants. Rpd3p is a histone deacetylase. Rpd3 mutants show hyperacetylation of histones and generally an increase in transcription of genes assayed. An exception to this rule, however, occurs in the case of silenced chromatin at yeast telomeres and rDNA, where silencing actually increases in the mutant. The increase in silencing can occur as a result of hyperacetylation of the lysines in the N-terminal tail that are recognized by Sir2. NAT1/ARD1 encode subunits of an N-terminal acetyltransferase. Mutations in either gene abolish silencing in yeast. It is possible that the nat1 or ard1 mutants have underacetylation of histone residues that potentiate Sir2 activity. Additionally, or alternatively, the effects of these mutants can be indirect.

Mammalian Sir2 Proteins

SIR2 homologs have been found in a variety of organisms. Human SIR2 homologs that all correspond to the same gene, mSIR2β, which is most related to yeast HST2 have been reported (Afshar, et al., *Gene* 234:161-168 (1999); Frye, *Biochem. Biophys. Res. Commun.* 260:273-279 (1999); Sherman, et al., *Mol. Biol. Cell* 10:3045-3059 (1999)). In contrast, the human SIR2 gene appears to correspond to a fragment of a homolog of mSIR2α. Of all mammalian SIR2 homologs analyzed to date, mSIR2α shows the greatest homology to ySir2p in the evolutionarily conserved core domain. Nonetheless, there are some significant differences between ySir2p and mSir2α. mSir2α has a diverged N-terminal portion and a longer C-terminal tail and is almost twice the size of ySir2p. It is possible that these mSir2α-specific regions may be involved in species-specific or cell type-specific protein-protein interactions.

In yeast, the Sir complex moves to sites of DNA double strand breaks. Since ADP-ribosylation has been associated with sites of DNA repair in mammalian cells, it is likely that mammalian Sir2 proteins are recruited to DNA damage. Mono-ADP-ribosylation of histones near sites of DNA damage in yeast and mammals likely have an important biological role.

Link Between Energy Metabolism, Heterochromatin and Aging

The substrate for Sir2 modification of chromatin, NAD, may be an indicator of the energy status of cells. Cells grown under energy limitation may have a high NAD/NADH ratio, while cells growing under energy surplus would have a low ratio. Since NAD but not NADH is expected to function as a substrate in the mono-ADP-ribosylation reaction, Sir2 activity can be highest under conditions of energy limitation. Thus, the rate of energy metabolism may control gene expression of certain chromosomal domains by regulating the activity of Sir2.

Recent studies indicate that Sir2p is a limiting component in the determination of the life span of yeast mother cells for example, overexpression of Sir2p extends the life span beyond wild type. Caloric or dietary restriction is associated with an extension of life span in rodents, C. elegans, and even yeast. Caloric restriction may exert of its effect, in part, by creating a condition of energy limitation, which would activate Sir2 and promote ADP-ribosylation of chromatin and gene silencing. ADP-ribosylation is a biochemical event which has been suggested to play a role in aging. Alterations in the maintenance of Sir2-silenced chromatin could result in normal mammalian aging and by slowing caloric restriction. The fact that Sir2 proteins are simple enzymes suggests a strategy for intervening in non genetic ways to influence life span. Small molecules that are agonists for this enzyme can extend life span in yeast cells and in mammals.

The present invention shows that yeast Sir2p and its mouse homolog mSir2α are ADP-ribosyltransferases and NAD hydrolases with specific histone substrates, the N-terminal tails of H3 and H4. Both activities are stimulated by acetylation in the histone tails, in particular Lys9Ac and Lys14Ac for H3, and Lys16Ac for H4. Acetylation of these lysine residues is important for silencing of chromatin in vivo. Mutations in the conserved sequences of mSir2α reduce ADP-ribosyltransferase activity in vitro and chromatin of the silencing activity in mouse NIH3T3 cells. The mSir2α protein is localized in the nuclei of mouse cells shown that acetylation-terminal tails of H3 and H4 trigger ADP-ribosyltransferase and NAD hydrolase activities of Sir2 proteins. The ADP-ribosylation and acetylation of histones proteins can be important in the formation of heterchromatin in eukaryotic cells.

The present invention shows that Sir2 proteins are novel NAD-dependent deacetylases specific for the N-terminal tail of histone H3. Although NAD and NADH are frequent enzyme cofactors in oxidation/reduction reactions, this is the first time NAD has been shown to drive a distinct enzymatic reaction in a substrate, such as a peptide of the amino-terminal tail of histone H3 di-acetylated at lysines 9 and 14.

Since histones in silenced chromatin are hypoacetylated, and because overexpressed Sir2p promotes global deacetylation of histones in yeast (Braunstein, M., et al., *Genes Dev* 7: 592-604 (1993); (Braunstein, M., et al., *Mol. Cell. Biol.* 16: 4349-4356 (1996)), it was originally proposed that Sir2p might be a histone deacetylase. However, such an activity could not be demonstrated until now, presumably because of its absolute requirement for NAD. The present invention is consistent with studies that show mutating lysines in the tails of histones H3 and H4 can reduce silencing in vivo (Thompson, J. S., et al., *Nature* 369: 245-247 (1994); (Braunstein, M., et al., *Mol. Cell. Biol.* 16: 4349-4356 (1996)) and suggest that this NAD-dependent deacetylation of histones per se is sufficient to establish silencing in vivo. These data show that SIR2 mutations reduce or eliminate deacetylase activity show corresponding defects in silencing, suppression of recombination, and life span in vivo. The nature of the requirement of NAD for deacetylation is not yet clear, but at the concentrations of about one hundred μM, NAD may serve as an allosteric effector to activate the histone deacetylase activity of Sir2. The failure of NADH, NADP, or NADPH to function as such reveals a remarkable specificity of Sir2p for the oxidized form of NAD. Sir2 proteins catalyze the putative transfer of ADP-ribose from NAD to the proteins such as intact histone H3 or the amino-terminal peptide and labeled NAD, to allow the detection of low levels of $^{32}$P transfer. However, in reactions allowing a direct comparison between ADP-ribosylation and deacetylation (using the H3 peptide at 1 mM NAD), the reaction products displayed at least 27% conversion of the peptide to deacetylated species, and no detectable conversion to any ADP-ribosylated species. Thus, ADP ribosyltransferase reaction proceeds to a much lesser degree than deacetylation, at least with this H3 peptide substrate.

Coumermycin A1 is an inhibitor of mono-ADP-ribosyltransferases (Banasik, M., et al., *Mol. Cell. Biochem.* 138: 185-187 (1994)) and was shown to inhibit the putative ADP-ribose transferase activity as well as the accompanying NAD hydrolysis. However, coumermycin A1 did not inhibit the Sir2p deacetylase activity at all. These findings indicate that the putative ADP-ribosyltransferase activity is separable and may play a distinct role in vivo. The ADP-ribosylation of histones is known to occur when cells are treated with DNA damaging agents (Adamietz, P., et al., *J. Biol. Chem.* 259: 6841-6846 (1984); (Kreimeyer, A., et al., *J. Biol. Chem.* 259: 890-896 (1984); (Pero, R. W., et al., *Mutat. Res.* 142: 69-73 (1985)). Moreover, antibodies against mono-ADP-ribose react with mammalian nuclei only if when cells are treated with DNA-damaging agents. Thus ADP-ribosylation of histones and NAD hydrolysis may play a role in opening up chromatin to allow DNA repair. In this regard, the Sir proteins are known to move to sites of DNA breaks to aid their repair by non-homologous end joining (Mills, K. D., et al., *Cell* 97: 609-620 (1999); (Martin, S. G., et al., *Cell* 97: 621-633 (1999)).

There are four SIR2-related genes in yeast, HST1-4 (Brachmann, C. B., et al., *Genes Dev.* 9: 2888-2902 (1995)), but no single hst mutant affects silencing, although effects are observed in the hst3/hst4 double mutant. It is expected that the these gene products catalyze histone deacetylation. In mammals there are at least five homologs (Frye, R. A., *Biochem. Biophys. Res. Commun.* 260: 273-279 (1999); (Brachmann, C. B., et al., *Genes Dev.* 9: 2888-2902 (1995)), of which mSir2α is the most closely related to Sir2p. mSir2α is identical to yeast Sir2p in the deacetylation reaction, indicating that this activity is highly conserved in nature.

mSir2α is not at the rDNA, centromeres, or telomeres, but broadly distributed in nuclei (not shown) suggesting that Sir2 proteins may regulate silencing in widely distributed blocks of the mammalian genome. A distinction between Sir2-silenced heterochromatin and constitutive heterochromatin is illustrated by the disruption of centromeric heterochromatin in *S. pombe* by the general deacetylase inhibitor, trichostatin A (TSA) (Ekwall, K., et al., *Cell* 91: 1021-1032 (1997)), which does not affect the deacetylase activity of Sir2p. The involvement of a distantly related SIR2 family member, hst4+, in this centromeric silencing (Freeman-Cook, L. L., et al., *Molecular Biology of the Cell* 10: 3171-3186 (1999)) provides a hint that the more distant SIR2 family members may target constitutive heterochromatin, while closely related SIR2 genes target regulated blocks of silencing.

In addition to a role in silencing, Sir2p also extends life span of mother cells by repressing recombination in the rDNA (Gottlieb, S., et al., *Cell* 56: 771-776 (1989)), and reducing the production of toxic rDNA circles (Sinclair, D. A., et al., *Science* 277: 1313-1316 (1997); (Sinclair, D. A., et al., *Cell* 91: 1-20 (1997)). The fact that NAD but not NADH, NADP, or NADPH can activate deacetylation of histones by Sir2p may link chromatin silencing and ageing to the metabolic state of cells, i.e., Sir2 proteins can sense the energy or oxidation state of cells. Most of the NAD in eukaryotic cells is present in the nucleus (Rechsteiner, M., et al., *Nature* 259: 695-696 (1976)), where it turns over rapidly (Dai, Y., et al., *Mut. Res.* 191: 29-35 (1987)). Thus, a pool of NAD can regulate chromatin structure by controlling the histone deacetylase activity of Sir2 proteins.

It is interesting to note that caloric restriction slows ageing in a variety of organisms, including yeast (Muller, I., et al., *Mech. Ageing Dev.* 12: 47-52 (1980)), *C. elegans* (Lakowski, B., et al., *Proc. Natl. Acad. Sci. USA* 95: 13091-13096 (1998)), rodents (Weindruch, R. H., et al., *J. Nutrit.* 116: 641-654 (1986)), and probably primates (Roth, G. S., *J. Am. Geriatr. Soc.* 47: 896-903 (1999)). It is possible that the altered metabolic rate in calorically restricted cells exert at least part of its effect by increasing the availability of NAD in the nucleus, which, in turn, up-regulates Sir2 proteins and chromatin silencing. The hunkering down of the genome in the face of carbon limitation is sensible because it conserves energy and could explain the extended life span under this regimen. In normal ageing, NAD levels decline (Chapman, M. L., et al., *Mech. Of Aging and Dev.* 21: 157-167 (1983)), perhaps causing a decrease in Sir2 activity and a deleterious loss of genomic silencing.

It is clear that nuclei obtained from adult animals may be reprogrammed in oocytes to undergo embryonic development and produce viable progeny (Wilmut, I., et al., *nature* 385: 810-813 (1997); (Wakayama, T., et al., *Nature* 394: 369-374 (1998)). This cloning implies that there can be no irreversible changes in nuclei of ageing animals, such as DNA deletions or DNA circles. Were changes in chromatin structure the basis of ageing, then such a reversibility in oocytes would be theoretically possible. It is possible that reprogramming of adult nuclei, a slow and inefficient process, can be facilitated by the addition of chromatin modification factors, such as Sir2 to oocytes. Moreover, it possible that increasing the activity of Sir2 in metazoans extends their life span, as it does in yeast (Kaeberlein, M., et al., *Genes Dev.* 13: 2570-2580 (1999)). The most ready way to achieve this goal is to provide additional copies of SIR2 genes in transgenic animals. A more long term strategy with possible implications to humans is to intervene with small molecules that increase the deacetylation activity of Sir2. The latter approach offers the advantage of late intervention to avoid any unwanted side effects on development or fertility and could, in principle, afford the benefits of caloric restriction without the practical difficulties.

While this invention has been particularly shown and described with references to preferred embodiments thereof, it will be understood by those skilled in the art that various changes in form and details may be made therein without departing from the scope of the invention encompassed by the appended claims. The teachings of all references cited herein are hereby incorporated by reference in their entirety.

EXEMPLIFICATION

Materials and Methods
Data Base and Sequence analysis

TBLASTN searches were performed on the NCBI mouse EST sequence databases, using the amino acid sequence of ySir2p. All mouse EST sequences homologous to ySir2p were classified into three groups termed α, β, and γ, based on the homology results from the searches. Three representative EST cDNA clones were purchased for three mouse homolog groups from Genome Systems Inc (St. Louis, Mo.): AA199012 for α, AA105536 for β, and AA260334 for γ. The cDNA clones were partially or completely sequenced. All deduced amino acid sequences were aligned with the Clustal X program. To cover each core domain completely, amino acid sequences of AA137380 and AA212772 for β and γ respectively, were also used. A phylogenetic tree of the core domains of the yeast and mouse Sir2 families was generated with the Clustal X and NJPLOT program by using the following amino acid sequences: position 228-499 for ySir2p, 174-440 for yHst1p, 1-251 for yHst2p, 26-315 for yHst3p, 65-343 for yHst4, 215-460 for mSir2α, TLGL (SEQ ID NO:36) to LINKEK (SEQ ID NO: 32) for mSir2β, and FGGG (SEQ ID NO:37) to LINRDL (SEQ ID NO: 33) for mSIR2γ.

Northern Blotting

The multiple tissue Northern blot (heart, brain, spleen, lung, liver, skeletal, muscle, kidney, testis) was purchased from Clontech™ (Palo Alto, Calif.). Prehybridization and hybridization were performed at 65° C. in 5×SSPE, 5×Denhardt's solution, 1% SDS and 0.1 mg/ml poly(A). The cDNA fragments of AA199012, AA105536, and AA260334 were used as probes for mSIR2α, β, and γ, respectively. The human β actin fragment from the manufacturer was used as a control probe. Between each blotting, the probe was stripped off by boiling the membrane in 0.5% SDS for 1 min.

Molecular Cloning of mSIR2α

The mouse 15-day embryo 5' STRETCH PLUS™ cDNA library (Clontech™) was screened with the cDNA fragment of AA199012 as a probe. Five positive clones were obtained from approximately one million independent plaques. One of the five clones contained a 3.9 kb cDNA fragment. The nucleotide sequence of this fragment was determined with an Applied Biosystems 374 automated sequencer. Although more 5' sequences of mSIR2α cDNA were obtained by 5' RACE with the mouse liver Marathon-Ready cDNA (Clontech™), no stop codon could be found in the upstream of the first start codon (data not shown). This finding was confirmed on the genomic sequence of the mSIR2α gene (data not shown). Thus, the cDNA clone encodes the full-length mSir2α protein, as shown in FIG. 2B. The deduced amino acid sequence of mSir2α was aligned in the CLUSTAL X and SEQVU 1.1 programs with other Sir2 family members.

Antibody Production to mSIR2α

The 5' SalI-PvuI fragment of the mSIR2α cDNA was engineered to be cloned into BamHI site of pET16b vector (NOVAGEN®, Madison, Wis.). The BL21 (DE3) pLysS bacterial strain that also has an extra copy of arginine tRNA gene was transformed with the resultant plasmid. A transformed bacterial clone was induced in 1 mM IPTG at 37° C. for 7 hrs to produce 10×His-tagged N-terminal fragment of the mSir2α protein. The mSir2α N-terminal protein was purified with Ni-NTA agarose (QIAGEN®, Valencia, Calif.) under denaturing condition. Rabbit polyclonal antisera against this purified protein was produced at Covance Research Products (Denver, Pa.). Affinity purification of the antibody was performed with HiTrap NHS-activated column (Amersham Pharmacia Biotech™, Piscataway, N.J.) conjugated with the dialyzed mSir2α N-terminal protein.

Western Blotting and Immunoprecipitation

Mouse NIH3T3 cells were lysed directly in Laemmli's sample buffer for Western blotting or in extraction buffer (20 mM Tris-HCl [pH7.6], 150 mM NaCl, 0.5% IGEPAL CA-630 (SIGMA, St. Louis, Mo.), 1 mM EDTA, 0.5 mM PMSF, 10 μg/ml leupeptin, 10 μg/ml pepstatin A, 10 μg/ml aprotinin) for immunoprecipitation. The in vitro translated mSir2α protein was produced with the XbaI-linearized pBluescript containing the mSIR2α cDNA at SalI site and the STP3 T7 in vitro transcription/translation kit (NOVAGEN®). For Western blotting, 17 μg of the extract or 2 μl of the in vitro translation mixture was run on a 4-15% gradient SDS-PAGE gel and transferred onto an Immobilon-P PVDF membrane (MILLIPORE®, Bedford, Mass.). After preblocking strips of the membrane in TBS containing 0.1% Tween20 and 5% nonfat skim milk, the first antibody reaction was performed in the 1:2000 dilution of the affinity-purified antibody against mSir2α or control rabbit IgG. The mSir2α band was visualized with the secondary anti-rabbit IgG antibody conjugated with horse radish peroxidase and the ECL detection kit (Amersham Pharmacia Biotech). For immunoprecipitation, approximately 300 μg of the extract was incubated at 4° C. with 1 μg of the affinity-purified mSir2α antibody for 1 hr and then with Protein A-SEPHAROSE® beads (SIGMA®) for another 1 hr. The protein complex on beads was washed with extraction buffer three times and extracted in sample buffer. The protein was electrophoresed and blotted as described above.

Immunofluorescence

NIH3T3 cells or mouse embryonic fibroblasts were plated on 10-well multitest slideglasses (ICN Biomedicals, Aurora, Ohio). The cells were briefly washed with PBS, fixed in PBS containing 3.2% paraformaldehyde for 10 min, and then treated with PBS containing 0.5% IGEPAL-CA630 for 20 min. Preblocking reaction was performed with PBG buffer (PBS containing 0.2% cold water fish gelatin and 0.5% bovine serum albumin (SIGMA®)) at 37° C. for 20 min. After washing cells in PBS-T (PBS containing 0.2% Tween20) briefly, the first antibody reaction was performed at 37° C. for 1 hr in PBG containing the affinity-purified mSir2α antibody diluted to 1:500 and/or one of the anti-human nuclear antibodies (ANA-N for nucleolus or ANA-C for centromeres, SIGMA®) diluted to 1:5 or 1:10 or control rabbit IgG. The cells were washed in PBS-T for 5 min twice. The secondary antibody reaction was performed at 37° C. for 1 hr with the anti-rabbit IgG antibody conjugated with FITC (Jackson ImmunoResearch Laboratories, PA) and/or the anti-human IgG antibody conjugated with TEXAS-RED® (Vector Laboratories, CA). After washing in PBS-T for 5 min, the cells were counterstained in 200 ng/ml of DAPI for 1 min. They were washed in TBS-T for 5 min again and in dH$_2$O briefly, and then embedded under coverslips with VECTOR-SHIELD® (Vector Laboratories).

For the immuno-FISH of mSir2α and telomeres, the first antibody reaction for mSir2α was performed as described above. The cells with the first immune complex was then fixed with 3.2% paraformaldehyde for 10 min, permealized again in PBS containing 0.5% IGEPAL®-CA630 for 20 min, treated in 0.1M NaOH for 2 min to denature DNA, and immediately washed in ice-cold PBS. The synthesis of a telomeric probe, hybridization of the probe and visualization of the hybridized spots were done as described previously. The secondary antibody reaction to detect mSir2α was also done during the last visualization step.

All immunofluorescent digital images were obtained with the Nikon ECLIPSE® TE300 fluorescent microscope equipped with a CCD digital camera (HAMAMATSU® Photonics, Japan) and the METAMORPH® imaging system software (Universal Imaging Corp., PA).

Production of Recombinant Proteins

The yeast SIR2 gene or the mSIR2a full-length cDNA was cloned into pET28a vector (NOVAGEN®). BL21 (DE3) and BL21 (DE3) pLysS with an extra copy of arginine tRNA gene was transformed with the ySIR2 and mSIR2α plasmids, respectively. Each transformed bacterial clone was induced in 1 mM IPTG at 37° C. for 1 hr. The induced 6×His-tagged proteins were purified with Ni-NTA agarose under native condition (see FIG. 4A). The N-terminal fragment of mSir2α was prepared in the same way. The control elute was prepared from a bacterial clone carrying pET28a vector only. The recombinant proteins were aliquoted and kept at −70° C.

Site-directed mutagenesis of mSIR2α core domain was performed with the GeneEditor™ system (Promega, Madison, Wis.) according to the procedure provided by the manufacturer. The mutant recombinant proteins were prepared in the same way as described above.

ADP-Ribosylation Assay

The typical reaction was performed in 50 or 100 μl of the buffer containing 5 mM Tris-HCl [pH8.0 or 9.0], 4 mM MgCl$_2$, 0.2 mM DTT, 1 μM cold β-NAD$^+$ (SIGMA®) and 8 μCi nicotinamide adenine dinucleotide 5'[α-$^{32}$P]triphosphate (NAD) as a donor of ADP-ribose (∼1000 Ci/mmol, Amersham Pharmacia Biotech). To check the sensitivity to poly- or mono-ADP-ribosylation inhibitors, 3-aminobenzamide (ICN Pharmaceuticals, CA), benzamide, novobiocin and coumermycin A1 (SIGMA®) were added to the reactions prior to adding Sir2 proteins, respectively. The wild type or mutant recombinant proteins (0.5-1 μg for ySir2p and 10 μg of mSir2α) were added with 4 μg of each histone purchased from Roche Molecular Biochemicals (Indianapolis, Ind.). For the peptide experiments, 5-10 μg of unacetylated or acetylated N-terminal tail peptides (amino acids 1-20) of H3 and H4 purchased from Upstate Biotechnology™ (Lake Placid, N.Y.) were used as substrates of the yeast and mouse Sir2 recombinant proteins.

To detect the activity of the endogenous mSir2α, which was usually immunoprecipitated from 300-400 μg of the NIH3T3 whole cell extract, the reaction buffer and substrates were added directly to the immune complex on Protein A-Sepharose beads. The reaction mixture was incubated at room temperature for 1 hr. For the reaction of snake venom phosphodiesterase (Roche Molecular Biochemicals), 1-2 μl of the enzyme or the same volume of dH$_2$O was added to the reaction mixture, respectively, after finishing ADP-ribosylation reaction. Each mixture was incubated at 37° C. for 1 hr and the reaction was terminated as described below.

To analyze histone modification, 25 μl of 100% trichloroacetic acid (TCA) solution was mixed to the reaction mixture and left on ice for 15 min. The protein precipitates were centrifuged at 4° C. and washed with 5 or 20% TCA solution twice. The pellets were dissolved in 15 μl of Leammli's sample buffer and boiled for 1.5 min. The proteins were electrophoresed in a 10-20% gradient SDS-PAGE gel. The gel was stained with COOMASSIE® Brilliant Blue R-250 (GibcoBRL Life Technologies™, Frederick, Md.) to check equal loading of histones, dried, and exposed to KODAK® X-OMAT film.

To analyze modified peptides, 10 μl of each reaction mixture was spotted on a cellulose TLC plate (EM Science, Gibbstown, N.J.). The chromatography was performed for 9-10 hrs in a TLC chamber containing the 65:5:3:2:29 mixture of isobutyric acid, pyridine, acetic acid, butanol and water. The plate was dried and exposed to Kodak X-OMAT film. The peptide spots were visualized by ninhydrin staining.

Transient Transfection Assay

Effector plasmids of mSIR2α were constructed using DNA fragments corresponding to amino acids 220-500 of the wild type and mutant mSIR2α amplified by PCR with Pfu-Turbo® DNA polymerase (STRATAGEN®, La Jolla, Calif.) with primers that create EcoRI sites at both ends of each fragment. Fragments were cloned into the EcoRI site of pM mammalian expression vector (Clontech™) to produce the N-terminal fusion protein to the GAL4 DNA binding domain. The luciferase plasmid, pUAS$_4$tkluc, which has four GAL4 binding sites in the upstream of the luciferase gene, was employed as a reporter gene. Plasmids preparations were made using the QIAfilter™ plasmid midi kit (QIAGEN®).

NIH3T3 cells ($10^6$ cells) were plated a day before transfection. Cells were transfected using SuperFect™ transfection reagent (QIAGEN®) with 4 µg of the GAL4 DBD-core domain effector plasmid, 1 µg of the luciferase reporter gene and 1.5 µg of SV40 promoter-driven β-galactosidase gene to normalize the transfection efficiency. The extracts of the transfectants were prepared 48 hrs after transfection. The luciferase assay was performed using the luciferase assay system kit (Promega™) and the Optocomp I luminometer (GM Instruments™, CT), according to the procedures provided by the manufacturers.

Production of Recombinant Proteins

The yeast SIR2 gene or the mSIR2α full-length cDNA were cloned into pET28a vector (NOVAGEN®, WI). BL21 (DE3) and BL21(DE3)pLysS with an extra copy of arginine tRNA gene was transformed with the SIR2 and mSIR2α plasmids, respectively. Each transformed bacterial clone was induced in 1 mM IPTG at 37° C. for 1 hr. The induced 6×His-tagged proteins were purified with Ni-NTA agarose under native conditions. The control elute was prepared from a bacterial clone carrying pET28a vector only. The recombinant proteins were aliquoted and kept at −70° C.

Deacetylation and ADP-Ribosylation Assays

The typical reaction of Sir2 deacetylase activity was performed in 50 µl of buffer containing 50 mM Tris-HCl [pH 9.0], 4 mM $MgCl_2$, 0.2 mM DTT, variable concentration of cold nicotinamide adenine dinucleotide (NAD) or NAD derivatives (SIGMA®, MO), 5-10 µg of the purified recombinant Sir2 proteins, and 10 µg of the histone H3 N-terminal tail peptide (amino acid 1-20) di-acetylated at positions 9 and 14 (Upstate Biotechnology™, NY). This starting peptide material contains a contaminant with 100 Da smaller molecular weight, which also showed exactly the same patterns of deacetylation (data not shown). To detect the ADP-ribosylation activity, 8 µCi of NAD 5'-[α-$^{32}$P]triphosphate (~1000 Ci/mmol, Amersham Pharmacia Biotech™, NJ) was added to the same reaction containing 1 µM cold NAD. Histone H3 protein (4 µg) (Roche Molecular Biochemicals™, IN) were used for this assay. All reaction mixtures were incubated at room temperature for 1 hr. Trichostatin A and coumermycin A1 (SIGMA™) were prepared in dimethylsulfoxide (DMSO, SIGMA®), and 5 µl of solvent or inhibitor was added to the reactions prior to adding Sir2 proteins.

Analysis of Deacetylated or ADP-Ribosylated Products

After the incubation, the products were precipitated at −20° C. overnight by adding 50 µl of distilled water and 25 µl of 100% trichloroacetic acid (TCA) solution. For high pressure liquid chromatography (HPLC), the precipitates were reconstituted in 5% $CH_3CN$ and 0.1% trifluoroacetic acid (TFA) and run in the gradient concentration between 0.05% TFA and 0.043% TFA plus 80% $CH_3CN$ on Hewlett Packard Model 1100 HPLC system with 214TP52 column (VYDAC, CA). The chromatograms at the absorbance of 210 nm were digitally recorded and analyzed by Hewlett Packard ChemStation™ system (version A.06.03 [509]). Fractions of samples were collected every 1 min by Gilson™ Fraction Collector Model 203. Peptide sequencing was done by the Applied Biosystems PROCISE® 494 HT protein sequencing system. PTH amino acid chromatograms were recorded and analyzed by the ABI Model 610A2.1 data integration/analysis system.

Electron-spray mass spectroscopy (also referred to herein as mass spectroscopy) was done on the PE Sciex Model API365™ system. Matrix assisted laser desorption/ionization (MALDI) mass spectroscopy can also be used. The electron-spray mass spectroscopy data were analyzed by the Bio-MultiView Program™ (version 1.3.1). To detect the ADP-ribosylated intact H3 protein, the pellets were dissolved in 15 µl of Leammli sample buffer, boiled for 1.5 min and electrophoresed in a 10-20% gradient SDS-PAGE gel. The gel was stained with Coomassie Brilliant Blue to check equal loading of histones, dried, and exposed to KODAK® X-OMAT film. To analyze the ADP-ribosylated H3 peptides, 10 µl of each reaction mixture was spotted on a cellulose TLC plate (EM Science™, NJ). The chromatography was performed for 9-10 hrs in a TLC chamber containing the 65:5:3:2:29 mixture of isobutyric acid, pyridine, acetic acid, butanol and water (Scheidtmann, K. H., et al., J. Virol. 44:116-133 (1982)). The plate was dried and exposed to KODAK® X-OMAT film. The peptide spots were checked by ninhydrin staining.

Molecular Cloning of mSIR2α

The mouse 15-day embryo 5-STRETCH PLUS cDNA library (Clontech, CA) was screened with the EST cDNA fragment of AA199012 as a probe. Five positive clones were obtained from approximately one million independent plaques. One of the five clones contained a 3.9 kb cDNA fragment. The nucleotide sequence of this fragment was determined with an Applied Biosystems 374 automated sequencer. The isolated cDNA clone encodes the full-length mSir2α protein since the in vitro-translated protein from this cDNA clone showed an indistinguishable size (110-120 kD) to the protein in the mouse NIH3T3 extract recognized by a specific polyclonal antibody against a N-terminal portion of mSir2α (data not shown).

The amino acid sequences of mSir2α and other Sir2 family members were aligned in the Clustal X program and a phylogenetic tree was generated by using the NJPLOT program.

Strains, Plasmids, and Antibodies

All strains used were derivatives of W303a sir2Æ : W303R sir2Æ (MATa, ade2-1, leu2-3,112, trp1-1, ura3-52, his3-11, sir2::TRP1, rDNA-ADE2), W303RT sir2Æ (MATa, ade2-1, leu2-3,112, trp1-1, ura3-52, his3-11, rad5-535, sir2::TRP1, rDNA-ADE2, URA3-TEL???), and W303R sir2Æ/rpd3 Æ (MATa, ade2-1, leu2-3,112, trp1-1, ura3-52, his 3-11, rdp3:: URA3, sir2::TRP1, rDNA-ADE2). Two integrating plasmids that contain SIR2 driven by its native promoter were used: pRS305-SIR2 and pRS305-SIR2*, the latter expressing Sir2p at low levels. SIR2 and mutant sir2 strains were generated by cutting the plasmid within the LEU2 gene and integrated using standard yeast transformation protocols. Unless otherwise noted derivative strains were generated using pRS305-SIR2. Rabbit antibodies to Sir2p were generated by using full-length rSir2p isolated under denaturing conditions.

Generation of Core Domain Mutants

Site directed mutations were generated in the plasmid pRS305-SIR2* using the Gene Editor™ system (Promega™, Madison, Wis.) according to the procedure provided by the manufacturer. Sequences were verified by Sanger sequencing methods. The mutants were then subcloned into pRS305-SIR2 and pET28a.

ADP-Ribosylation and Deacetylation Assays

BL21 with SIR2 or the sir2 mutants subcloned into pET28a (NOVAGEN®) were induced with 1 mM IPTG for 1 hr. The recombinant proteins were purified by Nickel-NTA column under native condition. Ribosylation and deacetylation assays were performed using 1 µg of recombinant protein for the ribosylation assay and 5 µg for the deacetylation assay.

Silencing, Life Span and rDNA Recombination Assays

To evaluate silencing at the telomeres and rDNA, 10-fold dilutions of the derivatives of either W303RT or W303R Ærpd3 were spotted on media containing 5-FOA or media lacking adenine, respectively. To assay for HM silencing, W303R derivatives generated with pRS305-SIR2* were patched onto YPD with the tester strain CKy20(MATa, arg1, tsm11) and after overnight growth were replica plated to minimal media with no supplemented amino acids. Life span and rDNA recombination rates were measured as in Kaeberlein, et. al., (Kaeberlein, M., et al., *Genes Dev.* 13: 2570-2580 (1999)).

Duplication Strains of *C. elegans*

All strains were maintained and handled as previously described (Brenner, S. *Genetics*, 77:71-94 (1974) and Sulston, J., et al., Cold Spring Harbor Laboratory, *Methods*, 587-602 (1988)). Duplication strains were maintained by picking individual worms and examining the brood for proper segregants.

Transgenic *C. elegans* Worms

A 2.2 k.b. PCR fragment containing the entire sir-2.1 coding sequence as well as 400 bp upstream and 300 bp downstream was injected into *C. elegans* worms at 50 ng/µl with pRF4 at 100 ng/µl (Mello, C. C., et al., *EMBO*, J10:3959-3970 (1991)) to obtain stable extrachromosomal transgenic lines. Lines were maintained by picking roller animals.

Integration of sir-2.1 into *C. elegans*

For each of geEx1, geEx2 and geEx3, L4 heimaphrodites (n=10) were placed on 10 plates and subjected to gamma irradiation from a Gammacell 220$^{60}$Co source at 4000 rads. Worms (n=5) were placed onto each of 20 plates and allowed to starve the plate such that no bacteria remained at 20° C. Each of the 20 plates were then chunked onto a fresh plate. Two days later, a total of 20 worms was singly picked to a plate from every parent plate for a total of 400 worms per gamma irradiation. Four days later, plates were scored for the presence of rollers and non-rollers. Any plates with all rollers were kept and followed for an integrated line. From these plates a total of 5 individual hermaphrodites were singled to a new individual plates and scored 4 days later for all rollers. Integrants segregated all rollers on all of the five plates.

Strain Construction *C. elegans* daf-2

A daf-2 males were mated to the transgenic SIR2 lines at 15° C. Five to seven days later, putative roller cross progeny were transferred to individual plates at 25° C. Three days later, the plates were scored for the presence of dauers. Roller dauers were returned to 15° C. to recover and singled to individual plates. For integrated lines, 20 animals were transferred from the brood of the recovered dauers to individual plates and their progeny scored for the presence of 100% rollers.

daf-16 daf-16 males were mated to the sir-2.1 lines at 15° C. Five to seven days later, putative roller cross progeny were singled to individual plates at 15° C. Animals (n=12) were singled to plates from each of the F1 plates and allowed to lay eggs. Four to five days later, PCR was performed on the F2 parent to determine the daf-16 genotype using primers S077 and S078 (Ogg, S., et al., *Nature*, 389:994-999 (1997)). Strains were maintained by transferring roller animals to new plates.

daf-4/daf-1

Wild-type males were mated to either daf-1 or daf-4 hermaphrodites at 15° C. Five to seven days later, non-Daf F1 hermaphrodites were singled to plates at 25° C. Three days later, roller dauers were picked off the plate and allowed to recover individually on a plate at 15° C. to establish the strain. Strains were maintained by transferring roller animals to new plates.

*C. elegan* Strain Life Span and Development

Life span assays were performed at 20° C. Adult hermaphrodites were picked (4-10 per plate) from each strain and allowed to undergo one full generation at 15° C. or 20° C. From these plates, individual L4s or young adults were picked to plates at 20° C. containing 400 µ/ml FUDR which blocks DNA synthesis and causes animals to lay eggs that do not develop and eliminates the need to transfer animals throughout the life span assay (Apfeld, J., et al., *Cell*, 95:199-210 (1998)). Animals were tapped every two-four days and were scored as dead when they did not move after repeated taps with a pick. A limited number of experiments were carried out on plates without FUDR by transferring adult animals every one-two days to new plates and these revealed the same, long life spans of sir-2.1 transgenic animals. All statistical tests were done using JMP 4.0 software.

Timing of development was scored for each strain at 20° C. Plates were scored every 12-18 hours for developmental stage. No noticeable differences were observed comparing the roller strains with and without the sir-2.1 transgene. For 27° C. dauer formation, animals were allowed to lay eggs at 27° C. for four hours. Plates were scored two days later for the presence of dauers and non-dauers. Both wild type and unc-31(e928) animals were used as controls for dauer induction.

Results

Characterization of the Closest Mouse SIR2 Homolog, mSIR2α

At least three different sequences, mSir2α, β, and γ, related to yeast Sir2p (ySir2p) have been identified in the mouse EST database. mSir2α was identified as having the greatest homology to ySir2p and the related yeast protein, Hst1p (FIG. 1A). mSir2β and γ have significant homology to Hst2p, another member of yeast Sir2 family.

The tissue distribution of mSIR2α, β, and γ mRNA expression was examined (FIG. 1B). A major transcript encoding mSIR2α (~4.0 kb) is present in all tissues examined. Minor transcripts of various size are also detected in each tissue. mSIR2β has only one transcript (~1.9 kb). mSIR2α and β appear to be expressed ubiquitously, showing a high level of expression in liver. The mSIR2γ transcript (~4.6 kb) is also predominantly expressed in liver.

A 3.9 kb cDNA clone of mSIR2α was identified by screening a mouse embryonic cDNA library with the EST clone AA199012 as a probe. This cDNA clone encodes a predicted protein with 737 amino acids with a molecular weight of 80.3 kD. The deduced amino acid sequence of mSIR2α is shown in FIG. 2A. A predicted nuclear localization signal KRKKRK (SEQ ID NO: 29) is present.

A rabbit polyclonal antibody raised against the N-terminal 131 amino acids of the mSir2α protein recognized a 120 kD protein in the cell extracts of murine NIH3T3 cells (FIG. 2B) and embryonic fibroblasts (data not shown). The in vitro translated (IVT) protein from the cDNA clone has an indistinguishable size to the protein in the NIH3T3 extract, suggesting that this cDNA clone encodes a full length protein of mSir2α (right panel, FIG. 2B). The 120 kD band was not detected in immunoprecipitates incubated with rabbit IgG alone or the in vitro translation mixture containing no RNA (FIG. 2B). An asterisk indicates IgG in immunoprecipitates.

In the mSir2α, the greatest homology to ySir2p resides in the middle or core domain of the protein (FIG. 2C). The amino acid identity of the mSir2α core domain to ySir2p is 45.9% and the N-terminal region of the mSir2α protein also shows weak homology to ySir2p (13.4% identity). The mSir2α has a longer C-terminal region than ySir2p, but no significant homology to other proteins in this region. The highly conserved core domains of yeast and mouse SIR2 family members have homology to the *Salmonella typhimurium* CobB protein (Tsang, A. W., et al., *J. Biol. Chem.* 273: 31788-31794 (1998)) (20.3% identity in the core domain (FIG. 2D). Asterisks denote a motif of putative NAD binding clefts conserved in known mono-ADP-ribosyltransferases. (FIG. 2C).

Figure 3:
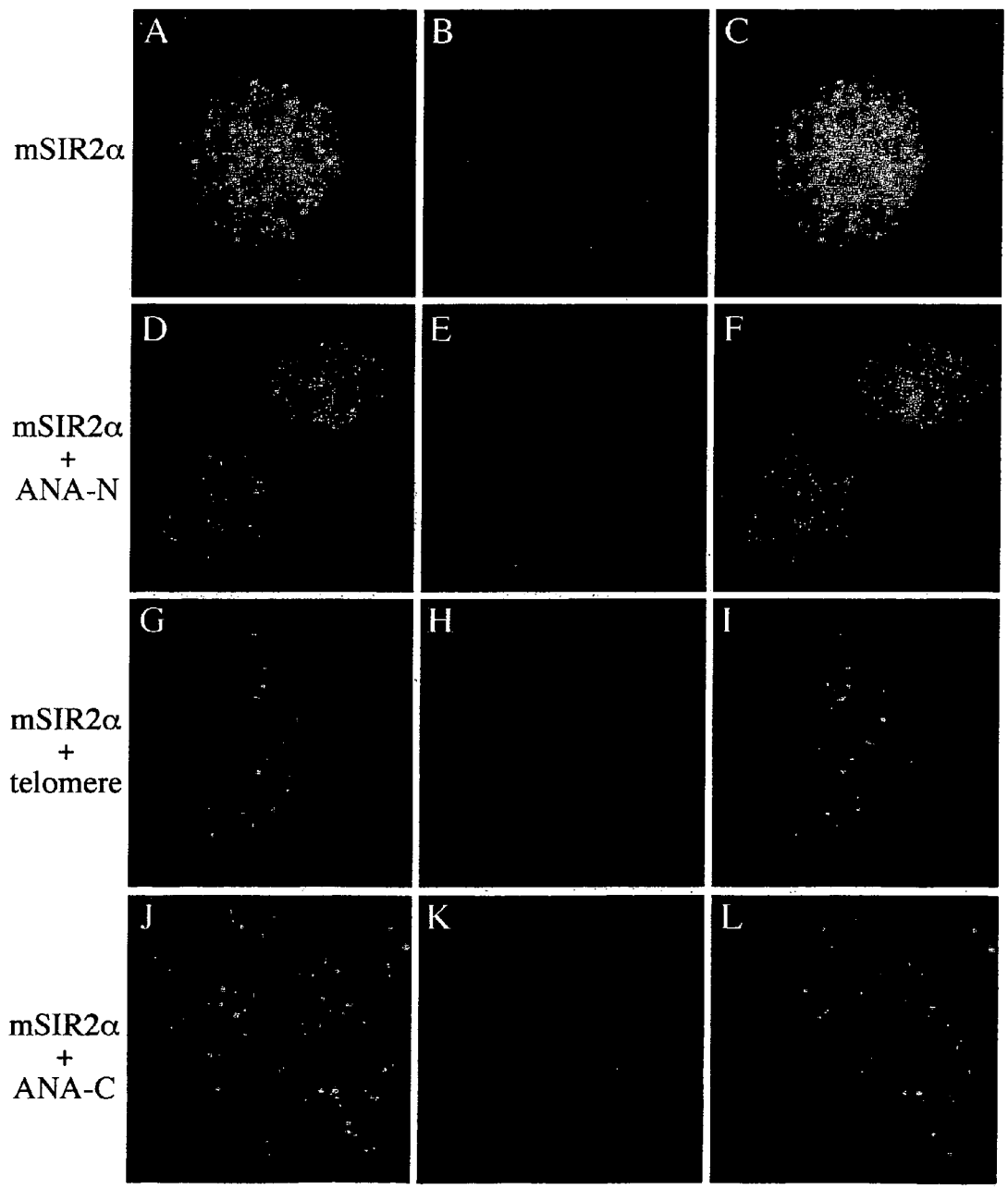
FIG. 3 depicts the immunocytochemical localization of mSir2α in mouse NIH3T3 cells (A, D, G, and J). Cells were counterstained with DAPI (B, E, H, and K). Nucleoli (E), telomeres (H), and centromeres (K) were visualized using an anti-human nucleolar antibody (ANA-N), telomeric FISH, and an anti-human centromeric antibody (ANA-C), respectively. Merged images are shown in C, F, I, and L.

In yeast, immunostaining revealed Sir2p localization in the nucleolus and telomeres (Gotta, M., et al., *Embo J.* 16: 3243-3255 (1997)). Immunostaining of mouse NIH3T3 cells with a polyclonal antibody raised against the N-terminal fragment of mSir2α localized mSir2α in the nucleus (FIG. 3A). DAPI-dense regions in nuclei, which correspond to mouse centromeres, were excluded (FIGS. 3B and C). This staining pattern was observed throughout the cell cycle except on mitotic chromosomes, which lacked staining (data not shown). Surprisingly, mSir2α was not localized to nucleoli, telomeres, or centromeres by co-immunofluorescence (FIG. 3, D-F, G-I, J-L) indicating that is not associated with the most highly repeated DNA in the mouse genome.

Yeast and Mouse Sir2 Proteins are Novel Nuclear Mono-ADP-Ribosyltransferases

The ADP-ribosylase activity of bacterial recombinant full-length proteins of ySir2p and mSir2α was determined in in vitro assays (FIG. 4A). Calf thymus histones were used as substrates and $^{32}$P-labeled nicotinamide adenine dinucleotide (NAD) as a donor of ADP-ribose. Reaction products were visualized by SDS-PAGE. The recombinant rySir2p and r-mSir2α proteins transferred radioactive ADP-ribose to H2B and H3, but not to H1, H2A and H4 (FIG. 4B, C). The Sir2 proteins modified H2B and H3 in a dose-dependent manner, the ADP-ribosylase activity did not reside in the mSir2α-specific N-terminal fragment N-ter (FIG. 4D). As shown in the upper panel of FIG. 4D, 5, 10, and 15 µg of recombinant full-length mSir2α (r-mSir2α) or its N-terminal fragment (N-ter) or control eluate (pET) were added to the reaction with histone H2B. Only the full-length protein showed the dose-dependent modification. As shown in the lower panel of FIG. 4D, 100, 250, 500, and 1000 ng of recombinant full-length ySir2p (r-ySir2p) were added to the reaction with histone H3. ADP-ribosylase activity was not observed when histone proteins were incubated with control pET alone (FIG. 4B).

To gain further evidence that this modification is due to ADP-ribose, the ySir2p- or mSir2α-modified H2B and H3 with snake venom phosphodiesterase (SVP) that can digest the phosphodiester bond in the ADP-ribose moiety (FIG. 4C, E). The radiolabeled $P^{32}$ (P*) is located at a position and the phosphodiester bond between radiolabeled and nonlabeled phosphates can be digested by snake venom phosphodiesterase (SVP), resulting in the removal of the radiolabel from ADP-ribosylated proteins (FIG. 4E). The radiolabel could be substantially removed from H2B and H3 by SVP (FIG. 4E). The label remaining in the histones may be due to the forward reaction by Sir2 enzymes and NAD during this treatment.

Histone products of Sir2 modification of unique molecular weights were observed in this assay, suggesting that this modification may not be poly-ADP-ribosylation, but mono-ADP-ribosylation. The sensitivity of the ADP-ribosylase activity of mSir2α to poly ADP-ribosylation inhibitors (3-aminobenzamide and benzamide) and mono-ADP-ribosylation inhibitors (novobiocin and coumermycin A1) was evaluated. (FIG. 4F). 3-aminobenzamide and benzamide did not inhibit the ADP-ribosylation activity of the mSir2α protein at concentrations of 40, 200 and 1000 µM (FIG. 4F, lanes 2 to 7) whereas novobiocin and coumermycin A1 strongly inhibited ADP-ribosylation at concentrations of 200 µM and 40 µM, respectively (FIG. 4F, lanes 9 and 12), consistent with their reported $IC_{50}$ concentrations of 370 and 27 µM. ySir2p showed the same sensitivity to those inhibitors (data not shown). Therefore, the sensitivity of the Sir2 enzymatic activities to those inhibitors demonstrates that these proteins are of the mono-ADP-ribosyltansferase class.

ADP-ribosyl-transferase activity could be detected for the endogenous mSir2α immunoprecipitated from NIH3T3 whole cell extracts (FIG. 4G). The endogenous mSir2α was immunoprecipitated from 300 µg of the NIH3T3 whole cell extract with an anti-mSir2α polyclonal antibody and the immune complex on Protein A-Sepharose beads was incubated in the reaction buffer containing $^{32}$P-labeled NAD and histone H1 or H2B.

ADP-Ribosyltransferase and NAD Hydrolase Activities of Yeast and Mouse Sir2 are Specifically Triggered by Acetylated H3 and H4 N-Terminal Tail Peptides Extended N-terminal tails of H3 and H4 are known to be important for the formation of Sir complex-mediated heterochromatin structure in yeast (Hecht, A., et al., *Cell* 80: 583-592 (1995)) and are targets for several different types of histone modification, such as acetylation, phosphorylation, and methylation (Hansen, J. C., et al., *Biochemistry* 37: 17637-17641 (1998)). The residues 1-20 of H3 are conserved through evolution and lysines 9 and 14 which are acetylated in the diacetylated peptide are indicated by asterisks in FIG. 5A. The residues 1-20 of monoacetylated H4 peptide originate from the human sequence and acetylated residues are indicated by asterisks FIG. 5A. Tetra-acetylated H4 peptide corresponds to the Tetrahymena sequence where all lysines are acetylated. The N-terminal tails of histones were evaluated as targets for ADP-ribosylation by Sir2 proteins.

Two synthetic peptides corresponding to the first 20 amino acids of H3 either unacetylated or diacetylated (on lysines 9 and 14) (FIG. 5A) were evaluated to determine whether yeast and mouse Sir2 proteins could modify these peptides. Reactions were carried out as above and analyzed by thin layer chromatography. Both the yeast and mouse Sir2 modified only the diacetylated H3 tail peptide (FIG. 5B). The indicated spot (bracket, FIG. 5B) was identified as the modified peptide because it migrated just below the ninhydrin-positive peptide spot on the chromatogram. Further, NAD hydrolase activity of both ySir2p and mSir2α was stimulated in the presence of the diacetylated peptide, indicated by the arrowhead in FIG. 5B. Since Lys9 and Lys14 of H3 are acetylated in vivo, this preferential utilization of the acetylated H3 peptide strongly suggests that the tail of H3 is a biologically relevant substrate for Sir2 proteins.

The extended N-terminal tail of histone H4 has four lysines at positions 5, 8, 12, and 16. (FIG. 5A). Mutational studies show the importance of these residues in silencing in vivo, and Lys5, 8, and 16 are hypoacetylated in yeast chromatin at HM loci. In mammalian cells, Lys16 of H4 is highly acetylated. H4 peptides (residues 1-20), which were acetylated singly at each of these lysines (5, 8, 12 or 16), were synthesized and evaluated for mSir2α stimulated ADP-ribosyltransferase and NAD hydrolase activities (FIG. 5C). A striking specificity in the acetylation pattern of the H4 tail was required to stimulate Sir2 activity. Both ADP-ribosylation and NAD hydrolysis were stimulated by the Lys16Ac peptide, but were affected weakly by the Lys5-, 8-, 12-, and tetra-acetylated peptides (FIG. 5C).

Highly Conserved Amino Acid Residues in the Core Domain are Essential for the Mono-ADP-Ribosylation Activity of mSir2α

To analyze the mono-ADP-ribosylation activity more precisely, ten highly conserved amino acid residues in the core domain of mSir2α were changed to alanine (FIG. 6A), mutant recombinant Sir2 proteins produced *E. coli*, and evaluated for ADP-ribosylation activities on H2B and H3 in vitro. Protocols for the production of mutant nucleic acid constructs and proteins are well known to the skilled artisan. (See, for example, Ausubel et al., "Current Protocols in Molecular Biology", John Wiley & Sons, NY, N.Y. (1999)).

Figures 6A, 6B:
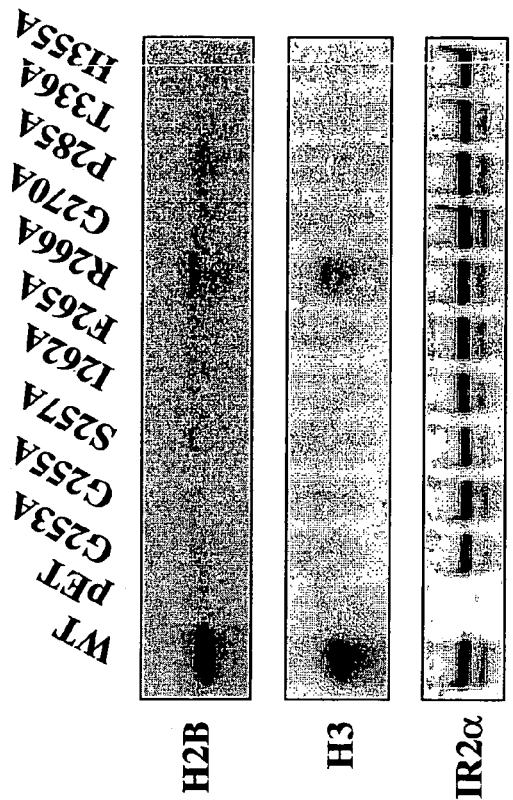
FIG. 6A depicts the highly conserved amino acid residues in the core domain of mSir2α (SEQ ID NO: 9) and ySir2 (SEQ ID NO: 10) proteins. Identical amino acids are boxed. Arrowheads depict the amino acid residues used to generate mutant Sir2 proteins which were evaluated for ADP-ribosylation activity.
FIG. 6B depicts the ADP-ribosylation activities of mSir2α proteins (Wildtype, WT; vector alone, pET; mutants G253A, G255A, S257A, I262A, F265A, R266A, G270A, P285A, T336A, H355A) on histones H2B and H3.

Aliquots of recombinant protein (10 µg) of the wild type recombinant mSir2α (WT), the pET control pET, and the mutant proteins (G253A, G255A, S257A, I262A, F265A, R266A, G270A, P285A, T336A, H355A) were incubated with H2B or H3. Western blot analysis showed that the amount of each full-length protein used was comparable (FIG. 5B, r-mSirα). All of the mutations of highly conserved residues dramatically affected the mono-ADP-ribosylation activity of mSir2α (FIG. 6B). The results were similar using H2B or H3.

Eight mutants (G253A, G255A, S257A, I262A, F265A, G270A, T336A, H355A) completely abolished the activity and the two mutants R266A and P285A showed some residual activities compared to the wild type activity (18% for R266A and 5% for P285A, see FIG. 6C). The radioactivity of H2B modified by the wild type is assigned to 100% and other data were normalized according to the wild type activity and blots quantitated by Phosphorimaging. The averages and the standard deviations were calculated from two independent experiments. In the core domain of ySir2p, mutations on highly conserved residues also affected the mono-ADP-ribosylation activity. Therefore, the core domain of Sir2 proteins contain the catalytic activity of mono-ADP-ribosylation and the evolutionarily conserved residues in the core domain are essential for this activity.

The mSir2α Core Domain Conveys Transcriptional Repressive Activity in Mouse Cells The in vivo function of the mSir2α mono-ADP-ribosylation activity, was evaluated by constructing expression vectors of wild-type (WT) and each of the mutant core domains (G253A, G255A, S257A, I262A, F265A, R266A, G270A, P285A, T336A, H355A) fused to the yeast Gal4 DNA binding domain (DBD) and transfecting the constructed NIH3T3 cells with a luciferase reporter plasmid containing four upstream Gal4 binding sites.

NIH3T3 cells $10^6$ were transfected with 4 µg of effector plasmids which fuse Sir2 sequences to the DBD, 1 µg of a reporter plasmid with luciferase expression driven by GAL4 DNA-binding sites and 1.5 µg of SV40 promoter-driven β-galactosidase gene to normalize the transfection efficiency. All luciferase activities after normalization were standardized to DBD alone. The averages and the standard deviations were calculated from three independent transfection experiments. The wild-type core domain was able to repress transcription four-fold, compared to the activity of the DBD only, which is known to activate transcription approximately two-fold in mammalian cells (FIG. 6D). The DBD-fused full-length ySir2p also showed similar repressive activity in NIH3T3 cells, suggesting that the shared mono-ADP-ribosylation activity can be involved in transcriptional repressive activity. All of the core domain mutants except for P285A reduced transcriptional repressive activity (FIG. 6D). One explanation for this discrepancy is that the P285A change does not inhibit the catalytic domain but causes the recombinant protein to be misfolded in E. coli. Another protein that binds to mSir2α can rescue such a mutant in mammalian cells.

Sir2p is an NAD-Dependent Deacetylase for Histone H3

Figure 8A:
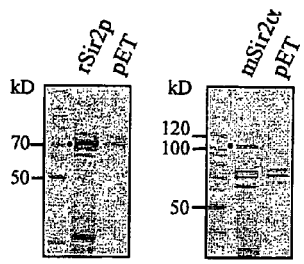
FIGS. 8a, 8b, 8c, 8d, 8e, 8f, and 8g illustrate the in vitro deacetylation of the H3 peptide (residues 1-20) di-acetylated at lysines 9 and 14 by recombinant yeast Sir2p.

The experiments employed purified recombinant Sir2p in a reaction with NAD and a peptide of the histone H3 amino-terminal tail (residues 1-20) di-acetylated at lysines 9 and 14. These lysines are hypoacetylated in silenced chromatin and mutations at these positions to glycine greatly reduce silencing in vivo (Thompson, J. S., et al., Nature 369: 245-247 (1994)). The products of a reaction containing 5 µg of recombinant yeast Sir2p (79 pmoles) (FIG. 8a), 10 µg of the H3 peptide (4.2 nmoles) increasing concentrations of NAD were analyzed s by high pressure liquid chromatography (HPLC).

Figure 8B:
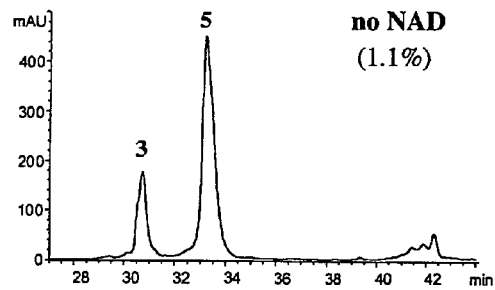
Figure 8E:
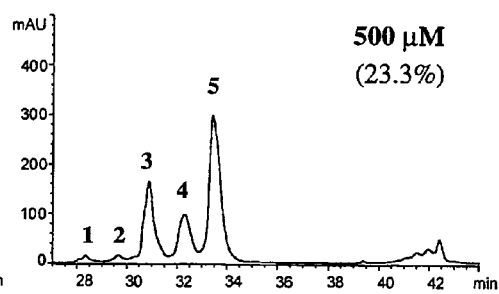
Figure 8C:
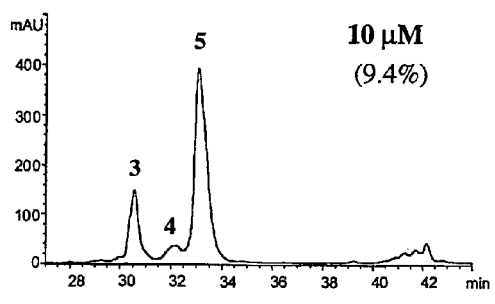
Figure 8F:
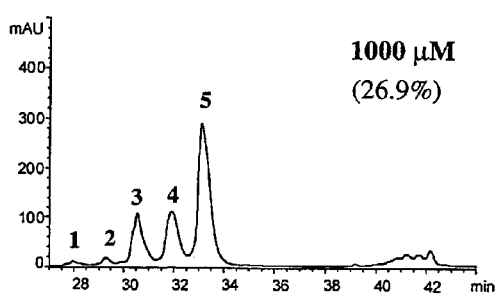
Figure 8D:
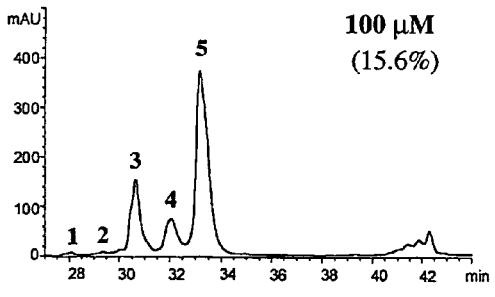
Figure 9A:
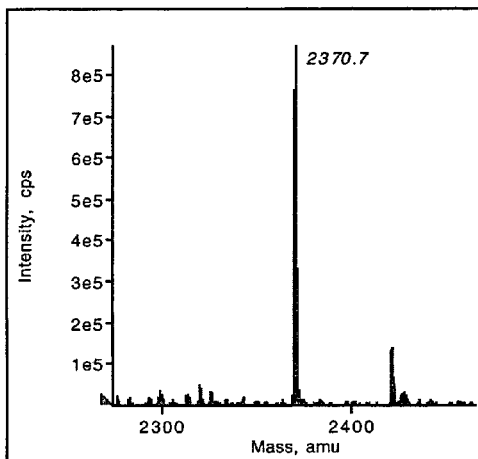
FIGS. 9a, 9b, 9c and 9d are electron-spray mass spectroscopy of peaks 3-5 of HPLC chromatogram.

As shown in FIG. 8b, the histone peptide reacted in the absence of NAD gave rise to two peaks (3 and 5) which were analyzed by electron-spray mass spectroscopy (FIGS. 9a and 9d) and correspond to monomer (MW2370) and dimer (MW4740) peptide, the latter likely due to oxidation of the peptide at the carboxyl cysteine residue. The same species were observed in reactions with a control bacterial preparation ("pET" in FIG. 8a) in the presence of NAD (not shown).

Figure 8G:
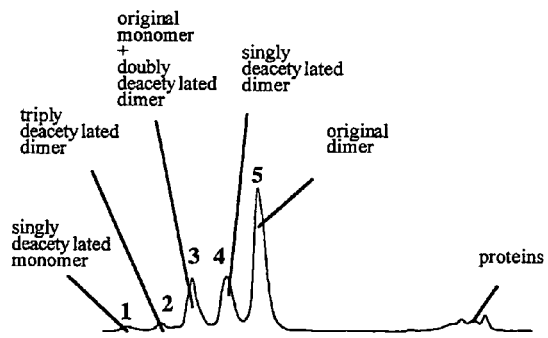
Figure 9B:
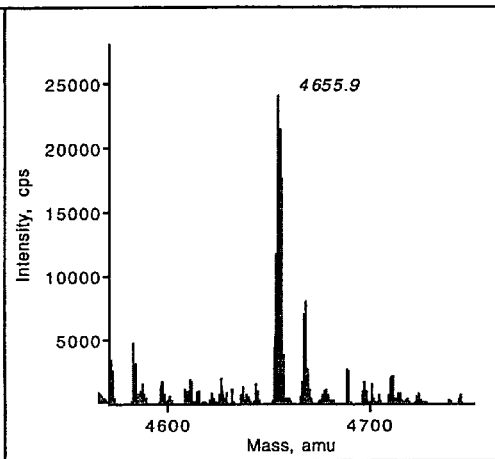
Figure 9C:
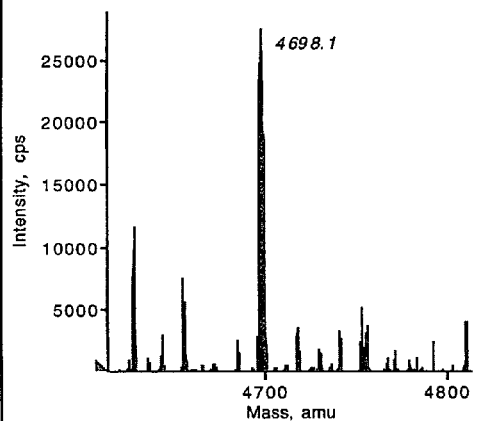
Figure 9D:
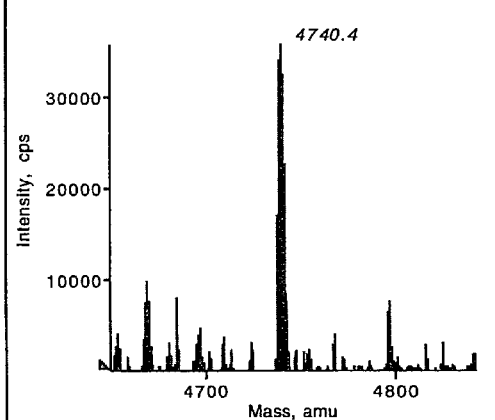

The addition of NAD to the reaction containing Sir2p gave rise to three additional peaks (1, 2, and 4), as well as an alteration in peak 3 (FIGS. 8c, 8d, 8e and 8f), which were also analyzed by electron-spray mass spectroscopy. Strikingly, these peaks did not correspond to ADP-ribosylated species, but rather to deacetylated species of peptide (see FIG. 8g). Peak 4 corresponded to the singly-deacetylated dimer (MW 4698) (FIG. 9c), peak 3 now also contained the doubly-deacetylated dimer (MW4656) (FIG. 9b). Because of their lower abundance, peak 1 and peak 2 were analyzed separately by matrix assisted laser desorption/ionization (MALDI) mass spectroscopy and peak 2 was found to correspond to the triply deacetylated dimer (MW4614) and peak 1 to the singly-deacetylated monomer (MW2328) (not shown). The relative areas under peaks 1, 2, and 4 was quantitated and at least 27% of the input peptide was deacetylated by Sir2p. The approximate Km of this deacetylation reaction for NAD was about 100 µM, at which the reaction proceeded to about 50% of the maximal level observed at higher concentrations of the cofactor.

Figures 10A, 10D:
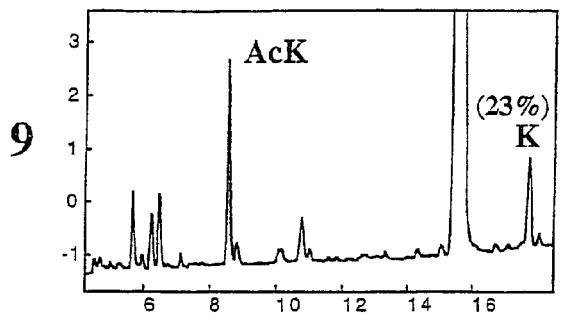
FIGS. 10a, 10b, 10c, 10d, 10e and 10f are the amino-terminal sequencing of peaks 4 and 5 of the deacetylase reaction at 1 mM NAD. Peaks 4 and 5 were subjected to sequencing by Edmann degradation. Chromatograms at positions 9, 14, and 18 are shown. In peak 4, about 23% of Lys9 (FIG. 10a) and 27% of Lys 14 (FIG. 10b) were deacetylated. In peak 5, both Lys 9 and 14 are essentially all acetylated (FIG. 10d and FIG. 10e). The unacetylated Lys18 of both peaks 4 and 5 are shown for comparison (FIG. 10c and FIG. 10f). The peak to the right of the acetylated lysine at position 14 corresponds to alanine, which is a preview of Ala 15.
Figures 10B, 10E:
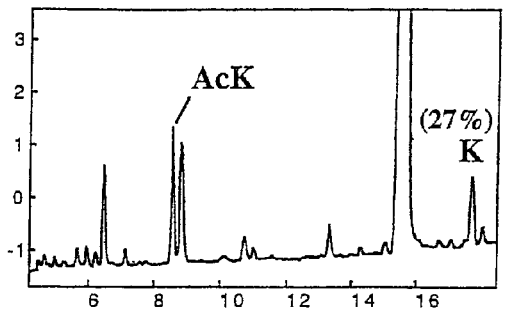
Figures 10C, 10F:
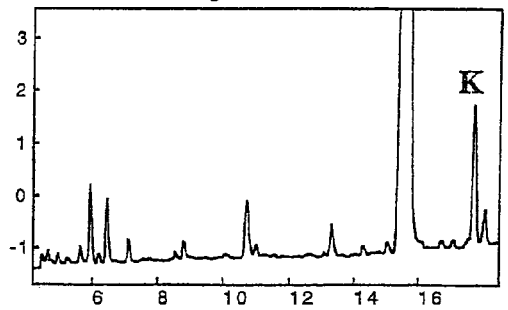

To analyze these reaction products further, peak 4, the singly deacetylated dimer, along with the input peak 5 were subjected to N-terminal protein sequencing by Edmann degradation (FIG. 10). The only differences between the input and reacted peaks occurred at lysines 9 and 14. Approximately 23-27% of the acetyl lysines at each position were deacetylated by Sir2p in the presence of NAD, in agreement with the calculated efficiency of the reaction and the mass spectroscopy data above. The unacetylated lysine 18 of peaks 4 and 5 is also shown for comparison. Thus, Sir2p is an NAD-dependent histone deacetylase which can deacetylate either lysine 9 or 14 of the H3N-terminus.

Effects of Inhibitors on Deacetylation and Putative ADP-Ribosylation

Figure 11A:
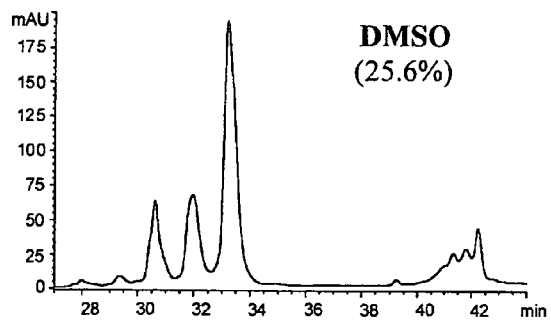
FIGS. 11a, 11b, 11c, 11d and 11e illustrate the effects of inhibitors on the deacetylase and putative ADP-ribosyltransferase activities of recombinant Sir2p (rSir2p). The HPLC chromatograms of the reactions in the presence of solvent only (FIG. 11a), 400 nM TSA (FIG. 11b) and 200 µM coumermycin A1 (Coumer) (FIG. 11e) are shown. The calculated efficiencies of the reactions are indicated. The effect of 200 µM coumermycin A1 on ADP-ribosylation of the intact histone H3 (FIG. 11c) and the H3 peptide (FIG. 11d) are examined on SDS-PAGE and TLC, respectively. pET corresponds to the vector control.
Figure 11B:
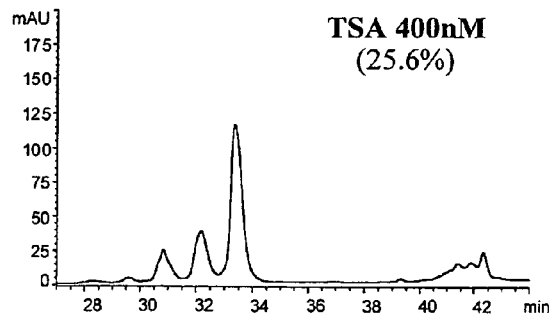

The effects of a potent inhibitor of histone deacetylases, trichostatin A (TSA) (Yoshida, M., et al., A. J. Biol. Chem. 265: 17174-17179 (1990)) was evaluated. TSA has been shown to act on constitutive heterochromatin in vivo, since it disrupts centromeric heterochromatin in S. pombe (Ekwall, K., et al., Cell 91: 1021-1032 (1997)). As shown in FIGS. 11a and 11b, TSA was totally incapable of inhibiting deacetylation, indicating that Sir2p is fundamentally different from the class of TSA-sensitive histone deacetylases, including Rpd3 (Taunton, J., et al., Science 272: 408-411 (1996)).

Figure 11E:
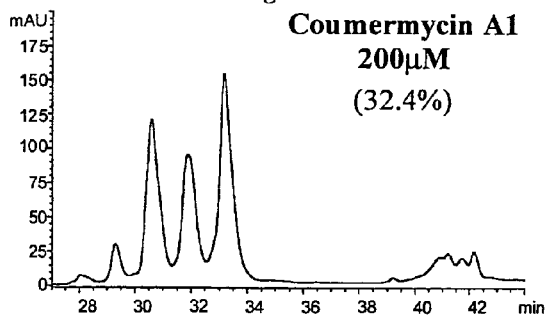
Figure 11C:
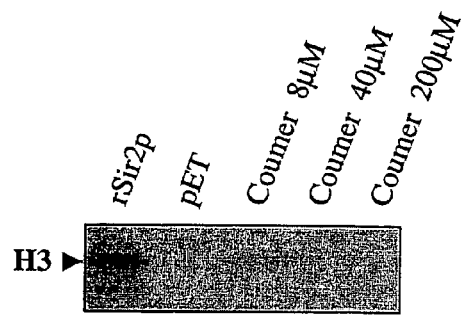
Figure 11D:
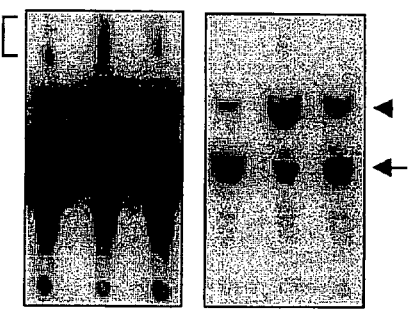
Figure 13A:
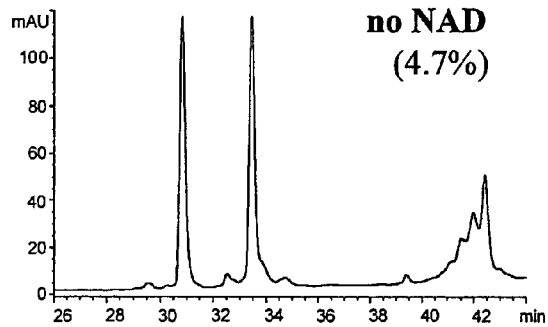
FIGS. 13a, 13b, 13c, 13d and 13e illustrate the effects of NAD derivatives on the Sir2p deacetylation activity of the H3 peptide. The HPLC chromatograms of the reactions with no NAD derivatives (FIG. 13a) and 1 mM concentration of NAD (FIG. 13b), NADH (FIG. 13c), NADP (FIG. 13d), and NADPH (FIG. 13e) are shown. The calculated efficiencies of the reactions are also indicated.
Figure 13D:
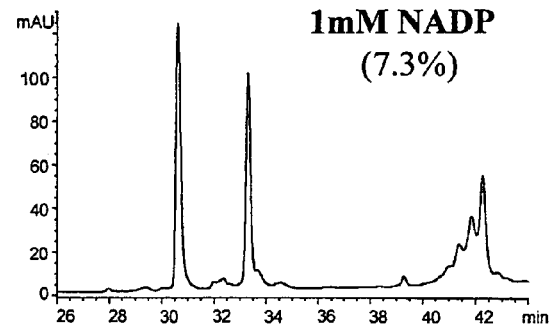
Figure 13B:
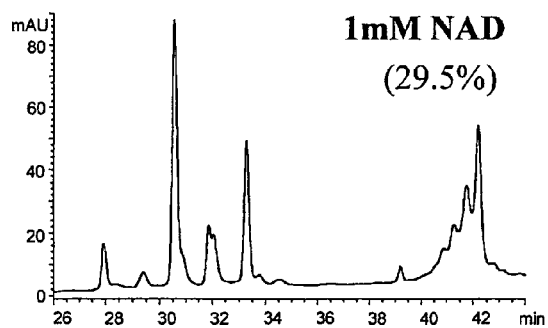
Figure 13E:
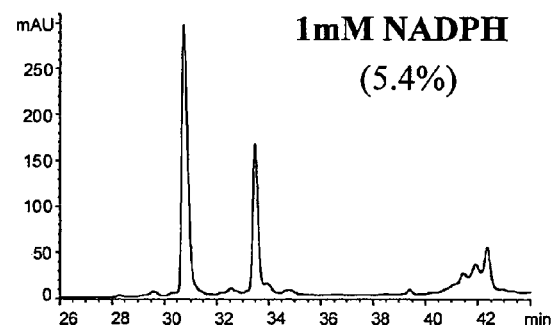
Figure 13C:
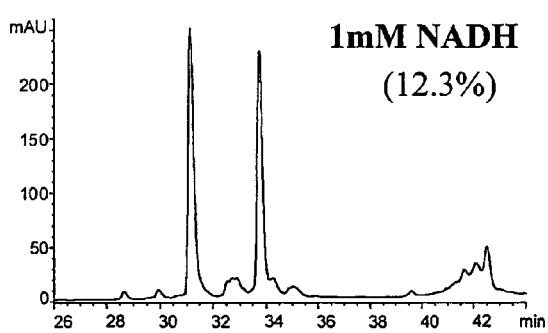
Figure 14B:
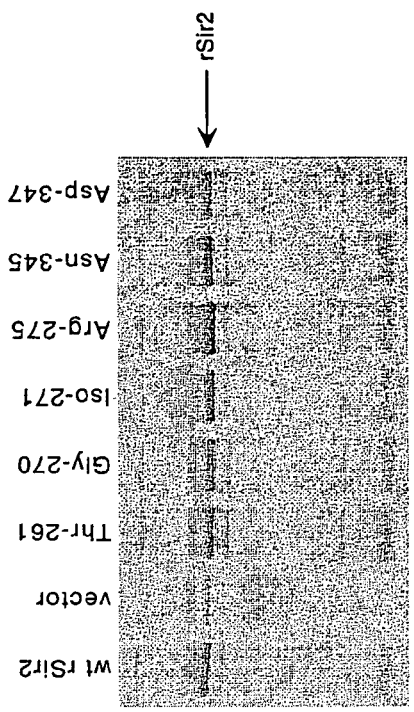
FIGS. 14a, 14b and 14c depict the putative ADP-ribosylation activities of Sir2 protein core domain mutants.
Figure 14C:
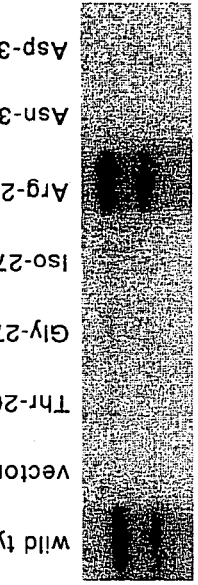
Figure 14A:
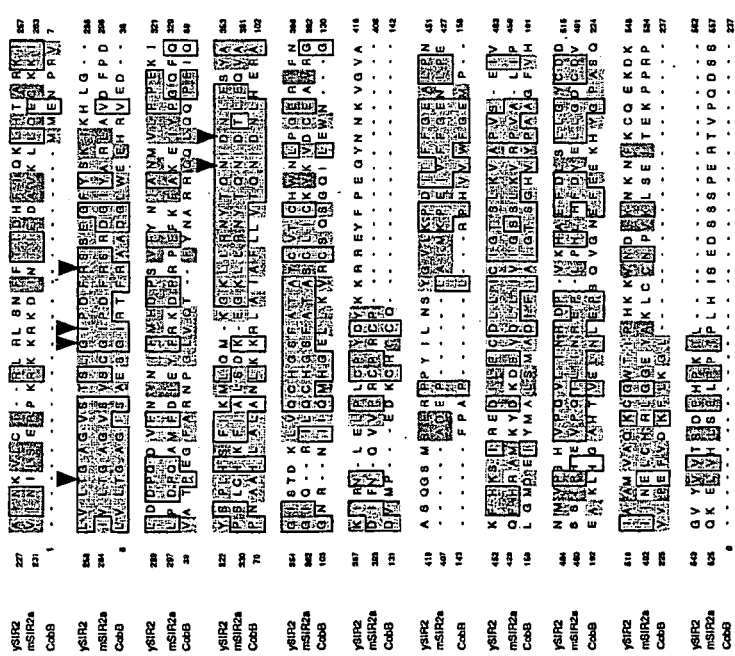

Sir2 proteins have been proposed to transfer a single ADP-ribose from NAD to protein (Frye, R. A., Biochem. Biophys. Res. Commun. 260: 273-279 (1999)). Consistent with this, we found that $^{32}$P was transferred from NAD to intact histone H3 (FIG. 11c) or to the H3 peptide (FIG. 11d). Transfer of label to the peptide was assayed using thin layer chromatography (TLC), which revealed not only this transfer but a substantial amount of NAD hydrolysis.

The effects of a known inhibitor of mono-ADP-ribosyl-transferases, coumermycin A1 (Banasik, M., et al., Mol. Cell. Biochem. 138: 185-187 (1994)) was evaluated. Both ADP-ribosylation (FIGS. 11c and 11d) and NAD hydrolysis (FIG.

11*d*) were inhibited by this drug at concentrations known to inhibit other mono-ADP-ribosyltransferases. Strikingly, coumermycin A1 was not capable of inhibiting deacetylation of the H3 tail by Sir2p (FIG. 11*e*). Thus, the ADP-ribosyltransferase and NAD hydrolase reactions are fundamentally distinct from this NAD-dependent deacetylation reaction. These two separable enzymatic activities of Sir2p may play distinct roles in vivo.

Mouse Sir2p also Catalyzes the Deacetylation of the Histone H3 Tail

A mouse Sir2 homolog was identified in the EST database and cloned the full length cDNA, termed mSir2α (FIG. 12*a*). The conserved region of this protein resembles yeast Sir2p more closely than do other mouse Sir2 proteins (FIG. 12*b*). To determine whether the mouse Sir2p homolog mSir2α would catalyze this deacetylation reaction, we incubated purified recombinant mSir2α with the di-acetylated H3 peptide and analyzed the reaction products by HPLC (FIG. 12*c*). The murine protein gave rise to the same array of products with a similar yield as the yeast enzyme, indicating that this deacetylation reaction is conserved from yeast to mammals.

NADH, NADP, and NADPH do not Activate Deacetylation by Sir2p

While there are literally hundreds of NAD-linked dehydrogenases that use NAD and NADH in oxidation/reduction reactions in cells, for example, glyceraldehyde-3-phosphate dehydrogenase, the requirement for NAD to drive any other enzymatic reaction is novel. This suggested that Sir2 proteins might be sensors of the energy or oxidation state of cells that transduces this status to the organization of chromatin structure. Catabolic reactions in cells, such as substrate level and oxidative phosphorylation in the utilization of glucose, are oxidative and use NAD to produce NADH. Biosynthetic reactions typically are reductive and use NADPH to produce NADP. It was thus of interest to determine whether NADH, NADP, and NADPH would function in the deacetylation reaction.

As shown in FIG. 13, NADP and NADPH did not function significantly, while NADH functioned weakly in the deacetylation of the H3 peptide by Sir2p. In fact, the small amount of deacetylated products in the NADH reaction can reasonably be attributed to a low level of oxidation of the NADH preparation. Also, neither NADH nor NADP significantly inhibited the deacetylase activity in a reaction with NAD (not shown). This remarkable specificity of Sir2p for NAD but not the other dinucleotides may allow Sir2 proteins to sense the energy or oxidation status of cells to link histone deacetylation and chromatin silencing to the metabolic rate.

Histone Deacetylase Defective Sir2p Mutants Show Defects in Silencing, Recombination Suppression and Life Span The present invention shows that mutations in Sir2 proteins reduce or eliminate the enzymatic activity of the protein affect these various functions, indicating that the histone deacetylase activity of Sir2p is important in vivo.

Figures 15A, 15B, 15C, 15D, 15E, 15F, 15G, 15H:
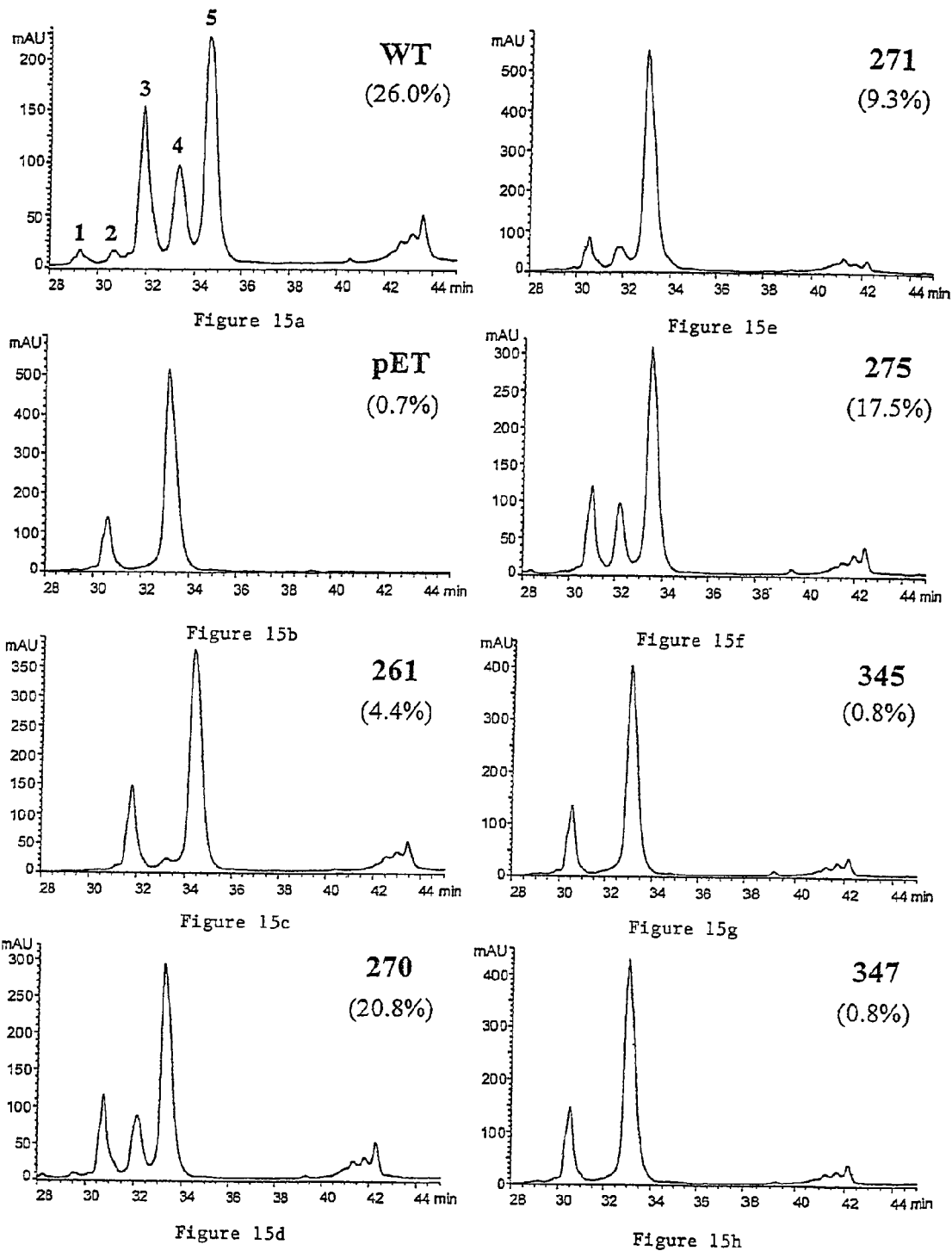
FIGS. 15a, 15b, 15c, 15d, 15e, 15f, 15g and 15h illustrate the effects of mutations in ySir2p on NAD dependent deacetylation of H3. The peptides were run on HPLC and the chromatograms based on the absorption at 220 nm recorded. The efficiency of reactions were determined by summing the area under the appropriate peaks.

A set of mutations in highly conserved residues of the core domain of SIR2 were constructed by site-directed mutagenesis (FIG. 17*a*) and cloned into vectors, along with the wild type, to allow expression of the recombinant proteins in *E. coli* or expression of single-copy genes from the native SIR2 promoter in *S. cerevisiae*. These 6×his (SEQ ID NO: 39) tagged proteins were purified from *E. coli* by a Ni-NTA column (FIG. 17*b*) and analyzed for the NAD-dependent histone H3 deacetylase activity in an assay with a di-acetylated H3 peptide (residues 1-20 acetylated on Lys9 and Lys14) and 1 mM NAD. HPLC separation of the reaction products yields five peaks of which 1, 2, a portion of 3 and 4 are deacetylated species of peptide (FIG. 15). In this deacetylase assay, mutants 345 and 347 were inactive, mutant 261 showed 17% of wild type activity, mutants 270 and 271 showed 80% and 36% wild type activity, respectively, and mutant 275 showed 67% wild type activity.

Figure 17A:
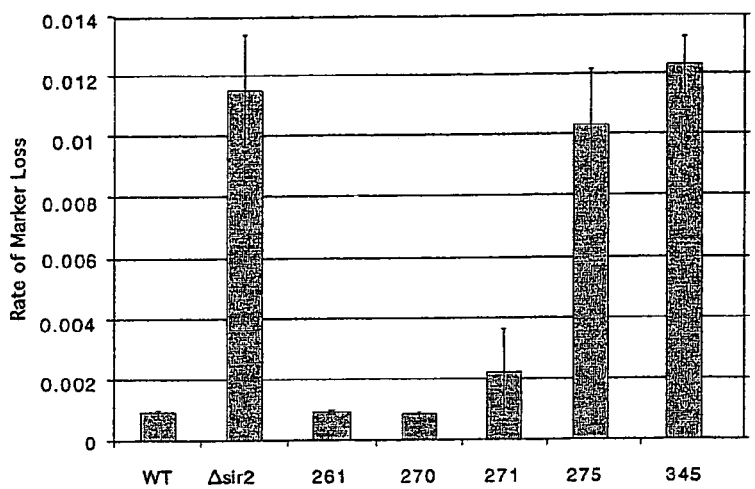
FIGS. 17a, 17b and 17c illustrate the effect of mutations in Sir2 on rDNA recombination and yeast life span.
Figure 17B:
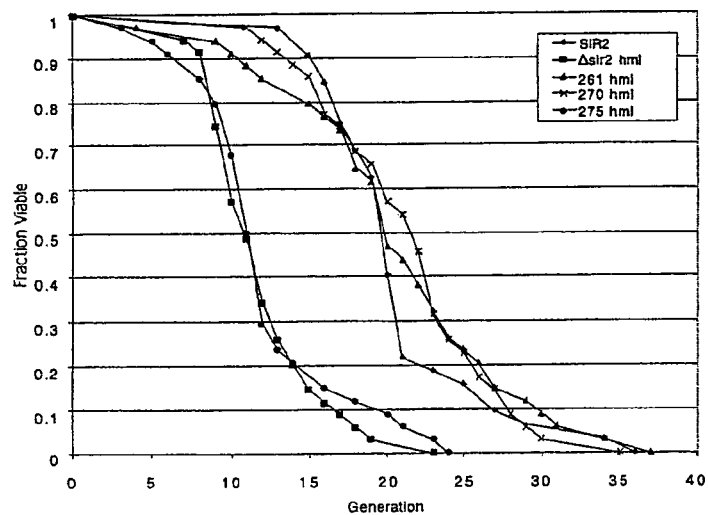
Figure 17C:
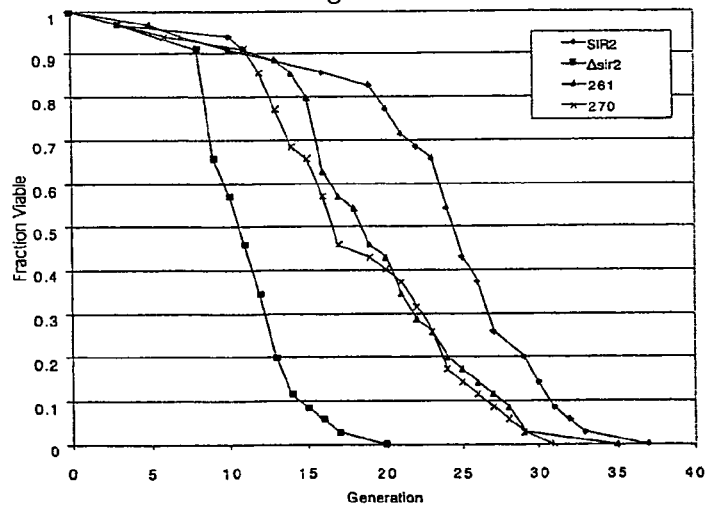

The Sir 2 mutant proteins were also analyzed for ADP-ribosyltransferase activity using the histone H3 substrate, (FIG. 17*c*). Mutants 345 and 347 were completely inactive, mutants 261, 270, and 271 displayed very weak activity, 4%, 7%, and 8%, respectively, and mutant 275 was about as active as wild type. The same pattern of activities was observed using a peptide of the N-terminal tail of histone H3 (not shown).

To examine the functions of these mutants in vivo, we studied yeast indicator strains in which the endogenous SIR2 had been deleted and the wild type and mutant SIR2 genes integrated back into the genome. All strains used are isogenic derivatives of W303R (Kaeberlein, M., et al., *Genes Dev.* 13: 2570-2580 (1999)) and all results are summarized in FIG. 18. The mutant proteins were visualized by Western blot and found to be expressed at approximately the same level as wild type, with a small reduction in the level of mutant 261 and perhaps 275, and 345 (FIG. 16*a*).

Silencing of the HMLα and HMRa mating loci was assayed by mating with a haploid strain of opposite mating type and monitoring the appearance of diploids on selective media. In this assay (FIG. 16*b*), mutants 261, 270, and 271 were mating proficient, indicating that silencing was essentially intact, and mutants 345, 347, and, surprisingly, 275 were defective. Telomere silencing was determined by repression of the telomere-positioned URA3 gene, which gives rise to growth on media containing 5-fluoro-orotic acid (FOA). Serial dilution of wild type and mutant strains on FOA plates indicated that mutant 261 silenced about as well as wild type, 270 showed partial silencing, and 271, 275, and 345 were defective (FIG. 16*c*). Silencing in the rDNA was determined by a serial dilution onto adenine-lacking media of strains with ADE2 inserted into the rDNA (Kaeberlein, M., et al., *Genes Dev.* 13: 2570-2580 (1999)). To facilitate detectable of differences in rDNA silencing, a rpd3Æ strain was used which displays enhanced silencing (Smith, J. S., et al., *Mol. Cell Biol.* 19: 3184-3197 (1999)). By this assay mutants 261 and 270 silenced about as well as the wild type, mutant 271 showed weak silencing, and mutants 275, and 345 were totally defective (FIG. 16*d*).

The data indicate a general, although not strictly quantitative, correlation between deacetylase activity in vitro and silencing in vivo (except for 275, see below). Mutant 345 is inactive for deacetylase activity in vitro and silencing in vivo. Mutants 261, 270, and 271, have intermediate levels of deacetylase activities in vitro and intermediate effects on silencing in vivo. Mutant 261 is proficient in all silencing assays, but does show a defect in a more sensitive silencing assay of life span, below. Mutant 270 is proficient in HM and rDNA silencing but intermediate in silencing at telomeres, and 271 is proficient in BM silencing, but intermediate to weak in silencing at telomeres and rDNA. An intermediate levels of deacetylase activity can are sufficient to mediate silencing, but the specific level of silencing may be modulated by other variables affected by these mutations, such as the interaction of Sir2p with partner proteins. The lack of silencing activity in mutant 275 was unexpected and may reflect an inability of that mutant protein to localize properly in the nucleus or to interact with important partners in vivo.

Replicative life span of mother cells is due in part to the accumulation of extrachromosomal rDNA circles (Sinclair, D. A., et al., *Science* 277: 1313-1316 (1997); (Sinclair, D. A., et al., *Cell* 91: 1-20 (1997)) that arise by homologous recombination (Park, P. U., et al., *Mol. Cell. Biol.* 19: 3848-3856 (1999)) in the tandem array of rDNA repeats on chromosome XII. This recombination is suppressed 5-10 fold by SIR2 (Gottlieb, S., et al., *Cell* 56: 771-776 (1989)), allowing cells to enjoy their normal life span. To measure recombination frequencies, wild type and Sir2 mutant strains containing the ADE2 gene inserted into the rDNA were plated on YPD media. This media is limiting in adenine, causing ade2– colonies to accumulate a red pigment. Half-red/white sectored colonies indicate ADE2 loss in the first generation after plating, and the frequency of these colonies compared to Ade+ colonies is a direct measure of the recombination rate in the rDNA. By this assay, SIR2 suppressed recombination about 12-fold compared to the SIR2 deletion strain (FIG. 17a). Mutants 261 and 270, showed a high degree of suppression in the range of wild type, mutant 271 showed partial suppression, and mutants 275, and 345 were as defective as the SIR2 deletion. Thus, the activities of these mutants in this recombination assay are similar to their activities in the rDNA silencing assay, above.

Previous findings show that the short life span of SIR2 deletion mutants in strain W303R is a composite of a failure to suppress rDNA recombination and also a failure to repress transcription of the copies of mating type information at HM loci yielding the a/α cell type (Kaeberlein, M., et al., *Genes Dev.* 13: 2570-2580 (1999)). Expression of a/α leads to a higher rate of recombination in the rDNA. The life spans of representative mutants were first determined in strains in which HMLα was deleted to avoid any contribution of the a/α cell type if weak derepression occurred at those loci. The sir2 deletion shortened life span about 50% compared to wild type, as expected (FIG. 17b). Mutants 261 and 270 complemented the sir2 deletion to give a wild type life span and mutant 275 was completely defective in complementing the life span defect, consistent with the activities of these mutants in the recombination assay.

Life span determination in wild type HM strains is a very sensitive known assay for Sir2 activity in vivo, i.e. in this assay even SIR2/SIR2 heterozygous diploids show a pronounced defect (Kaeberlein, M., et al., *Genes Dev.* 13: 2570-2580 (1999)). Thus, the life spans of SIR2 mutants were also determined in otherwise wild type haploid strains (FIG. 17c). Now a partial defect was observed in the 261 and 270 mutants, which can be attributed to a slight defect in the maintenance of repression at HM loci. Mutant 275 was again defective. Thus, with this sensitive assay, the 261 and 270 SIR2 mutants show defects, which parallel their enzymatic defects in vitro. Mutant 275 is exceptional, as in the above assays.

Previous studies indicate that the acetylation state of lysines in the amino-terminal tails of histones H3 and H4 is crucial for silencing in vivo (Braunstein, M., et al., *Genes Dev* 7: 592-604 (1993); (Braunstein, M., et al., *Mol. Cell. Biol.* 16: 4349-4356 (1996); (Turner, B. M., et al., *Cell* 69: 408-411 (1992)). Lysines 9 and 14 of H3 and lysines 5, 8, and 16 of H4 are hypoacetylated in silenced chromatin and return to their acetylated state in SIR mutants (Braunstein, M., et al., *Genes Dev* 7: 592-604 (1993); (Braunstein, M., et al., *Mol. Cell. Biol.* 16: 4349-4356 (1996)). Moreover, mutations in the lysines of the H3 tail, especially to uncharged residues, cause a loss of silencing (Thompson, J. S., et al., *Nature* 369: 245-247 (1994)). These data show that Sir2 mutations which eliminate deacetylase activity show silencing defects in vivo.

Taken together these findings suggest that the NAD-dependent histone deacetylase activity of Sir2p sufficiently explains the SIR2 functions of silencing, suppression of rDNA recombination, and life span extension in vivo. H3 and H4 are acetylated as a prerequisite to their recognition by chromatin assembly factors (Ma, X. J., et al., *Proc. Nat. Acad. Sci.* 95: 6693-6698 (1998)). Sir2p can be a target to specific genomic sites and initiates silencing by deacetylating H3 and, most likely, H4. It is possible that the putative ADP-ribosyltransferase activity of Sir2p also plays some role in these in vivo functions.

These data show that histone deacetylation by Sir2p has an absolute requirement for NAD. These data are striking and can couple chromatin silencing to the energy status of cells. Caloric restriction (Weindruch, R. H., et al., *J. Nutrit.* 116: 641-654 (1986)) increases life span in a wide variety of eukaryotic species. This regimen may increase available NAD and trigger the activity of Sir2 proteins, leading to greater silencing and a longer life span. Similarly normal aging can be caused, in part, by a decrease in the activity of Sir2 proteins, perhaps owing to a reduction in available NAD, causing a loss of silencing and the deleterious alteration in the pattern of gene expression.

Mouse Sir2p homolog mSir2α has histone deacetylase activity that closely resembles yeast Sir2p. The Sir2 proteins described herein and related mammalian Sir2 proteins (Brachmann, C. B., et al., *Genes Dev.* 9: 2888-2902 (1995); (Frye, R. A., *Biochem. Biophys. Res. Commun.* 260: 273-279 (1999)) could play regulated roles in chromatin structure, which might include changes in genome organization during cellular differentiation and in response to physiological stimuli, including caloric restriction. If aging were due, at least in part, to a loss of silencing, then interventions to increase the activity of Sir2 proteins can slow aging in mammals.

Increased Dosage of a *C. elegans* sir-2 Gene Extends Life Span in Worms

The dietary regimen of calorie restriction extends life span in a wide variety of species ranging from yeast to mammals (Pugh, T. D., *Neurobiol. Aging,* 20:157-165 (1999)). Genes regulating life span have been postulated in several model organisms, but a universal mechanism regulating aging has not emerged. For example, in mice, deletion of p66shc, a gene that signals an apoptotic response to DNA damage, appears to extend life span (Migliaccio, E. et al., *Nature,* 402:309-313 (1999)). In *Drosophila*, a mutation reducing the activity of a putative membrane protein methuselah also extends life span (Lin, Y. J. et al., *Science,* 282:943-946 (1998)).

In *C. elegans*, life span is regulated by a signal transduction pathway that also controls entry into a dormant larval state, termed dauer, when nutriens are scarce. Mutations reducing the activity of an insulin-like receptor (daf-2) or a PI(3) kinase (age-1) favor entry into the dauer state during larval development and also extend life span in adults (Kenyon, C., *Cold Spring Harbor Lab. Press,* 791-813 (1997); Kimura, K. et al., *Science* 277:942-946 (1997); Tissenbaum, et al., *Genetics,* 148: 703-717 (1998)). Down-regulation of this pathway activiates a forkhead transcription factor (daf-16), which may regulate targets that promote dauer formation in larvae and stress resistance and longevity in adults (Lin, et al., *Science,* 278: 1319-1322 (1997); Ogg, S., et al., *Nature,* 389:994-999 (1997)). A second class of mutations that extend life span in *C. elegans*, termed clk, appears to affect an increase in the time of development from embryo to adulthood (Lakowski, B. et al., *Science* 272:1010-1013 (1996)). A molecular link to metabolism is made by clk-1 mutations, which reduce levels of the electron carrier coenzyme Q (Ewbank, J. J., et al., *Science,* 275: 980-983 (1997); Felkai, S., et al., *EMBO Journal,* 18: 1783-1792 (1999)).

In yeast, the activity of the SIR2 gene determines the life span of mother cells. As shown herein, the addition of one extra copy of SIR2 extends life span significantly (FIGS. 17a, 17b, 17c). Sir2p mediates chromatin silencing at mating type genes (Rine, J., et al., *Genetics*, 116:9-22 (1987)), telomeres (Gottschling, D. E., et al., Cell, 63:751-762 (1990)) and ribosomal DNA (rDNA) (Gottlieb, S., et al., *Cell*, 56:771-776 (1989); Bryk, M., et al., *Genes Devel.*, 11:255-269 (1997); Smith, J. S., et al., *Genes Devel.*, 11:241-254 (1997)). As shown herein, silencing is regulated by the histone deacetylase enzymatic activity of Sir2p that, unlike other histone deacetylases, depends on NAD as a cofactor. The ability of calorie restriction to extend life span in yeast requires SIR2 and NPT1, a gene involved in NAD synthesis. Thus, by responding to levels of available NAD, yeast Sir2p links nutrient availability and life span by mediating the strength of chromatin silencing.

Figure 23:
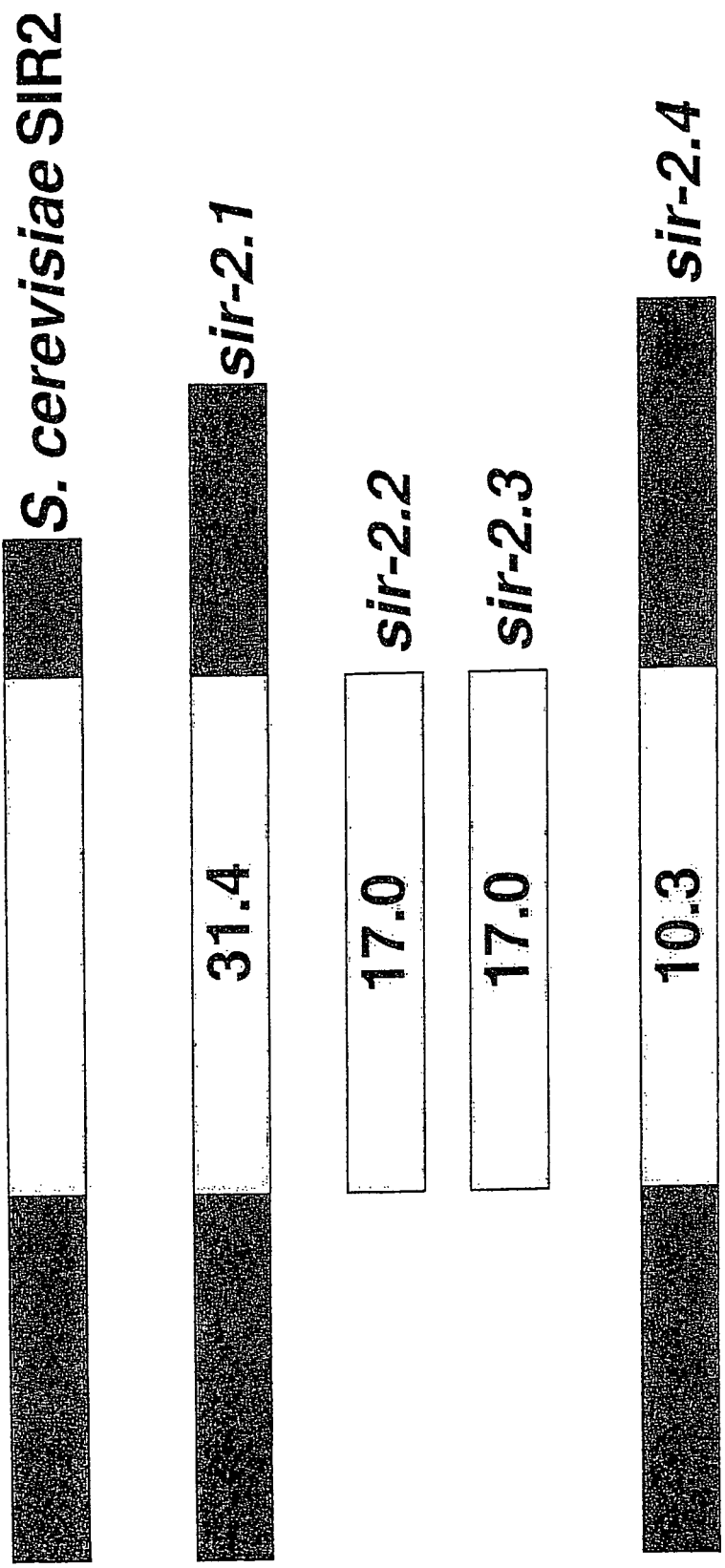
FIG. 23 depicts the similarity (31.4%, 17.0%, 17%, 10.3%) of the C. elegans sir-2 family (sir-2.1, sir-2.2, sir-2.3 and sir-2.4) to S. cerevisiae SIR2.

Since Sir2p homologues in higher eukaryotes, including ammals, display the NAD-dependent histone deacetylase activity (Imai, S., et al., *Nature*, 403:795-800 (2000)), these proteins might function generally in coupling nutrient availability to life span. The *C. elegans* genome has four genes with similarity to yeast SIR2 (Frye, R. A., *Biochemical and Biophysical Research Communication*, 273:793-798 (2000)). The sir-2.1 gene has 35% identity to yeast Sir2p in the conserved core domain (FIG. 23). Other sir-2 genes (2.2, 2.3, 2.4) are between 10-20% identical in their conserved domains.

Figure 24A:
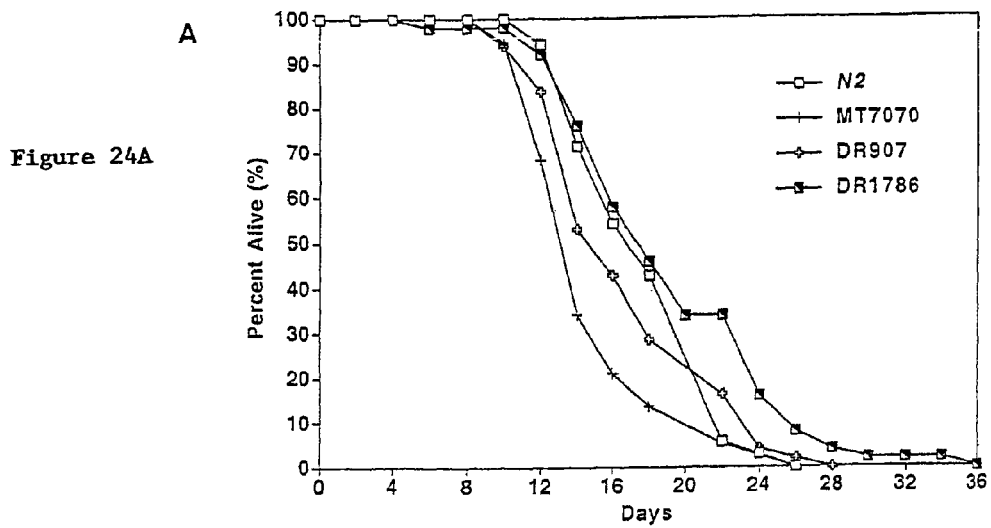
FIG. 24A depicts extension of lifespan in C elegans with duplication of the sir-2.1 gene in C. elegans.

To determine whether the sir-2 genes of *C. elegans* might regulate life span, strains with duplication of many chromosomal regions, including duplications covering these loci, were evaluated. Free or attached duplications are stably maintained in *C. elegans* and the dosage of genes is increased by 50% compared to normal hermaphrodites (Herman, R. K., et al., *Developmental Biology*, 49:200-219 (1979)). Strains containing 35 different duplications, covering approximately half of the *C. elegans* genome (Table 1) were evaluated. Most of these strains, including those with extra copies of the sir-2.2, 2.3 and 2.4, exhibited life spans similar to or shorter than the parental strain (Table 1). Interestingly, strain DR1786 which contains the free duplication mDp4 showed a significant extension in both the mean and maximum life span (Table 1 and FIG. 24A). As shown in FIG. 24A, the mean value for each strain is as follows: mean±standard error, and the number of trials is in parentheses. The number of animals scored is designated as "n": N2=17.6±0.2 (13), n=451; MT7070=14.6±0.6 (1), n=38; DR907=16.6±0.7 (1), n=49; DR1786=19.4±0.6 (2), n=50; p<0.05 compared to N2.

This duplication, a part of chromosome IV, includes the sir-2.1 locus. Another chromosome IV duplication (mDp1; present in strains DR907 and MT7070; (FIG. 24A) includes approximately two-thirds of the mDp4 duplication, but not the region carrying the sir-2.1 locus, and does not extend life span.

TABLE 1

Life span analysis of duplication strains

| Strain | Duplication; Location | Mean Life Span (n) | Range |
|---|---|---|---|
| N2 | | 15.2 ± 0.5 (47) | (9-23) |
| KR1293 | hDp12; sir-2.4p | 11.7 ± 0.3 (31) | (8-14) |
| KR1725 | hDp44; sir-2.4 | 14.7 ± 0.3 (41) | (10-20) |
| KR1722 | hDp52; sir-2.4 | 15.8 ± 0.4 (40) | (10-22) |
| SP75 | mnDp25; I | 14.0 ± 0.5 (31) | (5-20) |
| KR1704 | hDp68; sir-2.4p | 14.0 ± 0.4 (32) | (12-18) |
| TY1912 | yDp7; sir-2.4p | 15.8 ± 0.6 (43) | (6-24) |
| DR1786 | mDp4; sir-2.1 | 17.3 ± 1.0 (24)[a] | (6-28) |
| SP116 | mnDp9; sir-2.2, .3p | 16.8 ± 0.5 (75) | (8-26) |
| SP117 | mnDp10; sir-2.2, .3 | 13.7 ± 0.6 (19) | (10-18) |
| N2 | | 15.1 ± 0.3 (41) | (12-20) |
| KR1732 | hDp48; sir-2.4 | 17.3 ± 0.5 (36)[b] | (12-28) |
| RW6011 | mnDp34; II | 17.6 ± 1.0 (24)[c] | (12-30) |
| DR1786 | mDp4; sir-2.1 | 21.1 ± 1.0 (27)[d] | (12-36) |
| TY1909 | yDp4; sir-2.2, .3p | 14.0 ± 0.6 (38) | (9-20) |
| SP125 | mnDp5; X | 18.8 ± 1.0 (31)[e] | (12-30) |
| N2 | | 17.8 ± 0.6 (34) | (11-25) |
| MT7070 | mDp1; IV | 14.6 ± 0.6 (38) | (9-25) |
| DR907 | mDp1; IV | 16.6 ± 0.7 (49) | (7-28) |
| N2 | | 18.1 ± 0.8 (30) | (14-26) |
| KR1108 | hDp8; I | 18.7 ± 0.8 (38) | (12-30) |
| KR1110 | hDp11; I | 19.7 ± 0.7 (35) | (10-26) |
| KR1112 | hDp9; I | 18.7 ± 0.9 (30) | (10-26) |
| KR1236 | hDp2; sir-2.4 | 15.3 ± 0.6 (23) | (12-22) |
| KR1284 | hDp15; I | 12.8 ± 0.4 (19) | (10-18) |
| KR1280 | hDp13; I | 10.2 ± 0.3 (36) | (8-14) |
| KR1548 | hDp22; sir-2.4 | 14.5 ± 0.4 (29) | (10-18) |
| KR1282 | hDp16; sir-2.4 | 10.9 ± 0.6 (34) | (8-26) |
| KR1815 | hDp30; sir-2.4p | 12.5 ± 1.0 (21) | (6-28) |
| SP1911 | mnDp1; III; X | 14.3 ± 0.4 (37) | (8-22) |

Life span is expressed as the mean ± standard error at 20° C. Data were analyzed by Wilcoxen Rank test to determine significance. Statistical significance indicated by letter [a] = p < 0.05; [b] = p < 0.0001; [c] = p > 0.05; [d] = p < 0.0001; [e] = p < 0.0003. The number of animals tested is indicated as "n". Duplications whose endpoints have not been determined precisely enough to be certain that the duplication contains sir-2.1 are depicted by "p". Data is shown from an experiment using plates containing FUDR. Each grouping refers to a set of strains tested at the same time.

Figure 24B:
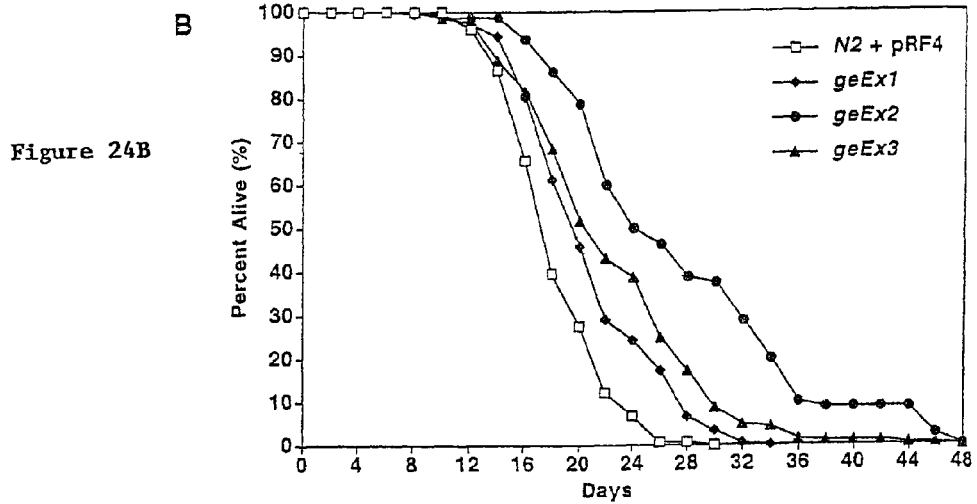
FIG. 24B depicts extension of lifespan in C. elegans following insertion of the sir-2.1 transgene.

To determine whether sir-2.1 was responsible for extension of life span, a 2.2 kb genomic fragment of sir-2.1 was injected into the N2 parental strain along with the transformation marker gene rol-6 using well-established methods. Three independent transgenic lines were identified. All three transgenic lines containing sir-2.1 (geEx1, geEx2, and geEx3) showed significantly extended life spans (p<0.05; mean life span 20.9±0.3, 27.4±1.0, and 22.4±0.4, respectively) compared to animals transgenic for rol-6(su1066) alone (mean life span 18.2±03) or the N2 parent (mean life span 17.6±0.2; FIG. 24B). As shown in FIG. 24B, the mean value for each strain is as follows: mean±standard error, number of trials in parentheses. The number of animals scored is designated as "n": N2+pRF4=18.3±0.3 (3), n=142; geEx1=20.9±0.3 (6), n=214; geEx2=27.4±1.0 (4), n=80; geEx3=22.4±0.4 (6), n=209, p<0.05 for all three extrachromosomal array lines when compared to wild type. There was no significant effect of rol-6 on life span (mean life span 18.2±0.3 with rol-6; 17.6±0.2 wild type alone).

Figure 24C:
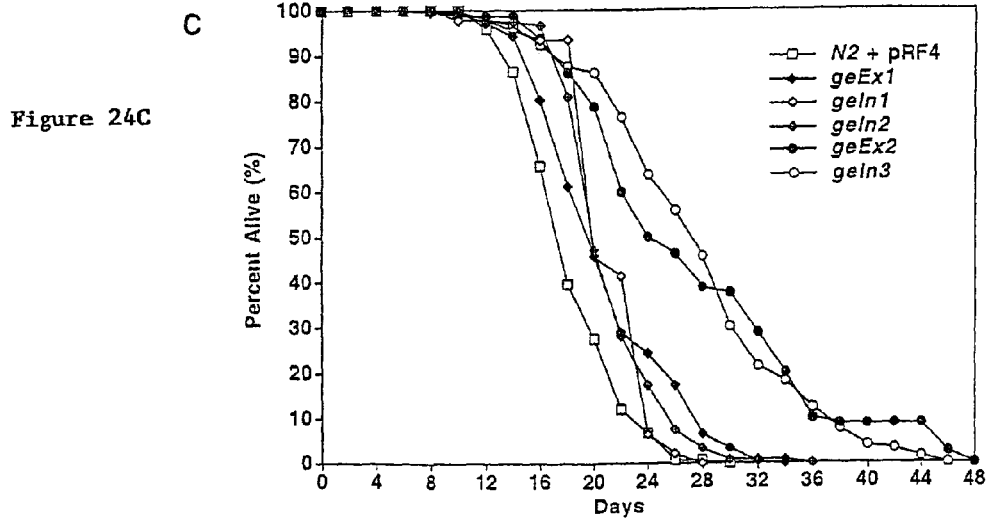
FIG. 24C depicts life span extension in C. elegans to the free array following integration of extrachromosomal arrays of the sir-2.1 gene.

Transgenic worms carrying the SIR2 extrachomosomal array were used to derive stably integrated lines using routine techniques. Integrants derived from both geEx1 (geIn1, geIn2) and geEx2 (geIn3) had an increase in sir-2.1 copy number of at least several-fold by Southern blotting compared to the N2 control. These lines exhibited the same long life spans as lines containing extrachromosomal arrays (geEx1=20.9±0.3, geIn1=21.6±0.3, and geIn2=21.5±0.5; geEx2=27.4±1.0 and geIn3=27.6±0.4; (FIG. 24C). As shown in FIG. 24C, the mean value for each strain is as follows: mean±standard error, number of trials in parentheses. The number of animals scored is designated as "n": N2+pRF4=18.3±0.3 (3); geEx1=20.9±0.3 (6), n=214; geIn1=21.6±0.3 (2), n=46; geIn2=21.5±0.5 (3), n=121; geEx2=27.4±1.0 (4), n=80; and geIn3=27.5±0.4 (7), n=276.

Thus, in yeast, increasing the dosage of a SIR2 gene extends the life span of *C. elegans* (FIGS. 17a, 17b and 17c). Since the mean and maximum life spans of the sir-2.1 transgenic animals were extended beyond animals bearing mDp4, genes detrimental to life span when increased in dosage may be present on the free duplication Alternatively, the increase in dosage of the sir-2.1 transgene may be the cause of life span extension beyond that of the free duplication.

Additional experiments were performed to determine whether sir-2.1 extends life span by acting through one of the known *C. elegans* pathways. The extension in life span by mutations in the insulin-like signaling dauer pathway (daf-2, age-1, or pdk-1) is abolished in strains mutant in the downstream gene daf-16 (Kenyon, C., *Cold Spring Harbor Lab. Press*, 791-813 (1997); Tissenbaum, H. A., et al., *Genetics*, 148:703-717 (1998); Paradis, S. et al., *Genes Devel.*, 13:1438-1452 (1999)). Therefore, to determine whether sir-2.1 acts in this pathway, the effect of a mutation in daf-16 on sir-2.1-mediated longevity was determined.

Figure 25A:
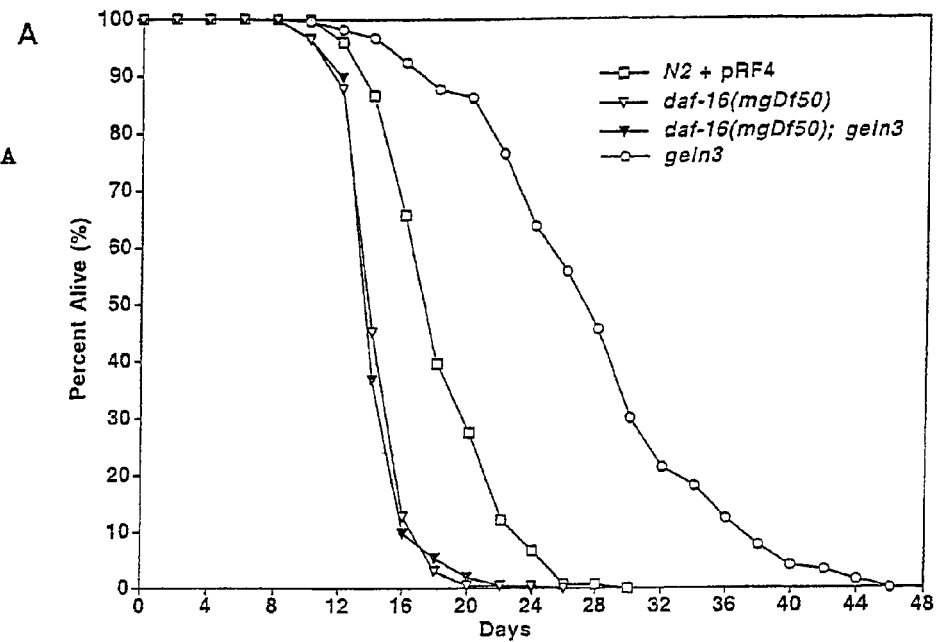
FIG. 25A depicts suppression of life span extension in C. elegans containing the sir-2.1 transgene by daf-16.

The extrachromosomal array or integrated sir-2.1 were thus crossed into a daf-16 null background. daf-16(mgDf50) is a large deletion that eliminates most of the daf-16 coding region (Ogg, S., et al., *Nature*, 389:994-999 (1997)). In all cases, the extension of life span by sir-2.1 was abolished in the daf-16(mgDf50) background (FIG. 25A). As shown in FIG. 25A, the mean value for each strain is as follows: mean±standard error, number of trials in parentheses. The number of animals scored in the given experiment is designated as "n". N2+pRF4=18.3±0.3 (3), n=142; daf-16 (mgDf50)=14.6±0.1 (5), n=274; daf-16(mgDf50); geIn3=13.7±0.2 (4), n=204; geIn3=27.5±0.4 (7) n=276. Similar finding were seen with the extrachromosomal array lines: daf-16(mgDf50); geEx1=14.2±0.5 (1) n=40, daf-16 (mgDf50); geEx2=14.0±0.3 (1) n=29; daf-16(mgDf50); geEx3=14.4±0.4 (1) n=47. This experiment was repeated on different independent isolates from both daf-16(mgDf50); geEx1 and daf-16(mgDf50); ge Ex3 with similar results.

daf-16(mgDf50) animals displayed a shorter mean life span than wilde type animals (daf-16(mgDf50)=14.6±0.1 versus N2=17.6±0.2) similar to other alleles of daf-16 (Lin, K., et al., *Science*, 278:1319-1322 (1997); Ogg, S., et al., *Nature*, 389:994-999 (1997)). Life span of geIn3 animals was 27.6±0.4 and was reduced to 13.7±0.2 in daf-16(mgDf50); geIn3 animals, similar to the life span of daf-16(mgDf50) mutants alone. When daf-16(mgDf50) was crossed to any of the three extrachromosomal arrays a similar reduction in life span to the level of daf-16 mutant alone was observed (FIG. 25B).

Figure 25B:
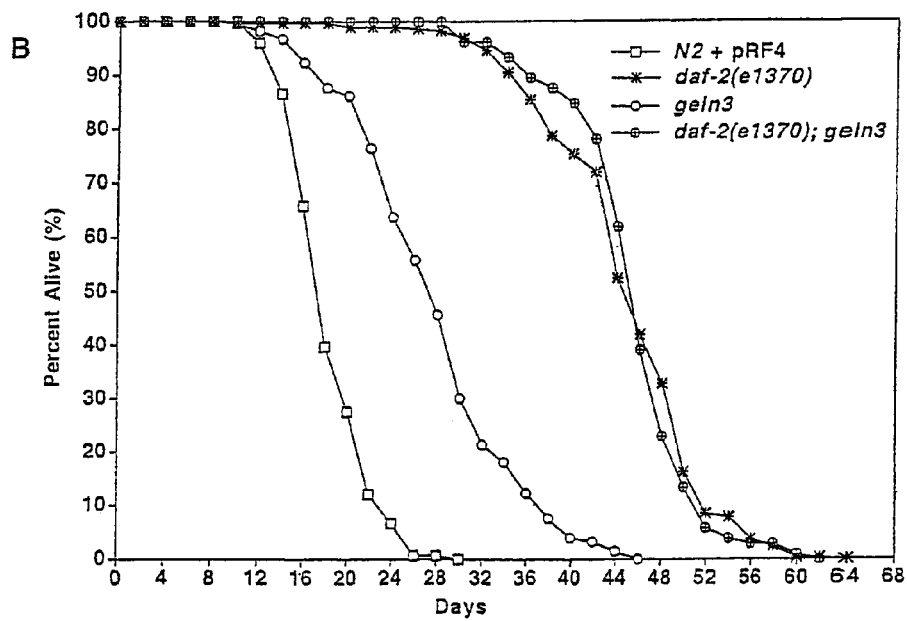
FIG. 25B illustrates daf-2 does not synergize with sir-2.1 transgene in C. elegans to extend life span.

As shown in FIG. 25B, the mean value for each strain is as follows: mean±standard error, number of trials in parentheses. The number of animals scored in the given experiment is designated as "n": N2+pRF4=18.3±0.3 (3), n=142; daf-2 (e1370)=44.7±0.4 (6), n=293; daf-2(e1370); geIn3=45.0±0.5 (2), n=105; geIn3=27.5±0.4 (7) n=276. Similar values were seen with another independent isolate of daf-2(e1370); geIn3. When crossed into a daf-2 background geEx1 and geEx3 showed similar finding with the means similar to daf-2 (e1370) alone: daf-2(e1370); geEx1=41.9±1.1 (2), n=63; and daf-2(e1370); geEx3=47.2±1.4 (1) n=36. This experiment was repeated on different independent isolates from both daf-2(e1370); geEx1 and daf-2(e1370); geEx3 with similar results. Side by side comparisons showed that the rol-6 (su1066) extrachromosomal array did not affect the mean or maximum life spans of the daf-2(e1370) mutant. Therefore, the life span extension of the overexpressed sir-2.1 requires DAF-16 activity, indicating sir-2.1 acts in the insulin-like signaling pathway.

The sir-2.1 transgene should not further extend the life span of a daf-2 mutant, in which the pathway has been inactivated. Sir-2.1 transgenic arrays were crossed into a daf-2(e1370) mutant background. The daf-2 mutation increased life span dramtically, similar to previously published data (Kenyon, C., *Cold Spring Harbor Lab. Press*, 791-813 (1997); Hsin, H., et al., *Nature*, 399: 362-366 (1999)) (FIG. 25B). However, no further extension was observed in a strain bearing the transgene and daf-2(e1370) animals (FIG. 25B). Thus, the sir-2.1 transgene functions to extend life span in the daf-16 dauer signaling pathway.

Although many mutations in the insulin-like signaling pathway extend life span, they also show other pleiotropies, including dauer formation, a reduced brood size and early larval lethality (daf-2 and age-1 mutations, Tissenbaum, et al., *Genetics*, 148: 703-717 (1998); Gems, D., et al., *Genetics*, 150:129-155 (1998)) and dauer formation at high temperature (27° C.) (e.g. unc-31 and unc-64, Ailion, M., et al., *Proceedings of the National Academy of Sciences*, 96:7394-7397 (1999)). Additionally, mutations in clk-1, which extend life span independent of the insulin-like signaling pathway, have the phenotype of a reduced rate of development (Lakowski, B. et al., *Science* 272:1010-1013 (1996)). Therefore, it was determined whether sir-2.1 extrachromosomal transgenic animals displayed any of these other pleiotropic phenotypes.

Brood size and time of development from hatching through the four larval stages to adulthood were normal in these animals when compared to wild type animals carrying a rol-6(su1066) extrachromosomal array (Table 2). Additionally, no inverse correlation between the mean brood size of the animals and the life span extension was evident. The extrachromosomal array that caused the greatest increase in life span (mean life span geEx2=27.7) had the largest mean brood size (288) (Table 2). Furthermore, there was little dauer formation at 27° C. or at lower temperatures in any of the transgenic SIR2 strains compared to wild type animals with or without the rol-6(su1066) extrachromosomal array. Thus, sir-2.1 transgenes do not affect fertility, early development or dauer formation, unlike the previously isolated mutations that increase life span in *C. elegans*.

TABLE 2 sir2.1 transgenes do not increase life span by decreasing fertility

| Transgene | Brood Size | Life Span |
|---|---|---|
| pRF4 | 242.0 (6) | 18.2 (142) |
| geEx1 | 245.0 (7) | 20.9 (214) |
| geEx2 | 281.0 (6) | 27.4 (80) |
| geEx3 | 228.0 (6) | 22.4 (209) |

For each worm, the total number of eggs laid were counted and the resulting number of progeny from these eggs were counted three days later. The number of animals tested is indicated as "n". A comparison of the number of progeny to the number of eggs indicated that no dead eggs or arrested larvae were observed in any of the broods. Brood counts are mean ± standard error for one experiment.

Mutations in several genes in the insulin-like signaling pathway including, daf-2, unc-31 and unc-64 are also known to synergize with mutations in a parallel TGF-β signaling pathway, represented by daf-4 and daf-1 (Ogg, S., et al., *Nature*, 389:994-999 (1997); Ailion, M., et al., *Proceedings of the National Academy of Sciences*, 96:7394-7397 (1999)). daf-1 and daf-4 are Type I and Type II TGF-β receptors and mutations in either of these two genes cause a temperature-sensitive dauer-constitutive phenotype in larvae but do not affect life span in adults (Kenyon, C., *Cold Spring Harbor Lab. Press*, 791-813, (1997); Estevez, M., et al., *Nature*, 365: 644-649 (1993); Georgi, L. L., et al., *Cell*, 61:635-645 (1990).

The sir-2.1 transgenic lines were crossed into daf-1 (m40) or daf-4(m63) mutants to determine if sir-2.1 synergizes with the TGF β pathway, which would further implicate sir-2.1 in the daf-16 dauer pathway. An increase in dauer formation at the permissive temperature of 20° in sir-2.1 transgenic animals in combination with either daf-4 or daf-1 mutations was observed (Table 3). Moreover, the tendency to form dauers correlated with the life span extension of the two transgenic lines tested. For example, at 20° C., 48% of the roller progeny formed dauers in daf-4 animals bearing geEx2, which increases life span 1.5x, while 29% of the roller progeny formed dauers in the daf-4 animals bearing geEx3, which increases life span 1.2x (Table 3). Even at 15° C., both daf-4; geEx2 and daf-4; geEx3 animals had a significant increase in dauer formation (Table 3). While daf-1 mutants bearing the sir-2.1 transgene showed little synergy at 15° C., these animals showed a significant increase in dauer formation at 20° C. (Table 3). Thus similar to mutations of other components of the daf-16 dependent dauer pathway, sir-2.1 transgenes synergize with TGF-β signaling pathway mutations, further supporting that sir-2.1 exerts its effect on the insulin-like signaling pathway. The effect of the sir-2.1 transgene alone may be too subtle to trigger dauer formation without the sensitizing daf-1 or daf-4 mutations.

TABLE 3

The sir-2.1 transgene synergizes with TGF-β signaling mutants for dauer formation

| Genotype | % Dauer Formation | | Lifespan of Array |
|---|---|---|---|
| | 15° C.(n) | 20° C.(n) | |
| daf-4(m63) | 0.7 (449) | 10.0 (981) | — |
| daf-4(m63) + pRF4 | 1.0 (209) | 11.6 (353) | 18.2 |
| daf-4(m63); geEx2 | 15.0 (301) | 48.0 (229) | 27.4 |
| daf-4(m63); geEx3 | 12.4 (431) | 29.2 (380) | 22.4 |
| daf-1(m40) | 0.6 (179) | 2.7 (670) | — |
| daf-1(m40) + pRF4 | 0 (692) | 0 (350) | 18.2 |
| daf-1(m40); geEx2 | 0 (30) | 29.5 (285) | 27.4 |
| daf-1(m40); geEx3 | 1.3 (79) | 13.0 (339) | 22.4 |

Adult hermaphrodites were allowed to lay eggs for 4-18 hours at 15° C. after which they were removed and the plate placed at either 15° C. or 20° C. Eggs and L1 larvae were counted. Either three (20° C.) or six (15° C.) days later, plates were scored for dauer, nondauer, roller and nonroller. Data are the result of at least two independent experiments. The number of animals tested is indicated as "n". Since daf-1 mutations are a maternal effect, hermaphrodites were allowed to lay eggs at 20° C. for this mutant.

These data show that sir-2.1 may act at the interface between nutrient availability and developmental decisions, for example, whether to form dauer larvae and, in animals that proceed to adulthood, how long to live. sir-2.1 may normally function by silencing genes upstream of daf-16 in cells that respond to the DAF-2 ligand, by silencing genes that result in production of the ligand in signaling cells, or both. Overexpression of sir-2.1 would promote longevity and predispose animals to dauer formation by hyper-repressing these genes.

A less likely possibility is that sir-2.1 is the primary downstream target activated by the daf-16 forkhead transcription factor to mediate dauer formation and longevity. In either case, the NAD-dependence of Sir2 proteins may effectively couple the degree of signaling through this pathway to nutrient availability in wild type animals. It was previously indicated that mutants of *C. Elegans* defective in pharyngeal pumping (eat mutants) might provide a model for calorie restriction that is independent of the daf-16 pathway (Lakowski, B., et al., *Proceedings of the National Academy of Scienes,* 95:13091-13096 (1998)). Since SIR2 appears to be an integral part of the life span extension due to calorie restriction in yeast, these data in *C. elegans,* sir-1 and the daf-16-dependent dauer pathway may also contribute to the benefit of calorie restriction in *C. elegans.*

Sir2 proteins may more generally couple nutrient availability to life decisions by slowing or suspending aging when conditions are poor. In addition to regulating longevity in mother cells, yeast Sir2p also indirectly controls the ability of haploid cells to enter the dormant state of sporulation under nutrient deprivation, by repressing the silent mating type genes and preserving haploid fertility. In sir2 mutants, haploids can not mate to form a a/a diploid cell type required for sporulation.

Thus, replicative aging in yeast mother cells and post-mitotic aging in the soma of adult worms are both regulated by Sir2 proteins. In yeast, one beneficial effect of Sir2p appears to occur in the rDNA, where Sir2-silencing represses recombination and may also coordinate rRNA synthesis to growth rate. In *C. elegans,* silencing by Sir2 may couple nutrient availability to the level of signaling through the daf-16 pathway. Sir2 proteins may regulate the rate of aging in other eukaryotes, which contain both dividing and post-mitotic cells in their soma. SIR2 genese may provide a link that coordinates aging in these two kinds of tissues to nutrient availability in an underlying and pervasive regulatory mechanism.

The life span of 35 different strains of *C. elegans* with duplications spanning about 50% of the genome's. This duplication contains the *C. elegans* gene sir-2.1 homologous to yeast SIR2. Transgenic *C. elegans* worms with extra copies of sir-2.1 also had extended life span compared to non-transgenic worms. Double mutant analysis indicates that the sir-2.1 transgene functions upstream of daf-16 in the insulin-like signaling pathway that regulates longevity in adult worms and entry into the dormant dauer state in larvae. These data show that Sir2 proteins couple longevity to nutrient availability in a wide variety of eukaryotic organisms.

What is claimed is:

1. A method of identifying an agent that alters NAD-dependent deacetylation activity of a Sir2 protein, comprising the steps of:
   a) combining an acetylated protein, the agent to be tested and the Sir2 protein or a fragment of the Sir2 protein, wherein the fragment of the Sir2 protein comprises an amino acid sequence selected from the group consisting of the amino acid sequence of SEQ ID NO 2, SEQ ID NO: 3, SEQ ID NO: 4, SEQ ID NO: 5, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 27, SEQ ID NO: 28 and SEQ ID NO: 38;
   b) measuring NAD-dependent deacetylation activity of the Sir2 protein or the fragment of the Sir2 protein with respect to at least one lysine residue in the acetylated protein; and
   c) comparing the NAD-dependent deacetylation activity of the Sir2 protein or the fragment of the Sir2 protein with respect to at least one lysine residue in the acetylated protein in the presence of the agent with the NAD-dependent deacetylation activity of the Sir2 protein or the fragment of the Sir2 protein with respect to at least one lysine residue in the acetylated protein in the absence of the agent,
   wherein a difference in the NAD-dependent deacetylation activity of the Sir2 protein or the fragment of the Sir2 protein with respect to at least one lysine residue in the acetylated protein in the presence of the agent identifies the agent that alters NAD-dependent deacetylation of the Sir2 protein.

2. The method of claim 1, wherein the acetylated protein is a nuclear protein.

3. The method according to claim 2, wherein the nuclear protein is a histone protein.

4. The method of claim 1, wherein the acetylated protein is a cytoplasmic protein.

5. The method according to claim 1, wherein the Sir2 protein is a Sir2α protein.

6. The method of claim 5, wherein the Sir2α protein comprises the amino acid sequence of SEQ ID NO: 1.

7. The method of claim 1, wherein the Sir2 protein is an isolated Sir2 protein.

8. The method of claim 7, wherein the isolated Sir2 protein is a recombinant Sir2 protein.

9. The method of claim 1, wherein the Sir2 protein is a human Sir2 protein.

10. The method of claim 9, wherein the human Sir2 protein comprises SEQ ID NO: 38.

11. The method of claim 1, wherein the Sir2 protein is an isolated nuclear protein.

12. The method of claim 1, wherein the difference in NAD-dependent deacetylation activity of the Sir2 protein or the fragment of the Sir2 protein is an increase in NAD-dependent deacetylation activity and identifies the agent that increases NAD-dependent deacetylation activity of the Sir2 protein.

13. The method of claim 12, wherein the agent is an agonist of NAD-dependent deacetylation activity of the Sir2 protein.

14. The method of claim 1, wherein the difference in NAD-dependent deacetylation activity of the Sir2 protein or the fragment of the Sir2 protein is a decrease in NAD-dependent deacetylation activity and identifies the agent that decreases NAD-dependent deacetylation activity.

15. The method of claim 14, wherein the agent is an antagonist of NAD-dependent deacetylation activity of the Sir2 protein.

16. The method of claim 1, wherein the fragment of the Sir2 protein comprises the amino acid sequence of SEQ ID NO: 9.

17. The method of claim 1, wherein the fragment of the Sir2 protein comprises the amino acid sequence of SEQ ID NO: 19.

18. The method of claim 1, wherein the fragment of the Sir2 protein comprises the amino acid sequence of SEQ ID NO: 38.

* * * * *

SEQUENCE LISTING

```
<160> NUMBER OF SEQ ID NOS: 39

<210> SEQ ID NO 1
<211> LENGTH: 737
<212> TYPE: PRT
<213> ORGANISM: Mus musculus

<400> SEQUENCE: 1

Met Ala Asp Glu Val Ala Leu Ala Leu Gln Ala Ala Gly Ser Pro Ser
 1               5                   10                  15

Ala Ala Ala Ala Met Glu Ala Ala Ser Gln Pro Ala Asp Glu Pro Leu
            20                  25                  30

Arg Lys Arg Pro Arg Arg Asp Gly Pro Gly Leu Gly Arg Ser Pro Gly
```

-continued

```
                35                  40                  45
Glu Pro Ser Ala Ala Val Ala Pro Ala Ala Gly Cys Glu Ala Ala
 50                  55                  60
Ser Ala Ala Ala Pro Ala Ala Leu Trp Arg Glu Ala Ala Gly Ala Ala
 65                  70                  75                  80
Ala Ser Ala Glu Arg Glu Ala Pro Ala Thr Ala Val Ala Gly Asp Gly
                 85                  90                  95
Asp Asn Gly Ser Gly Leu Arg Arg Glu Pro Arg Ala Ala Asp Asp Phe
                100                 105                 110
Asp Asp Asp Glu Gly Glu Glu Asp Glu Ala Ala Ala Ala Ala
                115                 120                 125
Ala Ala Ala Ile Gly Tyr Arg Asp Asn Leu Leu Leu Thr Asp Gly Leu
130                 135                 140
Leu Thr Asn Gly Phe His Ser Cys Glu Ser Asp Asp Asp Arg Thr
145                 150                 155                 160
Ser His Ala Ser Ser Asp Trp Thr Pro Arg Pro Arg Ile Gly Pro
                165                 170                 175
Tyr Thr Phe Val Gln Gln His Leu Met Ile Gly Thr Asp Pro Arg Thr
                180                 185                 190
Ile Leu Lys Asp Leu Leu Pro Glu Thr Ile Pro Pro Glu Leu Asp
                195                 200                 205
Asp Met Thr Leu Trp Gln Ile Val Ile Asn Ile Leu Ser Glu Pro Pro
210                 215                 220
Lys Arg Lys Lys Arg Lys Asp Ile Asn Thr Ile Glu Asp Ala Val Lys
225                 230                 235                 240
Leu Leu Gln Glu Cys Lys Lys Ile Ile Val Leu Thr Gly Ala Gly Val
                245                 250                 255
Ser Val Ser Cys Gly Ile Pro Asp Phe Arg Ser Arg Asp Gly Ile Tyr
                260                 265                 270
Ala Arg Leu Ala Val Asp Phe Pro Asp Leu Pro Asp Pro Gln Ala Met
                275                 280                 285
Phe Asp Ile Glu Tyr Phe Arg Lys Asp Pro Arg Pro Phe Phe Lys Phe
290                 295                 300
Ala Lys Glu Ile Tyr Pro Gly Gln Phe Gln Pro Ser Leu Cys His Lys
305                 310                 315                 320
Phe Ile Ala Leu Ser Asp Lys Glu Gly Lys Leu Leu Arg Asn Tyr Thr
                325                 330                 335
Gln Asn Ile Asp Thr Leu Glu Gln Val Ala Gly Ile Gln Arg Ile Leu
                340                 345                 350
Gln Cys His Gly Ser Phe Ala Thr Ala Ser Cys Leu Ile Cys Lys Tyr
                355                 360                 365
Lys Val Asp Cys Glu Ala Val Arg Gly Asp Ile Phe Asn Gln Val Val
370                 375                 380
Pro Arg Cys Pro Arg Cys Pro Ala Asp Glu Pro Leu Ala Ile Met Lys
385                 390                 395                 400
Pro Glu Ile Val Phe Phe Gly Glu Asn Leu Pro Glu Gln Phe His Arg
                405                 410                 415
Ala Met Lys Tyr Asp Lys Asp Glu Val Asp Leu Leu Ile Val Ile Gly
                420                 425                 430
Ser Ser Leu Lys Val Arg Pro Val Ala Leu Ile Pro Ser Ser Ile Pro
                435                 440                 445
His Glu Val Pro Gln Ile Leu Ile Asn Arg Glu Pro Leu Pro His Leu
                450                 455                 460
```

```
His Phe Asp Val Glu Leu Leu Gly Asp Cys Asp Val Ile Ile Asn Glu
465                 470                 475                 480

Leu Cys His Arg Leu Gly Gly Glu Tyr Ala Lys Leu Cys Cys Asn Pro
            485                 490                 495

Val Lys Leu Ser Glu Ile Thr Glu Lys Pro Pro Arg Pro Gln Lys Glu
        500                 505                 510

Leu Val His Leu Ser Glu Leu Pro Pro Thr Pro Leu His Ile Ser Glu
    515                 520                 525

Asp Ser Ser Pro Glu Arg Thr Val Pro Gln Asp Ser Ser Val Ile
530                 535                 540

Ala Thr Leu Val Asp Gln Ala Thr Asn Asn Val Asn Asp Leu Glu
545                 550                 555                 560

Val Ser Glu Ser Cys Val Glu Glu Lys Pro Gln Glu Val Gln Thr
                565                 570                 575

Ser Arg Asn Val Glu Asn Ile Asn Val Glu Asn Pro Asp Phe Lys Ala
            580                 585                 590

Val Gly Ser Ser Thr Ala Asp Lys Asn Glu Arg Thr Ser Val Ala Glu
        595                 600                 605

Thr Val Arg Lys Cys Trp Pro Asn Arg Leu Ala Lys Glu Gln Ile Ser
610                 615                 620

Lys Arg Leu Glu Gly Asn Gln Tyr Leu Phe Val Pro Pro Asn Arg Tyr
625                 630                 635                 640

Ile Phe His Gly Ala Glu Val Tyr Ser Asp Ser Glu Asp Val Leu
                645                 650                 655

Ser Ser Ser Ser Cys Gly Ser Asn Ser Asp Ser Gly Thr Cys Gln Ser
                660                 665                 670

Pro Ser Leu Glu Glu Pro Leu Glu Asp Glu Ser Glu Ile Glu Glu Phe
            675                 680                 685

Tyr Asn Gly Leu Glu Asp Asp Thr Glu Arg Pro Glu Cys Ala Gly Gly
        690                 695                 700

Ser Gly Phe Gly Ala Asp Gly Gly Asp Gln Glu Val Val Asn Glu Ala
705                 710                 715                 720

Ile Ala Thr Arg Gln Glu Leu Thr Asp Val Asn Tyr Pro Ser Asp Lys
                725                 730                 735

Ser

<210> SEQ ID NO 2
<211> LENGTH: 272
<212> TYPE: PRT
<213> ORGANISM: Saccharomyces cerevisiae

<400> SEQUENCE: 2

Ile Asn Lys Val Leu Cys Thr Arg Leu Arg Leu Ser Asn Phe Phe Thr
1               5                   10                  15

Ile Asp His Phe Ile Gln Lys Leu His Thr Ala Arg Lys Ile Leu Val
            20                  25                  30

Leu Thr Gly Ala Gly Val Ser Thr Ser Leu Gly Ile Pro Asp Phe Arg
        35                  40                  45

Ser Ser Glu Gly Phe Tyr Ser Lys Ile Lys His Leu Gly Leu Asp Asp
    50                  55                  60

Pro Gln Asp Val Phe Asn Tyr Asn Ile Phe Met His Asp Pro Ser Val
65                  70                  75                  80

Phe Tyr Asn Ile Ala Asn Met Val Leu Pro Pro Glu Lys Ile Tyr Ser
                85                  90                  95

Pro Leu His Ser Phe Ile Lys Met Leu Gln Met Lys Gly Lys Leu Leu
```

```
            100                 105                 110
Arg Asn Tyr Thr Gln Asn Ile Asp Asn Leu Glu Ser Tyr Ala Gly Ile
        115                 120                 125

Ser Thr Asp Lys Leu Val Gln Cys His Gly Ser Phe Ala Thr Ala Thr
        130                 135                 140

Cys Val Thr Cys His Trp Asn Leu Pro Gly Glu Arg Ile Phe Asn Lys
145                 150                 155                 160

Ile Arg Asn Leu Glu Leu Pro Leu Cys Pro Tyr Cys Tyr Lys Lys Arg
                165                 170                 175

Arg Glu Tyr Phe Pro Glu Gly Tyr Asn Asn Lys Val Gly Val Ala Ala
                180                 185                 190

Ser Gln Gly Ser Met Ser Glu Arg Pro Pro Tyr Ile Leu Asn Ser Tyr
            195                 200                 205

Gly Val Leu Lys Pro Asp Ile Thr Phe Phe Gly Glu Ala Leu Pro Asn
        210                 215                 220

Lys Phe His Lys Ser Ile Arg Glu Asp Ile Leu Glu Cys Asp Leu Leu
225                 230                 235                 240

Ile Cys Ile Gly Thr Ser Leu Lys Val Ala Pro Val Ser Glu Ile Val
                245                 250                 255

Asn Met Val Pro Ser His Val Pro Gln Val Leu Ile Asn Arg Asp Pro
                260                 265                 270

<210> SEQ ID NO 3
<211> LENGTH: 267
<212> TYPE: PRT
<213> ORGANISM: Saccharomyces cerevisiae

<400> SEQUENCE: 3

Ile Asn Lys Val Leu Ser Thr Arg Leu Arg Leu Pro Asn Phe Asn Thr
1               5                   10                  15

Ile Asp His Phe Thr Ala Thr Leu Arg Asn Ala Lys Lys Ile Leu Val
                20                  25                  30

Leu Thr Gly Ala Gly Val Ser Thr Ser Leu Gly Ile Pro Asp Phe Arg
            35                  40                  45

Ser Ser Glu Gly Phe Tyr Ser Lys Ile Arg His Leu Gly Leu Glu Asp
        50                  55                  60

Pro Gln Asp Val Phe Asn Leu Asp Ile Phe Leu Gln Asp Pro Ser Val
65                  70                  75                  80

Phe Tyr Asn Ile Ala His Met Val Leu Pro Pro Glu Asn Met Tyr Ser
                85                  90                  95

Pro Leu His Ser Phe Ile Lys Met Leu Gln Asp Lys Gly Lys Leu Leu
                100                 105                 110

Arg Asn Tyr Thr Gln Asn Ile Asp Asn Leu Glu Ser Tyr Ala Gly Ile
        115                 120                 125

Asp Pro Asp Lys Leu Val Gln Cys His Gly Ser Phe Ala Thr Ala Ser
        130                 135                 140

Cys Val Thr Cys His Trp Gln Ile Pro Gly Glu Lys Ile Phe Glu Asn
145                 150                 155                 160

Ile Arg Asn Leu Glu Leu Pro Leu Cys Pro Tyr Cys Tyr Gln Lys Arg
                165                 170                 175

Lys Gln Tyr Phe Pro Met Ser Asn Gly Asn Asn Thr Val Gln Thr Asn
        180                 185                 190

Ile Asn Phe Asn Ser Pro Ile Leu Lys Ser Tyr Gly Val Leu Lys Pro
            195                 200                 205

Asp Met Thr Phe Phe Gly Glu Ala Leu Pro Ser Arg Phe His Lys Thr
```

```
                    210                 215                 220
Ile Arg Lys Asp Ile Leu Glu Cys Asp Leu Leu Ile Cys Ile Gly Thr
225                 230                 235                 240

Ser Leu Lys Val Ala Pro Val Ser Glu Ile Val Asn Met Val Pro Ser
                245                 250                 255

His Val Pro Gln Ile Leu Ile Asn Arg Asp Met
                260                 265

<210> SEQ ID NO 4
<211> LENGTH: 245
<212> TYPE: PRT
<213> ORGANISM: Mus musculus

<400> SEQUENCE: 4

Val Ile Asn Ile Leu Ser Glu Pro Pro Lys Arg Lys Lys Arg Lys Asp
1               5                   10                  15

Ile Asn Thr Ile Glu Asp Ala Val Lys Leu Leu Gln Glu Cys Lys Lys
                20                  25                  30

Ile Ile Val Leu Thr Gly Ala Gly Val Ser Val Ser Cys Gly Ile Pro
            35                  40                  45

Asp Phe Arg Ser Arg Asp Gly Ile Tyr Ala Arg Leu Ala Val Asp Phe
        50                  55                  60

Pro Asp Leu Pro Asp Pro Gln Ala Met Phe Asp Ile Glu Tyr Phe Arg
65                  70                  75                  80

Lys Asp Pro Arg Pro Phe Phe Lys Phe Ala Lys Glu Ile Tyr Pro Gly
                85                  90                  95

Gln Phe Gln Pro Ser Leu Cys His Lys Phe Ile Ala Leu Ser Asp Lys
                100                 105                 110

Glu Gly Lys Leu Leu Arg Asn Tyr Thr Gln Asn Ile Asp Thr Leu Glu
            115                 120                 125

Gln Val Ala Gly Ile Gln Arg Ile Leu Gln Cys His Gly Ser Phe Ala
        130                 135                 140

Thr Ala Ser Cys Leu Ile Cys Lys Tyr Lys Val Asp Cys Glu Ala Val
145                 150                 155                 160

Arg Gly Asp Ile Phe Asn Gln Val Val Pro Arg Cys Pro Arg Cys Pro
                165                 170                 175

Ala Asp Glu Pro Leu Ala Ile Met Lys Pro Glu Ile Val Phe Phe Gly
                180                 185                 190

Glu Asn Leu Pro Glu Gln Phe His Arg Ala Met Lys Tyr Asp Lys Asp
            195                 200                 205

Glu Val Asp Leu Leu Ile Val Ile Gly Ser Ser Leu Lys Val Arg Pro
        210                 215                 220

Val Ala Leu Ile Pro Ser Ser Ile Pro His Glu Val Pro Gln Ile Leu
225                 230                 235                 240

Ile Asn Arg Glu Pro
                245

<210> SEQ ID NO 5
<211> LENGTH: 237
<212> TYPE: PRT
<213> ORGANISM: Salmonella typhimurium

<400> SEQUENCE: 5

Met Met Glu Asn Pro Arg Val Leu Val Leu Thr Gly Ala Gly Ile Ser
1               5                   10                  15

Ala Glu Ser Gly Ile Arg Thr Phe Arg Ala Ala Asp Gly Leu Trp Glu
                20                  25                  30
```

-continued

Glu His Arg Val Glu Asp Val Ala Thr Pro Glu Gly Phe Ala Arg Asn
            35                  40                  45

Pro Gly Leu Val Gln Thr Phe Tyr Asn Ala Arg Arg Gln Gln Leu Gln
    50                  55                  60

Gln Pro Glu Ile Gln Pro Asn Ala Ala His Leu Ala Leu Ala Asn Leu
65                  70                  75                  80

Lys Lys Arg Leu Ala Ile Ala Phe Leu Leu Val Thr Gln Asn Ile Asp
                85                  90                  95

Asn Leu His Glu Arg Ala Gly Asn Arg Asn Ile Ile Gln Met His Gly
            100                 105                 110

Glu Leu Leu Lys Val Arg Cys Ser Gln Ser Gly Gln Ile Leu Glu Trp
        115                 120                 125

Asn Gly Asp Val Met Pro Glu Asp Lys Cys His Cys Cys Gln Phe Pro
    130                 135                 140

Ala Pro Leu Arg Pro His Val Val Trp Phe Gly Glu Met Pro Leu Gly
145                 150                 155                 160

Met Asp Glu Ile Tyr Met Ala Leu Ser Met Ala Asp Ile Phe Ile Ala
                165                 170                 175

Ile Gly Thr Ser Gly His Val Tyr Pro Ala Ala Gly Phe Val His Glu
            180                 185                 190

Ala Lys Leu His Gly Ala His Thr Val Glu Leu Asn Leu Glu Pro Ser
        195                 200                 205

Gln Val Gly Asn Glu Phe Glu Glu Lys His Tyr Gly Pro Ala Ser Gln
    210                 215                 220

Val Val Pro Glu Phe Val Asp Lys Phe Leu Lys Gly Leu
225                 230                 235

<210> SEQ ID NO 6
<211> LENGTH: 21
<212> TYPE: PRT
<213> ORGANISM: Homo sapiens

<400> SEQUENCE: 6

Ala Arg Thr Lys Gln Thr Ala Arg Lys Ser Thr Gly Gly Lys Ala Pro
1               5                   10                  15

Arg Lys Gln Leu Cys
            20

<210> SEQ ID NO 7
<211> LENGTH: 20
<212> TYPE: PRT
<213> ORGANISM: Homo sapiens

<400> SEQUENCE: 7

Ser Gly Arg Gly Lys Gly Gly Lys Gly Leu Gly Lys Gly Gly Ala Lys
1               5                   10                  15

Arg His Arg Cys
            20

<210> SEQ ID NO 8
<211> LENGTH: 19
<212> TYPE: PRT
<213> ORGANISM: Homo sapiens

<400> SEQUENCE: 8

Ala Gly Gly Lys Gly Gly Lys Gly Met Gly Lys Val Gly Ala Lys Arg
1               5                   10                  15

His Ser Cys

<210> SEQ ID NO 9
<211> LENGTH: 128
<212> TYPE: PRT
<213> ORGANISM: Mus musculus

<400> SEQUENCE: 9

```
Ile Val Leu Thr Gly Ala Gly Val Ser Val Ser Cys Gly Ile Pro Asp
 1               5                  10                  15

Phe Arg Ser Arg Asp Gly Ile Tyr Ala Arg Leu Ala Val Asp Phe Pro
                20                  25                  30

Asp Leu Pro Asp Pro Gln Ala Met Phe Asp Ile Glu Tyr Phe Arg Lys
            35                  40                  45

Asp Pro Arg Pro Phe Phe Lys Phe Ala Lys Glu Ile Tyr Pro Gly Gln
        50                  55                  60

Phe Gln Pro Ser Leu Cys His Lys Phe Ile Ala Leu Ser Asp Lys Glu
65                  70                  75                  80

Gly Lys Leu Leu Arg Asn Tyr Thr Gln Asn Ile Asp Thr Leu Glu Gln
                85                  90                  95

Val Ala Gly Ile Gln Arg Ile Leu Gln Cys His Gly Ser Phe Ala Thr
            100                 105                 110

Ala Ser Cys Leu Ile Cys Lys Tyr Lys Val Asp Cys Glu Ala Val Arg
        115                 120                 125
```

<210> SEQ ID NO 10
<211> LENGTH: 128
<212> TYPE: PRT
<213> ORGANISM: Saccharomyces cerevisiae

<400> SEQUENCE: 10

```
Leu Val Leu Thr Gly Ala Gly Val Ser Thr Ser Leu Gly Ile Pro Asp
 1               5                  10                  15

Phe Arg Ser Ser Glu Gly Phe Tyr Ser Lys Ile Lys His Leu Gly Leu
                20                  25                  30

Asp Asp Pro Gln Asp Val Phe Asn Tyr Asn Ile Phe Met His Asp Pro
            35                  40                  45

Ser Val Phe Tyr Asn Ile Ala Asn Met Val Leu Pro Pro Glu Lys Ile
        50                  55                  60

Tyr Ser Pro Leu His Ser Phe Ile Lys Met Leu Gln Met Lys Gly Lys
65                  70                  75                  80

Leu Leu Arg Asn Tyr Thr Gln Asn Ile Asp Asn Leu Glu Ser Tyr Ala
                85                  90                  95

Gly Ile Ser Thr Asp Lys Leu Val Gln Cys His Gly Ser Phe Ala Thr
            100                 105                 110

Ala Thr Cys Val Thr Cys His Trp Asn Leu Pro Gly Glu Arg Ile Phe
        115                 120                 125
```

<210> SEQ ID NO 11
<211> LENGTH: 336
<212> TYPE: PRT
<213> ORGANISM: Saccharomyces cerevisiae

<400> SEQUENCE: 11

```
Ala Ile Asn Lys Val Leu Cys Thr Arg Leu Arg Leu Ser Asn Phe Phe
 1               5                  10                  15

Thr Ile Asp His Phe Ile Gln Lys Leu His Thr Ala Arg Lys Ile Leu
                20                  25                  30

Val Leu Thr Gly Ala Gly Val Ser Thr Ser Leu Gly Ile Pro Asp Phe
```

```
                35                40                 45
Arg Ser Ser Glu Gly Phe Tyr Ser Lys Ile Lys His Leu Gly Leu Asp
 50                  55                      60
Asp Pro Gln Asp Val Phe Asn Tyr Asn Ile Phe Met His Asp Pro Ser
 65                     70                      75                  80
Val Phe Tyr Asn Ile Ala Asn Met Val Leu Pro Glu Lys Ile Tyr
                     85                      90                  95
Ser Pro Leu His Ser Phe Ile Lys Met Leu Gln Met Lys Gly Lys Leu
                100                     105                 110
Leu Arg Asn Tyr Thr Gln Asn Ile Asp Asn Leu Glu Ser Tyr Ala Gly
                115                     120                 125
Ile Ser Thr Asp Lys Leu Val Gln Cys His Gly Ser Phe Ala Thr Ala
 130                     135                     140
Thr Cys Val Thr Cys His Trp Asn Leu Pro Gly Glu Arg Ile Phe Asn
 145                     150                     155                 160
Lys Ile Arg Asn Leu Glu Leu Pro Leu Cys Pro Tyr Cys Tyr Lys Lys
                     165                     170                 175
Arg Arg Glu Tyr Phe Pro Glu Gly Tyr Asn Asn Lys Val Gly Val Ala
                     180                     185                 190
Ala Ser Gln Gly Ser Met Ser Glu Arg Pro Pro Tyr Ile Leu Asn Ser
                195                     200                 205
Tyr Gly Val Leu Lys Pro Asp Ile Thr Phe Phe Gly Glu Ala Leu Pro
 210                     215                     220
Asn Lys Phe His Lys Ser Ile Arg Glu Asp Ile Leu Glu Cys Asp Leu
 225                     230                     235                 240
Leu Ile Cys Ile Gly Thr Ser Leu Lys Val Ala Pro Val Ser Glu Ile
                     245                     250                 255
Val Asn Met Val Pro Ser His Val Pro Gln Val Leu Ile Asn Arg Asp
                260                     265                 270
Pro Val Lys His Ala Glu Phe Asp Leu Ser Leu Leu Gly Tyr Cys Asp
                275                     280                 285
Asp Ile Ala Ala Met Val Ala Gln Lys Cys Gly Trp Thr Ile Pro His
 290                     295                     300
Lys Lys Trp Asn Asp Leu Lys Asn Lys Asn Phe Lys Cys Gln Glu Lys
 305                     310                     315                 320
Asp Lys Gly Val Tyr Val Thr Ser Asp Glu His Pro Lys Thr Leu
                     325                     330                 335

<210> SEQ ID NO 12
<211> LENGTH: 327
<212> TYPE: PRT
<213> ORGANISM: Mus musculus

<400> SEQUENCE: 12

Val Ile Asn Ile Leu Ser Glu Pro Pro Lys Arg Lys Lys Arg Lys Asp
  1               5                  10                  15
Ile Asn Thr Ile Glu Asp Ala Val Lys Leu Leu Gln Glu Cys Lys Lys
                 20                  25                  30
Ile Ile Val Leu Thr Gly Ala Gly Val Ser Val Ser Cys Gly Ile Pro
                 35                  40                  45
Asp Phe Arg Ser Arg Asp Gly Ile Tyr Ala Arg Leu Ala Val Asp Phe
     50                  55                  60
Pro Asp Leu Pro Asp Pro Gln Ala Met Phe Asp Ile Glu Tyr Phe Arg
 65                  70                  75                  80
Lys Asp Pro Arg Pro Phe Phe Lys Phe Ala Lys Glu Ile Tyr Pro Gly
```

```
Gln Phe Gln Pro Ser Leu Cys His Lys Phe Ile Ala Leu Ser Asp Lys
         85                  90                  95
Glu Gly Lys Leu Leu Arg Asn Tyr Thr Gln Asn Ile Asp Thr Leu Glu
    100                 105                 110
Gln Val Ala Gly Ile Gln Arg Ile Leu Gln Cys His Gly Ser Phe Ala
115                 120                 125
Thr Ala Ser Cys Leu Ile Cys Lys Tyr Lys Val Asp Cys Glu Ala Val
130                 135                 140
Arg Gly Asp Ile Phe Asn Gln Val Val Pro Arg Cys Pro Arg Cys Pro
145                 150                 155                 160
Ala Asp Glu Pro Leu Ala Ile Met Lys Pro Glu Ile Val Phe Phe Gly
    165                 170                 175
Glu Asn Leu Pro Glu Gln Phe His Arg Ala Met Lys Tyr Asp Lys Asp
180                 185                 190
    195                 200                 205
Glu Val Asp Leu Leu Ile Val Ile Gly Ser Ser Leu Lys Val Arg Pro
    210                 215                 220
Val Ala Leu Ile Pro Ser Ser Ile Pro His Glu Val Pro Gln Ile Leu
225                 230                 235                 240
Ile Asn Arg Glu Pro Leu Pro His Leu His Phe Asp Val Glu Leu Leu
            245                 250                 255
Gly Asp Cys Asp Val Ile Ile Asn Glu Leu Cys His Arg Leu Gly Gly
        260                 265                 270
Glu Tyr Ala Lys Leu Cys Cys Asn Pro Val Lys Leu Ser Glu Ile Thr
    275                 280                 285
Glu Lys Pro Pro Arg Pro Gln Lys Glu Leu Val His Leu Ser Glu Leu
290                 295                 300
Pro Pro Thr Pro Leu His Ile Ser Glu Asp Ser Ser Pro Glu Arg
305                 310                 315                 320
Thr Val Pro Gln Asp Ser Ser
            325

<210> SEQ ID NO 13
<211> LENGTH: 237
<212> TYPE: PRT
<213> ORGANISM: Salmonella typhimurium

<400> SEQUENCE: 13

Met Met Glu Asn Pro Arg Val Leu Val Leu Thr Gly Ala Gly Ile Ser
 1               5                  10                  15
Ala Glu Ser Gly Ile Arg Thr Phe Arg Ala Ala Asp Gly Leu Trp Glu
            20                  25                  30
Glu His Arg Val Glu Asp Val Ala Thr Pro Glu Gly Pro Ala Arg Asn
        35                  40                  45
Pro Gly Leu Val Gln Thr Phe Tyr Asn Ala Arg Arg Gln Gln Leu Gln
    50                  55                  60
Gln Pro Glu Ile Gln Pro Asn Ala Ala His Leu Ala Leu Ala Asn Leu
65                  70                  75                  80
Lys Lys Arg Leu Ala Ile Ala Phe Leu Leu Val Thr Gln Asn Ile Asp
            85                  90                  95
Asn Leu His Glu Arg Ala Gly Asn Arg Asn Ile Ile Gln Met His Gly
            100                 105                 110
Glu Leu Leu Lys Val Arg Cys Ser Gln Ser Gly Gln Ile Leu Glu Trp
        115                 120                 125
Asn Gly Asp Val Met Pro Glu Asp Lys Cys His Cys Cys Gln Phe Pro
```

```
            130                 135                 140
Ala Pro Leu Arg Pro His Val Val Trp Phe Gly Glu Met Pro Leu Gly
145                 150                 155                 160

Met Asp Glu Ile Tyr Met Ala Leu Ser Met Ala Asp Ile Phe Ile Ala
                165                 170                 175

Ile Gly Thr Ser Gly His Val Tyr Pro Ala Ala Gly Phe Val His Glu
            180                 185                 190

Ala Lys Leu His Gly Ala His Thr Val Glu Leu Asn Leu Glu Pro Ser
        195                 200                 205

Gln Val Gly Asn Glu Phe Glu Glu Lys His Tyr Gly Pro Ala Ser Gln
    210                 215                 220

Val Val Pro Glu Phe Val Asp Lys Phe Leu Lys Gly Leu
225                 230                 235

<210> SEQ ID NO 14
<211> LENGTH: 106
<212> TYPE: PRT
<213> ORGANISM: Saccharomyces cerevisiae

<400> SEQUENCE: 14

Ile Leu Val Leu Thr Gly Ala Gly Val Ser Thr Ser Leu Gly Ile Pro
1               5                   10                  15

Asp Phe Arg Ser Ser Glu Gly Phe Tyr Ser Lys Ile Lys His Leu Gly
            20                  25                  30

Leu Asp Asp Pro Gln Asp Val Phe Asn Tyr Asn Ile Phe Met His Asp
        35                  40                  45

Pro Ser Val Phe Tyr Asn Ile Ala Asn Met Val Leu Pro Pro Glu Lys
    50                  55                  60

Ile Tyr Ser Pro Leu His Ser Phe Ile Lys Met Leu Gln Met Lys Gly
65                  70                  75                  80

Lys Leu Leu Arg Asn Tyr Thr Gln Asn Ile Asp Asn Leu Glu Ser Tyr
                85                  90                  95

Ala Gly Ile Ser Thr Asp Lys Leu Val Gln
            100                 105

<210> SEQ ID NO 15
<211> LENGTH: 106
<212> TYPE: PRT
<213> ORGANISM: Saccharomyces cerevisiae

<400> SEQUENCE: 15

Ile Leu Val Leu Thr Gly Ala Gly Val Ser Thr Ser Leu Gly Ile Pro
1               5                   10                  15

Asp Phe Arg Ser Ser Glu Gly Phe Tyr Ser Lys Ile Arg His Leu Gly
            20                  25                  30

Leu Glu Asp Pro Gln Asp Val Phe Asn Leu Asp Ile Phe Leu Gln Asp
        35                  40                  45

Pro Ser Val Phe Tyr Asn Ile Ala His Met Val Leu Pro Pro Glu Asn
    50                  55                  60

Met Tyr Ser Pro Leu His Ser Phe Ile Lys Met Leu Gln Asp Lys Gly
65                  70                  75                  80

Lys Leu Leu Arg Asn Tyr Thr Gln Asn Ile Asp Asn Leu Glu Ser Tyr
                85                  90                  95

Ala Gly Ile Asp Pro Asp Lys Leu Val Gln
            100                 105

<210> SEQ ID NO 16
```

```
<211> LENGTH: 107
<212> TYPE: PRT
<213> ORGANISM: Saccharomyces cerevisiae

<400> SEQUENCE: 16

Val Ile Phe Met Val Gly Ala Gly Ile Ser Thr Ser Cys Gly Ile Pro
 1               5                  10                  15

Asp Phe Arg Ser Pro Gly Thr Gly Leu Tyr His Asn Leu Ala Arg Leu
                20                  25                  30

Lys Leu Pro Tyr Pro Glu Ala Val Phe Asp Val Asp Phe Gln Ser
            35                  40                  45

Asp Pro Leu Pro Phe Tyr Thr Leu Ala Lys Glu Leu Tyr Pro Gly Asn
    50                  55                  60

Phe Arg Pro Ser Lys Phe His Tyr Leu Leu Lys Leu Phe Gln Asp Lys
65                  70                  75                  80

Asp Val Leu Lys Arg Val Tyr Thr Gln Asn Ile Asp Thr Leu Glu Arg
                85                  90                  95

Gln Ala Gly Val Lys Asp Asp Leu Ile Ile Glu
                100                 105

<210> SEQ ID NO 17
<211> LENGTH: 131
<212> TYPE: PRT
<213> ORGANISM: Saccharomyces cerevisiae

<400> SEQUENCE: 17

Ile Ala Cys Leu Thr Gly Ala Gly Ile Ser Cys Asn Ala Gly Ile Pro
 1               5                  10                  15

Asp Phe Arg Ser Ser Asp Gly Leu Tyr Asp Leu Val Lys Lys Asp Cys
                20                  25                  30

Ser Gln Tyr Trp Ser Ile Lys Ser Gly Arg Glu Met Phe Asp Ile Ser
            35                  40                  45

Leu Phe Arg Asp Asp Phe Lys Ile Ser Ile Phe Ala Lys Phe Met Glu
    50                  55                  60

Arg Leu Tyr Ser Asn Val Gln Leu Ala Lys Pro Thr Lys Thr His Lys
65                  70                  75                  80

Phe Ile Ala His Leu Lys Asp Arg Asn Lys Leu Leu Arg Cys Tyr Thr
                85                  90                  95

Gln Asn Ile Asp Gly Leu Glu Glu Ser Ile Gly Leu Thr Leu Ser Asn
                100                 105                 110

Arg Lys Leu Pro Leu Thr Ser Phe Ser Ser His Trp Lys Asn Leu Asp
            115                 120                 125

Val Val Gln
    130

<210> SEQ ID NO 18
<211> LENGTH: 117
<212> TYPE: PRT
<213> ORGANISM: Saccharomyces cerevisiae

<400> SEQUENCE: 18

Met Val Val Val Ser Gly Ala Gly Ile Ser Val Ala Ala Gly Ile Pro
 1               5                  10                  15

Asp Phe Arg Ser Ser Glu Gly Ile Phe Ser Thr Val Asn Gly Gly Ser
                20                  25                  30

Gly Lys Asp Leu Phe Asp Tyr Asn Arg Val Tyr Gly Asp Glu Ser Met
            35                  40                  45

Ser Leu Lys Phe Asn Gln Leu Met Val Ser Leu Phe Arg Leu Ser Lys
```

```
                50                  55                  60
Asn Cys Gln Pro Thr Lys Phe His Glu Met Leu Asn Glu Phe Ala Arg
 65                  70                  75                  80

Asp Gly Arg Leu Leu Arg Leu Tyr Thr Gln Asn Ile Asp Gly Leu Asp
                 85                  90                  95

Thr Gln Leu Pro His Leu Ser Thr Asn Val Pro Leu Ala Lys Pro Ile
                100                 105                 110

Pro Ser Thr Val Gln
        115

<210> SEQ ID NO 19
<211> LENGTH: 106
<212> TYPE: PRT
<213> ORGANISM: Mus musculus

<400> SEQUENCE: 19

Ile Ile Val Leu Thr Gly Ala Gly Val Ser Val Ser Cys Gly Ile Pro
  1               5                  10                  15

Asp Phe Arg Ser Arg Asp Gly Ile Tyr Ala Arg Leu Ala Val Asp Phe
                 20                  25                  30

Pro Asp Leu Pro Asp Pro Gln Ala Met Phe Asp Ile Glu Tyr Phe Arg
             35                  40                  45

Lys Asp Pro Arg Pro Phe Phe Lys Phe Ala Lys Glu Ile Tyr Pro Gly
 50                  55                  60

Gln Phe Gln Pro Ser Leu Cys His Lys Phe Ile Ala Leu Ser Asp Lys
 65                  70                  75                  80

Glu Gly Lys Leu Leu Arg Asn Tyr Thr Gln Asn Ile Asp Thr Leu Glu
                 85                  90                  95

Gln Val Ala Gly Ile Gln Arg Ile Leu Gln
                100                 105

<210> SEQ ID NO 20
<211> LENGTH: 107
<212> TYPE: PRT
<213> ORGANISM: Mus musculus

<400> SEQUENCE: 20

Val Ile Cys Leu Val Gly Ala Gly Ile Ser Thr Ser Ala Gly Ile Pro
  1               5                  10                  15

Asp Phe Arg Ser Pro Ser Thr Gly Leu Tyr Ala Asn Leu Glu Lys Tyr
                 20                  25                  30

His Leu Pro Tyr Pro Glu Ala Ile Phe Glu Ile Ser Tyr Phe Lys Lys
             35                  40                  45

His Pro Glu Pro Phe Phe Ala Leu Ala Lys Glu Leu Tyr Pro Gly Gln
 50                  55                  60

Phe Lys Pro Thr Ile Cys His Tyr Phe Ile Arg Leu Leu Lys Glu Lys
 65                  70                  75                  80

Gly Leu Leu Leu Arg Cys Tyr Thr Gln Asn Ile Asp Thr Leu Glu Arg
                 85                  90                  95

Val Ala Gly Leu Glu Pro Gln Asp Leu Val Glu
                100                 105

<210> SEQ ID NO 21
<211> LENGTH: 86
<212> TYPE: PRT
<213> ORGANISM: Mus musculus

<400> SEQUENCE: 21
```

-continued

Gly Thr Arg Leu Tyr Ser Asn Leu Gln Gln Tyr Asp Ile Pro Tyr Pro
1               5                   10                  15

Glu Ala Ile Phe Glu Leu Gly Phe Phe His Asn Pro Lys Pro Phe
            20                  25                  30

Phe Met Leu Ala Lys Glu Leu Tyr Pro Gly His Tyr Arg Pro Asn Val
        35                  40                  45

Thr His Tyr Phe Leu Arg Leu Leu His Asp Lys Glu Leu Leu Leu Arg
    50                  55                  60

Leu Tyr Thr Gln Asn Ile Asp Gly Leu Glu Arg Ala Ser Gly Ile Pro
65                  70                  75                  80

Ala Ser Lys Leu Val Glu
                85

<210> SEQ ID NO 22
<211> LENGTH: 85
<212> TYPE: PRT
<213> ORGANISM: Mus musculus

<400> SEQUENCE: 22

Val Val Phe His Thr Gly Ala Gly Ile Ser Thr Ala Ser Gly Ile Pro
1               5                   10                  15

Asp Phe Arg Gly Pro His Gly Val Trp Thr Met Glu Glu Arg Gly Leu
            20                  25                  30

Ala Pro Lys Phe Asp Thr Thr Phe Glu Asn Ala Arg Pro Ser Lys Thr
        35                  40                  45

His Met Ala Leu Val Gln Leu Glu Arg Met Gly Phe Leu Ser Phe Leu
    50                  55                  60

Val Ser Gln Asn Val Asp Gly Leu Asp Val Arg Ser Gly Phe Pro Arg
65                  70                  75                  80

Asp Lys Leu Ala Glu
                85

<210> SEQ ID NO 23
<211> LENGTH: 71
<212> TYPE: PRT
<213> ORGANISM: Mus musculus

<400> SEQUENCE: 23

Leu Leu Val Met Thr Gly Ala Gly Ile Ser Thr Glu Ser Gly Ile Pro
1               5                   10                  15

Asp Tyr Arg Ser Glu Lys Val Gly Leu Tyr Ala Arg Thr Asp Arg Arg
            20                  25                  30

Pro Ile Gln His Ile Asp Phe Val Pro Val Leu Arg Ser Ala Ser Gly
        35                  40                  45

Thr Trp Pro Glu Asn Leu Trp Ala Gly Leu Asn Ser Pro Leu Thr Asn
    50                  55                  60

Pro Thr Gln His Thr Trp Leu
65                  70

<210> SEQ ID NO 24
<211> LENGTH: 75
<212> TYPE: PRT
<213> ORGANISM: Mus musculus

<400> SEQUENCE: 24

Ile Ala Ile Ile Ser Gly Ala Gly Val Ser Ala Glu Ser Gly Val Pro
1               5                   10                  15

Thr Phe Arg Gly Ala Gly Gly Tyr Trp Arg Lys Trp Gln Ala Gln Asp
            20                  25                  30

```
Leu Ala Thr Pro Gln Ala Phe Ala Arg Asn Pro Ser Gln Val Trp Glu
         35                  40                  45

Phe Tyr His Tyr Arg Arg Glu Val Met Arg Ser Lys Glu Pro Asn Pro
     50                  55                  60

Gly His Leu Ala Ile Ala Gln Cys Glu Ala Arg
 65                  70                  75

<210> SEQ ID NO 25
<211> LENGTH: 3869
<212> TYPE: DNA
<213> ORGANISM: Mus musculus
<220> FEATURE:
<221> NAME/KEY: CDS
<222> LOCATION: (48)..(2258)

<400> SEQUENCE: 25
gcggagcaga ggaggcgagg gcggagggcc agagaggcag ttggaag atg gcg gac        56
                                                    Met Ala Asp
                                                     1 gag gtg gcg ctc gcc ctt cag gcc gcc ggc tcc cct tcc gcg gcg gcc       104
Glu Val Ala Leu Ala Leu Gln Ala Ala Gly Ser Pro Ser Ala Ala Ala
      5                  10                  15 gcc atg gag gcc gcg tcg cag ccg gcg gac gag ccg ctc cgc aag agg       152
Ala Met Glu Ala Ala Ser Gln Pro Ala Asp Glu Pro Leu Arg Lys Arg
 20                  25                  30                  35 ccc cgc cga gac ggg cct ggc ctc ggg cgc agc ccg ggc gag ccg agc       200
Pro Arg Arg Asp Gly Pro Gly Leu Gly Arg Ser Pro Gly Glu Pro Ser
                 40                  45                  50 gca gca gtg gcg ccg gcg gcc gcg ggg tgt gag gcg gcg agc gcc gcg       248
Ala Ala Val Ala Pro Ala Ala Ala Gly Cys Glu Ala Ala Ser Ala Ala
             55                  60                  65 gcc ccg gcg gcg ctg tgg cgg gag gcg gca ggg gcg gcg gcg agc gcg       296
Ala Pro Ala Ala Leu Trp Arg Glu Ala Ala Gly Ala Ala Ala Ser Ala
         70                  75                  80 gag cgg gag gcc ccg gcg acg gcc gtg gcc ggg gac gga gac aat ggg       344
Glu Arg Glu Ala Pro Ala Thr Ala Val Ala Gly Asp Gly Asp Asn Gly
     85                  90                  95 tcc ggc ctg cgg cgg gag ccg agg gcg gct gac gac ttc gac gac gac       392
Ser Gly Leu Arg Arg Glu Pro Arg Ala Ala Asp Asp Phe Asp Asp Asp
100                 105                 110                 115 gag ggc gag gag gag gac gag gcg gcg gcg gca gcg gcg gcg gca gcg       440
Glu Gly Glu Glu Glu Asp Glu Ala Ala Ala Ala Ala Ala Ala Ala Ala
                120                 125                 130 atc ggc tac cga gac aac ctc ctg ttg acc gat gga ctc ctc act aat       488
Ile Gly Tyr Arg Asp Asn Leu Leu Leu Thr Asp Gly Leu Leu Thr Asn
            135                 140                 145 ggc ttt cat tcc tgt gaa agt gat gac gat gac aga acg tca cac gcc       536
Gly Phe His Ser Cys Glu Ser Asp Asp Asp Asp Arg Thr Ser His Ala
        150                 155                 160 agc tct agt gac tgg act ccg cgg ccg cgg ata ggt cca tat act ttt       584
Ser Ser Ser Asp Trp Thr Pro Arg Pro Arg Ile Gly Pro Tyr Thr Phe
165                 170                 175 gtt cag caa cat ctc atg att ggc acc gat cct cga aca att ctt aaa       632
Val Gln Gln His Leu Met Ile Gly Thr Asp Pro Arg Thr Ile Leu Lys
180                 185                 190                 195 gat tta tta cca gaa aca att cct cca cct gag ctg gat gat atg acg       680
Asp Leu Leu Pro Glu Thr Ile Pro Pro Pro Glu Leu Asp Asp Met Thr
                200                 205                 210 ctg tgg cag att gtt att aat atc ctt tca gaa cca cca aag cgg aaa       728
Leu Trp Gln Ile Val Ile Asn Ile Leu Ser Glu Pro Pro Lys Arg Lys
            215                 220                 225
```

```
                              -continued aaa aga aaa gat atc aat aca att gaa gat gct gtg aag tta ctg cag     776
Lys Arg Lys Asp Ile Asn Thr Ile Glu Asp Ala Val Lys Leu Leu Gln
        230                 235                 240 gag tgt aaa aag ata ata gtt ctg act gga gct ggg gtt tct gtc tcc     824
Glu Cys Lys Lys Ile Ile Val Leu Thr Gly Ala Gly Val Ser Val Ser
245                 250                 255 tgt ggg att cct gac ttc aga tca aga gac ggt atc tat gct cgc ctt     872
Cys Gly Ile Pro Asp Phe Arg Ser Arg Asp Gly Ile Tyr Ala Arg Leu
260                 265                 270                 275 gcg gtg gac ttc cca gac ctc cca gac cct caa gcc atg ttt gat att     920
Ala Val Asp Phe Pro Asp Leu Pro Asp Pro Gln Ala Met Phe Asp Ile
                280                 285                 290 gag tat ttt aga aaa gac cca aga cca ttc ttc aag ttt gca aag gaa     968
Glu Tyr Phe Arg Lys Asp Pro Arg Pro Phe Phe Lys Phe Ala Lys Glu
            295                 300                 305 ata tat ccc gga cag ttc cag ccg tct ctg tgt cac aaa ttc ata gct    1016
Ile Tyr Pro Gly Gln Phe Gln Pro Ser Leu Cys His Lys Phe Ile Ala
        310                 315                 320 ttg tca gat aag gaa gga aaa cta ctt cga aat tat act caa aat ata    1064
Leu Ser Asp Lys Glu Gly Lys Leu Leu Arg Asn Tyr Thr Gln Asn Ile
325                 330                 335 gat acc ttg gag cag gtt gca gga atc caa agg atc ctt cag tgt cat    1112
Asp Thr Leu Glu Gln Val Ala Gly Ile Gln Arg Ile Leu Gln Cys His
340                 345                 350                 355 ggt tcc ttt gca aca gca tct tgc ctg att tgt aaa tac aaa gtt gat    1160
Gly Ser Phe Ala Thr Ala Ser Cys Leu Ile Cys Lys Tyr Lys Val Asp
                360                 365                 370 tgt gaa gct gtt cgt gga gac att ttt aat cag gta gtt cct cgg tgc    1208
Cys Glu Ala Val Arg Gly Asp Ile Phe Asn Gln Val Val Pro Arg Cys
            375                 380                 385 cct agg tgc cca gct gat gag cca ctt gcc atc atg aag cca gag att    1256
Pro Arg Cys Pro Ala Asp Glu Pro Leu Ala Ile Met Lys Pro Glu Ile
        390                 395                 400 gtc ttc ttt ggt gaa aac tta cca gaa cag ttt cat aga gcc atg aag    1304
Val Phe Phe Gly Glu Asn Leu Pro Glu Gln Phe His Arg Ala Met Lys
405                 410                 415 tat gac aaa gat gaa gtt gac ctc ctc att gtt att gga tct tct ctg    1352
Tyr Asp Lys Asp Glu Val Asp Leu Leu Ile Val Ile Gly Ser Ser Leu
420                 425                 430                 435 aaa gtg aga cca gta gca cta att cca agt tct ata ccc cat gaa gtg    1400
Lys Val Arg Pro Val Ala Leu Ile Pro Ser Ser Ile Pro His Glu Val
                440                 445                 450 cct caa ata tta ata aat agg gaa cct ttg cct cat cta cat ttt gat    1448
Pro Gln Ile Leu Ile Asn Arg Glu Pro Leu Pro His Leu His Phe Asp
            455                 460                 465 gta gag ctc ctt gga gac tgc gat gtt ata att aat gag ttg tgt cat    1496
Val Glu Leu Leu Gly Asp Cys Asp Val Ile Ile Asn Glu Leu Cys His
        470                 475                 480 agg cta ggt ggt gaa tat gcc aaa ctt tgt tgt aac cct gta aag ctt    1544
Arg Leu Gly Gly Glu Tyr Ala Lys Leu Cys Cys Asn Pro Val Lys Leu
485                 490                 495 tca gaa att act gaa aaa cct cca cgc cca caa aag gaa ttg gtt cat    1592
Ser Glu Ile Thr Glu Lys Pro Pro Arg Pro Gln Lys Glu Leu Val His
500                 505                 510                 515 tta tca gag ttg cca cca aca cct ctt cat att tcg gaa gac tca agt    1640
Leu Ser Glu Leu Pro Pro Thr Pro Leu His Ile Ser Glu Asp Ser Ser
                520                 525                 530 tca cct gaa aga act gta cca caa gac tct tct gtg att gct aca ctt    1688
Ser Pro Glu Arg Thr Val Pro Gln Asp Ser Ser Val Ile Ala Thr Leu
            535                 540                 545
```

```
gta gac caa gca aca aac aac aat gtt aat gat tta gaa gta tct gaa    1736
Val Asp Gln Ala Thr Asn Asn Asn Val Asn Asp Leu Glu Val Ser Glu
            550                 555                 560 tca agt tgt gtg gaa gaa aaa cca caa gaa gta cag act agt agg aat    1784
Ser Ser Cys Val Glu Glu Lys Pro Gln Glu Val Gln Thr Ser Arg Asn
565                 570                 575 gtt gag aac att aat gtg gaa aat cca gat ttt aag gct gtt ggt tcc    1832
Val Glu Asn Ile Asn Val Glu Asn Pro Asp Phe Lys Ala Val Gly Ser
580                 585                 590                 595 agt act gca gac aaa aat gaa aga act tca gtt gca gaa aca gtg aga    1880
Ser Thr Ala Asp Lys Asn Glu Arg Thr Ser Val Ala Glu Thr Val Arg
            600                 605                 610 aaa tgc tgg cct aat aga ctt gca aag gag cag att agt aag cgg ctt    1928
Lys Cys Trp Pro Asn Arg Leu Ala Lys Glu Gln Ile Ser Lys Arg Leu
                615                 620                 625 gag ggt aat caa tac ctg ttt gta cca cca aat cgt tac ata ttc cac    1976
Glu Gly Asn Gln Tyr Leu Phe Val Pro Pro Asn Arg Tyr Ile Phe His
                630                 635                 640 ggt gct gag gta tac tca gac tct gaa gat gac gtc ttg tcc tct agt    2024
Gly Ala Glu Val Tyr Ser Asp Ser Glu Asp Asp Val Leu Ser Ser Ser
645                 650                 655 tcc tgt ggc agt aac agt gac agt ggc aca tgc cag agt cca agt tta    2072
Ser Cys Gly Ser Asn Ser Asp Ser Gly Thr Cys Gln Ser Pro Ser Leu
660                 665                 670                 675 gaa gaa ccc ttg gaa gat gaa agt gaa att gaa gaa ttc tac aat ggc    2120
Glu Glu Pro Leu Glu Asp Glu Ser Glu Ile Glu Glu Phe Tyr Asn Gly
            680                 685                 690 ttg gaa gat gat acg gag agg ccc gaa tgt gct gga gga tct gga ttt    2168
Leu Glu Asp Asp Thr Glu Arg Pro Glu Cys Ala Gly Gly Ser Gly Phe
            695                 700                 705 gga gct gat gga ggg gat caa gag gtt gtt aat gaa gct ata gct aca    2216
Gly Ala Asp Gly Gly Asp Gln Glu Val Val Asn Glu Ala Ile Ala Thr
710                 715                 720 aga cag gaa ttg aca gat gta aac tat cca tca gac aaa tca              2258
Arg Gln Glu Leu Thr Asp Val Asn Tyr Pro Ser Asp Lys Ser
725                 730                 735 taacactatt gaagctgtcc ggattcagga attgctccac cagcattggg aactttagca   2318
tgtcaaaaaa atgaatgttt acttgtgaac ttgaacaagg aaatctgaaa gatgtattat   2378
ttatagactg gaaaatagat tgtcttcttg gataatttct aaagttccat catttctgtt   2438
tgtacttgta cattcaacac tgttggttga cttcatcttc cttcaaggt tcatttgtat    2498
gatacattcg tatgtatgta aattttgtt ttttgcctaa tgagtttcaa ccttttaaag    2558
ttttcaaaag ccattggaat gttaatgtaa agggaacagc ttatctagac caaagaatgg   2618
tatttcacac ttttttgttt gtaacattga atagtttaaa gccctcaatt tctgttctgc   2678
tgaacttta tttttaggac agttaacttt ttaaacactg gcatttcca aaacttgtgg     2738
cagctaactt tttaaaatca cagatgactt gtaatgtgag gagtcagcac cgtgtctgga   2798
gcactcaaaa cttgggctca gtgtgtgaag cgtacttact gcatcgtttt tgtacttgct   2858
gcagacgtgg taatgtccaa acaggcccct gagactaatc tgataaatga tttggaaatg   2918
tgtttcagtt gttctagaaa caatagtgcc tgtctatata ggtcccctta gtttgaatat   2978
ttgccattgt ttaattaaat acctatcact gtggtagagc ctgcatagat cttcaccaca   3038
aatactgcca agatgtgaat atgcaaagcc tttctgaatc taataatggt acttctactg   3098
gggagagtgt aatattttgg actgctgttt ttccattaat gaggaaagca ataggcctct   3158
taattaaagt cccaaagtca taagataaat tgtagctcaa ccagaaagta cactgttgcc   3218
```

-continued

```
tgttgaggat tggtgtaat gtatcccaag gtgttagcct tgtattatgg agatgaatac   3278
agatccaata gtcaaatgaa actagttctt agttatttaa aagcttagct tgccttaaaa   3338
ctagggatca attttctcaa ctgcagaaac ttttagcctt tcaaacagtt cacacctcag   3398
aaagtcagta tttattttac agacttcttt ggaacattgc ccccaaattt aaatattcat   3458
gtgggtttag tatttattac aaaaaaatga tttgaaatat agctgttctt tatgcataaa   3518
atacccagtt aggaccatta ctgccagagg agaaaagtat taagtagctc atttccctac   3578
ctaaaagata actgaattta tttggctaca ctaaagaatg cagtatattt agttttccat   3638
ttgcatgatg tgtttgtgct atagacaata ttttaaattg aaaaatttgt tttaaattat   3698
ttttacagtg aagactgttt tcagctcttt ttatattgta catagacttt tatgtaatct   3758
ggcatatgtt ttgtagaccg tttaatgact ggattatctt cctccaactt ttgaaataca   3818
aaaacagtgt tttatactaa aaaaaaaaaa agtcgacgcg gccgcgaatt c            3869
```

<210> SEQ ID NO 26
<211> LENGTH: 737
<212> TYPE: PRT
<213> ORGANISM: Mus musculus

<400> SEQUENCE: 26

```
Met Ala Asp Glu Val Ala Leu Ala Leu Gln Ala Gly Ser Pro Ser
  1               5                  10                  15

Ala Ala Ala Ala Met Glu Ala Ala Ser Gln Pro Ala Asp Glu Pro Leu
             20                  25                  30

Arg Lys Arg Pro Arg Arg Asp Gly Pro Gly Leu Gly Arg Ser Pro Gly
         35                  40                  45

Glu Pro Ser Ala Ala Val Ala Pro Ala Ala Ala Gly Cys Glu Ala Ala
     50                  55                  60

Ser Ala Ala Pro Ala Ala Leu Trp Arg Glu Ala Ala Gly Ala Ala
 65                  70                  75                  80

Ala Ser Ala Glu Arg Glu Ala Pro Ala Thr Ala Val Ala Gly Asp Gly
                 85                  90                  95

Asp Asn Gly Ser Gly Leu Arg Arg Glu Pro Arg Ala Ala Asp Asp Phe
            100                 105                 110

Asp Asp Asp Glu Gly Glu Glu Asp Glu Ala Ala Ala Ala Ala
        115                 120                 125

Ala Ala Ala Ile Gly Tyr Arg Asp Asn Leu Leu Leu Thr Asp Gly Leu
    130                 135                 140

Leu Thr Asn Gly Phe His Ser Cys Glu Ser Asp Asp Asp Arg Thr
145                 150                 155                 160

Ser His Ala Ser Ser Ser Asp Trp Thr Pro Arg Pro Arg Ile Gly Pro
                165                 170                 175

Tyr Thr Phe Val Gln Gln His Leu Met Ile Gly Thr Asp Pro Arg Thr
            180                 185                 190

Ile Leu Lys Asp Leu Leu Pro Glu Thr Ile Pro Pro Glu Leu Asp
        195                 200                 205

Asp Met Thr Leu Trp Gln Ile Val Ile Asn Ile Leu Ser Glu Pro Pro
    210                 215                 220

Lys Arg Lys Lys Arg Lys Asp Ile Asn Thr Ile Glu Asp Ala Val Lys
225                 230                 235                 240

Leu Leu Gln Glu Cys Lys Lys Ile Ile Val Leu Thr Gly Ala Gly Val
                245                 250                 255

Ser Val Ser Cys Gly Ile Pro Asp Phe Arg Ser Arg Asp Gly Ile Tyr
```

```
                   260                 265                 270
Ala Arg Leu Ala Val Asp Phe Pro Asp Leu Pro Asp Pro Gln Ala Met
            275                 280                 285

Phe Asp Ile Glu Tyr Phe Arg Lys Asp Pro Arg Pro Phe Phe Lys Phe
        290                 295                 300

Ala Lys Glu Ile Tyr Pro Gly Gln Phe Gln Pro Ser Leu Cys His Lys
305                 310                 315                 320

Phe Ile Ala Leu Ser Asp Lys Glu Gly Lys Leu Leu Arg Asn Tyr Thr
                325                 330                 335

Gln Asn Ile Asp Thr Leu Glu Gln Val Ala Gly Ile Gln Arg Ile Leu
            340                 345                 350

Gln Cys His Gly Ser Phe Ala Thr Ala Ser Cys Leu Ile Cys Lys Tyr
        355                 360                 365

Lys Val Asp Cys Glu Ala Val Arg Gly Asp Ile Phe Asn Gln Val Val
        370                 375                 380

Pro Arg Cys Pro Arg Cys Pro Ala Asp Glu Pro Leu Ala Ile Met Lys
385                 390                 395                 400

Pro Glu Ile Val Phe Phe Gly Glu Asn Leu Pro Glu Gln Phe His Arg
                405                 410                 415

Ala Met Lys Tyr Asp Lys Asp Glu Val Asp Leu Leu Ile Val Ile Gly
            420                 425                 430

Ser Ser Leu Lys Val Arg Pro Val Ala Leu Ile Pro Ser Ser Ile Pro
        435                 440                 445

His Glu Val Pro Gln Ile Leu Ile Asn Arg Glu Pro Leu Pro His Leu
        450                 455                 460

His Phe Asp Val Glu Leu Leu Gly Asp Cys Asp Val Ile Ile Asn Glu
465                 470                 475                 480

Leu Cys His Arg Leu Gly Gly Glu Tyr Ala Lys Leu Cys Cys Asn Pro
                485                 490                 495

Val Lys Leu Ser Glu Ile Thr Glu Lys Pro Pro Arg Pro Gln Lys Glu
            500                 505                 510

Leu Val His Leu Ser Glu Leu Pro Pro Thr Pro Leu His Ile Ser Glu
        515                 520                 525

Asp Ser Ser Ser Pro Glu Arg Thr Val Pro Gln Asp Ser Ser Val Ile
530                 535                 540

Ala Thr Leu Val Asp Gln Ala Thr Asn Asn Asn Val Asn Asp Leu Glu
545                 550                 555                 560

Val Ser Glu Ser Ser Cys Val Glu Glu Lys Pro Gln Glu Val Gln Thr
                565                 570                 575

Ser Arg Asn Val Glu Asn Ile Asn Val Glu Asn Pro Asp Phe Lys Ala
            580                 585                 590

Val Gly Ser Ser Thr Ala Asp Lys Asn Glu Arg Thr Ser Val Ala Glu
        595                 600                 605

Thr Val Arg Lys Cys Trp Pro Asn Arg Leu Ala Lys Glu Gln Ile Ser
        610                 615                 620

Lys Arg Leu Glu Gly Asn Gln Tyr Leu Phe Val Pro Pro Asn Arg Tyr
625                 630                 635                 640

Ile Phe His Gly Ala Glu Val Tyr Ser Asp Ser Glu Asp Val Leu
                645                 650                 655

Ser Ser Ser Ser Cys Gly Ser Asn Ser Asp Ser Gly Thr Cys Gln Ser
            660                 665                 670

Pro Ser Leu Glu Glu Pro Leu Glu Asp Glu Ser Glu Ile Glu Glu Phe
        675                 680                 685
```

```
Tyr Asn Gly Leu Glu Asp Asp Thr Glu Arg Pro Glu Cys Ala Gly Gly
            690                 695                 700

Ser Gly Phe Gly Ala Asp Gly Asp Gln Glu Val Val Asn Glu Ala
705                 710                 715                 720

Ile Ala Thr Arg Gln Glu Leu Thr Asp Val Asn Tyr Pro Ser Asp Lys
                725                 730                 735

Ser

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: Leu or Ala

<400> SEQUENCE: 27

Gly Ala Gly Ile Ser Thr Ser Xaa Gly Ile Pro Asp Phe Arg
1               5                   10

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Tyr Thr Gln Asn Ile Asp
1               5

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Lys Arg Lys Lys Arg Lys
1               5

<210> SEQ ID NO 30
<211> LENGTH: 5
<212> TYPE: PRT
<213> ORGANISM: Saccharomyces cerevisiae

<400> SEQUENCE: 30

Val Ser Thr Ser Leu
1               5

<210> SEQ ID NO 31
<211> LENGTH: 5
<212> TYPE: PRT
<213> ORGANISM: Mus musculus

<400> SEQUENCE: 31

Val Ser Val Ser Cys
1               5
```

-continued

```
<210> SEQ ID NO 32
<211> LENGTH: 6
<212> TYPE: PRT
<213> ORGANISM: Mus musculus

<400> SEQUENCE: 32

Leu Ile Asn Lys Glu Lys
 1               5

<210> SEQ ID NO 33
<211> LENGTH: 6
<212> TYPE: PRT
<213> ORGANISM: Mus musculus

<400> SEQUENCE: 33

Leu Ile Asn Arg Asp Leu
 1               5

<210> SEQ ID NO 34
<211> LENGTH: 699
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (3)..(698)

<400> SEQUENCE: 34
```

| | | | | | | | | | | | | | | | | |
|---|---|---|---|---|---|---|---|---|---|---|---|---|---|---|---|---|
| cc acg | cgt | ccg | cgg | acg | cgt | ggg | cac | ggg | aca | gag | cag | tcg | gtg | aca | | 47 |
| Thr | Arg | Pro | Arg | Thr | Arg | Gly | His | Gly | Thr | Glu | Gln | Ser | Val | Thr | | |
| | 1 | | | 5 | | | | 10 | | | | | 15 | | | |
| gtc | ccg | agg | gcc | ccc | acc | ccg | ttc | cca | tgg | ccg | agc | cgg | acc | gat | tca | 95 |
| Val | Pro | Arg | Ala | Pro | Thr | Pro | Phe | Pro | Trp | Pro | Ser | Arg | Thr | Asp | Ser | |
| | | | 20 | | | | | 25 | | | | | 30 | | | |
| gac | tcg | gac | act | gag | gga | gga | gcc | act | ggt | gga | gag | gca | gag | atg | gac | 143 |
| Asp | Ser | Asp | Thr | Glu | Gly | Gly | Ala | Thr | Gly | Gly | Glu | Ala | Glu | Met | Asp | |
| | | 35 | | | | | 40 | | | | | 45 | | | | |
| ttc | ctg | agg | aat | tta | ttc | acc | cag | acc | ctg | ggc | ctg | ggt | tcc | caa | aag | 191 |
| Phe | Leu | Arg | Asn | Leu | Phe | Thr | Gln | Thr | Leu | Gly | Leu | Gly | Ser | Gln | Lys | |
| 50 | | | | | 55 | | | | | 60 | | | | | | |
| gag | cgt | ctt | cta | gac | gag | ctg | acc | ctc | gaa | gga | gtg | aca | cgc | tac | atg | 239 |
| Glu | Arg | Leu | Leu | Asp | Glu | Leu | Thr | Leu | Glu | Gly | Val | Thr | Arg | Tyr | Met | |
| 65 | | | | | 70 | | | | | 75 | | | | | | |
| cag | agc | gag | cgc | tgc | cgc | aag | gtc | atc | tgt | ttg | gtg | gga | gcc | gga | atc | 287 |
| Gln | Ser | Glu | Arg | Cys | Arg | Lys | Val | Ile | Cys | Leu | Val | Gly | Ala | Gly | Ile | |
| 80 | | | | 85 | | | | | 90 | | | | | 95 | | |
| tcc | acg | tcc | gcg | ggt | atc | cct | gac | ttc | cgc | tcc | ccg | tcc | act | ggc | ctc | 335 |
| Ser | Thr | Ser | Ala | Gly | Ile | Pro | Asp | Phe | Arg | Ser | Pro | Ser | Thr | Gly | Leu | |
| | | | 100 | | | | | 105 | | | | | 110 | | | |
| tat | gca | aac | ctg | gag | aag | tac | cac | ctt | cct | tac | cca | gag | gcc | atc | ttt | 383 |
| Tyr | Ala | Asn | Leu | Glu | Lys | Tyr | His | Leu | Pro | Tyr | Pro | Glu | Ala | Ile | Phe | |
| | | 115 | | | | | 120 | | | | | 125 | | | | |
| gag | atc | agc | tac | ttc | aag | aaa | cat | ccg | gaa | ccc | ttc | ttt | gcc | ctt | gcc | 431 |
| Glu | Ile | Ser | Tyr | Phe | Lys | Lys | His | Pro | Glu | Pro | Phe | Phe | Ala | Leu | Ala | |
| | 130 | | | | | 135 | | | | | 140 | | | | | |
| aag | gag | ctc | tat | ccc | ggg | cag | ttc | aag | cca | acc | atc | tgc | cac | tac | ttc | 479 |
| Lys | Glu | Leu | Tyr | Pro | Gly | Gln | Phe | Lys | Pro | Thr | Ile | Cys | His | Tyr | Phe | |
| 145 | | | | | 150 | | | | | 155 | | | | | | |
| atc | cgc | ctg | ctg | aag | gag | aag | ggg | ctg | ctg | cgc | tgc | tac | acg | cag | | 527 |
| Ile | Arg | Leu | Leu | Lys | Glu | Lys | Gly | Leu | Leu | Arg | Cys | Tyr | Thr | Gln | | |
| 160 | | | | | 165 | | | | | 170 | | | | 175 | | |
| aac | ata | gac | acg | ctg | gaa | cga | gtg | gcg | ggg | ctg | gag | ccc | cag | gac | ctg | 575 |

```
Asn Ile Asp Thr Leu Glu Arg Val Ala Gly Leu Glu Pro Gln Asp Leu
                180                 185                 190 gtg gag gcc cac ggc acc ttc tac aca tca cac tgt gtc aac acc tcc      623
Val Glu Ala His Gly Thr Phe Tyr Thr Ser His Cys Val Asn Thr Ser
                195                 200                 205 tgc aga aaa gaa tac acg atg ggc tgg atg aaa gag aag att tct cag      671
Cys Arg Lys Glu Tyr Thr Met Gly Trp Met Lys Glu Lys Ile Ser Gln
                210                 215                 220 aag caa ctc cca ggt gtg agc agt gtc a                                699
Lys Gln Leu Pro Gly Val Ser Ser Val
        225                 230
```

<210> SEQ ID NO 35
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

```
Thr Arg Pro Arg Thr Arg Gly His Gly Thr Glu Gln Ser Val Thr Val
 1               5                  10                  15

Pro Arg Ala Pro Thr Pro Phe Pro Trp Pro Ser Arg Thr Asp Ser Asp
                20                  25                  30

Ser Asp Thr Glu Gly Gly Ala Thr Gly Gly Glu Ala Glu Met Asp Phe
            35                  40                  45

Leu Arg Asn Leu Phe Thr Gln Thr Leu Gly Leu Gly Ser Gln Lys Glu
        50                  55                  60

Arg Leu Leu Asp Glu Leu Thr Leu Glu Gly Val Thr Arg Tyr Met Gln
 65                  70                  75                  80

Ser Glu Arg Cys Arg Lys Val Ile Cys Leu Val Gly Ala Gly Ile Ser
                85                  90                  95

Thr Ser Ala Gly Ile Pro Asp Phe Arg Ser Pro Ser Thr Gly Leu Tyr
                100                 105                 110

Ala Asn Leu Glu Lys Tyr His Leu Pro Tyr Pro Glu Ala Ile Phe Glu
            115                 120                 125

Ile Ser Tyr Phe Lys Lys His Pro Glu Pro Phe Phe Ala Leu Ala Lys
        130                 135                 140

Glu Leu Tyr Pro Gly Gln Phe Lys Pro Thr Ile Cys His Tyr Phe Ile
145                 150                 155                 160

Arg Leu Leu Lys Glu Lys Gly Leu Leu Leu Arg Cys Tyr Thr Gln Asn
                165                 170                 175

Ile Asp Thr Leu Glu Arg Val Ala Gly Leu Glu Pro Gln Asp Leu Val
            180                 185                 190

Glu Ala His Gly Thr Phe Tyr Thr Ser His Cys Val Asn Thr Ser Cys
        195                 200                 205

Arg Lys Glu Tyr Thr Met Gly Trp Met Lys Glu Lys Ile Ser Gln Lys
            210                 215                 220

Gln Leu Pro Gly Val Ser Ser Val
225                 230
```

<210> SEQ ID NO 36
<211> LENGTH: 4
<212> TYPE: PRT
<213> ORGANISM: Mus musculus

<400> SEQUENCE: 36

Thr Leu Gly Leu

```
<210> SEQ ID NO 37
<211> LENGTH: 4
<212> TYPE: PRT
<213> ORGANISM: Mus musculus

<400> SEQUENCE: 37

Phe Gly Gly Gly
 1

<210> SEQ ID NO 38
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: Val or Ile
<220> FEATURE:
<221> NAME/KEY: MOD_RES
<222> LOCATION: (6)
<223> OTHER INFORMATION: Thr or Val
<220> FEATURE:
<221> NAME/KEY: MOD_RES
<222> LOCATION: (8)
<223> OTHER INFORMATION: Leu, Cys or Ala

<400> SEQUENCE: 38

Gly Ala Gly Xaa Ser Xaa Ser Xaa Gly Ile Pro Asp Phe Arg Ser
 1               5                  10                  15

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 39

His His His His His His
 1               5
```